United States Patent
Liu et al.

(10) Patent No.: US 10,011,658 B2
(45) Date of Patent: Jul. 3, 2018

(54) CONSTRUCTS TARGETING AFP PEPTIDE/MHC COMPLEXES AND USES THEREOF

(71) Applicant: EUREKA THERAPEUTICS, INC., Emeryville, CA (US)

(72) Inventors: Cheng Liu, Emeryville, CA (US); Hong Liu, El Sobrante, CA (US); Yiyang Xu, Pleasanton, CA (US); Jingyi Xiang, Walnut Creek, CA (US); Li Long, Lafayette, CA (US)

(73) Assignee: EUREKA THERAPEUTICS, INC., Emeryville, CA (US)

( * ) Notice: Subject to any disclaimer, the term of this patent is extended or adjusted under 35 U.S.C. 154(b) by 0 days.

(21) Appl. No.: 15/829,783

(22) Filed: Dec. 1, 2017

(65) Prior Publication Data

US 2018/0079815 A1    Mar. 22, 2018

Related U.S. Application Data

(63) Continuation of application No. 15/563,912, filed as application No. PCT/US2016/025755 on Apr. 1, 2016.

(60) Provisional application No. 62/142,958, filed on Apr. 3, 2015, provisional application No. 62/244,653, filed on Oct. 21, 2015, provisional application No. 62/304,915, filed on Mar. 7, 2016.

(51) Int. Cl.
| | |
|---|---|
| *A61K 48/00* | (2006.01) |
| *C07K 16/18* | (2006.01) |
| *C07K 16/28* | (2006.01) |
| *C12N 5/0783* | (2010.01) |
| *C12N 5/10* | (2006.01) |
| *C07K 16/30* | (2006.01) |
| *C07K 14/705* | (2006.01) |
| *C07K 14/725* | (2006.01) |
| *A61K 39/00* | (2006.01) |
| *A61K 38/00* | (2006.01) |

(52) U.S. Cl.
CPC ...... *C07K 16/2833* (2013.01); *C07K 14/7051* (2013.01); *C07K 14/70596* (2013.01); *C07K 16/2809* (2013.01); *C07K 16/303* (2013.01); *A61K 38/00* (2013.01); *A61K 2039/54* (2013.01); *C07K 2317/31* (2013.01); *C07K 2317/565* (2013.01); *C07K 2317/622* (2013.01); *C07K 2317/734* (2013.01); *C07K 2317/92* (2013.01); *C07K 2319/02* (2013.01); *C07K 2319/03* (2013.01)

(58) Field of Classification Search
CPC .......... C07K 16/2833; C07K 2317/622; C07K 16/18; C07K 2319/70; C07K 2317/565; C12N 5/0636; C12N 2510/00; A61K 48/00

USPC ..... 424/93.21; 435/328, 330, 331, 332, 334; 530/387.3, 388.22

See application file for complete search history.

(56) References Cited

U.S. PATENT DOCUMENTS

| | | |
|---|---|---|
| 3,773,919 A | 11/1973 | Boswell et al. |
| 4,676,980 A | 6/1987 | Segal et al. |
| 4,816,567 A | 3/1989 | Cabilly et al. |
| 4,975,278 A | 12/1990 | Senter et al. |
| 4,994,560 A | 2/1991 | Kruper, Jr. et al. |
| 5,199,942 A | 4/1993 | Gillis |
| 5,208,020 A | 5/1993 | Chari et al. |
| 5,229,275 A | 7/1993 | Goroff |
| 5,274,119 A | 12/1993 | Frazier et al. |
| 5,342,604 A | 8/1994 | Wilson et al. |
| 5,350,674 A | 9/1994 | Boenisch et al. |
| 5,399,346 A | 3/1995 | Anderson et al. |
| 5,428,139 A | 6/1995 | Kiefer et al. |
| 5,435,990 A | 7/1995 | Cheng et al. |
| 5,489,425 A | 2/1996 | Kruper, Jr. et al. |
| 5,500,362 A | 3/1996 | Robinson et al. |
| 5,505,931 A | 4/1996 | Pribish |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,580,859 A | 12/1996 | Feigner et al. |
| 5,585,362 A | 12/1996 | Wilson et al. |
| 5,589,466 A | 12/1996 | Felgner et al. |
| 5,591,669 A | 1/1997 | Krimpenfort et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,652,361 A | 7/1997 | Simon et al. |
| 5,661,016 A | 8/1997 | Lonberg et al. |

(Continued)

FOREIGN PATENT DOCUMENTS

| | | |
|---|---|---|
| CN | 102321167 B | 4/2013 |
| CN | 103965361 A | 8/2014 |

(Continued)

OTHER PUBLICATIONS

Sela-Culang et al. (2013) Frontiers in Immunology, vol. 4, pp. 1-13.*

(Continued)

*Primary Examiner* — Anne Marie S Wehbe

(74) *Attorney, Agent, or Firm* — Morrison & Foerster LLP

(57) ABSTRACT

The present application provides constructs comprising an antibody moiety that specifically binds to a complex comprising an AFP peptide and an MHC class I protein. Also provided are methods of making and using these constructs.

24 Claims, 27 Drawing Sheets

(56) References Cited

U.S. PATENT DOCUMENTS

| | | | |
|---|---|---|---|
| 5,696,239 | A | 12/1997 | Wilson et al. |
| 5,714,631 | A | 2/1998 | Wilson et al. |
| 5,731,168 | A | 3/1998 | Carter et al. |
| 5,750,373 | A | 5/1998 | Garrard et al. |
| 5,756,065 | A | 5/1998 | Wilson et al. |
| 5,808,003 | A | 9/1998 | Subramanian et al. |
| 5,821,337 | A | 10/1998 | Carter et al. |
| 5,858,358 | A | 1/1999 | June et al. |
| 5,883,223 | A | 3/1999 | Gray |
| 6,194,551 | B1 | 2/2001 | Idusogie et al. |
| 6,326,193 | B1 | 12/2001 | Liu et al. |
| 6,352,694 | B1 | 3/2002 | June et al. |
| 6,534,055 | B1 | 3/2003 | June et al. |
| 6,602,684 | B1 | 8/2003 | Umaña et al. |
| 6,692,964 | B1 | 2/2004 | June et al. |
| 6,737,056 | B1 | 5/2004 | Presta |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,098,306 | B2 | 8/2006 | Economou et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 7,300,655 | B2 | 11/2007 | Hansen et al. |
| 7,332,581 | B2 | 2/2008 | Presta |
| 7,371,826 | B2 | 5/2008 | Presta |
| 7,446,190 | B2 | 11/2008 | Sadelain et al. |
| 7,521,541 | B2 | 4/2009 | Eigenbrot et al. |
| 7,741,465 | B1 | 6/2010 | Eshhar et al. |
| 2002/0031520 | A1 | 3/2002 | Economou et al. |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0014934 | A1 | 1/2005 | Hinton et al. |
| 2005/0079574 | A1 | 4/2005 | Bond |
| 2005/0119455 | A1 | 6/2005 | Fuh et al. |
| 2005/0123546 | A1 | 6/2005 | Umana et al. |
| 2005/0266000 | A1 | 12/2005 | Bond et al. |
| 2006/0121005 | A1 | 6/2006 | Berenson et al. |
| 2007/0117126 | A1 | 5/2007 | Sidhu et al. |
| 2007/0160598 | A1 | 7/2007 | Dennis et al. |
| 2007/0237764 | A1 | 10/2007 | Birtalan et al. |
| 2007/0292936 | A1 | 12/2007 | Barthelemy et al. |
| 2009/0002360 | A1 | 1/2009 | Chen et al. |
| 2012/0251579 | A1 | 10/2012 | Zender |
| 2013/0287748 | A1 | 10/2013 | June et al. |
| 2014/0322129 | A1 | 10/2014 | Leong et al. |

FOREIGN PATENT DOCUMENTS

| | | |
|---|---|---|
| CN | 103965362 A | 8/2014 |
| CN | 104087592 A | 10/2014 |
| CN | 105153315 A | 12/2015 |
| CN | 105331586 A | 2/2016 |
| CN | 103319595 B | 12/2016 |
| EP | 0 003 089 A1 | 7/1979 |
| EP | 0 404 097 A2 | 12/1990 |
| EP | 1 391 213 A1 | 2/2004 |
| WO | WO-1991/00360 A1 | 10/1991 |
| WO | WO-1992/20373 A1 | 11/1992 |
| WO | WO-1993/08829 A1 | 5/1993 |
| WO | WO-1993/11161 A1 | 6/1993 |
| WO | WO-1993/21232 A1 | 10/1993 |
| WO | WO-1994/11026 A2 | 5/1994 |
| WO | WO-1994/29351 A2 | 12/1994 |
| WO | WO-1997/04801 A1 | 2/1997 |
| WO | WO-1997/17852 A1 | 5/1997 |
| WO | WO-1997/30087 A1 | 8/1997 |
| WO | WO-1998/56418 A1 | 12/1998 |
| WO | WO-1998/58964 A1 | 12/1998 |
| WO | WO-1999/22764 A1 | 5/1999 |
| WO | WO-1999/51642 A1 | 10/1999 |
| WO | WO-2000/42072 A2 | 7/2000 |
| WO | WO-2000/61739 A1 | 10/2000 |
| WO | WO-2001/29058 A1 | 4/2001 |
| WO | WO-2001/29246 A1 | 4/2001 |
| WO | WO-2001/72768 A2 | 10/2001 |
| WO | WO-2001/96584 A2 | 12/2001 |
| WO | WO-2002/031140 A1 | 4/2002 |
| WO | WO-2003/011878 A2 | 2/2003 |
| WO | WO-2003/048731 A2 | 6/2003 |
| WO | WO-2003/068201 A2 | 8/2003 |
| WO | WO-2003/070752 A2 | 8/2003 |
| WO | WO-2003/084570 A1 | 10/2003 |
| WO | WO-2003/085107 A1 | 10/2003 |
| WO | WO-2003/085119 A1 | 10/2003 |
| WO | WO-2004/056312 A2 | 7/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/100402 A1 | 10/2005 |
| WO | WO-2006/029879 A2 | 3/2006 |
| WO | WO-2008/077546 A1 | 7/2008 |
| WO | WO-2009/067800 A1 | 6/2009 |
| WO | WO-2009/089004 A1 | 7/2009 |
| WO | WO-2009/108372 A2 | 9/2009 |
| WO | WO-2011/056983 A1 | 5/2011 |
| WO | WO-2011/133886 A2 | 10/2011 |
| WO | WO-2012/109659 A1 | 8/2012 |
| WO | WO-2014/093855 A1 | 6/2014 |
| WO | WO-2015/011450 A1 | 1/2015 |

OTHER PUBLICATIONS

Oren et al. (2014) J. Immunol., vol. 193,5733-5743.*

Almasbak et al. (2016) J. Immunol. Res., vol. 2016, pp. 1-10, Article ID 5474602.*

Baldwin, R.W. et al. (Mar. 15, 1986). "Monoclonal Antibodies in Cancer Treatment," *Lancet*. 327(8481):603-605.

Behboudi, S. et al. (Apr. 2010). "Cell-Mediated Immune Responses to α-Fetoprotein and Other Antigens in Hepatocellular Carcinoma," *Liver International* 30(4):521-526.

Berge, I.J.M. et al. (Dec. 1998). "Selective Expansion of a Peripheral Blood CD8+ Memory T Cell Subset Expressing Both Granzyme B and L-Selectin During Primary Viral Infection in Renal Allograft Recipients," *Transplant Proc.* 30(8):3975-3977.

Boerner, P. et al. (Jul. 1, 1991). "Production of Antigen-Specific Human Monoclonal Antibodies From In Vitro-Primed Human Splenocytes," *The Journal of Immunology* 147(1): 86-95.

Brentjens, R.J. et al. (Nov. 3, 2011). "Safety and Persistence of Adoptively Transferred Autologous CD19-Targeted T Cells in Patients With Relapsed or Chemotherapy Refractory B-Cell Leukemias," *Blood* 118(18):4817-4828.

Brischwein, K. et al. (Mar. 2006). "MT110: A Novel Bispecific Single-Chain Antibody Construct With High Efficacy in Eradicating Established Tumors," *Molecular Immunology* 43(8):1129-1143.

Brodeur, B.R. et al. (1987). "Mouse-Human Myeloma Partners for the Production of Heterohybridomas," Chapter 4 in *Monoclonal Antibody Production Techniques and Applications*, Marcel Dekker, Inc., New York, pp. 51-63.

Brüggemann, M. et al. (1993). "Designer Mice: The Production of Human Antibody Repertoires in Transgenic Animals," *Year in Immunol.* 7:33-40.

Brüggemann, M. et al. (Nov. 1, 1987). "Comparison of the Effector Functions of Human Immunoglobulins Using a Matched Set of Chimeric Antibodies," *J. Exp. Med.* 166:1351-1361.

Burton, D.R. (Mar. 1985). "Immunoglobulin G: Functional Sites," *Molecular Immunology* 22(3):161-206.

Butterfield, L.H. et al. (Dec. 1, 2003). "T-Cell Responses to HLA-A*0201 Immunodominant Peptides Derived from α-Fetoprotein in Patients with Hepatocellular Cancer," *Clinical Cancer Research* 9(16 pt. 1):5902-5908.

(56) References Cited

OTHER PUBLICATIONS

Butterfield, L.H. et al. (2014). "Alpha Fetoprotein DNA Prime and Adenovirus Boost Immunization of Two Hepatocellular Cancer Patients," *Journal of Translational Medicine* 12:86, pp. 1-9.
Butterfield, L.H. et al. (Apr. 15, 2001). "T Cell Responses to HLA-A*0201-Restricted Peptides Derived from Human α Fetoprotein," *The Journal of Immunology* 166(8):5300-5308.
Capel, P.J.A. et al. (Feb. 1994). "Heterogeneity of Human IgG Fc Receptors," *Immunomethods* 4(1):25-34.
Chames, P. et al. (Jul. 5, 2000). "Direct Selection of a Human Antibody Fragment Directed Against the Tumor T-Cell Epitope HLA-A1-MAGE-A1 From a Nonimmunized Phage-Fab Library," *Proc. Natl. Acad. Sci. USA* 97(14):7969-7974.
Chari, R.V.J. et al. (Jan. 1, 1992). "Immunoconjugates Containing Novel Maytansinoids: Promising Anticancer Drugs," *Cancer Research* 52:127-131.
Chothia, C. et al. (1987). "Canonical Structures for the Hypervariable Regions of Immunoglobulins," *J. Mol. Biol.* 196:901-917 (1987).
Chowdhury, P.S. (2008). "Engineering Hot Spots for Affinity Enhancement of Antibodies," Chapter 11 in *Methods in Molecular Biology*, M. Welschof (eds.) et al., Humana Press Inc., Totowa, NJ, 207:179-196.
Clackson et al. (Aug. 15, 1991). "Making Antibody Fragments Using Phage Display Libraries," *Nature* 352:624-628.
Clynes et al. (Jan. 1998). "Fc Receptors are Required in Passive and Active Immunity to Myeloma," *Proc. Nat'l Acad. Sci. USA* 95:652-656 (1998).
Colcher, D. et al. (1986). "Use of Monoclonal Antibodies as Radiopharmaceuticals for the Localization of Human Carcinoma Xenografts in Athymic Mice," *Methods in Enzymology* 121:802-816.
Cole et al. (1985). "The EBV-Hybridoma Technique and Its Application to Human Lung Cancer," in *Monoclonal Antibodies and Cancer Therapy*, Ralph A. Reisfeld (ed.) et al., Alan R. Liss, Inc. p. 77-96.
Cragg, M.S. et al. (Feb. 1, 2003). "Complement-mediated Lysis by Anti-CD20 mAb Correlates with Segregation into Lipid Rafts," *Blood* 101(3):1045-1052.
Cragg, M.S.et al. (Apr. 1, 2004). "Antibody Specificity Controls In Vivo Effector Mechanisms of Anti-CD20 Reagents," *Blood* 103(7):2738-2743.
Cunningham, B.C. et al. (Jun. 2, 1989). "High Resolution Epitope Mapping of hGH-Receptor Interactions by Alanine-Scanning Mutagenesis," *Science* 244:1081-1085.
Daëron, M. (1997). "Fc Receptor Biology," *Annu. Rev. Immunol.* 15:203-234.
Dao, T. et al. (Mar. 13, 2013). "Targeting the Intracellular WT1 Oncogene Product With a Therapeutic Human Antibody," *Sci. Transl. Med.* 5(176):176ra33, twenty two pages.
David, G.S. et al. (1974). "Protein Iodination with Solid State Lactoperoxidase," *Biochemistry* 13(5):1014-1021.
De-Haas, M. et al. (1995). "Fcγ Receptors of Phagocytes," *J. Lab. Clin. Med*.126:330-341.
Denkberg, G. et al. (Apr. 2006). "Recombinant Antibodies with T-Cell Receptor-Like Specificity: Novel Tools to Study MHC Class I Presentation," *Autoimmunity Reviews* 5(4):252-257.
Duncan, A.R. et al. (Apr. 1988). "The Binding C1q on IgG," *Nature* 332:738-740.
Edgar, R.C. (2004; e-published on Mar. 19, 2004). "MUSCLE: Multiple Sequence Alignment With High Accuracy and High Throughput," *Nucleic Acids Research* 32(5):1792-1797.
Edgar, R.C. (Aug. 19, 2004). "MUSCLE: A Multiple Sequence Alignment Method With Reduced Time and Space Complexity," *BMC Bioinformatics* 5(1):113, pp. 1-19.
Fellouse, F.A. et al. (Aug. 24, 2004). "Synthetic Antibodies from a Four-Amino-Acid Code: A Dominant Role for Tyrosine in Antigen Recognition," *Proc. Natl. Acad. Sci. USA* 101(34):12467-12472.
Ferrara, C. et al. (Apr. 5, 2006). "Modulation of Therapeutic Antibody Effector Functions by Glycosylation Engineering: Influence of Golgi Enzyme Localization Domain and Co Expression of Heterologous β1, 4-N-acetylglucosaminyltransferase III and Golgi α-mannosidase II," *Biotechnology and Bioengineering* 93(5):851-861.
Fishwild, D.M. et al. (Jul. 1996). "High-avidity Human IgGk Monoclonal Antibodies from a Novel Strain of Minilocus Transgenic Mice," *Nature Biotechnology* 14:845-851.
Fraker, P.J. et al. (Feb. 28, 1978). "Protein and Cell Membrane Iodinations with a Sparingly Soluble Chloroamide, 1,3,4,6-Tetrachloro-3a, 6a-Diphenylglycoluril," *Biochemical and Biophysical Research Communications* 80(4):849-857.
Garland, R.J. et al. (Jul. 30, 1999). "The Use of Teflon Cell Culture Bags to Expand Functionally Active CD8+ Cytotoxic T Lymphocytes," *Journal of Immunological Methods* 227(1-2):53-63.
Gazzano-Santoro, H. et al. (1997). "A Non-Radioactive Complement-Dependent Cytotoxicity Assay for Anti-CD20 Monoclonal Antibody," *Journal of Immunological Methods* 202:163-171.
Ghetie, V. et al. (2000). "Multiple Roles for the Major Histocompatibility Complex Class I-Related Receptor FcRn," *Annu. Rev. Immunal.* 18:739-766.
Goding, J.W. (1986). "Production of Monoclonal Antibodies," Chapter 3 in *Monoclonal Antibodies: Principles and Practice*, Academic Press, New York, pp. 56-103.
Griffiths, A.D. et al. (1993). "Human Anti-Self Antibodies with High Specificity from Phage Display Libraries," *The EMBO Journal* 12(2):725-734.
Grillo-López, A.J. (Jun. 2002). "Anticd20 mAbs: Modifying Therapeutic Strategies and Outcomes in the Treatment of Lymphoma Patients," *Expert Review of Anticancer Therapy* 2(3):323-329.
Gu, J. et al. (2012). "Generation of Dual-Variable-Domain Immunoglobulin Molecules for Dual-Specific Targeting," *Methods Enzymol.* 502:25-41.
Guyer, R.L. et al. (Aug. 1976). "Immunoglobulin Binding by Mouse Intestinal Epithelial Cell Receptors," *The Journal of Immunology* 117(2):587-593.
Haanen, J. et al. (Nov. 1, 1999). "Selective Expansion of Cross-reactive $CD8^+$ Memory T Cells by Viral Variants," *J. Exp. Med.* 190(9):1319-1328.
Held, G. et al. (2004). "Dissecting Cytotoxic T Cell Responses Towards the NY-ESO-1 Protein by Peptide/MHC-Specific Antibody Fragments," *Eur. J. Immunol.* 34:2919-2929.
Hellström, I et al. (Mar. 1895). "Strong Antitumor Activities of IgG3 Antibodies to a Human Melanoma-Associated Ganglioside," *Proc. Nat'l Acad. Sci. USA* 82:1499-1502.
Hellström, I et al. (Sep. 1986). "Antitumor Effect of L6, an IgG2a Antibody that Reacts with Most Human Carcinomas," *Proc. Nat'l Acad. Sci. USA* 83:7059-7063.
Hinman, L.M. et al. (Jul. 15, 1993). "Preparation and Characterization of Monoclonal Antibody Conjugates of the Calicheamicins: A Novel and Potent family of Antitumor Antibiotics," *Cancer Research* 53:3336-3342.
Hoet, R.M. et al. (Mar. 2005; e-published on Feb. 20, 2005). "Generation of High-Affinity Human Antibodies by Combining Donor-Derived and Synthetic Complementarity-Determining-Region Diversity," *Nature Biotechnology* 23(3):344-348.
Hollinger, P. et al. (Jul. 1993). ""Diabodies": Small Bivalent and Bispecific Antibody Fragments," *Proc. Natl. Acad. Sci. USA* 90:6444-6448.
Hoogenboom, H.R. (2001). "Overview of Antibody Phage-Display Technology and Its Applications," Chapter 1 in *Methods in Molecular Biology*, O'Brien (ed.) et al., Human Press, Totowa, NJ, 178:1-37.
Hoogenboom, H.R. et al. (1992). "By-Passing Immunization—Human Antibodies from Synthetic Repertoires of Germline $V_H$ Gene Segments Rearranged in Vitro," *J. Mol. Biol.* 227:381-388 (1992).
Hunter, W.M. et al. (May 5, 1962). "Preparation of Iodine-131 Labelled Human Growth Hormone of High Specific Activity," *Nature* 144(4827):495-496.
Idusogie, E.E. et al. (2000). "Mapping of the C1q Binding Site on Rituxan, a Chimeric Antibody with a Human IgG1 Fc," *The Journal of Immunology* 164: 4178-4184.

(56) References Cited

OTHER PUBLICATIONS

Jakobovits, A. et al. (Mar. 18, 1993). "Germ-Line Transmission and Expression of a Human-Derived Yeast Artificial Chromosome," *Nature* 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," *PNAS USA* 90:2551-2555.

Jiang, Y. et al. (Jun. 18, 2015). "T-cell Exhaustion in the Tumor Microenvironment," *Cell Death & Disease* 6(6):e1792, pp. 1-9.

Jones, K.L. et al. (Dec. 2009). "Evolving Novel Anti-HER2 Strategies," *The Lancet Oncology* 10(12):1179-1187.

Jones, P.T. et al. (May 29, 1986). "Replacing the Complementarity Determining Regions in a Human Antibody with those from a Mouse," *Nature* 321:522-525.

Kabat, E.A. et al. (1991). U.S. Department of Health and Human Services—Public Health Service National Institutes of health, in *Sequences of Proteins of Immunological Interest*, eighty five pages.

Kabat, E.A. et al. (Oct. 10, 1977). "Unusual Distributions of Amino Acids in Complementarity-Determining (Hypervariable) Segments of Heavy and Light Chains of Immunoglobulins and their Possible Roles in Specificity of Antibody-combining Sites," *The Journal of Biological Chemistry* 252(19):6609-6616.

Kam, N.W.S. et al. (Aug. 16, 2005). "Carbon Nanotubes as Multifunctional Biological Transporters and Near-Infrared Agents for Selective Cancer Cell Destruction," *Proc. Natl. Acad. Sci. USA* 102(33):11600-11605.

Kanda, Y. et al. (Jul. 5, 2006). "Comparison of Cell Lines for Stable Production of Fucose-Negative Antibodies With Enhanced ADCC," *Biotechnology and Bioengineering* 94(4):680-688.

Kim, J. et al. (1994). "Localizations of the Site of the Murine IgG1 Molecule that is Involved in Binding to the Murine Intestinal Fc Receptor," *Eur. J. Immunol.* 24:2429-2434.

Klechevsky, E. et al. (Aug. 1, 2008). "Antitumor Activity of Immunotoxins with T-Cell Receptor-like Specificity against Human Melanoma Xenografts," *Cancer Research* 68(15):6360-6367.

Kochenderfer, J.N. et al. (Nov. 18, 2010; e-published on Jul. 28, 2010). "Eradication of B-Lineage Cells and Regression of Lymphoma in a Patient Treated With Autologous T Cells Genetically Engineered to Recognize CD19," *Blood* 116(20):4099-4102.

Köhler G. et al. (Aug. 7, 1975). "Continuous Cultures of Fused Cells Secreting Antibody of Predefined Specificity," *Nature* 256:495-497.

König, R. (Feb. 2002). "Interactions Between MHC Molecules and Co-Receptors of the TCR," *Curr. Opin. Immunol.* 14(1):75-83.

Kostelny S.A. et al. (Mar. 1, 1992). "Formation of a Bispecific Antibody by the Use of Leucine Zippers," *The Journal of Immunology* 148(5):1547-1553.

Kozbor, D. et al. (Dec. 1984). "A Human Hybrid Myeloma for Production of Human Monoclonal Antibodies," *The Journal of Immunology* 133(6):3001-3005.

Labrigin, A.F. et al. (Mar. 26, 2013; e-published on Mar. 11, 2013). "Efficient Generation of Stable Bispecific IgG1 by Controlled Fab-Arm Exchange," *Proc. Natl. Acad. Sci.* 110(13):5145-5150.

Lee, C.V. et al. (2004). "Bivalent Antibody Phage Display Mimics Natural Immunoglobulin," *Journal of Immunological Methods* 284(1-2):119-132.

Lee, C.V. et al. (2004). "High-Affinity Human Antibodies from Phage-Displayed Synthetic Fab Libraries with a Single Framework Scaffold," *J. Mol. Biol.* 340(5):1073-1093.

Lev, A. et al. (Jun. 1, 2002). "Isolation and Characterization of Human Recombinant Antibodies Endowed with the Antigen-specific, Major Histocompatibility Complex-restricted Specificity of T Cells Directed toward the Widely Expressed Tumor T-cell Epitopes of the Telomerase Catalytic Subunit," *Cancer Research* 62(11):3184-3194.

Lindhofer, H. et al. (Jul. 1, 1995). "Preferential Species-Restricted Heavy/Light Chain Pairing in Rat/Mouse Quadromas. Implications for a Single-Step Purification of Bispecific Antibodies," *The Journal of Immunology* 155(1):219-225.

Liu, C. et al. (Aug. 1996). "Eradication of Large Colon Tumor Xenografts by Targeted Delivery of Maytansinoids," *Proc. Natl. Acad. Sci. USA* 93:8618-8623.

Liu, Y. et al. (Jul. 1, 2006). "Hierarchy of a Fetoprotein (AFP)-Specific T Cell Responses in Subjects with AFP-Positive Hepatocellular Cancer," *The Journal of Immunology* 177(1):712-721.

Lode, H.N. et al. (Jul. 15, 1998). "Targeted Therapy with a Novel Enediyene Antibiotic Calicheamicin $\Theta^1{}_1$ Effectively Suppresses Growth and Dissemination of Liver Metastases in a Syngeneic Model of Murine Neuroblastoma," *Cancer Research* 58:2925-2928.

Lonberg, N. et al. (1995). "Human Antibodies from Transgenic Mice," *Intern. Rev. Immunol.*, 13:65-93.

Lonberg, N. et al. (Apr. 28, 1994). "Antigen-Specific Human Antibodies from Mice Comprising Four Distinct Genetic Modifications," *Nature* 368:856-859.

Louis, C.U. et al. (Dec. 1, 2011; e-published on Oct. 7, 2011). "Antitumor Activity and Long-Term Fate of Chimeric Antigen Receptor-Positive T Cells in Patients With Neuroblastoma," *Blood* 118(23):6050-6056.

MacCallum, R.M. et al. (1996). "Antibody-Antigen Interactions: Contact Analysis and Binding Site Topography," *J. Mol. Biol.* 262:732-745.

Mack et al. (Jul. 1995). "A Small Bispecific Antibody Construct Expressed as a Functional Single-Chain Molecule With High Tumor Cell Cytotoxicity," *Proc. Natl. Acad. Sci.* 92:7021-7025.

Mackall, C.L. et al. (Dec. 2014; e-published on Oct. 28, 2014). "Immune-based Therapies for Childhood Cancer," *Nature Reviews Clinical Oncology* 11(12):693-703., pp. 1-11.

Mandler, R. et al. (2000). "Synthesis and Evaluation of Antiproliferative Activity of a Geldanamycin-Herceptin™ Immunoconjugate," *Bioorganic & Medicinal Chemistry Letters* 10:1025-1028.

Mandler, R. et al. (2002; e-published on Jun. 19, 2002). "Modifications in Synthesis Strategy Improve the Yield and Efficacy of Geldanamycin-Herceptin Immunoconjugates," *Bioconjugate Chem.* 13:786-791.

Mandler, R. et al. (Oct. 4, 2000). "Immunoconjugates of Geldanamycin and Anti-HER2 Monoclonal Antibodies: Antiproliferative Activity on Human Breast Carcinoma Cell Lines," *Journal of National Cancer Institute* 92(19):1573-1581.

Marks, J.D. et al. (1991). "By-Passing Immunization—Human Antibodies from V-Gene Libraries Displayed on Phage," *J. Mol. Biol.* 222:581-597.

Marks, J.D. et al. (2004). "Selection of Human Antibodies from Phage Display Libraries," Chapter 8 in *Methods in Molecular Biology*, B.K.C. Lo, ed., Humana Press Inc., Totowa, N.J., 248:161-175.

Marks, J.D. et al. (Jul. 1992). "By-Passing Immunization: Building High Affinity Human Antibodies by Chain Shuffling," *Bio/Technology*, 10:779-783.

Martin, S.F. et al. (Mar. 1998). "Application of AlMe$_3$-mediated Amidation Reactions to Solution Phase Peptide Synthesis," *Tetrahedron Letters* 39(12):1517-1520.

Maude, S.L. et al. (Oct. 16, 2014). "Chimeric Antigen Receptor T Cells for Sustained Remissions in Leukemia," *N Engl J Med.* 371(16):1507-1517.

McCafferty, J. et al. (Dec. 6, 1990). "Phage Antibodies: Filamentous Phage Displaying Antibody Variable Domains," *Nature* 348:552-554.

Milenic, D.E. (Sep. 2002). "Monoclonal Antibody-Based Therapy Strategies: Providing Options for the Cancer Patient," 8(19):1749-1764.

Milstein et al. (Oct. 6, 1983). "Hybrid Hybridomas and their Use in Immunohistochemistry," *Nature* 305:537-540.

Mizukoshi, E. et al. (Mar. 1, 2006). "Identification of A-Fetoprotein-Derived Peptides Recognized by Cytotoxic T Lymphocytes in HLA-A24+ Patients With Hepatocellular Carcinoma," *International Journal of Cancer* 118(5):1194-1204.

Morris, E. et al. (Mar. 2006). "Generation of Tumor-Specific T-Cell Therapies," *Blood Reviews* 20(2):61-69.

Morrison, S.L. (Apr. 28, 1994). "Success in Specification," *Nature* 368:812-813.

(56) References Cited

OTHER PUBLICATIONS

Morrison, S.L. et al. (Nov. 1984). "Chimeric Human Antibody Molecules: Mouse Antigen-Binding Domains with Human Constant Region Domains," *Proc. Natl. Acad. Sci. USA* 81:6851-6855.
Munson, P.J. et al. (1980). "LIGAND: A Versatile Computerized Approach for Characterization of Ligand-Binding Systems," *Analytical Biochemistry* 107:220-239.
Neuberger, M. (Jul. 1996). "Generating High-Avidity Human Mabs in Mice," *Nature Biotechnology* 14:826, one page.
Neuberger, M.S. et al. (Dec. 13, 1984). "Recombinant Antibodies Possessing Novel Effector Functions," *Nature* 312:604-608.
Niculescu-Duvaz, I. et al. (1997). "Antibody-Directed Enzyme Prodrug Therapy (ADEPT): A Review," *Advanced Drug Delivery Reviews* 26:151-172.
Noy, R. et al. (2005). "T-Cell Receptor-Like Antibodies: Novel Reagents for Clinical Cancer Immunology and Immunotherapy," *Expert Review of Anticancer Therapy* 5(3):523-536.
Nygren, H. (1982). "Conjugation of Horseradish Peroxide to Fab Fragments with Different Homobifunctional and Hetrobifunctional Cross-Linking Reagents," *J. Histochem. and Cytochem.* 30:407-412.
Okazaki, A. et al. (2004). "Fucose Depletion from Human IgG1 Oligosaccharide Enhances Binding Enthalpy and Association Rate Between IgG1 and FcγRIIIa," *J. Mol. Biol.* 336:1239-1249.
Osol, A. ed. (1980). *Remington's Pharmaceutical Sciences*, 16th edition, Table of Contents only, two pages.
Pain, D. et al. (1981). "Preparation of Protien A-Peroxidase Monoconjugate Using a Heterobifunctional Reagent, and its use in Enzyme Immunoassays," *Journal of Immunological Methods* 40:219-230.
Palucka, K. et al. (Apr. 2012). "Cancer Immunotherapy via Dendritic Cells," *Nature Reviews Cancer* 12(4):265-277.
Pardee, A.D. et al. (Jan./Feb. 2012). "Immunotherapy of Hepatocellular Carcinoma," *Oncoimmunology* 1(1):48-55.
Petkova, S.B. et al. (2006; advanced Access Publication on Oct. 31, 2006). "Enhanced Half-Life of Genetically Engineered Human IgG1 Antibodies in a Humanized FcRn Mouse Model: Potential Application in Humorally Mediated Autoimmune Disease," *International Immunology* 18(12):1759-1769.
Plückthun, A. (1994). "Antibodies from *Escherichia coli*," Chapter 11 in *The Pharmacology of Monoclonal Antibodies*, M. Rosenburg (ed.) et al., Springer-Verlag, New York, 113:269-315.
Presta, L.G. (1992). "Antibody Engineering," *Current Opinion in Structural Biology* 2:593-596.
Pullarkat, V. et al. (1999). "A Phase I Study of a HER2/neu Bispecific Antibody With Granulocyte-Colony-Stimulating Factor in Patients With Metastatic Breast Cancer That Overexpresses HER2/Neu," *Cancer Immunol Immunother* 48:9-21.
Ravetch, J.V. et al. (1991). "Fc Receptors," *Annu. Rev. Immunol.* 9:457-492.
Reddy, M.M. et al. (Mar. 2012). "Targeting JAK2 in the Therapy of Myeloproliferative Neoplasms," *Expert Opin. Ther. Targets* 16(3):313-324.
Ridgway, J.B.B. et al. (1996). ""Knobs-into-Holes," Engineering of Antibody $C_H3$ Domains for Heavy Chain Heterodimerization," *Protein Engineering* 9(7):617-621.
Riechmann, et al. (Mar. 24, 1988). "Reshaping Human Antibodies for Therapy," *Nature* 332:323-327.
Ripka, J. et al. (Sep. 1986). "Two Chinese Hamster Ovary Glycosylation Mutants Affected in the Conversion of GDP-Mannose to GDP-Fucose," *Archives of Biochemistry and Biophysics* 249(2):533-545.
Rosenberg, S.A. et al. (Dec. 22, 1988). "Use of Tumor-Infiltrating Lymphocytes and Interleukin-2 in the Immunotherapy of Patients with Metastatic Melanoma—A preliminary Report," *The New England Journal of Medicine* 319:1676-1680.
Rossi, E.A. et al. (May 2, 2006). "Stably Tethered Multifunctional Structures of Defined Composition Made by the Dock and Lock Method for Use in Cancer Targeting," *Proc. Natl. Acad. Sci.*, 103(18):6841-6846.

Rowland et al. (1986). "Drug Localisation and Growth Inhibition Studies of Vindesine-Monoclonal Anti-CEA Conjugates in a Human Tumour Xenograft," *Cancer Immunol. Immunother.* 21:183-187.
Roychowdhury, S. et al. (Nov. 2011; e-published on Oct. 6, 2011). "Managing Resistance in Chronic Myeloid Leukemia," *Blood Reviews* 25(6):279-290.
Sergeeva, A. et al. (Apr. 21, 2011). "An Anti-PR1/HLA-A2 T-Cell Receptor-Like Antibody Mediates Complement-Dependent Cytotoxicity Against Acute Myeloid Leukemia Progenitor Cells," *Blood* 117(16):4262-4272.
Shibata, T et al. (2014; e-published on Jan. 28, 2014). "Exploration of Liver Cancer Genomes," *Nat. Rev. Gastroenterol. Hepatol.* 11(6):340-349.
Shields, R.L. et al. (Mar. 2, 2001). "High Resolution Mapping of the Binding Site on Human IgG1 for FcγRII, FcγRIII, and FcRn and Design of IgG1 Variants with Improved Binding to the FcγR," *The Journal of Biological Chemistry* 276(9):6591-6604.
Sidhu, S.S. et al. (2004). "Phage-Displayed Antibody Libraries of Synthetic Heavy Chain Complementarity Determining Regions," *J. Mol. Biol.* 338(2): 299-310.
Singh, H. et al. (Dec. 1, 2001). "ProPred: prediction of HLA-DR binding sites," *Bioinformatics* 17(12):1236-1237.
Suresh, M.R. et al. (1986). "Bispecific Monoclonal Antibodies from Hybrid Hybridomas," *Methods in Enzymology* 121:210-228.
Syrigos, K.N. et al. (1999). "Antibody Directed Enzyme Prodrug Therapy (ADEPT): A Review of the Experimental and Clinical Considerations," *Anticancer Research* 19:605-614.
Takeuchi, K. et al. (2011). "Receptor Tyrosine Kinases and Targeted Cancer Therapeutics,".*Biol. Pharm. Bull.* 34(12):1774-1780.
Terentiev, A.A. et al. (e-published on Jun. 14, 2013). "Alpha-Fetoprotein: A Renaissance," *Tumour Biol.* 34(4):2075-2091.
Thorpe, P.E. (1985). "Antibody Carriers of Cytotoxic Agents in Cancer Therapy: A Review," in *Monoclonal Antibodies '84: Biological and Clinical Applications*, A. Pinchera et al. (eds.), Editrice Kurtis-Milano, pp. 475-506.
Tomimatsu, K. et al. (2009). "Production of Human Monoclonal Antibodies against FcεRIα by a Method Combining in Vitro Immunization with Phage Display," *Biosci. Biotechnol. Biochem.* 73(7):1465-1469.
Traunecker, A. et al. (1991). "Bispecific Single Chain Molecules (Janusins) Target Cytotoxic Lymphocytes on HIV Infected Cells," *The EMBO Journal* 10:3655-3659.
Tutt, A. et al. (Jul. 1, 1991). "Trispecific F(ab')₃ Derivatives That Use Cooperative Signaling Via the TCR/CD3 Complex and CD2 to Activate and Redirect Resting Cytotoxic T Cells," *The Journal of Immunology* 147(1):60-69.
Ui-Tei, K. et al. (Aug. 18, 2000). "Sensitive Assay of RNA Interference in *Drosophila* and Chinese Hamster Cultured Cells Using Firefly Luciferase Gene as Target," *FEBS Letters* 479(3):79-82.
Vallanueva, A. et al. (Jan. 2013; e-published Nov. 13, 2012). "Medical Therapies for Hepatocellular Carcinoma: A Critical View of the Evidence," *Nat. Rev. Gastroenterol. Hepatol.* 10(1):34-42.
Veomett, N, et al. (Aug. 1, 2014; e-published on May 21, 2014). "Therapeutic Efficacy of an Fc-Enhanced TCR-Like Antibody to the Intracellular WT1 Oncoprotein," *Clin. Cancer Res.* 20(15):4036-4046.
Verhoeyen, M. et al. (1988). "Reshaping Human Antibodies: Grafting and Antilysozyme Activity," *Science* 239:1534-1536.
Veri, M. et al. (Jul. 2010). "Therapeutic Control of B Cell Activation Via Recruitment of Fcγ Receptor IIb (CD32B) Inhibitory Function With a Novel Bispecific Antibody Scaffold," *Arthritis Rheum.* 62(7):1933-1943.
Vita, R. et al. (Jan. 2015; e-published on Oct. 9, 2014). "The Immune Epitope Database (IEDB) 3.0.," *Nucleic Acids Res.* 43(Database Issue):D405-D412.
Vitetta, E.S. et al. (1987). "Redesigning Nature's Poisons to Create Anti-Tumor Reagents," *Science* 238:1098-1104.
Wherry, E. J. (Jun. 2011). "T Cell Exhaustion," *Nature immunology* 12(6):492-499.
Winter, G. et al. (1994). "Making Antibodies by Phage Display Technology," *Ann. Rev. Immunol.*, 12:433-455.

(56) References Cited

OTHER PUBLICATIONS

World Health Organization (International Agency for Research Center). (2012). "All Cancers (excluding non-melanoma skin cancer)—Estimated Incidence, Mortality and Prevalence Worldwide in 2012," located at <http://globocan.iarc.fr/Pages/fact_sheets_cancer.aspx> last visited on Sep. 29, 2017.

Wright, A. et al. (Jan. 1997). "Effect of Glycosylation on Antibody Function: Implications for Genetic Engineering," *TIBTECH* 15:26-32.

Yamane-Ohnuki, N. et al. (Sep. 5, 2004). "Establishment of *FUT8* Knockout Chinese Hamster Ovary Cells: An Ideal Host Cell Line for Producing Completely Defucosylated Antibodies with Enhanced Antibody-Dependent Cellular Cytotoxicity," *Biotechnology and Bioengineering* 87(5):614-622.

International Preliminary Report on Patentability dated Oct. 12, 2017 for PCT Patent Application No. PCT/US2016/25755, filed on Apr. 1, 2016, six pages.

International Search Report dated Jul. 15, 2016, for PCT Patent Application No. PCT/US2016/25755, filed on Apr. 1, 2016, four pages.

Written Opinion dated Jul. 15, 2016, for PCT Patent Application No. PCT/US2016/25755, filed on Apr. 1, 2016, four pages.

Butterfield, L.H. et al. (Jul. 1, 1999). "Generation of Human T-Cell Responses to an HLA-A2.1-Restricted Peptide Epitope Derived From α-Fetoprotein," *Cancer Res.* 59(13):3134-3142.

Cohen, C.J. et al. (Sep./Oct. 2003). "Recombinant Antibodies with MHC-Restricted, Peptide-Specific, T-Cell Receptor-Like Specificity: New Tools to Study Antigen Presentation and TCR—Peptide—MHC Interactions," *Journal of Molecular Recognition* 16(5):324-332.

\* cited by examiner

| Peptide | Ala Position | FACS MFI |
|---|---|---|
| FMNKFIYEI | WT | 37900 |
| AMNKFIYEI | 1 | 468 |
| FMAKFIYEI | 3 | 4470 |
| FMNAFIYEI | 4 | 20.9 |
| FMNKAIYEI | 5 | 21800 |
| FMNKFAYEI | 6 | 18900 |
| FMNKFIAEI | 7 | 42500 |
| FMNKFIYAI | 8 | 38500 |

52

61

76

79

\* Dunnet's test, P<0.05
\*\*\* Dunnet's test, P<0.001

1. ET1402 mIgG1 52, REDUCED.
2. ET1402 mIgG1 61, REDUCED.
3. ET1402 mIgG1 76, REDUCED.
4. ET1402 mIgG1 79, REDUCED.
5. ET1402 mIgG1 control antibody, REDUCED.
6. ET1402 mIgG1 52, NON-REDUCED, NO HEAT.
7. ET1402 mIgG1 61, NON-REDUCED, NO HEAT.
8. ET1402 mIgG1 76, NON-REDUCED, NO HEAT.
9. ET1402 mIgG1 79, NON-REDUCED, NO HEAT.
10. ET1402 mIgG1 control antibody, NON-REDUCED, NO HEAT.

SK-Hep1-MG tumors: Group 6

Biocare anti-human CD3 (1:50), pH 6.2 Ag Retrieval, Biocare Universal Detection, 20X

CONSTRUCTS TARGETING AFP PEPTIDE/MHC COMPLEXES AND USES THEREOF

CROSS-REFERENCE TO RELATED APPLICATIONS

This application is a continuation of U.S. patent application Ser. No. 15/563,912, filed on Oct. 2, 2017, which is a U.S. national phase application under 35 U.S.C. § 371 of International Application No. PCT/US2016/025755, filed on Apr. 1, 2016, which claims priority to U.S. Provisional Application No. 62/142,958, filed on Apr. 3, 2015, U.S. Provisional Application No. 62/244,653, filed on Oct. 21, 2015, and U.S. Provisional Application No. 62/304,915, filed on Mar. 7, 2016, all of which are hereby incorporated by reference in their entireties.

FIELD OF THE INVENTION

This invention pertains to antibody constructs that specifically bind MHC molecules complexed with AFP peptides, and uses thereof including treating and diagnosing diseases.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750042000101SEQLIST.txt, date recorded: Nov. 28, 2017, size: 66 KB).

BACKGROUND OF THE INVENTION

Cell surface proteins constitute only a small fraction of the cellular proteins and these proteins are often not tumor-specific. Because of the inability to easily penetrate cells, marketed therapeutic monoclonal antibodies (mAbs) recognize these cell surface proteins, most of which are lineage or differentiation antigens (Milenic, E. D., Curr. Pharm. Des. 8:1794-1764, 2002; Grillo-Lopez, A. J., Expert Rev. Anticancer Ther. 2(3):323-329, 2002; Jones, K. L. & Buzdat, A. U., Lancet Oncol. 10(12):1179-1187, 2009). In contrast, mutated or oncogenic tumor-associated proteins are typically nuclear, cytoplasmic or secreted, which are currently best addressed either by small molecule drugs, or in the case of secreted proteins, hardly addressed as anti-cancer drug targets (Reddy et al., Expert Opin. Ther. Targets 3:313-324, 2012; Takeuchi, K. & Ito, F., Biol. Pharm. Bull. 34(12): 1774-1780; Roychowdhury, S. & Talpaz, M., Blood Rev. 6:279-290, 2011). However, most intracellular proteins can be proteosomally degraded, processed and presented by MHC molecules on the cell surface as T cell peptide epitopes in the context of MHC molecules that are recognized by T cell receptors (TCRs) (Morris et al., Blood Rev. 20:61-69, 2006; Konnig, R., Curr. Opin. Immunol. 14(1): 75-83, 2002). Therefore, generating therapeutic mAbs that recognize the secreted or intracellular tumor antigen-derived peptide/MHC complexes on the cell surface will take advantage of the enhanced specificity and therapeutic potency offered by mAbs. Recent advances in using phage display to generate mAbs have made it possible to select agents with exquisite specificity against defined epitopes from large antibody repertoires. A number of such mAbs specific for solid tumor antigens, in the context of HLA-A01 and HLA-A02, have been successfully selected from phage display libraries (Noy et al., Expert Rev. Anticancer Ther. 5(3):523-536, 2005; Chames et al., Proc. Natl. Acad. Sci. USA 97:7969-7974, 2000; Held et al., Eur. J. Immunol. 34:2919-2929, 2004; Lev et al., Cancer Res. 62:3184-3194, 2002; Klechevsky et al., Cancer Res. 68(15):6360-6367, 2008). More recently, a human mAb specific for human WT1/HLA-A02 complex, a well-described T cell epitope, has been shown to inhibit multiple cancer cell lines and primary cancer cells via Fc-mediated effector cell function (Dao et al., Sci. Transl. Med. 5:176ra33, 2013; Veomett et al., Clin. Cancer Res. doi: 10.1158/1078-0432, 2014) in cellular assays and in in vivo models.

Alpha-fetoprotein (AFP) is a 69 kD glycoprotein produced in the yolk sac and fetal liver and secreted into circulation. The synthesis of AFP decreases dramatically after birth and only trace amounts are present in the adult liver. In normal adult human blood serum, AFP concentration is usually as low as 5-7 ng/ml (Terentiev, A. A. & Moldogazieva, N. T., Tumour Biol. 34(4):2075-2091, 2013). However, expression of the AFP gene is reactivated in adults during liver regeneration, hepatocarcinogensis, germ cell tumor or in some cases of viral infection (HBV/HCV). The measurement of serum AFP, therefore, plays an important role in diagnosis and in monitoring responses to the treatment of AFP-positive cancers. Currently, AFP is considered a "gold standard" among tumor-specific molecular biomarkers. However, because AFP is not a cell-surface protein, targeting AFP has not been a very active area for anti-cancer antibody drug development.

Primary liver cancer is the fifth most common form of cancer worldwide and the second most common cause of cancer-related death. In 2012, there were about 782,000 new cancer cases globally, and about 746,000 liver cancer related deaths (http://globocan.iarc.fr/Pages/fact_sheets_cancer.aspx). 90-95% of liver cancers are hepatocellular carcinoma (HCC). Chronic liver damage, such as that caused by chronic hepatitis, liver cirrhosis and fatty liver disease, is closely associated with the occurrence of HCC. Hepatitis virus infection (e.g. HBV, HCV), aflatoxin B exposure, alcohol intake and other metabolic diseases (e.g. obesity and diabetes) are well-known risk factors for HCC. The incidence of HCC is high in East Asian and African countries due to the prevalence in HBV and HCV in these regions (Shibata, T. & Aburatani, H., Nat. Rev. Gastroenterol. Hepatol. 11(6):340-349, 2014). However, the number of patients infected with HCV has been rapidly increasing in Western countries, especially in the USA where viral hepatitis infection is partly mediated through drug abuse. Meanwhile, the incidences of cirrhosis owing to nonalcoholic steatohepatitis (NASH) and obesity also increased in Western countries. In the US, HCC is the $9^{th}$ most common cancer (Vallanueva et al., Nat. Rev. Gastroenterol. Hepatol. 10(1):34-42).

Mean survival of patients with HCC is 3 months from diagnosis. However this is closely related to the stage of the tumor and the extent of underlying liver disease. As only a minority of HCC patients is considered suitable for resection and transplantation at the time of diagnosis, treatment for the majority of patients with HCC is mainly palliative. Non-surgical treatments, such as trans-arterial chemoembolization (TACE/TAE), radio-frequency ablation and systemic targeted agent like sorafenib, have been shown to reduce tumor burden and improve survival rate but these treatments do not eradicate cancer cells and the patients frequently relapse. Therefore, the development of more effective therapies remains a pressing field of research (Behboudi et al., Liver Int. 30(4):521-526, 2010).

AFP expression is reactivated in approximately 80% of HCC Immunotherapy studies aimed at generating AFP-specific cytotoxic CD8 T cell responses that recognize peptides presented on HCC cancer cell surface by MHC class I proteins have reported many human AFP peptides as T-cell epitopes (Butterfield et al., *J. Immunol.* 166:5300-5308, 2001; Pardee, A. D. & Butterfield, L. H., *Oncolmmunol.* 1:48-55, 2012; Butterfield et al., *J. Trans. Med.* 12:86, 2014; Liu et al., *J. Immunol.* 177 (1):712-721, 2006; Mizukoshi et al., *Int. J. Cancer* 118 (5):1194-1204, 2006). Among these peptides, FMNKFIYEI (AFP158) is an immunodominant T-cell epitope restricted by HLA-A*02:01. AFP/HLA-A*02:01 complex induced peptide-specific T cells in vitro from normal HLA-A*02:01 donors. These AFP158 specific T cells recognized HLA-A*02:01 positive and AFP positive tumor cells in both cytotoxicity assays and IFNγ ELISPOT assays. AFP158 was identified by mass spectrometric analysis of surface peptides from an HLA-A*02:01 positive HCC cell line, HepG2, but not from a HLA-A*02:01 negative cancer cell line, Hep3B (Butterfield et al., *J. Immunol.* 166:5300-5308, 2001). These data support that AFP158 is indeed processed and presented by HLA-A*02:01 molecules in AFP-positive cancer cells. Therefore, AFP158/HLA-A*02:01 is a good target candidate for mAb cancer drug development.

Traditional approaches to using AFP as a therapeutic target for treating cancers that overexpress AFP have relied on using antibodies that target the AFP protein or vaccination with various AFP peptides. Antibodies directed against the AFP protein have little therapeutic efficacy since AFP is not a cell-surface protein, and may be present at high circulating levels, thus reducing any specific targeting of the antibody to the cells expressing AFP. While vaccination with various MHC-restricted AFP peptides and variants thereof has been observed to lead to activation of AFP-specific T cells and increased cytotoxicity of AFP-presenting cells in vitro, a clinically significant therapeutic benefit has yet to be observed.

The disclosures of all publications, patents, patent applications and published patent applications referred to herein are hereby incorporated herein by reference in their entirety.

BRIEF SUMMARY OF THE INVENTION

The present application in one aspect provides constructs (such as isolated constructs) that bind to a complex comprising an AFP peptide and an MHC class I protein (referred to herein as an "AFP/MHC class I complex," or "AMC"). In some embodiments, the constructs ("anti-AMC constructs") comprise an antibody moiety (referred to herein as an "anti-AMC antibody moiety") that specifically binds to a complex comprising an AFP peptide and an MHC class I protein.

Thus, in some embodiments, there is provided an anti-AMC construct (such as an isolated anti-AMC construct) comprising an antibody moiety that specifically binds to a complex comprising an AFP peptide and an MHC class I protein. In some embodiments, the AFP/MHC class I complex is present on a cell surface. In some embodiments, the AFP/MHC class I complex is present on the surface of a cancer cell.

In some embodiments, the anti-AMC construct comprises an antibody moiety that specifically binds to a complex comprising an AFP peptide and an MHC class I protein, wherein the MHC class I protein is HLA-A. In some embodiments, the MHC class I protein is HLA-A02. In some embodiments, the MHC class I protein is the HLA-A*02:01 subtype of the HLA-A02 allele.

In some embodiments, according to any of the anti-AMC constructs (such as isolated anti-AMC constructs) described above, the anti-AMC construct comprises an antibody moiety that specifically binds to a complex comprising an AFP peptide and an MHC class I protein, wherein the antibody moiety cross-reacts with a complex comprising the AFP peptide and a second MHC class I protein having a different HLA allele than the MHC class I protein. In some embodiments, the antibody moiety cross-reacts with a complex comprising an interspecies variant of the AFP peptide and the MHC class I protein. In some embodiments, the antibody moiety cross-reacts with a complex comprising a variant of the AFP peptide comprising one amino acid substitution (such as a conservative amino acid substitution) and the MHC class I protein.

In some embodiments, according to any of the anti-AMC constructs (such as isolated anti-AMC constructs) described above, the anti-AMC construct comprises an antibody moiety that specifically binds to a complex comprising an AFP peptide and an MHC class I protein, wherein the AFP peptide is about 8 to about 12 (such as about any of 8, 9, 10, 11, or 12) amino acids in length. In some embodiments, the AFP peptide is derived from human AFP. In some embodiments, the AFP peptide has an amino acid sequence selected from the group consisting of SEQ ID NOs: 3-13 and 16. In some embodiments, the AFP peptide has the amino acid sequence FMNKFIYEI (SEQ ID NO: 4).

In some embodiments, according to any of the anti-AMC constructs (such as isolated anti-AMC constructs) described above, the anti-AMC construct comprises an antibody moiety that specifically binds to a complex comprising an AFP peptide and an MHC class I protein, wherein the antibody moiety is a full-length antibody, a Fab, a Fab', a (Fab')2, an Fv, or a single chain Fv (scFv). In some embodiments, the antibody moiety is fully human, semi-synthetic with human antibody framework regions, or humanized.

In some embodiments, according to any of the anti-AMC constructs (such as isolated anti-AMC constructs) described above, the anti-AMC construct comprises an antibody moiety that specifically binds to a complex comprising an AFP peptide and an MHC class I protein, wherein the antibody moiety binds to the AFP/MHC class I complex with an equilibrium dissociation constant ($K_d$) between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the isolated anti-AMC construct binds to the AFP/MHC class I complex with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values).

In some embodiments, the anti-AMC construct comprises an antibody moiety that specifically binds to a complex comprising an AFP peptide and an MHC class I protein, wherein the antibody moiety comprises: i) a heavy chain variable domain comprising a heavy chain complementarity determining region (HC-CDR) 1 comprising the amino acid sequence of G-F/Y-S/T-F-D/S/T-D/N/S-Y/A-A/G/W (SEQ ID NO: 87), or a variant thereof comprising up to about 3 (such as about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (such as about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (such as about any of 1, 2, or 3) amino acid substitutions; and ii) a light chain variable domain comprising a light chain complementarity determining region (LC-CDR) 1 comprising the amino acid sequence of S/T-G/S-D/N-I/V-A/G-A/S/V-X-H/Y (SEQ ID NO: 120), or a variant thereof comprising up to about 3 (such as about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (such as about any of 1, 2, or 3) amino acid substitutions, wherein X can be any amino acid.

In some embodiments, the anti-AMC construct comprises an antibody moiety that specifically binds to a complex comprising an AFP peptide and an MHC class I protein, wherein the antibody moiety comprises: i) a heavy chain variable domain comprising an HC-CDR1 comprising (and in some embodiments consisting of) the amino acid sequence of any one of SEQ ID NOs: 57-66, or a variant thereof comprising up to about 5 (such as about any of 1, 2, 3, 4, or 5) amino acid substitutions, an HC-CDR2 comprising (and in some embodiments consisting of) the amino acid sequence of any one of SEQ ID NOs: 67-76, or a variant thereof comprising up to about 5 (such as about any of 1, 2, 3, 4, or 5) amino acid substitutions, and an HC-CDR3 comprising (and in some embodiments consisting of) the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising (and in some embodiments consisting of) the amino acid sequence of any one of SEQ ID NOs: 90-99, or a variant thereof comprising up to about 5 (such as about any of 1, 2, 3, 4, or 5) amino acid substitutions, an LC-CDR2 comprising (and in some embodiments consisting of) the amino acid sequence of any one of SEQ ID NOs: 100-109, or a variant thereof comprising up to about 3 (such as about any of 1, 2, or 3) amino acid substitutions, and an LC-CDR3 comprising (and in some embodiments consisting of) the amino acid sequence of any one of SEQ ID NOs: 110-119, or a variant thereof comprising up to about 5 (such as about any of 1, 2, 3, 4, or 5) amino acid substitutions.

In some embodiments, the anti-AMC construct comprises an antibody moiety that specifically binds to a complex comprising an AFP peptide and an MHC class I protein, wherein the antibody moiety comprises: i) a heavy chain variable domain comprising (and in some embodiments consisting of) an HC-CDR1 comprising (and in some embodiments consisting of) the amino acid sequence of any one of SEQ ID NOs: 57-66, an HC-CDR2 comprising (and in some embodiments consisting of) the amino acid sequence of any one of SEQ ID NOs: 67-76, and an HC-CDR3 comprising (and in some embodiments consisting of) the amino acid sequence of any one of SEQ ID NOs: 77-86; or a variant thereof comprising up to about 5 (such as about any of 1, 2, 3, 4, or 5) amino acid substitutions in the HC-CDR regions; and ii) a light chain variable domain comprising an LC-CDR1 comprising (and in some embodiments consisting of) the amino acid sequence of any one of SEQ ID NOs: 90-99, an LC-CDR2 comprising (and in some embodiments consisting of) the amino acid sequence of any one of SEQ ID NOs: 100-109, and an LC-CDR3 comprising (and in some embodiments consisting of) the amino acid sequence of any one of SEQ ID NOs: 110-119; or a variant thereof comprising up to about 5 (such as about any of 1, 2, 3, 4, or 5) amino acid substitutions in the LC-CDR regions.

In some embodiments, the anti-AMC construct comprises an antibody moiety that specifically binds to a complex comprising an AFP peptide and an MHC class I protein, wherein the antibody moiety comprises a) a heavy chain variable domain comprising (and in some embodiments consisting of) the amino acid sequence of any one of SEQ ID NOs: 17-26 or a variant thereof having at least about 95% (such as at least about any of 95%, 96%, 97%, 98%, or 99%) sequence identify to any one of SEQ ID NOs: 17-26; and b) a light chain variable domain comprising (and in some embodiments consisting of) the amino acid sequence of any one of SEQ ID NOs: 27-36 or a variant thereof having at least about 95% (such as at least about any of 95%, 96%, 97%, 98%, or 99%) sequence identity to any one of SEQ ID NOs: 27-36. In some embodiments, the antibody moiety comprises a heavy chain variable domain comprising (and in some embodiments consisting of) the amino acid sequence of any one of SEQ ID NOs: 17-26 and a light chain variable domain comprising (and in some embodiments consisting of) the amino acid sequence of any one of SEQ ID NOs: 27-36.

In some embodiments, the anti-AMC construct comprises a first antibody moiety that competes for binding to a target AFP/MHC class I complex with a second antibody moiety according to any of the antibody moieties described above. In some embodiments, the first antibody moiety binds to the same, or substantially the same, epitope as the second antibody moiety. In some embodiments, binding of the first antibody moiety to the target AFP/MHC class I complex inhibits binding of the second antibody moiety to the target AFP/MHC class I complex by at least about 70% (such as by at least about any of 75%, 80%, 85%, 90%, 95%, 98% or 99%), or vice versa. In some embodiments, the first antibody moiety and the second antibody moiety cross-compete for binding to the target AFP/MHC class I complex, i.e., each of the first and second antibody moieties competes with the other for binding to the target AFP/MHC class I complex.

In some embodiments, according to any of the anti-AMC constructs (such as isolated anti-AMC constructs) described above, the isolated anti-AMC construct is a full-length antibody. In some embodiments, the isolated anti-AMC construct is monospecific. In some embodiments, the isolated anti-AMC construct is multi-specific. In some embodiments, the isolated anti-AMC construct is bispecific. In some embodiments, the isolated anti-AMC molecule is a tandem scFv, a diabody (Db), a single chain diabody (scDb), a dual-affinity retargeting (DART) antibody, a dual variable domain (DVD) antibody, a knob-into-hole (KiH) antibody, a dock and lock (DNL) antibody, a chemically cross-linked antibody, a heteromultimeric antibody, or a heteroconjugate antibody. In some embodiments, the isolated anti-AMC construct is a tandem scFv comprising two scFvs linked by a peptide linker. In some embodiments, the peptide linker comprises (and in some embodiments consists of) the amino acid sequence GGGGS.

In some embodiments, according to any of the anti-AMC constructs (such as isolated anti-AMC constructs) described above, the anti-AMC construct comprises an antibody moiety that specifically binds to a complex comprising an AFP peptide and an MHC class I protein, wherein the isolated anti-AMC construct further comprises a second antigen-binding moiety that specifically binds to a second antigen. In some embodiments, the second antigen-binding moiety is an antibody moiety. In some embodiments, the second antigen is an antigen on the surface of a T cell. In some embodiments, the T cell is selected from the group consisting of a cytotoxic T cell, a helper T cell, and a natural killer T cell.

In some embodiments, the second antigen is selected from the group consisting of CD3γ, CD3δ, CD3ε, CD3ζ, CD28, OX40, GITR, CD137, CD27, CD40L, and HVEM. In some embodiments, the second antigen is CD3ε, and the isolated anti-AMC construct is a tandem scFv comprising an N-terminal scFv specific for the AFP/MHC class I complex and a C-terminal scFv specific for CD3ε. In some embodiments, the second antigen is an antigen on the surface of a natural killer cell, a neutrophil, a monocyte, a macrophage, or a dendritic cell.

In some embodiments, according to any of the anti-AMC constructs (such as isolated anti-AMC constructs) described above, the anti-AMC construct comprises an antibody moiety that specifically binds to a complex comprising an AFP peptide and an MHC class I protein, wherein the isolated anti-AMC construct is a chimeric antigen receptor. In some embodiments, the chimeric antigen receptor comprises an extracellular domain comprising the antibody moiety, a transmembrane domain, and an intracellular signaling domain. In some embodiments, the intracellular signaling domain comprises a CD3ζ intracellular signaling sequence and a co-stimulatory signaling sequence. In some embodiments, the co-stimulatory signaling sequence is a CD28 intracellular signaling sequence.

In some embodiments, according to any of the anti-AMC constructs (such as isolated anti-AMC constructs) described above, the anti-AMC construct comprises an antibody moiety that specifically binds to a complex comprising an AFP peptide and an MHC class I protein, wherein the isolated anti-AMC construct is an immunoconjugate comprising the antibody moiety and an effector molecule. In some embodiments, the effector molecule is a therapeutic agent selected from the group consisting of a drug, a toxin, a radioisotope, a protein, a peptide, and a nucleic acid. In some embodiments, the therapeutic agent is a drug or a toxin. In some embodiments, the effector molecule is a label.

In yet other embodiments, there is provided a pharmaceutical composition comprising an anti-AMC construct (such as an isolated anti-AMC construct) according to any of the embodiments described above. In some embodiments, the pharmaceutical composition further comprises a cell (such as an effector cell) associated with the anti-AMC construct. In some embodiments, there is provided a host cell expressing or associated with an anti-AMC construct or polypeptide component thereof. In some embodiments, there is provided a nucleic acid encoding an anti-AMC construct or polypeptide component thereof. In some embodiments, there is provided a vector comprising the nucleic acid. In some embodiments, there is provided an effector cell expressing or associated with an anti-AMC construct. In some embodiments, the effector cell is a T cell.

In some embodiments, there is provided a method of detecting a cell presenting a complex comprising an AFP peptide and an MHC class I protein on its surface, comprising contacting the cell with an anti-AMC construct (such as an isolated anti-AMC construct) according to any of the embodiments described above comprising a) an antibody moiety that specifically binds to a complex comprising the AFP peptide and the MHC class I protein and b) a label, and detecting the presence of the label on the cell.

In some embodiments, there is provided a method of treating an individual having an AFP-positive disease, comprising administering to the individual an effective amount of a pharmaceutical composition comprising an anti-AMC construct (such as an isolated anti-AMC construct) according to any of the embodiments described above. In some embodiments, the pharmaceutical composition further comprises a cell (such as an effector cell) associated with the isolated anti-AMC construct. In some embodiments, there is provided a method of treating an individual having an AFP-positive disease, comprising administering to the individual an effective amount of an effector cell expressing any of the anti-AMC CARs described above. In some embodiments, the effector cell is a T cell. In some embodiments, the administration is to an injection site distal to a first disease site in the individual. In some embodiments, the injection site is a first tumor distal to the first disease site. In some embodiments, the first disease site is an AFP-positive tumor. In some embodiments, the AFP-positive disease is cancer. In some embodiments, the cancer is hepatocellular carcinoma or germ cell tumor. In some embodiments, the cancer is hepatocellular carcinoma. In some embodiments, the cancer is hepatocellular carcinoma and metastasis is inhibited. In some embodiments, the cancer is metastatic hepatocellular carcinoma.

In some embodiments, there is provided a method of diagnosing an individual having an AFP-positive disease, comprising: a) administering an effective amount of an isolated anti-AMC construct according to any of the embodiments described above to the individual; and b) determining the level of the label in the individual, wherein a level of the label above a threshold level indicates that the individual has the AFP-positive disease. In some embodiments, there is provided a method of diagnosing an individual having an AFP-positive disease, comprising: a) contacting a sample derived from the individual with an isolated anti-AMC construct according to any of the embodiments described above; and b) determining the number of cells bound with the isolated anti-AMC construct in the sample, wherein a value for the number of cells bound with the isolated anti-AMC construct above a threshold level indicates that the individual has the AFP-positive disease. In some embodiments, the AFP-positive disease is cancer. In some embodiments, the cancer is hepatocellular carcinoma or germ cell tumor. In some embodiments, the cancer is hepatocellular carcinoma. In some embodiments, the cancer is hepatocellular carcinoma and metastasis is inhibited. In some embodiments, the cancer is metastatic hepatocellular carcinoma.

Also provided are methods of making any of the constructs described herein, articles of manufacture, and kits that are suitable for the methods described herein.

BRIEF DESCRIPTION OF THE DRAWINGS

FIG. 25 shows flow cytometry analysis of the degranulation of AFP158 CAR-transduced T cells after co-culturing with target cells (HepG2, SK-HEP-1 or SK-Hep1-MiniG); transduced T-cells were gated for CAR and CD8 expression and stained for anti-CD107a.

DETAILED DESCRIPTION OF THE INVENTION

Figure 1:
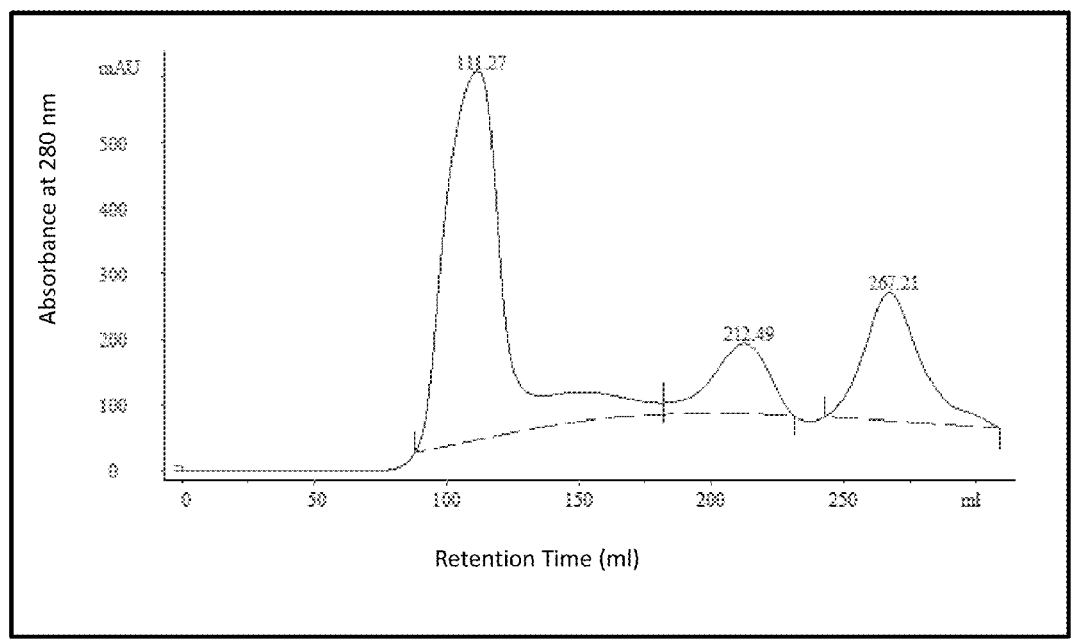
FIG. 1 shows the size exclusion chromatography (SEC) chromatogram of AFP158 peptide/HLA-A*02:01 complex following concentration by ultrafiltration. Properly folded peptide/MHC complex monomers: 212.49 mL; misfolded aggregates: 111.27 mL; free β2M: 267.21 mL.

The present application provides isolated constructs (referred to herein as "anti-AMC constructs") that comprise an antibody moiety (referred to herein as an "anti-AMC antibody moiety") that specifically binds to a complex comprising an AFP peptide and an MHC class I protein (referred to herein as an "AFP/MHC class I complex," or "AMC"). The anti-AMC constructs specifically recognize AFP/MHC class I complexes (such as MHC-presented AFP peptides on the surface of cells expressing AFP), as opposed to circulating AFP protein or free AFP peptides. When armed as anti-CD3 bispecific antibodies or present in a chimeric antigen receptor (CAR) expressed by a T cell, the anti-AMC antibody moiety specifically redirected human T cells to kill AMC-presenting target cells, such as AMC-presenting cancer cells. This strategy provides a significant technical advantage over using antibodies directed against the AFP protein, which cannot specifically target AMC-presenting cells (i.e., cells presenting on their surface an AFP peptide bound to an MHC class I molecule). Furthermore, when fused to a detectable moiety, the anti-AMC antibody moiety allows for diagnosis and prognosis of AFP-positive diseases or disorders with high sensitivity to changes in the number and distribution of AMC-presenting cells, a potentially more relevant measure of disease progression than circulating AFP levels.

Using phage display technology, we generated multiple monoclonal antibodies that are specific and high affinity against human AFP158 peptide/HLA-A*02:01 complex, as well as AFP158/MHC complexes formed in the context of other subtypes of the HLA-A02 allele. Flow cytometry and T-cell mediated cytotoxicity assays demonstrated that the antibodies recognized AFP peptide-pulsed T2 cells and AMC-presenting cancer cell lines, in an AFP- and HLA-A*02:01-restricted manner. When armed as anti-CD3 bispecific antibodies or CAR T cells, the antibodies re-directed human T cells to kill AFP-positive and HLA-A*02:01-positive target cancer cells. The data presented herein demonstrate that antibodies against a secreted cancer antigen in the context of an HLA complex can be effective therapeutic agents for cancer indications, such as solid tumor indications.

The present application thus provides constructs (such as isolated constructs) comprising an antibody moiety that specifically binds to a complex comprising an AFP peptide and an MHC class I protein. The construct can be, for example, a full-length anti-AMC antibody, a multi-specific anti-AMC molecule (such as a bispecific anti-AMC antibody), an anti-AMC chimeric antigen receptor ("CAR"), or an anti-AMC immunoconjugate.

In another aspect, there are provided nucleic acids encoding the anti-AMC constructs or the anti-AMC antibody moiety portion of the constructs.

In another aspect, there are provided compositions comprising an anti-AMC construct comprising an antibody moiety that specifically binds to a complex comprising an AFP-peptide and an MHC class I protein. The composition can be a pharmaceutical composition comprising an anti-AMC construct or an effector cell expressing or associated with the anti-AMC construct (for example a T cell expressing an anti-AMC CAR).

Also provided are methods of making and using the anti-AMC constructs (or cells expressing or associated with the anti-AMC constructs) for treatment or diagnostic purposes, as well as kits and articles of manufacture useful for such methods.

Definitions

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the invention contemplate any one or more of these aspects of treatment.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

"Activation", as used herein in relation to T cells, refers to the state of a T cell that has been sufficiently stimulated to induce detectable cellular proliferation. Activation can also be associated with induced cytokine production, and detectable effector functions.

The term "antibody moiety" includes full-length antibodies and antigen-binding fragments thereof. A full-length antibody comprises two heavy chains and two light chains. The variable regions of the light and heavy chains are responsible for antigen binding. The variables region in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody moiety "competes" for binding to a target AMC with a second antibody moiety when the first antibody moiety inhibits target AMC binding of the second antibody moiety by at least about 50% (such as at least about any of 55%, 60%, 65%, 70%, 75%, 80%, 85%, 90%, 95%, 98% or 99%) in the presence of an equimolar concentration of the first antibody moiety, or vice versa. A high throughput process for "binning" antibodies based upon their cross-competition is described in PCT Publication No. WO 03/48731.

As use herein, the term "specifically binds" or "is specific for" refers to measurable and reproducible interactions, such as binding between a target and an antibody or antibody moiety, that is determinative of the presence of the target in the presence of a heterogeneous population of molecules, including biological molecules. For example, an antibody or antibody moiety that specifically binds to a target (which can be an epitope) is an antibody or antibody moiety that binds this target with greater affinity, avidity, more readily, and/or with greater duration than its bindings to other targets. In some embodiments, an antibody or antibody moiety that specifically binds to an antigen reacts with one or more antigenic determinants of the antigen (for example an AFP peptide/MHC class I protein complex) with a binding affinity that is at least about 10 times its binding affinity for other targets.

An "isolated" anti-AMC construct as used herein refers to an anti-AMC construct that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR DEFINITIONS

|  | Kabat[1] | Chothia[2] | MacCallum[3] |
| --- | --- | --- | --- |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32 (5):1792-1797, 2004; Edgar, R. C., *BMC Bioinformatics* 5 (1):113, 2004).

The terms "Fc receptor" or "FcR" are used to describe a receptor that binds to the Fc region of an antibody. In some embodiments, an FcR of this invention is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.*22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent $K_d$ or $IC_{50}$ value) than the parent polypeptide or a native sequence IgG Fc. According to some embodiments, the improvement in binding compared to a parent polypeptide is about 3 fold, such as about any of 5, 10, 25, 50, 60, 100, 150, 200, or up to 500 fold, or about 25% to 1000% improvement in binding. The polypeptide variant which "exhibits decreased binding" to an FcR, binds at least one FcR with lower affinity (e.g., higher apparent $K_d$ or higher $IC_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

The polypeptide comprising a variant Fc region which "exhibits increased ADCC" or mediates antibody-dependent cell-mediated cytotoxicity (ADCC) in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g. in an animal model etc. In some embodiments, the variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an anti-AMC construct or composition as disclosed herein, is an amount sufficient to carry out a specifically stated purpose. An "effective amount" can be determined empirically and by known methods relating to the stated purpose.

The term "therapeutically effective amount" refers to an amount of an anti-AMC construct or composition as disclosed herein, effective to "treat" a disease or disorder in an individual. In the case of cancer, the therapeutically effective amount of the anti-AMC construct or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-AMC construct or composition as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that extends the survival of a patient. In some embodiments, the therapeutically effective amount is an amount that improves progression free survival of a patient.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "label" when used herein refers to a detectable compound or composition which can be conjugated directly or indirectly to the anti-AMC antibody moiety. The label may be detectable by itself (e.g., radioisotope labels or fluorescent labels) or, in the case of an enzymatic label, may catalyze chemical alteration of a substrate compound or composition which is detectable.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "or," and "the" include plural referents unless the context clearly dictates otherwise.

Anti-AMC Constructs

In one aspect, the present invention provides AFP/MHC class I complex-specific constructs (anti-AMC constructs) that comprise an antibody moiety that specifically binds to a complex comprising an AFP peptide and an MHC class I protein ("AFP/MHC class I complex," or "AMC"). The specificity of the anti-AMC construct derives from an anti-AMC antibody moiety, such as a full-length antibody or antigen-binding fragment thereof, that specifically binds to the AMC. In some embodiments, reference to a moiety (such as an antibody moiety) that specifically binds to a complex comprising an AFP peptide and an MHC class I protein means that the moiety binds to the AMC with a) an affinity that is at least about 10 (including for example at least about any of 10, 20, 30, 40, 50, 75, 100, 200, 300, 400, 500, 750, 1000 or more) times its binding affinity for each of full-length AFP, free AFP peptide, MHC class I protein not bound to a peptide, and MHC class I protein bound to a non-AFP peptide; or b) a $K_d$ no more than about 1/10 (such as no more than about any of 1/10, 1/20, 1/30, 1/40, 1/50, 1/75, 1/100, 1/200, 1/300, 1/400, 1/500, 1/750, 1/1000 or less) times its $K_d$ for binding to each of full-length AFP, free AFP peptide, MHC class I protein not bound to a peptide, and MHC class I protein bound to a non-AFP peptide. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, Biacore instruments, or kinetic exclusion assay (KinExA) utilizing, for example, Sapidyne instruments.

Contemplated anti-AMC constructs include, for example, full-length anti-AMC antibodies, multi-specific (such as bispecific) anti-AMC molecules, anti-AMC chimeric antigen receptors (CARs), and anti-AMC immunoconjugates.

For example, in some embodiments, there is provided an anti-AMC construct (such as an isolated anti-AMC construct) comprising an anti-AMC antibody moiety that specifically binds to a complex comprising an AFP peptide and an MHC class I protein. In some embodiments, the AFP peptide is AFP158 (SEQ ID NO: 4). In some embodiments, the MHC class I protein is HLA-A02. In some embodiments, the MHC class I protein is HLA-A*02:01 (GenBank Accession No. AAO20853). In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the anti-AMC construct binds the AMC with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-AMC construct cross-reacts with at least one (such as at least any of 2, 3, 4, 5, or 6) complex comprising the MHC class I protein and a variant of the AFP peptide having one amino acid substitution (such as a conservative amino acid substitution). In some embodiments, the anti-AMC construct cross-reacts with at least one (such as at least any of 2, 3, 4, or 5) complex comprising the AFP peptide and a different subtype of the MHC class I protein.

In some embodiments, there is provided an anti-AMC construct comprising an anti-AMC antibody moiety that specifically binds to a complex comprising an AFP158 peptide (SEQ ID NO: 4) and HLA-A*02:01. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the anti-AMC construct binds the AMC with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-AMC construct cross-reacts with at least one (such as at least any of 2, 3, 4, 5, or 6) complex comprising the MHC class I protein and a variant of the AFP peptide having one amino acid substitution (such as a conservative amino acid substitution). In some embodiments, the anti-AMC construct cross-reacts with at least one (such as at least any of 2, 3, 4, or 5) complex comprising the AFP peptide and a different subtype of the MHC class I protein.

In some embodiments, there is provided an anti-AMC construct comprising an anti-AMC antibody moiety that specifically binds to a complex comprising an AFP peptide and an MHC class I protein, wherein the anti-AMC antibody moiety comprises: i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89); or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the anti-AMC construct binds the AMC with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-AMC construct cross-reacts with at least one (such as at least any of 2, 3, 4, 5, or 6) complex comprising the MHC class I protein and a variant of the AFP peptide having one amino acid substitution (such as a conservative amino acid substitution). In some embodiments, the anti-AMC construct cross-reacts with at least one (such as at least any of 2, 3, 4, or 5) complex comprising the AFP peptide and a different subtype of the MHC class I protein.

In some embodiments, there is provided an anti-AMC construct comprising an anti-AMC antibody moiety that specifically binds to a complex comprising an AFP peptide and an MHC class I protein, wherein the anti-AMC antibody moiety comprises: i) a heavy chain variable domain sequence comprising an HC-CDR1 comprising (and in some embodiments consisting of) the amino acid sequence of any one of SEQ ID NOs: 57-66; or a variant thereof comprising up to about 5 (for example about any of 1, 2, 3, 4, or 5) amino acid substitutions; an HC-CDR2 comprising (and in some embodiments consisting of) the amino acid sequence of any one of SEQ ID NOs: 67-76; or a variant thereof comprising up to about 5 (for example about any of 1, 2, 3, 4, or 5) amino acid substitutions; and an HC-CDR3 comprising (and in some embodiments consisting of) the amino acid sequence of any one of SEQ ID NOs: 77-86; or a variant thereof comprising up to about 5 (for example about any of 1, 2, 3, 4, or 5) amino acid substitutions; and ii) a light chain variable domain sequence comprising an LC-CDR1 comprising (and in some embodiments consisting of) the amino acid sequence of any one of SEQ ID NOs: 90-99; or a variant thereof comprising up to about 5 (for example about any of 1, 2, 3, 4, or 5) amino acid substitutions; an LC-CDR2 comprising (and in some embodiments consisting of) the amino acid sequence of any one of SEQ ID NOs: 100-109; or a variant thereof comprising up to about 3 (for example about any of 1, 2, or 3) amino acid substitutions; and an LC-CDR3 comprising (and in some embodiments consisting of) the amino acid sequence of any one of SEQ ID NOs: 110-119; or a variant thereof comprising up to about 5 (for example about any of 1, 2, 3, 4, or 5) amino acid substitutions. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the anti-AMC construct binds the AMC with a Kd between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-AMC construct cross-reacts with at least one (such as at least any of 2, 3, 4, 5, or 6) complex comprising the MHC class I protein and a variant of the AFP peptide having one amino acid substitution (such as a conservative amino acid substitution). In some embodiments, the anti-AMC construct cross-reacts with at least one (such as at least any of 2, 3, 4, or 5) complex comprising the AFP peptide and a different subtype of the MHC class I protein.

In some embodiments, there is provided an anti-AMC construct comprising an anti-AMC antibody moiety that specifically binds to a complex comprising an AFP peptide and an MHC class I protein, wherein the anti-AMC antibody moiety comprises: i) a heavy chain variable domain sequence comprising an HC-CDR1 comprising (and in some embodiments consisting of) the amino acid sequence of any one of SEQ ID NOs: 57-66; an HC-CDR2 comprising (and in some embodiments consisting of) the amino acid sequence of any one of SEQ ID NOs: 67-76; and an HC-CDR3 comprising (and in some embodiments consisting of) the amino acid sequence of any one of SEQ ID NOs: 77-86; or a variant thereof comprising up to about 5 (for example about any of 1, 2, 3, 4, or 5) amino acid substitutions in the HC-CDR sequences; and ii) a light chain variable domain sequence comprising an LC-CDR1 comprising (and in some embodiments consisting of) the amino acid sequence of any one of SEQ ID NOs: 90-99; an LC-CDR2 comprising (and in some embodiments consisting of) the amino acid sequence of any one of SEQ ID NOs: 100-109; and an LC-CDR3 comprising (and in some embodiments consisting of) the amino acid sequence of any one of SEQ ID NOs: 110-119; or a variant thereof comprising up to about 5 (for example about any of 1, 2, 3, 4, or 5) amino acid substitutions in the LC-CDR sequences. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the anti-AMC construct binds the AMC with a Kd between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-AMC construct cross-reacts with at least one (such as at least any of 2, 3, 4, 5, or 6) complex comprising the MHC class I protein and a variant of the AFP peptide having one amino acid substitution (such as a conservative amino acid substitution). In some embodiments, the anti-AMC construct cross-reacts with at least one (such as at least any of 2, 3, 4, or 5) complex comprising the AFP peptide and a different subtype of the MHC class I protein.

In some embodiments, there is provided an anti-AMC construct comprising an anti-AMC antibody moiety that specifically binds to a complex comprising an AFP peptide and an MCH class I protein, wherein the anti-AMC antibody moiety comprises a heavy chain variable domain comprising (and in some embodiments consisting of) the amino acid sequence of any one of SEQ ID NOs: 17-26, or a variant thereof having at least about 95% (for example at least about any of 96%, 97%, 98%, or 99%) sequence identity, and a light chain variable domain comprising (and in some embodiments consisting of) the amino acid sequence of any one of SEQ ID NOs: 27-36, or a variant thereof having at least about 95% (for example at least about any of 96%, 97%, 98%, or 99%) sequence identity. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the anti-AMC construct binds the AMC with a Kd between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-AMC construct cross-reacts with at least one (such as at least any of 2, 3, 4, 5, or 6) complex comprising the MHC class I protein and a variant of the AFP peptide having one amino acid substitution (such as a conservative amino acid substitution). In some embodiments, the anti-AMC construct cross-reacts with at least one (such as at least any of 2, 3, 4, or 5) complex comprising the AFP peptide and a different subtype of the MHC class I protein.

In some embodiments, there is provided an anti-AMC construct comprising a first anti-AMC antibody moiety that competes for binding to a target AFP/MHC class I complex with a second anti-AMC antibody moiety according to any of the anti-AMC antibody moieties described herein. In some embodiments, the first anti-AMC antibody moiety binds to the same, or substantially the same, epitope as the second anti-AMC antibody moiety. In some embodiments, binding of the first anti-AMC antibody moiety to the target AFP/MHC class I complex inhibits binding of the second anti-AMC antibody moiety to the target AFP/MHC class I complex by at least about 70% (such as by at least about any of 75%, 80%, 85%, 90%, 95%, 98% or 99%), or vice versa. In some embodiments, the first anti-AMC antibody moiety and the second anti-AMC antibody moiety cross-compete for binding to the target AFP/MHC class I complex, i.e., each of the first and second antibody moieties competes with the other for binding to the target AFP/MHC class I complex.

The different aspects are discussed in various sections below in further detail.

Anti-AMC Antibody Moiety

The anti-AMC constructs comprise an anti-AMC antibody moiety that specifically binds to a complex comprising an AFP peptide and an MHC class I protein.

In some embodiments, the anti-AMC antibody moiety specifically binds to an AMC present on the surface of a cell. In some embodiments, the cell presents on its surface abnormally high levels of AFP. In some embodiments, the cell is a cancer cell. In some embodiments, the cancer cell is in a solid tumor. In some embodiments, the cancer cell is a metastatic cancer cell.

In some embodiments, the AFP peptide is an MHC class I-restricted peptide. In some embodiments, the AFP peptide is from about 8 to about 12 (such as about any of 8, 9, 10, 11, or 12) amino acids in length. In some embodiments, the AFP peptide is derived from human AFP (hAFP), mouse AFP (mAFP), or rat AFP (rAFP).

In some embodiments, the AFP peptide is derived from hAFP. In some embodiments, the AFP peptide comprises (and in some embodiments consists of) the sequence of amino acids 137-145 of hAFP (PLFQVPEPV, SEQ ID NO: 3), amino acids 158-166 of hAFP (FMNKFIYEI, SEQ ID NO: 4, also referred to herein as "AFP158"), amino acids 325-334 of hAFP (GLSPNLNRFL, SEQ ID NO: 5), or amino acids 542-50 of hAFP (GVALQTMKQ, SEQ ID NO: 6).

In some embodiments, the AFP peptide is derived from mAFP. In some embodiments, the AFP peptide comprises the sequence of amino acids 154-162 of mAFP (FMNRFIYEV, SEQ ID NO: 16).

In some embodiments, the MHC class I protein is HLA-A, HLA-B, HLA-C, HLA-E, HLA-F, or HLA-G. In some embodiments, the MHC class I protein is HLA-A. In some embodiments, the HLA-A is HLA-A02. In some embodiments, the HLA-A02 is HLA-A*02:01.

In some embodiments, the anti-AMC antibody moiety is a full-length antibody. In some embodiments, the anti-AMC antibody moiety is an antigen-binding fragment, for example an antigen-binding fragment selected from the group consisting of a Fab, a Fab', a F(ab')2, an Fv fragment, a disulfide stabilized Fv fragment (dsFv), and a single-chain antibody molecule (scFv). In some embodiments, the anti-AMC antibody moiety is an scFv. In some embodiments, the anti-AMC antibody moiety is human, humanized, or semi-synthetic.

In some embodiments, the anti-AMC antibody moiety specifically binds to the N-terminal portion of the AFP peptide in the complex. In some embodiments, the anti-AMC antibody moiety specifically binds to the C-terminal portion of the AFP peptide in the complex. In some embodiments, the anti-AMC antibody moiety specifically binds to the middle portion of the AFP peptide in the complex.

In some embodiments, the anti-AMC antibody moiety specifically binds to a complex comprising an AFP peptide and an MHC class I protein, wherein the anti-AMC antibody moiety cross-reacts with at least one complex comprising the AFP peptide and an allelic variant of the MHC class I protein. In some embodiments, the allelic variant has up to about 10 (such as about any of 1, 2, 3, 4, 5, 6, 7, 8, 9, or 10) amino acid substitutions when compared to the MHC class I protein. In some embodiments, the allelic variant is the same serotype as the MHC class I protein. In some embodiments, the allelic variant is a different serotype than the MHC class I protein. In some embodiments, the anti-AMC antibody moiety does not cross-react with a complex comprising the AFP peptide and any allelic variant of the MHC class I protein.

In some embodiments, the anti-AMC antibody moiety specifically binds to a complex comprising an AFP peptide and an MHC class I protein, wherein the anti-AMC antibody moiety cross-reacts with at least one complex comprising the MHC class I protein and a variant of the AFP peptide having one amino acid substitution (such as a conservative substitution). In some embodiments, the anti-AMC antibody moiety does not cross-react with a complex comprising the MHC class I protein and any variant of the AFP peptide.

In some embodiments, the anti-AMC antibody moiety specifically binds to a complex comprising an AFP peptide and an MHC class I protein, wherein the anti-AMC antibody moiety cross-reacts with at least one complex comprising the MHC class I protein and an interspecies variant of the AFP peptide. In some embodiments, for example, the AFP peptide is human AFP peptide and the interspecies variant of the AFP peptide is a mouse or rat variant thereof. In some embodiments, the anti-AMC antibody moiety does not cross-react with a complex comprising the MHC class I protein and any interspecies variant of the AFP peptide.

In some embodiments, the anti-AMC antibody moiety (or the anti-AMC construct comprising the anti-AMC antibody moiety) binds to the complex comprising the AFP peptide and the MHC class I protein with an affinity that is at least about 10 (including for example at least about any of 10, 20, 30, 40, 50, 75, 100, 200, 300, 400, 500, 750, 1000 or more) times its binding affinity for each of full-length AFP, free AFP peptide, MHC class I protein not bound to a peptide, and MHC class I protein bound to a non-AFP peptide. In some embodiments, the anti-AMC antibody moiety (or the anti-AMC construct comprising the anti-AMC antibody moiety) binds to the complex comprising the AFP peptide and the MHC class I protein with a $K_d$ no more than about $\frac{1}{10}$ (such as no more than about any of $\frac{1}{10}$, $\frac{1}{20}$, $\frac{1}{30}$, $\frac{1}{40}$, $\frac{1}{50}$, $\frac{1}{75}$, $\frac{1}{100}$, $\frac{1}{200}$, $\frac{1}{300}$, $\frac{1}{400}$, $\frac{1}{500}$, $\frac{1}{750}$, $\frac{1}{1000}$ or less) times its $K_d$ for binding to each of full-length AFP, free AFP peptide, MHC class I protein not bound to a peptide, and MHC class I protein bound to a non-AFP peptide.

In some embodiments, the anti-AMC antibody moiety (or the anti-AMC construct comprising the anti-AMC antibody moiety) binds to the complex comprising the AFP peptide and the MHC class I protein with a Kd between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-AMC antibody moiety (or the anti-AMC construct comprising the anti-AMC antibody moiety) binds to the complex comprising the AFP peptide and the MHC class I protein with a Kd between about 1 pM to about 250 pM (such as about any of 1, 10, 25, 50, 75, 100, 150, 200, or 250 pM, including any ranges between these values). In some embodiments, the anti-AMC antibody moiety (or the anti-AMC construct comprising the anti-AMC antibody moiety) binds to the complex comprising the AFP peptide and the MHC class I protein with a Kd between about 1 nM to about 500 nM (such as about any of 1, 10, 25, 50, 75, 100, 150, 200, 250, 300, 350, 400, 450, or 500 nM, including any ranges between these values).

In some embodiments, the anti-AMC antibody moiety specifically binds to a complex comprising AFP158 (SEQ ID NO: 4) and an MHC class I protein (such as HLA-A02, for example HLA-A*02:01). In some embodiments, the anti-AMC antibody moiety further binds to at least one (including at least about any of 2, 3, 4, 5, 6, or 7) of: a complex comprising an AFP peptide of SEQ ID NO: 7 and an MHC class I protein (such as HLA-A02, for example HLA-A*02:01); a complex comprising an AFP peptide of SEQ ID NO: 8 and an MHC class I protein (such as HLA-A02, for example HLA-A*02:01); a complex comprising an AFP peptide of SEQ ID NO: 9 and an MHC class I protein (such as HLA-A02, for example HLA-A*02:01); a complex comprising an AFP peptide of SEQ ID NO: 10 and an MHC class I protein (such as HLA-A02, for example HLA-A*02:01); a complex comprising an AFP peptide of SEQ ID NO: 11 and an MHC class I protein (such as HLA-A02, for example HLA-A*02:01); a complex comprising an AFP peptide of SEQ ID NO: 12 and an MHC class I protein (such as HLA-A02, for example HLA-A*02:01); and a complex comprising an AFP peptide of SEQ ID NO: 13 and an MHC class I protein (such as HLA-A02, for example HLA-A*02:01).

In some embodiments, the anti-AMC antibody moiety specifically binds to: a complex comprising an AFP peptide of SEQ ID NO: 4 and an MHC class I protein (such as HLA-A02, for example HLA-A*02:01); a complex comprising an AFP peptide of SEQ ID NO: 10 and an MHC class I protein (such as HLA-A02, for example HLA-A*02:01); a complex comprising an AFP peptide of SEQ ID NO: 11 and an MHC class I protein (such as HLA-A02, for example HLA-A*02:01); a complex comprising an AFP peptide of SEQ ID NO: 12 and an MHC class I protein (such as HLA-A02, for example HLA-A*02:01); and a complex comprising an AFP peptide of SEQ ID NO: 13 and an MHC class I protein (such as HLA-A02, for example HLA-A*02:01).

In some embodiments, the anti-AMC antibody moiety specifically binds to: a complex comprising an AFP peptide of SEQ ID NO: 4 and an MHC class I protein (such as HLA-A02, for example HLA-A*02:01); a complex comprising an AFP peptide of SEQ ID NO: 7 and an MHC class I protein (such as HLA-A02, for example HLA-A*02:01); and a complex comprising an AFP peptide of SEQ ID NO: 8 and an MHC class I protein (such as HLA-A02, for example HLA-A*02:01).

In some embodiments, the anti-AMC antibody moiety specifically binds to: a complex comprising an AFP peptide of SEQ ID NO: 4 and an MHC class I protein (such as HLA-A02, for example HLA-A*02:01); a complex comprising an AFP peptide of SEQ ID NO: 8 and an MHC class I protein (such as HLA-A02, for example HLA-A*02:01); a complex comprising an AFP peptide of SEQ ID NO: 10 and an MHC class I protein (such as HLA-A02, for example HLA-A*02:01); a complex comprising an AFP peptide of SEQ ID NO: 11 and an MHC class I protein (such as HLA-A02, for example HLA-A*02:01); a complex comprising an AFP peptide of SEQ ID NO: 12 and an MHC class I protein (such as HLA-A02, for example HLA-A*02:01); and a complex comprising an AFP peptide of SEQ ID NO: 13 and an MHC class I protein (such as HLA-A02, for example HLA-A*02:01).

In some embodiments, the anti-AMC antibody moiety specifically binds to: a complex comprising an AFP peptide of SEQ ID NO: 4 and an MHC class I protein (such as HLA-A02, for example HLA-A*02:01); a complex comprising an AFP peptide of SEQ ID NO: 7 and an MHC class I protein (such as HLA-A02, for example HLA-A*02:01); and a complex comprising an AFP peptide of SEQ ID NO: 13 and an MHC class I protein (such as HLA-A02, for example HLA-A*02:01).

In some embodiments, the anti-AMC antibody moiety specifically binds to: a complex comprising an AFP peptide of SEQ ID NO: 4 and an MHC class I protein (such as HLA-A02, for example HLA-A*02:01); a complex comprising an AFP peptide of SEQ ID NO: 7 and an MHC class I protein (such as HLA-A02, for example HLA-A*02:01); a complex comprising an AFP peptide of SEQ ID NO: 9 and an MHC class I protein (such as HLA-A02, for example HLA-A*02:01); a complex comprising an AFP peptide of SEQ ID NO: 11 and an MHC class I protein (such as HLA-A02, for example HLA-A*02:01); and a complex comprising an AFP peptide of SEQ ID NO: 13 and an MHC class I protein (such as HLA-A02, for example HLA-A*02:01).

In some embodiments, the anti-AMC antibody moiety specifically binds to a complex comprising AFP158 (SEQ ID NO: 4) and HLA-A*02:01. In some embodiments, the anti-antibody moiety cross-reacts with at least one (including at least about any of 2, 3, 4, 5, or 6) of: a complex comprising AFP158 (SEQ ID NO: 4) and HLA-A*02:02 (GenBank Accession No. AFL91480), a complex comprising AFP158 (SEQ ID NO: 4) and HLA-A*02:03 (GenBank Accession No. AAA03604), a complex comprising AFP158 (SEQ ID NO: 4) and HLA-A*02:05 (GenBank Accession No. AAA03603), a complex comprising AFP158 (SEQ ID NO: 4) and HLA-A*02:06 (GenBank Accession No. CCB78868), a complex comprising AFP158 (SEQ ID NO: 4) and HLA-A*02:07 (GenBank Accession No. ACR55712), and a complex comprising AFP158 (SEQ ID NO: 4) and HLA-A*02:11 (GenBank Accession No. CAB56609). In some embodiments, the anti-AMC antibody moiety cross-reacts with each of a complex comprising AFP158 (SEQ ID NO: 4) and HLA-A*02:02, a complex comprising AFP158 (SEQ ID NO: 4) and HLA-A*02:03, and a complex comprising AFP158 (SEQ ID NO: 4) and HLA-A*02:11. In some embodiments, the anti-AMC antibody moiety cross-reacts with each of a complex comprising AFP158 (SEQ ID NO: 4) and HLA-A*02:02, a complex comprising AFP158 (SEQ ID NO: 4) and HLA-A*02:05, a complex comprising AFP158 (SEQ ID NO: 4) and HLA-A*02:06, a complex comprising AFP158 (SEQ ID NO: 4) and HLA-A*02:07, and a complex comprising AFP158 (SEQ ID NO: 4) and HLA-A*02:11.

In some embodiments, the anti-AMC antibody moiety is a semi-synthetic antibody moiety comprising fully human sequences and one or more synthetic regions. In some embodiments, the anti-AMC antibody moiety is a semi-synthetic antibody moiety comprising a fully human light chain variable domain and a semi-synthetic heavy chain variable domain comprising fully human FR1, HC-CDR1, FR2, HC-CDR2, FR3, and FR4 regions and a synthetic HC-CDR3. In some embodiments, the semi-synthetic heavy chain variable domain comprises a fully synthetic HC-CDR3 having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length. In some embodiments, the semi-synthetic heavy chain variable domain or the synthetic HC-CDR3 is obtained from a semi-synthetic library (such as a semi-synthetic human library) comprising fully synthetic HC-CDR3s having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length, wherein each amino acid in the sequence is randomly selected from the standard human amino acids, minus cysteine. In some embodiments, the synthetic HC-CDR3 is from about 10 to about 19 (such as about any of 10, 11, 12, 13, 14, 15, 16, 17, 18 or 19) amino acids in length.

The anti-AMC antibody moieties in some embodiments comprise specific sequences or certain variants of such sequences. In some embodiments, the amino acid substitutions in the variant sequences do not substantially reduce the ability of the anti-AMC antibody moiety to bind the AMC. For example, alterations that do not substantially reduce AMC binding affinity may be made. Alterations that substantially improve AMC binding affinity or affect some other property, such as specificity and/or cross-reactivity with related variants of the AMC, are also contemplated.

In some embodiments, the anti-AMC antibody moiety comprises i) a heavy chain variable domain comprising an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid.

In some embodiments, the anti-AMC antibody moiety comprises i) a heavy chain variable domain comprising an HC-CDR3 comprising the amino acid sequence of A/G-X-W/Y-Y-X-X-X-F/Y-D (SEQ ID NO: 89); and ii) a light chain variable domain comprising an LC-CDR3 comprising the amino acid sequence of Q-S/T-Y/W-D/T-S/T-A/S (SEQ ID NO: 121); wherein X can be any amino acid.

In some embodiments, the anti-AMC antibody moiety comprises i) a heavy chain variable domain comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/ N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/ T-A/S (SEQ ID NO: 121), or a variant thereof comprising up to about 3 (for example about any of 1, 2, or 3) amino acid substitutions; wherein X can be any amino acid.

In some embodiments, the anti-AMC antibody moiety comprises i) a heavy chain variable domain comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/ S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/ T-A/S (SEQ ID NO: 121); wherein X can be any amino acid.

In some embodiments, the anti-AMC antibody moiety comprises i) a heavy chain variable domain comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); or a variant thereof comprising up to about 3 (such as about any of 1, 2, or 3) amino acid substitutions in the HC-CDR sequences; and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); or a variant thereof comprising up to about 3 (such as about any of 1, 2, or 3) amino acid substitutions in the LC-CDR sequences; wherein X can be any amino acid.

In some embodiments, the anti-AMC antibody moiety comprises i) a heavy chain variable domain comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid. The sequences of the CDRs noted herein are provided in Table 2 below.

TABLE 2

| | | | |
|---|---|---|---|
| HC-CDR1 consensus | SEQ ID NO: 87 | G-F/Y-S/T-F-D/S/T-D/N/S-Y/A-A/G/W |
| HC-CDR2 consensus | SEQ ID NO: 88 | I/S-K/S-X-H/Y-X-G-X-T |
| HC-CDR3 consensus | SEQ ID NO: 89 | A/G-X-W/Y-Y-X-X-X-F/Y-D |
| LC-CDR1 consensus | SEQ ID NO: 120 | S/T-G/S-D/N-I/V-A/G-A/S/V-X-H/Y |
| LC-CDR3 consensus | SEQ ID NO: 121 | Q-S/T-Y/W-D/T-S/T-A/S |

In some embodiments, the anti-AMC antibody moiety comprises i) a heavy chain variable domain comprising an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR3 comprising the amino acid sequence of any one of SEQ ID NOs: 110-119, or a variant thereof comprising up to about 5 (such as about any of 1, 2, 3, 4, or 5) amino acid substitutions.

In some embodiments, the anti-AMC antibody moiety comprises i) a heavy chain variable domain comprising an HC-CDR3 comprising the amino acid sequence of any one of SEQ ID NOs: 77-86; and ii) a light chain variable domain comprising an LC-CDR3 comprising the amino acid sequence of any one of SEQ ID NOs: 110-119.

In some embodiments, the anti-AMC antibody moiety comprises i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions.

In some embodiments, the anti-AMC antibody moiety comprises i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119.

In some embodiments, the anti-AMC antibody moiety comprises i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences.

In some embodiments, the anti-AMC antibody moiety comprises i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions, wherein the amino acid substitutions are in HC-CDR1 or HC-CDR2; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions, wherein the amino acid substitutions are in HC-CDR1 or HC-CDR2.

In some embodiments, the anti-AMC antibody moiety comprises i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119. The sequences of the HC-CDRs noted herein are provided in Table 3 below and the LC-CDRs noted herein are provided in Table 4 below.

TABLE 3

| SEQ ID NO: 57 17 HC-CDR1 | GYTFTSYG | SEQ ID NO: 67 17 HC-CDR2 | ISAYNGNT | SEQ ID NO: 77 17 HC-CDR3 | ARYQDWWYLGQFDQ |
|---|---|---|---|---|---|
| SEQ ID NO: 58 33 HC-CDR1 | VSSNSAAWN | SEQ ID NO: 68 33 HC-CDR2 | YRSKWYN | SEQ ID NO: 78 33 HC-CDR3 | ARGSYYSGRYDA |
| SEQ ID NO: 59 44 HC-CDR1 | GGTFSSYA | SEQ ID NO: 69 44 HC-CDR2 | IIPIFGTA | SEQ ID NO: 79 44 HC-CDR3 | AREIRGYYYYYGMDV |

TABLE 3-continued

| | | |
|---|---|---|
| SEQ ID NO: 60 GFTFDDYA 48 HC-CDR1 | SEQ ID NO: 70 ISWNSGRI 48 HC-CDR2 | SEQ ID NO: 80 ARADDYGAPYYYYGMDV 48 HC-CDR3 |
| SEQ ID NO: 61 GGSISSSNW 50 HC-CDR1 | SEQ ID NO: 71 IYHSGST 50 HC-CDR2 | SEQ ID NO: 81 ATGYGGYFDY 50 HC-CDR3 |
| SEQ ID NO: 62 GYTFTSYG 52 HC-CDR1 | SEQ ID NO: 72 ISAYNGNT 52 HC-CDR2 | SEQ ID NO: 82 ARDSYYYYYGMDV 52 HC-CDR3 |
| SEQ ID NO: 63 GYSFPNYW 61 HC-CDR1 | SEQ ID NO: 73 IDPGDSYT 61 HC-CDR2 | SEQ ID NO: 83 ARYVSLVDI 61 HC-CDR3 |
| SEQ ID NO: 64 GFTFSNAW 76 HC-CDR1 | SEQ ID NO: 74 IRSKAYGGTT 76 HC-CDR2 | SEQ ID NO: 84 ARDGLYSSSWYDSDY 76 HC-CDR3 |
| SEQ ID NO: 65 GFTFDDYA 79 HC-CDR1 | SEQ ID NO: 75 ISWNSGSI 79 HC-CDR2 | SEQ ID NO: 85 AKDIHSGSYYGLLYYAMDV 79 HC-CDR3 |
| SEQ ID NO: 66 GYTFTSYG 17-13 HC-CDR1 | SEQ ID NO: 76 ISAYNGNT 17-13 HC-CDR2 | SEQ ID NO: 86 ARFQDWWYLGQFDQ 17-13 HC-CDR3 |

TABLE 4

| | | |
|---|---|---|
| SEQ ID NO: 90 GSDVGVYYY 17 LC-CDR1 | SEQ ID NO: 100 DVG 17 LC-CDR2 | SEQ ID NO: 110 ASYTNRNSLGYV 17 LC-CDR3 |
| SEQ ID NO: 91 SGSIASNY 33 LC-CDR1 | SEQ ID NO: 101 EDN 33 LC-CDR2 | SEQ ID NO: 111 QSYDSSTVV 33 LC-CDR3 |
| SEQ ID NO: 92 NIGTKS 44 LC-CDR1 | SEQ ID NO: 102 YDT 44 LC-CDR2 | SEQ ID NO: 112 QVWDSSSDHPV 44 LC-CDR3 |
| SEQ ID NO: 93 SSNIGAGYD 48 LC-CDR1 | SEQ ID NO: 103 GNS 48 LC-CDR2 | SEQ ID NO: 113 QSYDSSLSGSV 48 LC-CDR3 |
| SEQ ID NO: 94 NIGSKS 50 LC-CDR1 | SEQ ID NO: 104 YDS 50 LC-CDR2 | SEQ ID NO: 114 QVWDSSSDHVV 50 LC-CDR3 |
| SEQ ID NO: 95 TGAVTSGHY 52 LC-CDR1 | SEQ ID NO: 105 DAS 52 LC-CDR2 | SEQ ID NO: 115 LLSYSDALV 52 LC-CDR3 |
| SEQ ID NO: 96 SSDVGGYNY 61 LC-CDR1 | SEQ ID NO: 106 DVN 61 LC-CDR2 | SEQ ID NO: 116 SSYTTGSRAV 61 LC-CDR3 |
| SEQ ID NO: 97 SSNIGNNY 76 LC-CDR1 | SEQ ID NO: 107 DNN 76 LC-CDR2 | SEQ ID NO: 117 GTWDGSLYTML 76 LC-CDR3 |
| SEQ ID NO: 98 SSNIGAGYD 79 LC-CDR1 | SEQ ID NO: 108 GNS 79 LC-CDR2 | SEQ ID NO: 118 QSYDSSLSGSGV 79 LC-CDR3 |
| SEQ ID NO: 99 GSDVGVYYY 17-13 LC-CDR1 | SEQ ID NO: 109 DVD 17-13 LC-CDR2 | SEQ ID NO: 119 ASYTNRNSLGYV 17-13 LC-CDR3 |

In some embodiments, the anti-AMC antibody moiety comprises a heavy chain variable domain comprising the amino acid sequence of any one of SEQ ID NOs: 17-26, or a variant thereof having at least about 95% (including for example at least about any of 96%, 97%, 98%, or 99%) sequence identity, and a light chain variable domain comprising the amino acid sequence of any one of SEQ ID NOs: 27-36, or a variant thereof having at least about 95% (including for example at least any of 96%, 97%, 98%, or 99%) sequence identity.

In some embodiments, the anti-AMC antibody moiety comprises a heavy chain variable domain comprising the amino acid sequence of any one of SEQ ID NOs: 17-26 and a light chain variable domain comprising the amino acid sequence of any one of SEQ ID NOs: 27-36.

The heavy and light chain variable domains can be combined in various pair-wise combinations to generate a number of anti-AMC antibody moieties.

For example, in some embodiments, the anti-AMC antibody moiety comprises a heavy chain variable domain comprising an HC-CDR1 comprising the amino acid sequence of SEQ ID NO: 57, or a variant thereof comprising up to about 5 (for example about any of 1, 2, 3, 4, or 5) amino acid substitutions; an HC-CDR2 comprising the amino acid sequence of SEQ ID NO: 67, or a variant thereof comprising up to about 5 (for example about any of 1, 2, 3, 4, or 5) amino acid substitutions; and an HC-CDR3 comprising the amino acid sequence of SEQ ID NO: 77, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 90, or a variant thereof comprising up to about 5 (for example about any of 1, 2, 3, 4, or 5) amino acid substitutions; an LC-CDR2 comprising the amino acid sequence of SEQ ID NO: 100, or a variant thereof comprising up to about 3 (for example about any of 1, 2, or 3) amino acid substitutions; and an LC-CDR3 comprising the amino acid sequence of SEQ ID NO: 110, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 57, an HC-CDR2 comprising the amino acid sequence of SEQ ID NO: 67, and an HC-CDR3 comprising the amino acid sequence of SEQ ID NO: 77, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 90, an LC-CDR2 comprising the amino acid sequence of SEQ ID NO: 100, and an LC-CDR3 comprising the amino acid sequence of SEQ ID NO: 110, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 57, an HC-CDR2 comprising the amino acid sequence of SEQ ID NO: 67, and an HC-CDR3 comprising the amino acid sequence of SEQ ID NO: 77; and a light chain variable domain comprising an LC-CDR1 comprising the amino acid sequence of SEQ ID NO: 90, an LC-CDR2 comprising the amino acid sequence of SEQ ID NO: 100, and an LC-CDR3 comprising the amino acid sequence of SEQ ID NO: 110.

In some embodiments, the anti-AMC antibody moiety comprises a heavy chain variable domain comprising an HC-CDR1 comprising the amino acid sequence of SEQ ID NO: 58, or a variant thereof comprising up to about 5 (for example about any of 1, 2, 3, 4, or 5) amino acid substitutions; an HC-CDR2 comprising the amino acid sequence of SEQ ID NO: 68, or a variant thereof comprising up to about 5 (for example about any of 1, 2, 3, 4, or 5) amino acid substitutions; and an HC-CDR3 comprising the amino acid sequence of SEQ ID NO: 78, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 91, or a variant thereof comprising up to about 5 (for example about any of 1, 2, 3, 4, or 5) amino acid substitutions; an LC-CDR2 comprising the amino acid sequence of SEQ ID NO: 101, or a variant thereof comprising up to about 3 (for example about any of 1, 2, or 3) amino acid substitutions; and an LC-CDR3 comprising the amino acid sequence of SEQ ID NO: 111, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 58, an HC-CDR2 comprising the amino acid sequence of SEQ ID NO: 68, and an HC-CDR3 comprising the amino acid sequence of SEQ ID NO: 78, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 91, an LC-CDR2 comprising the amino acid sequence of SEQ ID NO: 101, and an LC-CDR3 comprising the amino acid sequence of SEQ ID NO: 111, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 58, an HC-CDR2 comprising the amino acid sequence of SEQ ID NO: 68, and an HC-CDR3 comprising the amino acid sequence of SEQ ID NO: 78; and a light chain variable domain comprising an LC-CDR1 comprising the amino acid sequence of SEQ ID NO: 91, an LC-CDR2 comprising the amino acid sequence of SEQ ID NO: 101, and an LC-CDR3 comprising the amino acid sequence of SEQ ID NO: 111.

In some embodiments, the anti-AMC antibody moiety comprises a heavy chain variable domain comprising an HC-CDR1 comprising the amino acid sequence of SEQ ID NO: 59, or a variant thereof comprising up to about 5 (for example about any of 1, 2, 3, 4, or 5) amino acid substitutions; an HC-CDR2 comprising the amino acid sequence of SEQ ID NO: 69, or a variant thereof comprising up to about 5 (for example about any of 1, 2, 3, 4, or 5) amino acid substitutions; and an HC-CDR3 comprising the amino acid sequence of SEQ ID NO: 79, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 92, or a variant thereof comprising up to about 5 (for example about any of 1, 2, 3, 4, or 5) amino acid substitutions; an LC-CDR2 comprising the amino acid sequence of SEQ ID NO: 102, or a variant thereof comprising up to about 3 (for example about any of 1, 2, or 3) amino acid substitutions; and an LC-CDR3 comprising the amino acid sequence of SEQ ID NO: 112, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 59, an HC-CDR2 comprising the amino acid sequence of SEQ ID NO: 69, and an HC-CDR3 comprising the amino acid sequence of SEQ ID NO: 79, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 92, an LC-CDR2 comprising the amino acid sequence of SEQ ID NO: 102, and an LC-CDR3 comprising the amino acid sequence of SEQ ID NO: 112, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 59, an HC-CDR2 comprising the amino acid sequence of SEQ ID NO: 69, and an HC-CDR3 comprising the amino acid sequence of SEQ ID NO: 79; and a light chain variable domain comprising an LC-CDR1 comprising the amino acid sequence of SEQ ID NO: 92, an LC-CDR2 comprising the amino acid sequence of SEQ ID NO: 102, and an LC-CDR3 comprising the amino acid sequence of SEQ ID NO: 112.

In some embodiments, the anti-AMC antibody moiety comprises a heavy chain variable domain comprising an HC-CDR1 comprising the amino acid sequence of SEQ ID NO: 60, or a variant thereof comprising up to about 5 (for example about any of 1, 2, 3, 4, or 5) amino acid substitutions; an HC-CDR2 comprising the amino acid sequence of SEQ ID NO: 70, or a variant thereof comprising up to about 5 (for example about any of 1, 2, 3, 4, or 5) amino acid substitutions; and an HC-CDR3 comprising the amino acid sequence of SEQ ID NO: 80, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 93, or a variant thereof comprising up to about 5 (for example about any of 1, 2, 3, 4, or 5) amino acid substitutions; an LC-CDR2 comprising the amino acid sequence of SEQ ID NO: 103, or a variant thereof comprising up to about 3 (for example about any of 1, 2, or 3) amino acid substitutions; and an LC-CDR3 comprising the amino acid sequence of SEQ ID NO: 113, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 60, an HC-CDR2 comprising the amino acid sequence of SEQ ID NO: 70, and an HC-CDR3 comprising the amino acid sequence of SEQ ID NO: 80, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 93, an LC-CDR2 comprising the amino acid sequence of SEQ ID NO: 103, and an LC-CDR3 comprising the amino acid sequence of SEQ ID NO: 113, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 60, an HC-CDR2 comprising the amino acid sequence of SEQ ID NO: 70, and an HC-CDR3 comprising the amino acid sequence of SEQ ID NO: 80; and a light chain variable domain comprising an LC-CDR1 comprising the amino acid sequence of SEQ ID NO: 93, an LC-CDR2 comprising the amino acid sequence of SEQ ID NO: 103, and an LC-CDR3 comprising the amino acid sequence of SEQ ID NO: 113.

In some embodiments, the anti-AMC antibody moiety comprises a heavy chain variable domain comprising an HC-CDR1 comprising the amino acid sequence of SEQ ID NO: 61, or a variant thereof comprising up to about 5 (for example about any of 1, 2, 3, 4, or 5) amino acid substitutions; an HC-CDR2 comprising the amino acid sequence of SEQ ID NO: 71, or a variant thereof comprising up to about 5 (for example about any of 1, 2, 3, 4, or 5) amino acid substitutions; and an HC-CDR3 comprising the amino acid sequence of SEQ ID NO: 81, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 94, or a variant thereof comprising up to about 5 (for example about any of 1, 2, 3, 4, or 5) amino acid substitutions; an LC-CDR2 comprising the amino acid sequence of SEQ ID NO: 104, or a variant thereof comprising up to about 3 (for example about any of 1, 2, or 3) amino acid substitutions; and an LC-CDR3 comprising the amino acid sequence of SEQ ID NO: 114, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 61, an HC-CDR2 comprising the amino acid sequence of SEQ ID NO: 71, and an HC-CDR3 comprising the amino acid sequence of SEQ ID NO: 81, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 94, an LC-CDR2 comprising the amino acid sequence of SEQ ID NO: 104, and an LC-CDR3 comprising the amino acid sequence of SEQ ID NO: 114, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 61, an HC-CDR2 comprising the amino acid sequence of SEQ ID NO: 71, and an HC-CDR3 comprising the amino acid sequence of SEQ ID NO: 81; and a light chain variable domain comprising an LC-CDR1 comprising the amino acid sequence of SEQ ID NO: 94, an LC-CDR2 comprising the amino acid sequence of SEQ ID NO: 104, and an LC-CDR3 comprising the amino acid sequence of SEQ ID NO: 114.

In some embodiments, the anti-AMC antibody moiety comprises a heavy chain variable domain comprising an HC-CDR1 comprising the amino acid sequence of SEQ ID NO: 62, or a variant thereof comprising up to about 5 (for example about any of 1, 2, 3, 4, or 5) amino acid substitutions; an HC-CDR2 comprising the amino acid sequence of SEQ ID NO: 72, or a variant thereof comprising up to about 5 (for example about any of 1, 2, 3, 4, or 5) amino acid substitutions; and an HC-CDR3 comprising the amino acid sequence of SEQ ID NO: 82, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 95, or a variant thereof comprising up to about 5 (for example about any of 1, 2, 3, 4, or 5) amino acid substitutions; an LC-CDR2 comprising the amino acid sequence of SEQ ID NO: 105, or a variant thereof comprising up to about 3 (for example about any of 1, 2, or 3) amino acid substitutions; and an LC-CDR3 comprising the amino acid sequence of SEQ ID NO: 115, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 62, an HC-CDR2 comprising the amino acid sequence of SEQ ID NO: 72, and an HC-CDR3 comprising the amino acid sequence of SEQ ID NO: 82, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 95, an LC-CDR2 comprising the amino acid sequence of SEQ ID NO: 105, and an LC-CDR3 comprising the amino acid sequence of SEQ ID NO: 115, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 62, an HC-CDR2 comprising the amino acid sequence of SEQ ID NO: 72, and an HC-CDR3 comprising the amino acid sequence of SEQ ID NO: 82; and a light chain variable domain comprising an LC-CDR1 comprising the amino acid sequence of SEQ ID NO: 95, an LC-CDR2 comprising the amino acid sequence of SEQ ID NO: 105, and an LC-CDR3 comprising the amino acid sequence of SEQ ID NO: 115.

In some embodiments, the anti-AMC antibody moiety comprises a heavy chain variable domain comprising an HC-CDR1 comprising the amino acid sequence of SEQ ID NO: 63, or a variant thereof comprising up to about 5 (for example about any of 1, 2, 3, 4, or 5) amino acid substitutions; an HC-CDR2 comprising the amino acid sequence of SEQ ID NO: 73, or a variant thereof comprising up to about 5 (for example about any of 1, 2, 3, 4, or 5) amino acid substitutions; and an HC-CDR3 comprising the amino acid sequence of SEQ ID NO: 83, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 96, or a variant thereof comprising up to about 5 (for example about any of 1, 2, 3, 4, or 5) amino acid substitutions; an LC-CDR2 comprising the amino acid sequence of SEQ ID NO: 106, or a variant thereof comprising up to about 3 (for example about any of 1, 2, or 3) amino acid substitutions; and an LC-CDR3 comprising the amino acid sequence of SEQ ID NO: 116, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 63, an HC-CDR2 comprising the amino acid sequence of SEQ ID NO: 73, and an HC-CDR3 comprising the amino acid sequence of SEQ ID NO: 83, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 96, an LC-CDR2 comprising the amino acid sequence of SEQ ID NO: 106, and an LC-CDR3 comprising the amino acid sequence of SEQ ID NO: 116, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 63, an HC-CDR2 comprising the amino acid sequence of SEQ ID NO: 73, and an HC-CDR3 comprising the amino acid sequence of SEQ ID NO: 83; and a light chain variable domain comprising an LC-CDR1 comprising the amino acid sequence of SEQ ID NO: 96, an LC-CDR2 comprising the amino acid sequence of SEQ ID NO: 106, and an LC-CDR3 comprising the amino acid sequence of SEQ ID NO: 116.

In some embodiments, the anti-AMC antibody moiety comprises a heavy chain variable domain comprising an HC-CDR1 comprising the amino acid sequence of SEQ ID NO: 64, or a variant thereof comprising up to about 5 (for example about any of 1, 2, 3, 4, or 5) amino acid substitutions; an HC-CDR2 comprising the amino acid sequence of SEQ ID NO: 74, or a variant thereof comprising up to about 5 (for example about any of 1, 2, 3, 4, or 5) amino acid substitutions; and an HC-CDR3 comprising the amino acid sequence of SEQ ID NO: 84, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 97, or a variant thereof comprising up to about 5 (for example about any of 1, 2, 3, 4, or 5) amino acid substitutions; an LC-CDR2 comprising the amino acid sequence of SEQ ID NO: 107, or a variant thereof comprising up to about 3 (for example about any of 1, 2, or 3) amino acid substitutions; and an LC-CDR3 comprising the amino acid sequence of SEQ ID NO: 117, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 64, an HC-CDR2 comprising the amino acid sequence of SEQ ID NO: 74, and an HC-CDR3 comprising the amino acid sequence of SEQ ID NO: 84, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 97, an LC-CDR2 comprising the amino acid sequence of SEQ ID NO: 107, and an LC-CDR3 comprising the amino acid sequence of SEQ ID NO: 117, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 64, an HC-CDR2 comprising the amino acid sequence of SEQ ID NO: 74, and an HC-CDR3 comprising the amino acid sequence of SEQ ID NO: 84; and a light chain variable domain comprising an LC-CDR1 comprising the amino acid sequence of SEQ ID NO: 97, an LC-CDR2 comprising the amino acid sequence of SEQ ID NO: 107, and an LC-CDR3 comprising the amino acid sequence of SEQ ID NO: 117.

In some embodiments, the anti-AMC antibody moiety comprises a heavy chain variable domain comprising an HC-CDR1 comprising the amino acid sequence of SEQ ID NO: 65, or a variant thereof comprising up to about 5 (for example about any of 1, 2, 3, 4, or 5) amino acid substitutions; an HC-CDR2 comprising the amino acid sequence of SEQ ID NO: 75, or a variant thereof comprising up to about 5 (for example about any of 1, 2, 3, 4, or 5) amino acid substitutions; and an HC-CDR3 comprising the amino acid sequence of SEQ ID NO: 85, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 98, or a variant thereof comprising up to about 5 (for example about any of 1, 2, 3, 4, or 5) amino acid substitutions; an LC-CDR2 comprising the amino acid sequence of SEQ ID NO: 108, or a variant thereof comprising up to about 3 (for example about any of 1, 2, or 3) amino acid substitutions; and an LC-CDR3 comprising the amino acid sequence of SEQ ID NO: 118, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 65, an HC-CDR2 comprising the amino acid sequence of SEQ ID NO: 75, and an HC-CDR3 comprising the amino acid sequence of SEQ ID NO: 85, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 98, an LC-CDR2 comprising the amino acid sequence of SEQ ID NO: 108, and an LC-CDR3 comprising the amino acid sequence of SEQ ID NO: 118, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 65, an HC-CDR2 comprising the amino acid sequence of SEQ ID NO: 75, and an HC-CDR3 comprising the amino acid sequence of SEQ ID NO: 85; and a light chain variable domain comprising an LC-CDR1 comprising the amino acid sequence of SEQ ID NO: 98, an LC-CDR2 comprising the amino acid sequence of SEQ ID NO: 108, and an LC-CDR3 comprising the amino acid sequence of SEQ ID NO: 118.

In some embodiments, the anti-AMC antibody moiety comprises a heavy chain variable domain comprising an HC-CDR1 comprising the amino acid sequence of SEQ ID NO: 66, or a variant thereof comprising up to about 5 (for example about any of 1, 2, 3, 4, or 5) amino acid substitutions; an HC-CDR2 comprising the amino acid sequence of SEQ ID NO: 76, or a variant thereof comprising up to about 5 (for example about any of 1, 2, 3, 4, or 5) amino acid substitutions; and an HC-CDR3 comprising the amino acid sequence of SEQ ID NO: 86, or a variant thereof comprising up to about 5 (such as about any of 1, 2, 3, 4, or 5) amino acid substitutions; and a light chain variable domain comprising an LC-CDR1 comprising the amino acid sequence of SEQ ID NO: 99, or a variant thereof comprising up to about 5 (for example about any of 1, 2, 3, 4, or 5) amino acid substitutions; an LC-CDR2 comprising the amino acid sequence of SEQ ID NO: 109, or a variant thereof comprising up to about 3 (for example about any of 1, 2, or 3) amino acid substitutions; and an LC-CDR3 comprising the amino acid sequence of SEQ ID NO: 119, or a variant thereof comprising up to about 5 (such as about any of 1, 2, 3, 4, or 5) amino acid substitutions.

In some embodiments, the anti-AMC antibody moiety comprises a heavy chain variable domain comprising an HC-CDR1 comprising the amino acid sequence of SEQ ID NO: 66, an HC-CDR2 comprising the amino acid sequence of SEQ ID NO: 76, and an HC-CDR3 comprising the amino acid sequence of SEQ ID NO: 86, or a variant thereof comprising up to about 5 (such as about any of 1, 2, 3, 4, or 5) amino acid substitutions in the HC-CDR sequences; and a light chain variable domain comprising an LC-CDR1 comprising the amino acid sequence of SEQ ID NO: 99, an LC-CDR2 comprising the amino acid sequence of SEQ ID NO: 109, and an LC-CDR3 comprising the amino acid sequence of SEQ ID NO: 119, or a variant thereof comprising up to about 5 (such as about any of 1, 2, 3, 4, or 5) amino acid substitutions in the LC-CDR sequences.

In some embodiments, the anti-AMC antibody moiety comprises a heavy chain variable domain comprising an HC-CDR1 comprising the amino acid sequence of SEQ ID NO: 66, an HC-CDR2 comprising the amino acid sequence of SEQ ID NO: 76, and an HC-CDR3 comprising the amino acid sequence of SEQ ID NO: 86; and a light chain variable domain comprising an LC-CDR1 comprising the amino acid sequence of SEQ ID NO: 99, an LC-CDR2 comprising the amino acid sequence of SEQ ID NO: 109, and an LC-CDR3 comprising the amino acid sequence of SEQ ID NO: 119.

In some embodiments, the anti-AMC antibody moiety comprises a heavy chain variable domain comprising the amino acid sequence set forth in SEQ ID NO: 17, or a variant thereof having at least about 95% (for example at least about any of 96%, 97%, 98%, or 99%) sequence identity, and a light chain variable domain comprising the amino acid sequence set forth in SEQ ID NO: 27, or a variant thereof having at least about 95% (including for example at least about any of 96%, 97%, 98%, or 99%) sequence identity. In some embodiments, the anti-AMC antibody moiety comprises a heavy chain variable domain comprising the amino acid sequence set forth in SEQ ID NO: 17 and a light chain variable domain comprising the amino acid sequence set forth in SEQ ID NO: 27.

In some embodiments, the anti-AMC antibody moiety comprises a heavy chain variable domain comprising the amino acid sequence set forth in SEQ ID NO: 18, or a variant thereof having at least about 95% (including for example at least about any of 96%, 97%, 98%, or 99%) sequence identity, and a light chain variable domain comprising the amino acid sequence set forth in SEQ ID NO: 28, or a variant thereof having at least about 95% (including for example at least about any of 96%, 97%, 98%, or 99%) sequence identity. In some embodiments, the anti-AMC antibody moiety comprises a heavy chain variable domain comprising the amino acid sequence set forth in SEQ ID NO: 18 and a light chain variable domain comprising the amino acid sequence set forth in SEQ ID NO: 28.

In some embodiments, the anti-AMC antibody moiety comprises a heavy chain variable domain comprising the amino acid sequence set forth in SEQ ID NO: 19, or a variant thereof having at least about 95% (for example at least about any of 96%, 97%, 98%, or 99%) sequence identity, and a light chain variable domain comprising the amino acid sequence set forth in SEQ ID NO: 29, or a variant thereof having at least about 95% (including for example at least about any of 96%, 97%, 98%, or 99%) sequence identity. In some embodiments, the anti-AMC antibody moiety comprises a heavy chain variable domain comprising the amino acid sequence set forth in SEQ ID NO: 19 and a light chain variable domain comprising the amino acid sequence set forth in SEQ ID NO: 29.

In some embodiments, the anti-AMC antibody moiety comprises a heavy chain variable domain comprising the amino acid sequence set forth in SEQ ID NO: 20, or a variant thereof having at least about 95% (for example at least about any of 96%, 97%, 98%, or 99%) sequence identity, and a light chain variable domain comprising the amino acid sequence set forth in SEQ ID NO: 30, or a variant thereof having at least about 95% (including for example at least about any of 96%, 97%, 98%, or 99%) sequence identity. In some embodiments, the anti-AMC antibody moiety comprises a heavy chain variable domain comprising the amino acid sequence set forth in SEQ ID NO: 20 and a light chain variable domain comprising the amino acid sequence set forth in SEQ ID NO: 30.

In some embodiments, the anti-AMC antibody moiety comprises a heavy chain variable domain comprising the amino acid sequence set forth in SEQ ID NO: 21, or a variant thereof having at least about 95% (for example at least about any of 96%, 97%, 98%, or 99%) sequence identity, and a light chain variable domain comprising the amino acid sequence set forth in SEQ ID NO: 31, or a variant thereof having at least about 95% (including for example at least about any of 96%, 97%, 98%, or 99%) sequence identity. In some embodiments, the anti-AMC antibody moiety comprises a heavy chain variable domain comprising the amino acid sequence set forth in SEQ ID NO: 21 and a light chain variable domain comprising the amino acid sequence set forth in SEQ ID NO: 31.

In some embodiments, the anti-AMC antibody moiety comprises a heavy chain variable domain comprising the amino acid sequence set forth in SEQ ID NO: 22, or a variant thereof having at least about 95% (for example at least about any of 96%, 97%, 98%, or 99%) sequence identity, and a light chain variable domain comprising the amino acid sequence set forth in SEQ ID NO: 32, or a variant thereof having at least about 95% (including for example at least about any of 96%, 97%, 98%, or 99%)

sequence identity. In some embodiments, the anti-AMC antibody moiety comprises a heavy chain variable domain comprising the amino acid sequence set forth in SEQ ID NO: 22 and a light chain variable domain comprising the amino acid sequence set forth in SEQ ID NO: 32.

In some embodiments, the anti-AMC antibody moiety comprises a heavy chain variable domain comprising the amino acid sequence set forth in SEQ ID NO: 23, or a variant thereof having at least about 95% (for example at least about any of 96%, 97%, 98%, or 99%) sequence identity, and a light chain variable domain comprising the amino acid sequence set forth in SEQ ID NO: 33, or a variant thereof having at least about 95% (including for example at least about any of 96%, 97%, 98%, or 99%) sequence identity. In some embodiments, the anti-AMC antibody moiety comprises a heavy chain variable domain comprising the amino acid sequence set forth in SEQ ID NO: 23 and a light chain variable domain comprising the amino acid sequence set forth in SEQ ID NO: 33.

In some embodiments, the anti-AMC antibody moiety comprises a heavy chain variable domain comprising the amino acid sequence set forth in SEQ ID NO: 24, or a variant thereof having at least about 95% (including for example at least about any of 96%, 97%, 98%, or 99%) sequence identity, and a light chain variable domain comprising the amino acid sequence set forth in SEQ ID NO: 34, or a variant thereof having at least about 95% (including for example at least about any of 96%, 97%, 98%, or 99%) sequence identity. In some embodiments, the anti-AMC antibody moiety comprises a heavy chain variable domain comprising the amino acid sequence set forth in SEQ ID NO: 24 and a light chain variable domain comprising the amino acid sequence set forth in SEQ ID NO: 34.

In some embodiments, the anti-AMC antibody moiety comprises a heavy chain variable domain comprising the amino acid sequence set forth in SEQ ID NO: 25, or a variant thereof having at least about 95% (for example at least about any of 96%, 97%, 98%, or 99%) sequence identity, and a light chain variable domain comprising the amino acid sequence set forth in SEQ ID NO: 35, or a variant thereof having at least about 95% (including for example at least about any of 96%, 97%, 98%, or 99%) sequence identity. In some embodiments, the anti-AMC antibody moiety comprises a heavy chain variable domain comprising the amino acid sequence set forth in SEQ ID NO: 25 and a light chain variable domain comprising the amino acid sequence set forth in SEQ ID NO: 35.

In some embodiments, the anti-AMC antibody moiety comprises a heavy chain variable domain comprising the amino acid sequence set forth in SEQ ID NO: 26, or a variant thereof having at least about 95% (including for example at least about any of 96%, 97%, 98%, or 99%) sequence identity, and a light chain variable domain comprising the amino acid sequence set forth in SEQ ID NO: 36, or a variant thereof having at least about 95% sequence identity. In some embodiments, the anti-AMC antibody moiety comprises a heavy chain variable domain comprising the amino acid sequence set forth in SEQ ID NO: 26 and a light chain variable domain comprising the amino acid sequence set forth in SEQ ID NO: 36.

In some embodiments, the anti-AMC antibody moiety competes for binding to a target AFP/MHC class I complex with a second anti-AMC antibody moiety according to any of the anti-AMC antibody moieties described herein. In some embodiments, the anti-AMC antibody moiety binds to the same, or substantially the same, epitope as the second anti-AMC antibody moiety. In some embodiments, binding of the anti-AMC antibody moiety to the target AFP/MHC class I complex inhibits binding of the second anti-AMC antibody moiety to the target AFP/MHC class I complex by at least about 70% (such as by at least about any of 75%, 80%, 85%, 90%, 95%, 98% or 99%), or vice versa. In some embodiments, the anti-AMC antibody moiety and the second anti-AMC antibody moiety cross-compete for binding to the target AFP/MHC class I complex, i.e., each of the antibody moieties competes with the other for binding to the target AFP/MHC class I complex.

Full-Length Anti-AMC Antibodies

The anti-AMC constructs in some embodiments are full-length antibodies comprising an anti-AMC antibody moiety (also referred to herein as a "full-length anti-AMC antibody"). In some embodiments, the full-length antibody is a monoclonal antibody.

In some embodiments, the full-length anti-AMC antibody comprises an Fc sequence from an immunoglobulin, such as IgA, IgD, IgE, IgG, and IgM. In some embodiments, the full-length anti-AMC antibody comprises an Fc sequence of IgG, such as any of IgG1, IgG2, IgG3, or IgG4. In some embodiments, the full-length anti-AMC antibody comprises an Fc sequence of a human immunoglobulin. In some embodiments, the full-length anti-AMC antibody comprises an Fc sequence of a mouse immunoglobulin. In some embodiments, the full-length anti-AMC antibody comprises an Fc sequence that has been altered or otherwise changed so that it has enhanced antibody dependent cellular cytotoxicity (ADCC) or complement dependent cytotoxicity (CDC) effector function.

Thus, for example, in some embodiments, there is provided a full-length anti-AMC antibody comprising a) an anti-AMC antibody moiety that specifically binds to a complex comprising an AFP peptide and an MHC class I protein, and b) an Fc region. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, there is provided a full-length anti-AMC antibody comprising a) an anti-AMC antibody moiety that specifically binds to a complex comprising an AFP158 peptide (SEQ ID NO: 4) and HLA-A*02:01, and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-AMC antibody comprising a) an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89); or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-AMC antibody comprising a) an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-AMC antibody comprising a) an anti-AMC antibody moiety that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-AMC antibody comprising a) an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences; and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-AMC antibody comprising a) an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-AMC antibody comprising a) an anti-AMC antibody moiety that specifically binds to a complex comprising an AFP peptide and an MHC class I protein comprising a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% sequence identity; and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-AMC antibody comprising a) an anti-AMC antibody moiety that specifically binds to a complex comprising an AFP peptide and an MHC class I protein comprising a heavy chain variable domain comprising the amino acid sequence of any one of SEQ ID NOs: 17-26 and a light chain variable domain comprising the amino acid sequence of any one of SEQ ID NOs: 27-36; and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, the full-length anti-AMC antibody binds to a complex comprising an AFP peptide and an MHC class I protein with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the full-length anti-AMC antibody binds to a complex comprising an AFP peptide and an MHC class I protein with a $K_d$ between about 1 pM to about 250 pM (such as about any of 1, 10, 25, 50, 75, 100, 150, 200, or 250 pM, including any ranges between these values).

Multi-Specific Anti-AMC Molecules

The anti-AMC constructs in some embodiments comprise a multi-specific anti-AMC molecule comprising an anti-AMC antibody moiety and a second binding moiety (such as a second antigen-binding moiety). In some embodiments, the multi-specific anti-AMC molecule comprises an anti-AMC antibody moiety and a second antigen-binding moiety.

Multi-specific molecules are molecules that have binding specificities for at least two different antigens or epitopes (e.g., bispecific antibodies have binding specificities for two antigens or epitopes). Multi-specific molecules with more than two valencies and/or specificities are also contemplated. For example, trispecific antibodies can be prepared. Tutt et al. *J. Immunol.* 147: 60 (1991). It is to be appreciated that one of skill in the art could select appropriate features of individual multi-specific molecules described herein to combine with one another to form a multi-specific anti-AMC molecule of the invention.

Thus, for example, in some embodiments, there is provided a multi-specific (e.g., bispecific) anti-AMC molecule comprising a) an anti-AMC antibody moiety that specifically binds to a complex comprising an AFP peptide and an MHC class I protein, and b) a second binding moiety (such as an antigen-binding moiety). In some embodiments, the second binding moiety specifically binds to a complex comprising a different AFP peptide bound to the MHC class I protein. In some embodiments, the second scFv specifically binds to a complex comprising the AFP peptide bound to a different MHC class I protein. In some embodiments, the second binding moiety specifically binds to a different epitope on the complex comprising the AFP peptide bound to the MHC class I protein. In some embodiments, the second binding moiety specifically binds to a different antigen. In some embodiments, the second binding moiety specifically binds to an antigen on the surface of a cell, such as a cytotoxic cell. In some embodiments, the second binding moiety specifically binds to an antigen on the surface of a lymphocyte, such as a T cell, an NK cell, a neutrophil, a monocyte, a macrophage, or a dendritic cell. In some embodiments, the second binding moiety specifically binds to an effector T cell, such as a cytotoxic T cell (also known as cytotoxic T lymphocyte (CTL) or T killer cell).

In some embodiments, there is provided a multi-specific anti-AMC molecule comprising a) an anti-AMC antibody moiety that specifically binds to a complex comprising an AFP peptide and an MHC class I protein, and b) a second antigen-binding moiety that binds specifically to CD3. In some embodiments, the second antigen-binding moiety specifically binds to CD3ε. In some embodiments, the second antigen-binding moiety specifically binds to an agonistic epitope of CD3ε. The term "agonistic epitope", as used herein, means (a) an epitope that, upon binding of the multi-specific molecule, optionally upon binding of several multi-specific molecules on the same cell, allows said multi-specific molecules to activate TCR signaling and induce T cell activation, and/or (b) an epitope that is solely composed of amino acid residues of the epsilon chain of CD3 and is accessible for binding by the multi-specific molecule, when presented in its natural context on T cells (i.e. surrounded by the TCR, the CD3γ chain, etc.), and/or (c) an epitope that, upon binding of the multi-specific molecule, does not lead to stabilization of the spatial position of CD3ε relative to CD3γ.

In some embodiments, there is provided a multi-specific anti-AMC molecule comprising a) an anti-AMC antibody moiety that specifically binds to a complex comprising an AFP peptide and an MHC class I protein, and b) a second antigen-binding moiety that binds specifically to an antigen on the surface of an effector cell, including for example CD3γ, CD3δ, CD3ε, CD3ζ, CD28, CD16a, CD56, CD68, and GDS2D.

In some embodiments, there is provided a multi-specific anti-AMC molecule comprising a) an anti-AMC antibody moiety that specifically binds to a complex comprising an AFP peptide and an MHC class I protein, and b) a second antigen-binding moiety that binds specifically to a component of the complement system, such as C1q. C1q is a subunit of the C1 enzyme complex that activates the serum complement system.

In some embodiments, the second antigen-binding moiety specifically binds to an Fc receptor. In some embodiments, the second antigen-binding moiety specifically binds to an Fcγ receptor (FcγR). The FcγR may be an FcγRIII present on the surface of natural killer (NK) cells or one of FcγRI, FcγRIIA, FcγRIIBI, FcγRIIB2, and FcγRIIIB present on the surface of macrophages, monocytes, neutrophils and/or dendritic cells. In some embodiments, the second antigen-binding moiety is an Fc region or functional fragment thereof. A "functional fragment" as used in this context refers to a fragment of an antibody Fc region that is still capable of binding to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis. A functional Fc fragment is capable of competitively inhibiting the binding of the original, full-length Fc portion to an FcR such as the activating FcγRI. In some embodiments, a functional Fc fragment retains at least 30%, 40%, 50%, 60%, 70%, 80%, 90% or 95% of its affinity to an activating FcγR. In some embodiments, the Fc region or functional fragment thereof is an enhanced Fc region or functional fragment thereof. The term "enhanced Fc region", as used herein, refers to an Fc region that is modified to enhance Fc receptor-mediated effector-functions, in particular antibody-dependent cell-mediated cytotoxicity (ADCC), complement-dependent cytotoxicity (CDC), and antibody-mediated phagocytosis. This can be achieved as known in the art, for example by altering the Fc region in a way that leads to an increased affinity for an activating receptor (e.g. FcγRIIIA (CD16A) expressed on natural killer (NK) cells) and/or a decreased binding to an inhibitory receptor (e.g. FcγRIIB1/B2 (CD32B)). In yet other embodiments, the second antigen-binding moiety is an antibody or antigen-binding fragment thereof that specifically binds to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis.

In some embodiments, the multi-specific anti-AMC molecule allows killing of AMC-presenting target cells and/or can effectively redirect CTLs to lyse AMC-presenting target cells. In some embodiments, the multi-specific (e.g., bispecific) anti-AMC molecule of the present invention shows an in vitro $EC_{50}$ ranging from 10 to 500 ng/ml, and is able to induce redirected lysis of about 50% of the target cells through CTLs at a ratio of CTLs to target cells of from about 1:1 to about 50:1 (such as from about 1:1 to about 15:1, or from about 2:1 to about 10:1).

In some embodiments, the multi-specific (e.g., bispecific) anti-AMC molecule is capable of cross-linking a stimulated or unstimulated CTL and the target cell in such a way that the target cell is lysed. This offers the advantage that no generation of target-specific T cell clones or common antigen presentation by dendritic cells is required for the multi-specific anti-AMC molecule to exert its desired activity. In some embodiments, the multi-specific anti-AMC molecule of the present invention is capable of redirecting CTLs to lyse the target cells in the absence of other activating signals. In some embodiments, the second antigen-binding moiety of the multi-specific anti-AMC molecule specifically binds to CD3 (e.g., specifically binds to CD3ε), and signaling through CD28 and/or IL-2 is not required for redirecting CTLs to lyse the target cells.

Methods for measuring the preference of the multi-specific anti-AMC molecule to simultaneously bind to two antigens (e.g., antigens on two different cells) are within the normal capabilities of a person skilled in the art. For example, when the second binding moiety specifically binds to CD3 the multi-specific anti-AMC molecule may be contacted with a mixture of CD3+/AFP− cells and CD3−/AFP+ cells. The number of multi-specific anti-AMC molecule-positive single cells and the number of cells cross-linked by multi-specific anti-AMC molecules may then be assessed by microscopy or fluorescence-activated cell sorting (FACS) as known in the art.

For example, in some embodiments, there is provided a multi-specific anti-AMC molecule comprising a) an anti-AMC antibody moiety that specifically binds to a complex comprising an AFP peptide and an MHC class I protein, and b) a second antigen-binding moiety. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the second antigen-binding moiety specifically binds to a complex comprising a different AFP peptide bound to the MHC class I protein. In some embodiments, the second antigen-binding moiety specifically binds to a complex comprising the AFP peptide bound to a different MHC class I protein. In some embodiments, the second antigen-binding moiety specifically binds to a different epitope on the complex comprising the AFP peptide bound to the MHC class I protein. In some embodiments, the second antigen-binding moiety specifically binds to another antigen. In some embodiments, the second antigen-binding moiety specifically binds to an antigen on the surface of a cell, such as an AMC-presenting cell. In some embodiments, the second antigen-binding moiety specifically binds to an antigen on the surface of a cell that does not express AFP. In some embodiments, the second antigen-binding moiety specifically binds to an antigen on the surface of a cytotoxic cell. In some embodiments, the second antigen-binding moiety specifically binds to an antigen on the surface of a lymphocyte, such as a T cell, an NK cell, a neutrophil, a monocyte, a macrophage, or a dendritic cell. In some embodiments, the second antigen-binding moiety specifically binds to an antigen on the surface of an effector T cell, such as a cytotoxic T cell. In some embodiments, the second antigen-binding moiety specifically binds to an antigen on the surface of an effector cell, including for example CD3γ, CD3δ, CD3ε, CD3ζ, CD28, CD16a, CD56, CD68, and GDS2D. In some embodiments, the anti-AMC antibody moiety is human, humanized, or semi-synthetic. In some embodiments, the second antigen-binding moiety is an antibody moiety. In some embodiments, the second antigen-binding moiety is a human, humanized, or semi-synthetic antibody moiety. In some embodiments, the multi-specific anti-AMC molecule further comprises at least one (such as at least about any of 2, 3, 4, 5, or more) additional antigen-binding moieties.

In some embodiments, there is provided a multi-specific anti-AMC molecule comprising a) an anti-AMC antibody moiety that specifically binds to a complex comprising an AFP158 peptide (SEQ ID NO: 4) and HLA-A*02:01, and b) a second antigen-binding moiety.

In some embodiments, there is provided a multi-specific anti-AMC molecule comprising a) an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, and b) a second antigen-binding moiety.

In some embodiments, there is provided a multi-specific anti-AMC molecule comprising a) an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, and b) a second antigen-binding moiety.

In some embodiments, there is provided a multi-specific anti-AMC molecule comprising a) an anti-AMC antibody moiety that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions; and b) a second antigen-binding moiety.

In some embodiments, there is provided a multi-specific anti-AMC molecule comprising a) an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences; and b) a second antigen-binding moiety.

In some embodiments, there is provided a multi-specific anti-AMC molecule comprising a) an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; and b) a second antigen-binding moiety.

In some embodiments, there is provided a multi-specific anti-AMC molecule comprising a) an anti-AMC antibody moiety comprising a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% sequence identity; and b) a second scFv.

In some embodiments, there is provided a multi-specific anti-AMC molecule comprising a) an anti-AMC antibody moiety comprising a heavy chain variable domain comprising the amino acid sequence of any one of SEQ ID NOs: 17-26 and a light chain variable domain comprising the amino acid sequence of any one of SEQ ID NOs: 27-36; and b) a second antigen-binding moiety.

In some embodiments, the multi-specific anti-AMC molecule is, for example, a diabody (Db), a single-chain diabody (scDb), a tandem scDb (Tandab), a linear dimeric scDb (LD-scDb), a circular dimeric scDb (CD-scDb), a di-diabody, a tandem scFv, a tandem di-scFv (e.g., a bispecific T cell engager), a tandem tri-scFv, a tri(a)body, a bispecific Fab2, a di-miniantibody, a tetrabody, an scFv-Fc-scFv fusion, a dual-affinity retargeting (DART) antibody, a dual variable domain (DVD) antibody, an IgG-scFab, an scFab-ds-scFv, an Fv2-Fc, an IgG-scFv fusion, a dock and lock (DNL) antibody, a knob-into-hole (KiH) antibody (bispecific IgG prepared by the KiH technology), a DuoBody (bispecific IgG prepared by the Duobody technology), a heteromultimeric antibody, or a heteroconjugate antibody. In some embodiments, the multi-specific anti-AMC molecule is a tandem scFv (e.g., a tandem di-scFv, such as a bispecific T cell engager).

Tandem scFv

The multi-specific anti-AMC molecule in some embodiments is a tandem scFv comprising a first scFv comprising an anti-AMC antibody moiety and a second scFv (also referred to herein as a "tandem scFv multi-specific anti-AMC antibody"). In some embodiments, the tandem scFv multi-specific anti-AMC antibody further comprises at least one (such as at least about any of 2, 3, 4, 5, or more) additional scFv.

In some embodiments, there is provided a tandem scFv multi-specific (e.g., bispecific) anti-AMC antibody comprising a) a first scFv that specifically binds to a complex comprising an AFP peptide and an MHC class I protein, and b) a second scFv. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the second scFv specifically binds to a complex comprising a different AFP peptide bound to the MHC class I protein. In some embodiments, the second scFv specifically binds to a complex comprising the AFP peptide bound to a different MHC class I protein. In some embodiments, the second scFv specifically binds to a different epitope on the complex comprising the AFP peptide bound to the MHC class I protein. In some embodiments, the second scFv specifically binds to another antigen. In some embodiments, the second scFv specifically binds to an antigen on the surface of a cell, such as an AMC-presenting cell. In some embodiments, the second scFv specifically binds to an antigen on the surface of a cell that does not express AFP. In some embodiments, the second scFv specifically binds to an antigen on the surface of a cytotoxic cell. In some embodiments, the second scFv specifically binds to an antigen on the surface of a lymphocyte, such as a T cell, an NK cell, a neutrophil, a monocyte, a macrophage, or a dendritic cell. In some embodiments, the second scFv specifically binds to an antigen on the surface of an effector T cell, such as a cytotoxic T cell. In some embodiments, the second scFv specifically binds to an antigen on the surface of an effector cell, including for example CD3γ, CD3δ, CD3ε, CD3ζ, CD28, CD16a, CD56, CD68, and GDS2D. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic. In some embodiments, the tandem scFv multi-specific anti-AMC antibody further comprises at least one (such as at least about any of 2, 3, 4, 5, or more) additional scFv.

In some embodiments, there is provided a tandem scFv multi-specific (e.g., bispecific) anti-AMC antibody comprising a) a first scFv that specifically binds to a complex comprising an AFP158 peptide (SEQ ID NO: 4) and HLA-A*02:01, and b) a second scFv.

In some embodiments, there is provided a tandem scFv multi-specific (e.g., bispecific) anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, and b) a second scFv.

In some embodiments, there is provided a tandem scFv multi-specific (e.g., bispecific) anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, and b) a second scFv.

In some embodiments, there is provided a tandem scFv multi-specific (e.g., bispecific) anti-AMC antibody comprising a) a first scFv that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions; and b) a second scFv.

In some embodiments, there is provided a tandem scFv multi-specific (e.g., bispecific) anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences; and b) a second scFv.

In some embodiments, there is provided a tandem scFv multi-specific (e.g., bispecific) anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; and b) a second scFv.

In some embodiments, there is provided a tandem scFv multi-specific (e.g., bispecific) anti-AMC antibody comprising a) a first scFv comprising a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% sequence identity; and b) a second scFv.

In some embodiments, there is provided a tandem scFv multi-specific (e.g., bispecific) anti-AMC antibody comprising a) a first scFv comprising a heavy chain variable domain comprising the amino acid sequence of any one of SEQ ID NOs: 17-26 and a light chain variable domain comprising the amino acid sequence of any one of SEQ ID NOs: 27-36; and b) a second scFv.

In some embodiments, there is provided a tandem scFv multi-specific (e.g., bispecific) anti-AMC antibody comprising a) a first scFv that specifically binds to a complex comprising an AFP peptide and an MHC class I protein, and b) a second scFv, wherein the tandem scFv multi-specific anti-AMC antibody is a tandem di-scFv or a tandem tri-scFv. In some embodiments, the tandem scFv multi-specific anti-AMC antibody is a tandem di-scFv. In some embodiments, the tandem scFv multi-specific anti-AMC antibody is a bispecific T-cell engager.

For example, in some embodiments, there is provided a tandem di-scFv bispecific anti-AMC antibody comprising a) a first scFv that specifically binds to a complex comprising an AFP peptide and an MHC class I protein, and b) a second scFv that specifically binds to an antigen on the surface of a T cell. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the second scFv specifically binds to an antigen on the surface of an effector T cell, such as a cytotoxic T cell. In some embodiments, the second scFv specifically binds to an antigen selected, for example, from the group consisting of CD3γ, CD3δ, CD3ε, CD3ζ, CD28, OX40, GITR, CD137, CD27, CD40L, and HVEM. In some embodiments, the second scFv specifically binds to an agonistic epitope on an antigen on the surface of a T cell, wherein the binding of the second scFv to the antigen enhances T cell activation. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv that specifically binds to a complex comprising an AFP158 peptide (SEQ ID NO: 4) and HLA-A*02:01, and b) a second scFv that specifically binds to an antigen on the surface of a T cell.

In some embodiments, there is provided a tandem di-scFv bispecific anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, and b) a second scFv that specifically binds to an antigen on the surface of a T cell.

In some embodiments, there is provided a tandem di-scFv bispecific anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, and b) a second scFv that specifically binds to an antigen on the surface of a T cell.

In some embodiments, there is provided a tandem di-scFv bispecific anti-AMC antibody comprising a) a first scFv that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions; and b) a second scFv that specifically binds to an antigen on the surface of a T cell.

In some embodiments, there is provided a tandem di-scFv bispecific anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences, and b) a second scFv that specifically binds to an antigen on the surface of a T cell.

In some embodiments, there is provided a tandem di-scFv bispecific anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of any one of SEQ ID NOs:

57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; and b) a second scFv that specifically binds to an antigen on the surface of a T cell.

In some embodiments, there is provided a tandem di-scFv bispecific anti-AMC antibody comprising a) a first scFv comprising a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% (for example at least about any of 96%, 97%, 98%, or 99%) sequence identity, and b) a second scFv that specifically binds to an antigen on the surface of a T cell.

In some embodiments, there is provided a tandem di-scFv bispecific anti-AMC antibody comprising a) a first scFv comprising a heavy chain variable domain comprising the amino acid sequence of any one of SEQ ID NOs: 17-26 and a light chain variable domain comprising the amino acid sequence of any one of SEQ ID NOs: 27-36, and b) a second scFv that specifically binds to an antigen on the surface of a T cell.

In some embodiments, there is provided a tandem di-scFv bispecific anti-AMC antibody comprising a) a first scFv that specifically binds to a complex comprising an AFP peptide and an MHC class I protein, and b) a second scFv that specifically binds to CD3ε. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence GGGGS. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv that specifically binds to a complex comprising an AFP158 peptide (SEQ ID NO: 4) and HLA-A*02:01, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence GGGGS. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence GGGGS. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence GGGGS. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence GGGGS. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence GGGGS.

In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence GGGGS. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv comprising a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% (for example at least about any of 96%, 97%, 98%, or 99%) sequence identity, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence GGGGS. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-AMC antibody comprising a) a first scFv comprising a heavy chain variable domain comprising the amino acid sequence of any one of SEQ ID NOs: 17-26 and a light chain variable domain comprising the amino acid sequence of any one of SEQ ID NOs: 27-36, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values)

amino acids in length. In some embodiments, the peptide linker comprises (and in some embodiments consists of) the amino acid sequence GGGGS. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, the tandem di-scFv bispecific anti-AMC antibody binds to a complex comprising an AFP peptide and an MHC class I protein with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the tandem di-scFv bispecific anti-AMC antibody binds to a complex comprising an AFP peptide and an MHC class I protein with a $K_d$ between about 1 nM to about 500 nM (such as about any of 1, 10, 25, 50, 75, 100, 150, 200, 250, 300, 350, 400, 450, or 500 nM, including any ranges between these values).

Chimeric Antigen Receptor (CAR) and CAR Effector Cells

The anti-AMC construct in some embodiments is a chimeric antigen receptor (CAR) comprising an anti-AMC antibody moiety (also referred to herein as an "anti-AMC CAR"). Also provided is a CAR effector cell (e.g., T cell) comprising a CAR comprising an anti-AMC antibody moiety (also referred to herein as an "anti-AMC CAR effector cell", e.g., "anti-AMC CAR T cell").

The anti-AMC CAR comprises a) an extracellular domain comprising an anti-AMC antibody moiety that specifically binds to a complex comprising an AFP peptide and an MHC class I protein and b) an intracellular signaling domain. A transmembrane domain may be present between the extracellular domain and the intracellular domain.

Between the extracellular domain and the transmembrane domain of the anti-AMC CAR, or between the intracellular domain and the transmembrane domain of the anti-AMC CAR, there may be a spacer domain. The spacer domain can be any oligo- or polypeptide that functions to link the transmembrane domain to the extracellular domain or the intracellular domain in the polypeptide chain. A spacer domain may comprise up to about 300 amino acids, including for example about 10 to about 100, or about 25 to about 50 amino acids.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the α, β, δ, or γ chain of the T-cell receptor, CD28, CD3ε, CD3ζ, CD45, CD4, CD5, CD8, CD9, CD16, CD22, CD33, CD37, CD64, CD80, CD86, CD134, CD137, or CD154. In some embodiments, the transmembrane domain may be synthetic, in which case it may comprise predominantly hydrophobic residues such as leucine and valine. In some embodiments, a triplet of phenylalanine, tryptophan and valine may be found at each end of a synthetic transmembrane domain. In some embodiments, a short oligo- or polypeptide linker, having a length of, for example, between about 2 and about 10 (such as about any of 2, 3, 4, 5, 6, 7, 8, 9, or 10) amino acids in length may form the linkage between the transmembrane domain and the intracellular signaling domain of the anti-AMC CAR. In some embodiments, the linker is a glycine-serine doublet.

In some embodiments, the transmembrane domain that naturally is associated with one of the sequences in the intracellular domain of the anti-AMC CAR is used (e.g., if an anti-AMC CAR intracellular domain comprises a CD28 co-stimulatory sequence, the transmembrane domain of the anti-AMC CAR is derived from the CD28 transmembrane domain). In some embodiments, the transmembrane domain can be selected or modified by amino acid substitution to avoid binding of such domains to the transmembrane domains of the same or different surface membrane proteins to minimize interactions with other members of the receptor complex.

The intracellular signaling domain of the anti-AMC CAR is responsible for activation of at least one of the normal effector functions of the immune cell in which the anti-AMC CAR has been placed in. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term "intracellular signaling sequence" is thus meant to include any truncated portion of the intracellular signaling domain sufficient to transduce the effector function signal.

Examples of intracellular signaling domains for use in the anti-AMC CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of intracellular signaling sequence: those that initiate antigen-dependent primary activation through the TCR (primary signaling sequences) and those that act in an antigen-independent manner to provide a secondary or co-stimulatory signal (co-stimulatory signaling sequences).

Primary signaling sequences regulate primary activation of the TCR complex either in a stimulatory way, or in an inhibitory way. Primary signaling sequences that act in a stimulatory manner may contain signaling motifs which are known as immunoreceptor tyrosine-based activation motifs or ITAMs. The anti-AMC CAR constructs in some embodiments comprise one or more ITAMs.

Examples of ITAM containing primary signaling sequences that are of particular use in the invention include those derived from TCRζ, FcRγ, FcRβ, CD3γ, CD3δ, CD3ε, CD5, CD22, CD79a, CD79b, and CD66d.

In some embodiments, the anti-AMC CAR comprises a primary signaling sequence derived from CD3ζ. For example, the intracellular signaling domain of the CAR can comprise the CD3ζ intracellular signaling sequence by itself or combined with any other desired intracellular signaling sequence(s) useful in the context of the anti-AMC CAR of the invention. For example, the intracellular domain of the anti-AMC CAR can comprise a CD3ζ intracellular signaling sequence and a costimulatory signaling sequence. The costimulatory signaling sequence can be a portion of the intracellular domain of a costimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the intracellular signaling domain of the anti-AMC CAR comprises the intracellular signaling sequence of CD3ζ and the intracellular signaling sequence of CD28. In some embodiments, the intracellular signaling domain of the anti-AMC CAR comprises the intracellular signaling sequence of CD3ζ and the intracellular signaling sequence of 4-1BB. In some embodiments, the intracellular signaling domain of the anti-AMC CAR comprises the intracellular signaling sequence of CD3ζ and the intracellular signaling sequences of CD28 and 4-1BB.

Thus, for example, in some embodiments, there is provided an anti-AMC CAR comprising a) an extracellular domain comprising an anti-AMC antibody moiety that specifically binds to a complex comprising an AFP peptide and an MHC class I protein, b) a transmembrane domain, and c) an intracellular signaling domain. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP158 peptide (SEQ ID NO: 4) and HLA-A*02:01, b) a transmembrane domain, and c) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, b) a transmembrane domain, and c) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); b) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions; b) a transmembrane domain, and c) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences; b) a transmembrane domain, and c) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; b) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% sequence identity; b) a transmembrane domain, and c) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising a heavy chain variable domain comprising the amino acid sequence of any one of SEQ ID NOs: 17-26 and a light chain variable domain comprising the amino acid sequence of any one of SEQ ID NOs: 27-36; b) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein, b) a transmembrane domain, and c) an intracellular signaling domain comprising a CD3ζ intracellular signaling sequence and a CD28 intracellular signaling sequence. In some embodiments, the AFP peptide is AFP158 (SEQ ID NO: 4). In some embodiments, the MHC class I protein is HLA-A02. In some embodiments, the MHC class I protein is HLA-A*02:01.

In some embodiments, there is provided an anti-AMC CAR comprising a) an extracellular domain comprising an anti-AMC antibody moiety that specifically binds to a complex comprising an AFP158 peptide (SEQ ID NO: 4) and HLA-A*02:01, b) a transmembrane domain, and c) an intracellular signaling domain comprising a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, b) a transmembrane domain, and c) an intracellular signaling domain comprising a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, b) a transmembrane domain, and c) an intracellular signaling domain comprising a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions; b) a transmembrane domain, and c) an intracellular signaling domain comprising a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences; b) a transmembrane domain, and c) an intracellular signaling domain comprising a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; b) a transmembrane domain, and c) an intracellular signaling domain comprising a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising i) a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% sequence identity; b) a transmembrane domain, and c) an intracellular signaling domain comprising a CD3ζ intracellular signaling sequence and a CD28 intracellular signaling sequence.

In some embodiments, there is provided an anti-AMC CAR comprising a) an extracellular domain comprising an anti-AMC antibody moiety that specifically binds to a complex comprising an AFP peptide and an MHC class I protein comprising a heavy chain variable domain comprising the amino acid sequence of any one of SEQ ID NOs: 17-26 and a light chain variable domain comprising the amino acid sequence of any one of SEQ ID NOs: 27-36; b) a transmembrane domain, and c) an intracellular signaling domain comprising a CD3ζ intracellular signaling sequence and a CD28 intracellular signaling sequence.

Also provided herein are effector cells (such as lymphocytes, e.g., T cells) expressing an anti-AMC CAR.

Also provided is a method of producing an effector cell expressing an anti-AMC CAR, the method comprising introducing a vector comprising a nucleic acid encoding the anti-AMC CAR into the effector cell. In some embodiments, introducing the vector into the effector cell comprises transducing the effector cell with the vector. In some embodiments, introducing the vector into the effector cell comprises transfecting the effector cell with the vector. Transduction or transfection of the vector into the effector cell can be carried about using any method known in the art.

Immunoconjugates

The anti-AMC constructs in some embodiments comprise an immunoconjugate comprising an anti-AMC antibody moiety attached to an effector molecule (also referred to herein as an "anti-AMC immunoconjugate"). In some embodiments the effector molecule is a therapeutic agent, such as a cancer therapeutic agent, which is either cytotoxic, cytostatic or otherwise provides some therapeutic benefit. In some embodiments, the effector molecule is a label, which can generate a detectable signal, either directly or indirectly.

In some embodiments, there is provided an anti-AMC immunoconjugate comprising an anti-AMC antibody moiety and a therapeutic agent (also referred to herein as an "antibody-drug conjugate", or "ADC"). In some embodiments, the therapeutic agent is a toxin that is either cytotoxic, cytostatic or otherwise prevents or reduces the ability of the target cells to divide. The use of ADCs for the local delivery of cytotoxic or cytostatic agents, i.e., drugs to kill or inhibit tumor cells in the treatment of cancer (Syrigos and Epenetos, *Anticancer Research* 19:605-614 (1999); Niculescu-Duvaz and Springer, *Adv. Drg. Del. Rev.* 26:151-172 (1997); U.S. Pat. No. 4,975,278) allows targeted delivery of the drug moiety to target cells, and intracellular accumulation therein, where systemic administration of these unconjugated therapeutic agents may result in unacceptable levels of toxicity to normal cells as well as the target cells sought to be eliminated (Baldwin et al., *Lancet* (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (eds.), pp. 475-506). Maximal efficacy with minimal toxicity is sought thereby. Importantly, since most normal cells do not present the AMC on their surface, they cannot bind the anti-AMC immunoconjugate, and are protected from the killing effect of the toxin or other therapeutic agents.

Therapeutic agents used in anti-AMC immunoconjugates include, for example, daunomycin, doxorubicin, methotrexate, and vindesine (Rowland et al., *Cancer Immunol. Immunother.* 21:183-187 (1986)). Toxins used in anti-AMC immunoconjugates include bacterial toxins such as diphtheria toxin, plant toxins such as ricin, small molecule toxins such as geldanamycin (Mandler et al., *J. Nat. Cancer Inst.* 92(19):1573-1581 (2000); Mandler et al., *Bioorganic & Med. Chem. Letters* 10:1025-1028 (2000); Mandler et al., *Bioconjugate Chem.* 13:786-791 (2002)), maytansinoids (EP 1391213; Liu et al., *Proc. Natl. Acad. Sci. USA* 93:8618-8623 (1996)), and calicheamicin (Lode et al., *Cancer Res.* 58:2928 (1998); Hinman et al., *Cancer Res.* 53:3336-3342 (1993)). The toxins may exert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Enzymatically active toxins and fragments thereof that can be used include, for example, diphtheria A chain, nonbinding active fragments of diphtheria toxin, exotoxin A chain (from *Pseudomonas aeruginosa*), ricin A chain, abrin A chain, modeccin A chain, α-sarcin, *Aleurites fordii* proteins, dianthin proteins, *Phytolaca americana* proteins (PAPI, PAPII, and PAP-S), *momordica charantia* inhibitor, curcin, crotin, *saponaria officinalis* inhibitor, gelonin, mitogellin, restrictocin, phenomycin, enomycin, and the tricothecenes. See, e.g., WO 93/21232 published Oct. 28, 1993.

Anti-AMC immunoconjugates of an anti-AMC antibody moiety and one or more small molecule toxins, such as a calicheamicin, maytansinoids, dolastatins, aurostatins, a trichothecene, and CC1065, and the derivatives of these toxins that have toxin activity, are also contemplated herein.

In some embodiments, there is provided an anti-AMC immunoconjugate comprising a therapeutic agent that has an intracellular activity. In some embodiments, the anti-AMC immunoconjugate is internalized and the therapeutic agent is a cytotoxin that blocks the protein synthesis of the cell, therein leading to cell death. In some embodiments, the therapeutic agent is a cytotoxin comprising a polypeptide having ribosome-inactivating activity including, for example, gelonin, bouganin, saporin, ricin, ricin A chain, bryodin, diphtheria toxin, restrictocin, *Pseudomonas* exotoxin A and variants thereof. In some embodiments, where the therapeutic agent is a cytotoxin comprising a polypeptide having a ribosome-inactivating activity, the anti-AMC immunoconjugate must be internalized upon binding to the target cell in order for the protein to be cytotoxic to the cells.

In some embodiments, there is provided an anti-AMC immunoconjugate comprising a therapeutic agent that acts to disrupt DNA. In some embodiments, the therapeutic agent that acts to disrupt DNA is, for example, selected from the group consisting of enediyne (e.g., calicheamicin and esperamicin) and non-enediyne small molecule agents (e.g., bleomycin, methidiumpropyl-EDTA-Fe(II)). Other cancer therapeutic agents useful in accordance with the present application include, without limitation, daunorubicin, doxorubicin, distamycin A, cisplatin, mitomycin C, ecteinascidins, duocarmycin/CC-1065, and bleomycin/pepleomycin.

The present invention further contemplates an anti-AMC immunoconjugate formed between the anti-AMC antibody moiety and a compound with nucleolytic activity (e.g., a ribonuclease or a DNA endonuclease such as a deoxyribonuclease; DNase).

In some embodiments, the anti-AMC immunoconjugate comprises an agent that acts to disrupt tubulin. Such agents may include, for example, rhizoxin/maytansine, paclitaxel, vincristine and vinblastine, colchicine, auristatin dolastatin 10 MMAE, and peloruside A.

In some embodiments, the anti-AMC immunoconjugate comprises an alkylating agent including, for example, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In some embodiments, the cancer therapeutic agent portion of the anti-AMC immunoconjugate of the present application may comprise an antimitotic agent including, without limitation, allocolchicine NSC 406042, Halichondrin B NSC 609395, colchicine NSC 757, colchicine derivative NSC 33410, dolastatin 10 NSC 376128 (NG—auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In some embodiments, the anti-AMC immunoconjugate comprises a topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In some embodiments, the anti-AMC immunoconjugate comprises a topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In some embodiments, the anti-AMC immunoconjugate comprises an RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, α-TGDR NSC 71851, aphidicolin glycinate NSC 303812, ara-C NSC 63878, 5-aza-2'-deoxycytidine NSC 12771643, β-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

In some embodiments, the anti-AMC immunoconjugate comprises a highly radioactive atom. A variety of radioactive isotopes are available for the production of radioconjugated antibodies. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu.

In some embodiments, the anti-AMC antibody moiety can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

In some embodiments, an anti-AMC immunoconjugate may comprise an anti-AMC antibody moiety conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such anti-AMC immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibody moieties by recombinant DNA techniques well known in the art. See, e.g., Neuberger et al., *Nature* 312:604-608 (1984).

In some embodiments, the therapeutic portion of the anti-AMC immunoconjugates may be a nucleic acid. Nucleic acids that may be used include, but are not limited to, anti-sense RNA, genes or other polynucleotides, including nucleic acid analogs such as thioguanine and thiopurine.

The present application further provides anti-AMC immunoconjugates comprising an anti-AMC antibody moiety attached to an effector molecule, wherein the effector molecule is a label, which can generate a detectable signal, indirectly or directly. These anti-AMC immunoconjugates can be used for research or diagnostic applications, such as for the in vivo detection of cancer. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example $^{99}Tc$ or $^{123}I$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

In some embodiments, the anti-AMC immunoconjugate is detectable indirectly. For example, a secondary antibody that is specific for the anti-AMC immunoconjugate and contains a detectable label can be used to detect the anti-AMC immunoconjugate.

Thus, for example, in some embodiments, there is provided an anti-AMC immunoconjugate comprising a) an anti-AMC antibody moiety that specifically binds to a complex comprising an AFP peptide and an MHC class I protein, and b) an effector molecule. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the effector molecule is covalently attached to the anti-AMC antibody moiety. In some embodiments, the effector molecule is a therapeutic agent selected, for example, from the group consisting of a drug, a toxin, a radioisotope, a protein, a peptide, and a nucleic acid. In some embodiments, the effector molecular is a cancer therapeutic agent. In some embodiments, the cancer therapeutic agent is a chemotherapeutic. In some embodiments, the cancer therapeutic agent is a highly radioactive atom selected, for example, from the group consisting of $^{211}At$, $^{131}I$, $^{125}I$, $^{90}Y$, $^{186}Re$, $^{188}Re$, $^{153}Sm$, $^{212}Bi$, $^{32}P$, and $^{212}Pb$. In some embodiments, the effector molecule is a label that can generate a detectable signal, either directly or indirectly. In some embodiments, the label is a radioisotope selected, for example, from the group consisting of $^{3}H$, $^{14}C$, $^{32}P$, $^{35}S$, $^{123}I$, $^{125}I$, $^{131}I$. In some embodiments, the anti-AMC antibody moiety is an scFv. In some embodiments, the anti-AMC antibody moiety is human, humanized, or semi-synthetic.

In some embodiments, there is provided an anti-AMC immunoconjugate comprising a) an anti-AMC antibody moiety that specifically binds to a complex comprising an AFP158 peptide (SEQ ID NO: 4) and HLA-A*02:01, and b) an effector molecule. In some embodiments, the effector molecule is covalently attached to the anti-AMC antibody moiety. In some embodiments, the effector molecule is a therapeutic agent selected, for example, from the group consisting of a drug, a toxin, a radioisotope, a protein, a peptide, and a nucleic acid. In some embodiments, the effector molecular is a cancer therapeutic agent. In some embodiments, the cancer therapeutic agent is a chemotherapeutic. In some embodiments, the cancer therapeutic agent is a highly radioactive atom selected, for example, from the group consisting of $^{211}At$, $^{131}I$, $^{125}I$, $^{90}Y$, $^{186}Re$, $^{188}Re$, $^{153}Sm$, $^{212}Bi$, $^{32}P$, and $^{212}Pb$. In some embodiments, the effector molecule is a label that can generate a detectable signal, either directly or indirectly. In some embodiments, the label is a radioisotope selected, for example, from the group consisting of 3H $^{14}C$, $^{32}P$, $^{35}S$, $^{123}I$, $^{125}I$, and $^{131}I$. In some embodiments, the anti-AMC antibody moiety is an scFv. In some embodiments, the anti-AMC antibody moiety is human, humanized, or semi-synthetic.

In some embodiments, there is provided an anti-AMC immunoconjugate comprising a) an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, and b) an effector molecule.

In some embodiments, there is provided an anti-AMC immunoconjugate comprising a) an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, and b) an effector molecule.

In some embodiments, there is provided an anti-AMC immunoconjugate comprising a) an anti-AMC antibody moiety that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions, and b) an effector molecule.

In some embodiments, there is provided an anti-AMC immunoconjugate comprising a) an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109: and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences, and b) an effector molecule.

In some embodiments, there is provided an anti-AMC immunoconjugate comprising a) an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119, and b) an effector molecule.

In some embodiments, there is provided an anti-AMC immunoconjugate comprising a) an anti-AMC antibody moiety that specifically binds to a complex comprising an AFP peptide and an MHC class I protein comprising a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% (for example at least about any of 96%, 97%, 98%, or 99%) sequence identity, and b) an effector molecule.

In some embodiments, there is provided an anti-AMC immunoconjugate comprising a) an anti-AMC antibody moiety that specifically binds to a complex comprising an AFP peptide and an MHC class I protein comprising a heavy chain variable domain comprising the amino acid sequence of any one of SEQ ID NOs: 17-26 and a light chain variable domain comprising the amino acid sequence of any one of SEQ ID NOs: 27-36, b) an effector molecule.

Nucleic Acids

Nucleic acid molecules encoding the anti-AMC constructs or anti-AMC antibody moieties are also contemplated. In some embodiments, there is provided a nucleic acid (or a set of nucleic acids) encoding a full-length anti-AMC antibody. In some embodiments, there is provided a nucleic acid (or a set of nucleic acids) encoding a multi-specific anti-AMC molecule (e.g., a multi-specific anti-AMC antibody, a bispecific anti-AMC antibody, or a bispecific T-cell engager anti-AMC antibody), or polypeptide portion thereof. In some embodiments, there is provided a nucleic acid (or a set of nucleic acids) encoding an anti-AMC CAR. In some embodiments, there is provided a nucleic acid (or a set of nucleic acids) encoding an anti-AMC immunoconjugate, or polypeptide portion thereof.

The present application also includes variants to these nucleic acid sequences. For example, the variants include nucleotide sequences that hybridize to the nucleic acid sequences encoding the anti-AMC constructs or anti-AMC antibody moieties of the present application under at least moderately stringent hybridization conditions.

The present invention also provides vectors in which a nucleic acid of the present invention is inserted.

In brief summary, the expression of an anti-AMC construct (e.g., anti-AMC CAR) or polypeptide portion thereof by a natural or synthetic nucleic acid encoding the anti-AMC construct or polypeptide portion thereof can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

AFP and MHC Class I Proteins

Alpha-fetoprotein (AFP, α-fetoprotein; also referred to as alpha-1-fetoprotein, alpha-fetoglobulin, or alpha fetal protein) is a 591 amino acid glycoprotein that in humans is encoded by the AFP gene. The AFP gene is located on the q arm of chromosome 4 (4q25). AFP is a major plasma protein produced by the yolk sac and the liver during fetal development. It is thought to be the fetal form of serum albumin AFP binds to copper, nickel, fatty acids and bilirubin, and is found in monomeric, dimeric and trimeric forms. AFP is the most abundant plasma protein found in the human fetus. Plasma levels decrease rapidly after birth but begin decreasing prenatally starting at the end of the first trimester. Normal adult levels are usually achieved by the age of 8 to 12 months. The function of AFP in adult humans is unknown; however, in rodents it binds estradiol to prevent the transport of this hormone across the placenta to the fetus. The main function of this is to prevent the virilization of female fetuses. As human AFP does not bind estrogen, its function in humans is less clear.

Some of the diseases in which AFP will be elevated in a person include, for example, hepatocellular carcinoma/hepatoma, germ cell tumor, metastatic liver cancer, omphalocele, neural tube defects, yolk sac tumors, and ataxia telangiectasia.

MHC class I proteins are one of two primary classes of major histocompatibility complex (MHC) molecules (the other being MHC class II) and are found on nearly every nucleated cell of the body. Their function is to display fragments of proteins from within the cell to T cells; healthy cells will be ignored, while cells containing foreign proteins will be attacked by the immune system. Because MHC class I proteins present peptides derived from cytosolic proteins, the pathway of MHC class I presentation is often called the cytosolic or endogenous pathway. Class I MHC molecules bind peptides generated mainly from degradation of cytosolic proteins by the proteasome. The MHC I:peptide complex is then inserted into the plasma membrane of the cell. The peptide is bound to the extracellular part of the class I MHC molecule. Thus, the function of the class I MHC is to display intracellular proteins to cytotoxic T cells (CTLs). However, class I MHC can also present peptides generated from exogenous proteins, in a process known as cross-presentation.

MHC class I proteins consist of two polypeptide chains, α and β2-microglobulin (β2M). The two chains are linked noncovalently via interaction of b2m and the α3 domain. Only the α chain is polymorphic and encoded by a HLA gene, while the b2m subunit is not polymorphic and encoded by the β-2 microglobulin gene. The α3 domain is plasma membrane-spanning and interacts with the CD8 co-receptor of T-cells. The α3-CD8 interaction holds the MHC I molecule in place while the T cell receptor (TCR) on the surface of the cytotoxic T cell binds its α1-α2 heterodimer ligand, and checks the coupled peptide for antigenicity. The α1 and α2 domains fold to make up a groove for peptides to bind. MHC class I proteins bind peptides that are 8-10 amino acid in length.

The human leukocyte antigen (HLA) genes are the human versions of the MHC genes. The three major MHC class I proteins in humans are HLA-A, HLA-B, and HLA-C, while the 3 minor ones are HLA-E, HLA-F, and HLA-G. HLA-A is ranked among the genes in humans with the fastest-evolving coding sequence. As of December 2013, there were 2432 known HLA-A alleles coding for 1740 active proteins and 117 null proteins. The HLA-A gene is located on the short arm of chromosome 6 and encodes the larger, α-chain, constituent of HLA-A. Variation of HLA-A α-chain is key to HLA function. This variation promotes genetic diversity in the population. Since each HLA has a different affinity for peptides of certain structures, greater variety of HLAs means greater variety of antigens to be 'presented' on the cell surface, enhancing the likelihood that a subset of the population will be resistant to any given foreign invader. This decreases the likelihood that a single pathogen has the capability to wipe out the entire human population. Each individual can express up to two types of HLA-A, one from each of their parents. Some individuals will inherit the same HLA-A from both parents, decreasing their individual HLA diversity; however, the majority of individuals will receive two different copies of HLA-A. This same pattern follows for all HLA groups. In other words, a person can only express either one or two of the 2432 known HLA-A alleles.

All alleles receive at least a four digit classification, e.g., HLA-A*02:12. The A signifies which HLA gene the allele belongs to. There are many HLA-A alleles, so that classification by serotype simplifies categorization. The next pair of digits indicates this assignment. For example, HLA-A*02:02, HLA-A*02:04, and HLA-A*02:324 are all members of the A2 serotype (designated by the *02 prefix). This group is the primary factor responsible for HLA compatibility. All numbers after this cannot be determined by serotyping and are designated through gene sequencing. The second set of digits indicates what HLA protein is produced. These are assigned in order of discovery and as of December 2013 there are 456 different HLA-A02 proteins known (assigned names HLA-A*02:01 to HLA-A*02:456). The shortest possible HLA name includes both of these details. Each extension beyond that signifies a nucleotide change that may or may not change the protein.

In some embodiments, the anti-AMC antibody moiety specifically binds to a complex comprising an AFP peptide and an MHC class I protein, wherein the MHC class I protein is HLA-A, HLA-B, HLA-C, HLA-E, HLA-F, or HLA-G. In some embodiments, the MHC class I protein is HLA-A, HLA-B, or HLA-C. In some embodiments, the MHC class I protein is HLA-A. In some embodiments, the MHC class I protein is HLA-B. In some embodiments, the MHC class I protein is HLA-C. In some embodiments, the MHC class I protein is HLA-A01, HLA-A02, HLA-A03, HLA-A09, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, HLA-A69, HLA-A74, or HLA-A80. In some embodiments, the MHC class I protein is HLA-A02. In some embodiments, the MHC class I protein is any one of HLA-A*02:01-555, such as HLA-A*02:01, HLA-A*02:02, HLA-A*02:03, HLA-A*02:04, HLA-A*02:05, HLA-A*02:06, HLA-A*02:07, HLA-A*02:08, HLA-A*02:09, HLA-A*02:10, HLA-A*02:11, HLA-A*02:12, HLA-A*02:13, HLA-A*02:14, HLA-A*02:15, HLA-A*02:16, HLA-A*02:17, HLA-A*02:18, HLA-A*02:19, HLA-A*02:20, HLA-A*02:21, HLA-A*02:22, or HLA-A*02:24. In some embodiments, the MHC class I protein is HLA-A*02:01. HLA-A*02:01 is expressed in 39-46% of all Caucasians, and therefore represents a suitable choice of MHC class I protein for use in the present invention.

AFP peptides suitable for use in generating anti-AMC antibody moieties can be determined, for example, based on the presence of HLA-A*02:01-binding motifs and cleavage sites for proteasomes and immune-proteasomes using computer prediction models known to those of skill in the art. For predicting MHC binding sites, such models include, but are not limited to, IEDB (Vita et al., The immune epitope database (IEDB) 3.0. *Nucleic Acids Res.* 2014 Oct. 9. pii: gku938), ProPred1 (described in more detail in Singh and Raghava, *ProPred: prediction of HLA-DR binding sites.* BIOINFORMATICS 17(12):1236-1237, 2001), and SYFPEITHI (see Schuler et al. *SYFPEITHI, Database for Searching and T-Cell Epitope Prediction. in Immunoinformatics Methods in Molecular Biology*, vol 409(1): 75-93, 2007).

Once appropriate peptides have been identified, peptide synthesis may be done in accordance with protocols well known to those of skill in the art. Because of their relatively small size, the peptides of the invention may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method of preparing the peptides of the invention (See for example, Solid Phase Peptide Synthesis by John Morrow Stewart and Martin et al. *Application of Almez-mediated Amidation Reactions to Solution Phase Peptide Synthesis*, Tetrahedron Letters Vol. 39, pages 1517-1520, 1998).

The binding activity of candidate AFP peptides can be tested using the antigen-processing-deficient T2 cell line, which increases expression of HLA-A when stabilized by a peptide in the antigen-presenting groove. T2 cells are pulsed with the candidate peptide for a time sufficient to stabilize HLA-A expression on the cell surface, which can be measured using any methods known in the art, such as by immunostaining with a fluorescently labeled monoclonal antibody specific for HLA-A (for example, BB7.2) followed by fluorescence-activated cell-sorting (FACS) analysis.

Preparation of Anti-AMC Antibodies and Anti-AMC Antibody Moieties

In some embodiments, the anti-AMC antibody or anti-AMC antibody moiety is a monoclonal antibody. Monoclonal antibodies can be prepared, e.g., using hybridoma methods, such as those described by Kohler and Milstein, *Nature*, 256:495 (1975) and Sergeeva et al., *Blood*, 117(16):4262-4272, using the phage display methods described herein and in the Examples below, or using recombinant DNA methods (see, e.g., U.S. Pat. No. 4,816,567).

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest, or a complex comprising at least two molecules, such as a complex comprising an AFP peptide and an MHC class I protein. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. See, e.g., Goding, Monoclonal Antibodies: Principles and Practice (New York: Academic Press, 1986), pp. 59-103 Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.*, 133:3001 (1984); Brodeur et al. Monoclonal Antibody Production Techniques and Applications (Marcel Dekker, Inc. New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The anti-AMC antibodies or antibody moieties may also be identified by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248:161-175 (Lo, ed., Human Press, Totowa, N.J., 2003); Sidhu et al., *J. Mol. Biol.* 338 (2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284 (1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The antibodies or antigen-binding fragments thereof can be prepared using phage display to screen libraries for antibodies specific to a complex comprising an AFP peptide and an MHC class I protein. The library can be a human scFv phage display library having a diversity of at least one $\times 10^9$ (such as at least about any of $1 \times 10^9$, $2.5 \times 10^9$, $5 \times 10^9$, $7.5 \times 10^9$, $1 \times 10^{10}$, $2.5 \times 10^{10}$, $5 \times 10^{10}$, $7.5 \times 10^{10}$, or $1 \times 10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a non-human phage display library.

Phage clones that bind to the AMC with high affinity can be selected by iterative binding of phage to the AMC, which is bound to a solid support (such as, for example, beads for solution panning or mammalian cells for cell panning), followed by removal of non-bound phage and by elution of specifically bound phage. In an example of solution panning, the AMC can be biotinylated for immobilization to a solid support. The biotinylated AMC is mixed with the phage library and a solid support, such as streptavidin-conjugated Dynabeads M-280, and then AMC-phage-bead complexes are isolated. The bound phage clones are then eluted and used to infect an appropriate host cell, such as *E. coli* XL1-Blue, for expression and purification. In an example of cell panning, T2 cells (a TAP-deficient, HLA-A*02:01$^+$ lymphoblast cell line) loaded with the AFP peptide of the AMC are mixed with the phage library, after which the cells are collected and the bound clones are eluted and used to infect an appropriate host cell for expression and purification. The panning can be performed for multiple (such as about any of 2, 3, 4, 5, 6 or more) rounds with either solution panning, cell panning, or a combination of both, to enrich for phage clones binding specifically to the AMC. Enriched phage clones can be tested for specific binding to the AMC by any methods known in the art, including for example ELISA and FACS.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). Hybridoma cells as described above or AMC-specific phage clones of the invention can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a nonimmunoglobulin polypeptide. Such a nonimmunoglobulin polypeptide can be substituted for the constant domains of an antibody of the invention, or can be substituted for the variable domains of one antigen-combining site of an antibody of the invention to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology*, 121: 210 (1986).

Human and Humanized Antibodies

The anti-AMC antibodies or antibody moieties can be humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, scFv, or other antigen-binding subsequences of antibodies) that typically contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. In some embodiments, the humanized antibody will comprise at least a portion of an immunoglobulin constant region (Fc), typically that of a human immunoglobulin. See, e.g., Jones et al., *Nature*, 321: 522-525 (1986); Riechmann et al., *Nature*, 332: 323-329 (1988); Presta, *Curr. Op. Struct. Biol.*, 2:593-596 (1992).

Generally, a humanized antibody has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature*, 321: 522-525 (1986); Riechmann et al., *Nature*, 332: 323-327 (1988); Verhoeyen et al., *Science*, 239: 1534-1536 (1988)), by substituting rodent CDRs or CDR sequences for the corresponding sequences of a human antibody. Accordingly, such "humanized" antibodies are antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA*, 90:2551 (1993); Jakobovits et al., *Nature*, 362:255-258 (1993); Bruggemann et al., *Year in Immunol.*, 7:33 (1993); U.S. Pat. Nos. 5,545,806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); Lonberg and Huszar, *Intern. Rev. Immunol.*, 13: 65-93 (1995).

Human antibodies may also be generated by in vitro activated B cells (see U.S. Pat. Nos. 5,567,610 and 5,229,275) or by using various techniques known in the art, including phage display libraries. Hoogenboom and Winter, *J. Mol. Biol.*, 227:381 (1991); Marks et al., *J. Mol. Biol.*, 222:581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985) and Boerner et al., *J. Immunol.*, 147 (1): 86-95 (1991).

Multi-Specific Antibodies

In some embodiments, the anti-AMC construct is a multi-specific antibody. Suitable methods for making multi-specific (e.g., bispecific) antibodies are well known in the art. For example, the production of bispecific antibodies can based on the co-expression of two immunoglobulin heavy-chain/light-chain pairs, where the two pairs each have different specificities, and upon association result in a heterodimeric antibody (see, e.g., Milstein and Cuello, *Nature*, 305: 537-539 (1983); WO 93/08829, and Traunecker et al., *EMBO J.* 10: 3655 (1991)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., *EMBO*, 10: 3655-3659 (1991). Alternatively, the combining of heavy and light chains can be directed by taking advantage of species-restricted pairing (see, e.g., Lindhofer et al., *J. Immunol.*, 155:219-225 (1995)) and the pairing of heavy chains can be directed by use of "knob-into hole" engineering of CH3 domains (see, e.g., U.S. Pat. No. 5,731,168; Ridgway et al., *Protein Eng.*, 9 (7):617-621 (1996)). Multi-specific antibodies may also be made by engineering electrostatic steering effects for making antibody Fc-heterodimeric molecules (see, e.g., WO 2009/089004A1). In yet another method, stable bispecific antibodies can be generated by controlled Fab-arm exchange, where two parental antibodies having distinct antigen specificity and matched point mutations in the CH3 domains are mixed in reducing condition to allow for separation, reassembly, and reoxidation to form highly pure bispecific antibodies. Labrigin et al., *Proc. Natl. Acad. Sci.*, 110 (13):5145-5150 (2013). Such antibodies, comprising a mixture of heavy-chain/light-chain pairs, are also referred to herein as "heteromultimeric antibodies".

Antibodies or antigen-binding fragments thereof having different specificities can also be chemically cross-linked to generate multi-specific heteroconjugate antibodies. For example, two F(ab')2 molecules, each having specificity for a different antigen, can be chemically linked. Pullarkat et al., *Trends Biotechnol.*, 48:9-21 (1999). Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

In some embodiments, multi-specific antibodies can be prepared using recombinant DNA techniques. For example, a bispecific antibody can be engineered by fusing two scFvs, such as by fusing them through a peptide linker, resulting in a tandem scFv. One example of a tandem scFv is a bispecific T cell engager. Bispecific T cell engagers are made by linking an anti-CD3 scFv to an scFv specific for a surface antigen of a target cell, such as a tumor-associated antigen (TAA), resulting in the redirection of T cells to the target cells. Mack et al., *Proc. Natl. Acad. Sci.*, 92:7021-7025 (1995); Brischwein et al., *Mol. Immunol.*, 43 (8):1129-1143 (2006). By shortening the length of a peptide linker between two variable domains, they can be prevented from self-assembling and forced to pair with domains on a second polypeptide, resulting in a compact bispecific antibody called a diabody (Db). Holliger et al., *Proc. Natl. Acad. Sci.*, 90:6444-6448 (1993). The two polypeptides of a Db each comprise a VH connected to a VL by a linker which is too short to allow pairing between the two domains on the same chain. Accordingly, the VH and VL domains of one polypeptide are forced to pair with the complementary VL and VH domains of another polypeptide, thereby forming two antigen-binding sites. In a modification of this format, the two polypeptides are linked by another peptide linker, resulting in a single chain diabody (scDb). In yet another modification of the Db format, dual-affinity retargeting (DART) bispecific antibodies can be generated by introducing a disulfide linkage between cysteine residues at the C-terminus of each polypeptide, optionally including domains prior to the C-terminal cysteine residues that drive assembly of the desired heterodimeric structure. Veri et al., *Arthritis Rheum.*, 62 (7):1933-1943 (2010). Dual-variable-domain immunoglobulins (DVD-Ig™), in which the target-binding variable domains of two monoclonal antibodies are combined via naturally occurring linkers to yield a tetravalent, bispecific antibody, are also known in the art. Gu and Ghayur, *Methods Enzymol.*, 502:25-41 (2012). In yet another format, Dock and Lock (DNL), bispecific antibodies are prepared by taking advantage of the dimerization of a peptide (DDD2) derived from the regulatory subunit of human cAMP-dependent protein kinase (PKA) with a peptide (AD2) derived from the anchoring domains of human A kinase anchor proteins (AKAPs). Rossi et al., *Proc. Natl. Acad. Sci.*, 103:6841-6846 (2006).

Various techniques for making and isolating bispecific antibody fragments directly from recombinant cell culture have also been described. For example, bispecific antibodies have been produced using leucine zippers. Kostelny et al., *J. Immunol.*, 148 (5):1547-1553 (1992). This method can also be utilized for the production of antibody homodimers.

Anti-AMC Variants

In some embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. Sites of interest for substitutional mutagenesis include the HVRs and FRs Amino acid substitutions may be introduced into an antibody of interest and the products screened for a desired activity, e.g., retained/improved antigen binding, decreased immunogenicity, or improved ADCC or CDC.

Conservative substitutions are shown in Table 5 below.

TABLE 5

CONSERVATIVE SUBSTITITIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:
a. hydrophobic: Norleucine, Met, Ala, Val, Leu, Ile;
b. neutral hydrophilic: Cys, Ser, Thr, Asn, Gln;
c. acidic: Asp, Glu;
d. basic: His, Lys, Arg;
e. residues that influence chain orientation: Gly, Pro;
f. aromatic: Trp, Tyr, Phe.

Non-conservative substitutions will entail exchanging a member of one of these classes for another class.

An exemplary substitutional variant is an affinity matured antibody, which may be conveniently generated, e.g., using phage display-based affinity maturation techniques. Briefly, one or more CDR residues are mutated and the variant antibodies displayed on phage and screened for a particular biological activity (e.g. binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Fc Region Variants

In some embodiments, one or more amino acid modifications may be introduced into the Fc region of a full-length anti-AMC antibody provided herein, thereby generating an Fc region variant. In some embodiments, the Fc region variant has enhanced antibody dependent cellular cytotoxicity (ADCC) effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9 (2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-AMC antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, the invention contemplates an anti-AMC construct variant comprising an FC region that possesses some but not all effector functions, which makes it a desirable candidate for applications in which the half-life of the anti-AMC construct in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l Immunol.* 18 (12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9 (2): 6591-6604 (2001).)

In some embodiments, there is provided an anti-AMC construct (e.g., a full-length anti-AMC antibody) variant comprising a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-AMC construct (e.g., full-length anti-AMC antibody) variant comprises the following amino acid substitution in its variant Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, there is provided an anti-AMC construct (e.g., a full-length anti-AMC antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

Anti-AMC constructs (such as full-length anti-AMC antibodies) comprising any of the Fc variants described herein, or combinations thereof, are contemplated.

Glycosylation Variants

In some embodiments, an anti-AMC construct provided herein is altered to increase or decrease the extent to which the anti-AMC construct is glycosylated. Addition or deletion of glycosylation sites to an anti-AMC construct may be conveniently accomplished by altering the amino acid sequence of the anti-AMC construct or polypeptide portion thereof such that one or more glycosylation sites is created or removed.

Where the anti-AMC construct comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-AMC construct of the invention may be made in order to create anti-AMC construct variants with certain improved properties.

In some embodiments, anti-AMC construct (such as full-length anti-AMC antibody) variants are provided comprising an Fc region wherein a carbohydrate structure attached to the Fc region has reduced fucose or lacks fucose, which may improve ADCC function. Specifically, anti-AMC constructs are contemplated herein that have reduced fusose relative to the amount of fucose on the same anti-AMC construct produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-AMC construct is one wherein less than about 50%, 40%, 30%, 20%, 10%, or 5% of the N-linked glycans thereon comprise fucose. For example, the amount of fucose in such an anti-AMC construct may be from 1% to 80%, from 1% to 65%, from 5% to 65% or from 20% to 40%. In some embodiments, the anti-AMC construct is one wherein none of the N-linked glycans thereon comprise fucose, i.e., wherein the anti-AMC construct is completely without fucose, or has no fucose or is afucosylated. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication No. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as α-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94 (4):680-688 (2006); and WO2003/085107).

Anti-AMC construct (such as full-length anti-AMC antibody) variants are further provided with bisected oligosaccharides, e.g., in which a biantennary oligosaccharide attached to the Fc region of the anti-AMC construct is bisected by GlcNAc. Such anti-AMC construct (such as full-length anti-AMC antibody) variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering*, 93 (5): 851-861 (2006). Anti-AMC construct (such as full-length anti-AMC antibody) variants with at least one galactose residue in the oligosaccharide attached to the Fc region are also provided. Such anti-AMC construct variants may have improved CDC function. Such antibody variants are described, e.g., in WO 1997/30087 (Patel et al.); WO 1998/58964 (Raju, S.); and WO 1999/22764 (Raju, S.).

In some embodiments, the anti-AMC construct (such as full-length anti-AMC antibody) variants comprising an Fc region are capable of binding to an FcγRIII. In some embodiments, the anti-AMC construct (such as full-length anti-AMC antibody) variants comprising an Fc region have ADCC activity in the presence of human effector cells or have increased ADCC activity in the presence of human effector cells compared to the otherwise same anti-AMC construct (such as full-length anti-AMC antibody) comprising a human wild-type IgG1Fc region.

Cysteine Engineered Variants

In some embodiments, it may be desirable to create cysteine engineered anti-AMC constructs (such as full-length anti-AMC antibodies) in which one or more amino acid residues are substituted with cysteine residues. In some embodiments, the substituted residues occur at accessible sites of the anti-AMC construct. By substituting those residues with cysteine, reactive thiol groups are thereby positioned at accessible sites of the anti-AMC construct and may be used to conjugate the anti-AMC construct to other moieties, such as drug moieties or linker-drug moieties, to create an anti-AMC immunoconjugate, as described further herein. Cysteine engineered anti-AMC constructs (such as full-length anti-AMC antibodies) may be generated as described, e.g., in U.S. Pat. No. 7,521,541.

Derivatives

In some embodiments, an anti-AMC construct provided herein may be further modified to contain additional non-proteinaceous moieties that are known in the art and readily available. The moieties suitable for derivatization of the anti-AMC construct include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-AMC construct may vary, and if more than one polymer are attached, they can be the same or different molecules. In general, the number and/or type of polymers used for derivatization can be determined based on considerations including, but not limited to, the particular properties or functions of the anti-AMC construct to be improved, whether the anti-AMC construct derivative will be used in a therapy under defined conditions, etc.

In some embodiments, conjugates of an anti-AMC construct and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the anti-AMC construct-nonproteinaceous moiety are killed.

CAR Effector Cell Preparation

The present invention in one aspect provides effector cells (such as lymphocytes, for example T cells) expressing an anti-AMC CAR. Exemplary methods of preparing effector cells (such as T cells) expressing the anti-AMC CARs (anti-AMC CAR effector cells, such as anti-AMC CAR T cells) are provided herein.

In some embodiments, an anti-AMC CAR effector cell (such as T cell) can be generated by introducing a vector (including for example a lentiviral vector) comprising an anti-AMC CAR (for example a CAR comprising an anti-AMC antibody moiety and CD28 and CD3ζ intracellular signaling sequences) into the effector cell (such as T cell). In some embodiments, the anti-AMC CAR effector cells (such as T cells) of the invention are able to replicate in vivo, resulting in long-term persistence that can lead to sustained control of an AFP-positive disease (such as cancer, e.g., HCC).

In some embodiments, the invention relates to administering a genetically modified T cell expressing an anti-AMC CAR for the treatment of a patient having an AFP-positive disease or at risk of having an AFP-positive disease using lymphocyte infusion. In some embodiments, autologous lymphocyte infusion is used in the treatment. Autologous PBMCs are collected from a patient in need of treatment and T cells are activated and expanded using the methods described herein and known in the art and then infused back into the patient.

In some embodiments, the anti-AMC CAR T cell expresses an anti-AMC CAR comprising an anti-AMC antibody moiety (also referred to herein as an "anti-AMC CAR T cell"). In some embodiments, the anti-AMC CAR T cell expresses an anti-AMC CAR comprising an extracellular domain comprising an anti-AMC antibody moiety and an intracellular domain comprising intracellular signaling sequences of CD3ζ and CD28. The anti-AMC CAR T cells of the invention can undergo robust in vivo T cell expansion and can establish AMC-specific memory cells that persist at high levels for an extended amount of time in blood and bone marrow. In some embodiments, the anti-AMC CAR T cells of the invention infused into a patient can eliminate AMC-presenting cells, such as AMC-presenting cancer cells, in vivo in patients having an AFP-positive disease. In some embodiments, the anti-AMC CAR T cells of the invention infused into a patient can eliminate AMC-presenting cells, such as AMC-presenting cancer cells, in vivo in patients having an AFP-positive disease that is refractory to at least one conventional treatment.

In some embodiments, the anti-AMC CAR T cell expresses the anti-AMC CAR with even cell surface distribution. Even cell surface distribution can be characterized, for example, by staining patterns with continuous appearance and even thickness or signal intensity. For example, in some embodiments, a composition, such as a pharmaceutical composition, comprising anti-AMC CAR T cells comprises fewer than about 10% (such as fewer than about 10, 9, 8, 7, 6, 5, 4, 3, 2, or 1%) cells with aggregation of the anti-AMC CAR on the cell surface. Aggregation can be characterized, for example, by staining patterns with uneven thickness or signal intensity, or discontinuous, lumpy, punctate, and/or uneven distribution patterns. In some embodiments, the anti-AMC CAR T cell expresses the anti-AMC CAR with less than about 10% (such as less than about 10, 9, 8, 7, 6, 5, 4, 3, 2, or 1%) aggregation of the anti-AMC CAR on the cell surface. In some embodiments, the anti-AMC CAR T cell has a low level of antigen-independent anti-AMC CAR activation. In some embodiments, the anti-AMC CAR T cell has a low level of T cell exhaustion. T cell exhaustion naturally occurs during conditions of extended immune activation, such as with cancer or chronic infection, where T cells become dysfunctional. T cell exhaustion may be characterized by impaired effector function, prolonged expression of inhibitory receptors, and/or an altered transcriptional state compared to functional effector or memory T cells. Optimal clearance of tumor cells and infections is prevented by T cell exhaustion. T cell exhaustion of the anti-AMC CAR T cell can be characterized by any means known in the art, for example, by determining its functional and/or phenotypic profile (Wherry, E. J., *Nature immunology* 12 (6): 492-499, 2011; Jiang, Y., et al., *Cell death & disease* 6 (6): e1792, 2015). For example, in some embodiments, the anti-AMC CAR T cell expresses low levels of one or more markers of T cell exhaustion, including, for example, PD-1, LAG-3, TIM-3, CTLA-4, BTLA, and TIGIT. In some embodiments, the anti-AMC CAR T cell maintains levels characteristic of non-exhausted T cells for IL-2 production, TNF-α production, IFN-γ production, and granzyme B production, and/or maintains ex vivo killing capacity in the presence of target cells, suggesting that the anti-AMC CAR T cell is not undergoing self-activation and premature exhaustion.

Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell lines available in the art may be used. In some embodiments of the present invention, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as $Ca^{2+}$-free, $Mg^{2+}$-free PBS, PlasmaLyte A, or other saline solutions with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In some embodiments, the time period ranges from 30 minutes to 36 hours or longer and all integer values there between. In some embodiments, the time period is at least one, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such as in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD 14, CD20, CD11b, CD 16, HLA-DR, and CD8. In some embodiments, it may be desirable to enrich for or positively select for regulatory T cells which typically express $CD4^+$, $CD25^+$, CD62Lhi, $GITR^+$, and $FoxP3^+$. Alternatively, in some embodiments, T regulatory cells are depleted by anti-CD25 conjugated beads or other similar methods of selection.

For isolation of a desired population of cells by positive or negative selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/ml is used. In some embodiments, a concentration of about 1 billion cells/ml is used. In some embodiments, greater than about 100 million cells/ml is used. In some embodiments, a concentration of cells of about any of 10, 15, 20, 25, 30, 35, 40, 45, or 50 million cells/ml is used. In some embodiments, a concentration of cells of about any of 75, 80, 85, 90, 95, or 100 million cells/ml is used. In some embodiments, a concentration of about 125 or about 150 million cells/ml is used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In some embodiments of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in some embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express a desirable anti-AMC CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30 (8):3975-3977, 1998; Haanen et al., J. Exp. Med. 190 (9):13191328, 1999; Garland et al., J. Immunol. Meth. 227 (1-2):53-63, 1999).

Immunoconjugate Preparation

The anti-AMC immunoconjugates may be prepared using any methods known in the art. See, e.g., WO 2009/067800, WO 2011/133886, and U.S. Patent Application Publication No. 2014322129, incorporated by reference herein in their entirety.

The anti-AMC antibody moiety of an anti-AMC immunoconjugate may be "attached to" the effector molecule by any means by which the anti-AMC antibody moiety can be associated with, or linked to, the effector molecule. For example, the anti-AMC antibody moiety of an anti-AMC immunoconjugate may be attached to the effector molecule by chemical or recombinant means. Chemical means for preparing fusions or conjugates are known in the art and can be used to prepare the anti-AMC immunoconjugate. The method used to conjugate the anti-AMC antibody moiety and effector molecule must be capable of joining the binding protein with the effector molecule without interfering with the ability of the binding protein to bind to the antigen on the target cell.

The anti-AMC antibody moiety of an anti-AMC immunoconjugate may be linked indirectly to the effector molecule. For example, the anti-AMC antibody moiety of an anti-AMC immunoconjugate may be directly linked to a liposome containing the effector molecule of one of several types. The effector molecule(s) and/or the anti-AMC antibody moiety may also be bound to a solid surface.

In some embodiments, the anti-AMC antibody moiety of an anti-AMC immunoconjugate and the effector molecule are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the anti-AMC antibody moiety and/or effector molecule. In addition, if there are no reactive groups, a photoactivatible crosslinker can be used. In certain instances, it may be desirable to include a spacer between the anti-AMC antibody moiety and the effector molecule. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

In some embodiments, the anti-AMC antibody moiety of an anti-AMC immunoconjugate may be engineered with specific residues for chemical attachment of the effector molecule. Specific residues used for chemical attachment of molecule known to the art include lysine and cysteine. The crosslinker is chosen based on the reactive functional groups inserted on the anti-AMC antibody moiety, and available on the effector molecule.

An anti-AMC immunoconjugate may also be prepared using recombinant DNA techniques. In such a case a DNA sequence encoding the anti-AMC antibody moiety is fused to a DNA sequence encoding the effector molecule, resulting in a chimeric DNA molecule. The chimeric DNA sequence is transfected into a host cell that expresses the fusion protein. The fusion protein can be recovered from the cell culture and purified using techniques known in the art.

Examples of attaching an effector molecule, which is a label, to the binding protein include the methods described in Hunter, et al., *Nature* 144:945 (1962); David, et al., *Biochemistry* 13:1014 (1974); Pain, et al., *J. Immunol. Meth.* 40:219 (1981); Nygren, J. Histochem. and Cytochem. 30:407 (1982); Wensel and Meares, *Radioimmunoimaging And Radioimmunotherapy*, Elsevier, N.Y. (1983); and Colcher et al., "Use Of Monoclonal Antibodies As Radiopharmaceuticals For The Localization Of Human Carcinoma Xenografts In Athymic Mice", *Meth. Enzymol.*, 121:802-16 (1986).

The radio- or other labels may be incorporated in the immunoconjugate in known ways. For example, the peptide may be biosynthesized or may be synthesized by chemical amino acid synthesis using suitable amino acid precursors involving, for example, fluorine-19 in place of hydrogen. Labels such as $^{99}$Tc or $^{123}$I, $^{186}$Re, $^{188}$Re and $^{111}$In can be attached via a cysteine residue in the peptide. Yttrium-90 can be attached via a lysine residue. The IODOGEN method (Fraker et al., *Biochem. Biophys. Res. Commun.* 80:49-57 (1978)) can be used to incorporate iodine-123. "Monoclonal Antibodies in Immunoscintigraphy" (Chatal, CRC Press 1989) describes other methods in detail.

Immunoconjugates of the antibody moiety and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCI), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene tnaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

The anti-AMC immunoconjugates of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Pharmaceutical Compositions

Also provided herein are compositions (such as pharmaceutical compositions, also referred to herein as formulations) comprising an anti-AMC construct. In some embodiments, the composition further comprises a cell (such as an effector cell, e.g., a T cell) associated with the anti-AMC construct. In some embodiments, there is provided a pharmaceutical composition comprising an anti-AMC construct and a pharmaceutically acceptable carrier. In some embodiments, the pharmaceutical composition further comprises a cell (such as an effector cell, e.g., a T cell) associated with the anti-AMC construct.

Suitable formulations of the anti-AMC constructs are obtained by mixing an anti-AMC construct having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-AMC constructs of this invention into cells.

The formulation herein may also contain one or more active compounds in addition to the anti-AMC construct as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-AMC construct. Such molecules are suitably present in combination in amounts that are effective for the purpose intended. The effective amount of such other agents depends on the amount of anti-AMC construct present in the formulation, the type of disease or disorder or treatment, and other factors discussed above. These are generally used in the same dosages and with administration routes as described herein or about from 1 to 99% of the heretofore employed dosages.

The anti-AMC constructs may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980). Sustained-release preparations may be prepared.

Sustained-release preparations of the anti-AMC constructs can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydro gels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization of anti-AMC constructs depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-AMC construct is formulated in a buffer comprising a citrate, NaCl, acetate, succinate, glycine, polysorbate 80 (Tween 80), or any combination of the foregoing. In some embodiments, the anti-AMC construct is formulated in a buffer comprising about 100 mM to about 150 mM glycine. In some embodiments, the anti-AMC construct is formulated in a buffer comprising about 50 mM to about 100 mM NaCl. In some embodiments, the anti-AMC construct is formulated in a buffer comprising about 10 mM to about 50 mM acetate. In some embodiments, the anti-AMC construct is formulated in a buffer comprising about 10 mM to about 50 mM succinate. In some embodiments, the anti-AMC construct is formulated in a buffer comprising about 0.005% to about 0.02% polysorbate 80. In some embodiments, the anti-AMC construct is formulated in a buffer having a pH between about 5.1 and 5.6. In some embodiments, the anti-AMC construct is formulated in a buffer comprising 10 mM citrate, 100 mM NaCl, 100 mM glycine, and 0.01% polysorbate 80, wherein the formulation is at pH 5.5.

The formulations to be used for in vivo administration must be sterile. This is readily accomplished by, e.g., filtration through sterile filtration membranes.

Methods for Treatment using Anti-AMC Constructs

The anti-AMC constructs and/or compositions of the invention can be administered to individuals (e.g., mammals such as humans) to treat a disease and/or disorder involving abnormally high AFP expression (also referred to herein as an "AFP-positive" disease or disorder), including, for example, cancer (such as hepatocellular carcinoma, germ cell tumor, and breast cancer). The present application thus in some embodiments provides a method of treating an AFP-positive disease (such as cancer) in an individual comprising administering to the individual an effective amount of a composition (such as a pharmaceutical composition) comprising an anti-AMC construct comprising an anti-AMC antibody moiety, such as any one of the anti-AMC constructs described herein. In some embodiments, the composition further comprises a cell (such as an effector cell) associated with the anti-AMC construct. In some embodiments, the cancer is selected, for example, from the group consisting of hepatocellular carcinoma, germ cell tumor, and breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

For example, in some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP peptide and an MHC class I protein. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP158 peptide (SEQ ID NO: 4) and HLA-A*02:01. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP peptide and an MHC class I protein, wherein the anti-AMC antibody moiety comprises: i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP peptide and an MHC class I protein, wherein the anti-AMC antibody moiety comprises: i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP peptide and an MHC class I protein, wherein the anti-AMC antibody moiety comprises: i) a heavy chain variable domain sequence comprising an HC-CDR1 comprising the amino acid sequence of any one of SEQ ID NOs: 57-66, or a variant thereof comprising up to about 5 (for example about any of 1, 2, 3, 4, or 5) amino acid substitutions; an HC-CDR2 comprising the amino acid sequence of any one of SEQ ID NOs: 67-76, or a variant thereof comprising up to about 5 (for example about any of 1, 2, 3, 4, or 5) amino acid substitutions; and an HC-CDR3 comprising the amino acid sequence of any one of SEQ ID NOs: 77-86; or a variant thereof comprising up to about 5 (for example about any of 1, 2, 3, 4, or 5) amino acid substitutions; and ii) a light chain variable domain sequence comprising an LC-CDR1 comprising the amino acid sequence of any one of SEQ ID NOs: 90-99, or a variant thereof comprising up to about 5 (for example about any of 1, 2, 3, 4, or 5) amino acid substitutions; an LC-CDR2 comprising the amino acid sequence of any one of SEQ ID NOs: 100-109, or a variant thereof comprising up to about 5 (for example about any of 1, 2, 3, 4, or 5) amino acid substitutions; and an LC-CDR3 comprising the amino acid sequence of any one of SEQ ID NOs: 110-119; or a variant thereof comprising up to about 5 (for example about any of 1, 2, 3, 4, or 5) amino acid substitutions. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP peptide and an MHC class I protein, wherein the anti-AMC antibody moiety comprises:

i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (for example about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (for example about any of 1, 2, 3, 4, or 5) amino acid substitutions in the LC-CDR sequences. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP peptide and an MHC class I protein, wherein the anti-AMC antibody moiety comprises: i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP peptide and an MCH class I protein, wherein the anti-AMC antibody moiety comprises a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% (for example at least about any of 96%, 97%, 98%, or 99%) sequence identity. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an anti-AMC construct comprising an anti-AMC antibody moiety that specifically binds to a complex comprising an AFP peptide and an MCH class I protein, wherein the anti-AMC antibody moiety comprises a heavy chain variable domain comprising the amino acid sequence of any one of SEQ ID NOs: 17-26 and a light chain variable domain comprising the amino acid sequence of any one of SEQ ID NOs: 27-36. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the composition further comprises a cell (such as an effector cell) associated with the anti-AMC construct. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating metastatic hepatocellular carcinoma in an individual comprising administering to the individual an effective amount of a composition comprising an anti-AMC construct according to any of the embodiments described above. In some embodiments, the individual is human.

In some embodiments, there is provided a method of inhibiting (such as preventing) metastasis of hepatocellular carcinoma in an individual comprising administering to the individual an effective amount of a composition comprising an anti-AMC construct according to any of the embodiments described above. In some embodiments, the individual is human.

In some embodiments of any of the methods for treating an AFP-positive disease described above, the anti-AMC construct is conjugated to a cell (such as an immune cell, e.g., a T cell) prior to being administered to the individual. Thus, for example, there is provided a method of treating an AFP-positive disease in an individual comprising a) conjugating any one of the anti-AMC constructs described herein to a cell (such as an immune cell, e.g., a T cell) to form an anti-AMC construct/cell conjugate, and b) administering to the individual an effective amount of a composition comprising the anti-AMC construct/cell conjugate. In some embodiments, the cell is derived from the individual. In some embodiments, the cell is not derived from the individual. In some embodiments, the anti-AMC construct is conjugated to the cell by covalent linkage to a molecule on the surface of the cell. In some embodiments, the anti-AMC construct is conjugated to the cell by non-covalent linkage to a molecule on the surface of the cell. In some embodiments, the anti-AMC construct is conjugated to the cell by insertion of a portion of the anti-AMC construct into the outer membrane of the cell. In some embodiments, the anti-AMC construct is non-naturally occurring. In some embodiments, the anti-AMC construct is a full-length antibody. In some embodiments, the anti-AMC construct is a multi-specific (such as bispecific) molecule. In some embodiments, the anti-AMC construct is a chimeric antigen receptor. In some embodiments, the anti-AMC construct is an immunoconjugate. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with or genetically prone to one or more of the diseases or disorders described herein (such as hepatocellular carcinoma, germ cell tumor, and breast cancer). In some embodiments, the individual has one or more risk factors associated with one or more diseases or disorders described herein.

The present application in some embodiments provides a method of delivering an anti-AMC construct (such as any one of the anti-AMC constructs described herein) to a cell presenting on its surface a complex comprising an AFP peptide and an MHC class I protein in an individual, the method comprising administering to the individual a composition comprising the anti-AMC construct. In some embodiments, the anti-AMC construct to be delivered is associated with a cell (such as an effector cell, e.g., a T cell).

Many diagnostic methods for cancer (such as hepatocellular carcinoma, germ cell tumor, and breast cancer) or any other disease exhibiting abnormal AFP expression and the clinical delineation of those diseases are known in the art. Such methods include, but are not limited to, e.g., immunohistochemistry, PCR, and fluorescent in situ hybridization (FISH).

In some embodiments, the anti-AMC constructs and/or compositions of the invention are administered in combination with a second, third, or fourth agent (including, e.g., an antineoplastic agent, a growth inhibitory agent, a cytotoxic agent, or a chemotherapeutic agent) to treat diseases or disorders involving abnormal AFP expression. In some embodiments, the anti-AMC construct is administered in combination with an agent that increases the expression of MHC class I proteins and/or enhances the surface presentation of AFP peptides by MHC class I proteins. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, IFNβ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine.

In some embodiments, there is provided a method of treating an AFP-positive disease in an individual, wherein the cells expressing AFP do not normally present, or present at relatively low levels, a complex comprising an AFP protein and an MHC class I protein on their surface (such as germ cell tumor cells), the method comprising administering to the individual a composition comprising an anti-AMC construct in combination with an agent that increases the expression of MHC class I proteins and/or enhances the surface presentation of AFP peptides by MHC class I proteins. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, IFNβ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine.

Cancer treatments can be evaluated by, e.g., tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation $100-(T/C \times 100)$, where T is the mean relative tumor volume of the treated tumor, and C is the mean relative tumor volume of a non-treated tumor. In some embodiments, the % TGI is about 10%, about 20%, about 30%, about 40%, about 50%, about 60%, about 70%, about 80%, about 90%, about 91%, about 92%, about 93%, about 94%, about 95%, or more than 95%.

Dosing and Method of Administering the anti-AMC Construct Compositions

The dose of the anti-AMC construct compositions administered to an individual (such as a human) may vary with the particular composition, the mode of administration, and the type of disease being treated. In some embodiments, the amount of the composition is effective to result in an objective response (such as a partial response or a complete response). In some embodiments, the amount of the anti-AMC construct composition is sufficient to result in a complete response in the individual. In some embodiments, the amount of the anti-AMC construct composition is sufficient to result in a partial response in the individual. In some embodiments, the amount of the anti-AMC construct composition administered (for example when administered alone) is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the anti-AMC construct composition. Responses of an individual to the treatment of the methods described herein can be determined, for example, based on RECIST levels.

In some embodiments, the amount of the composition is sufficient to prolong progress-free survival of the individual. In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the anti-AMC construct composition.

In some embodiments, the amount of the composition, alone or in combination with a second, third, and/or fourth agent, is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the anti-AMC construct (e.g., full-length anti-AMC antibody, multi-specific anti-AMC molecule, anti-AMC CAR, or anti-AMC immunoconjugate) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regimen. In some embodiments, the amount of the composition is more than about any of 80%, 90%, 95%, or 98% of the MTD.

In some embodiments, the amount of an anti-AMC construct (e.g., full-length anti-AMC antibody, multi-specific anti-AMC molecule, anti-AMC CAR, or anti-AMC immunoconjugate) in the composition is included in a range of about 0.001 µg to about 1000 µg.

In some embodiments of any of the above aspects, the effective amount of an anti-AMC construct (e.g., full-length anti-AMC antibody, multi-specific anti-AMC molecule, anti-AMC CAR, or anti-AMC immunoconjugate) in the composition is in the range of about 0.1 µg/kg to about 100 mg/kg of total body weight.

The anti-AMC construct compositions can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion.

Anti-AMC CAR Effector Cell Therapy

The present application also provides methods of using an anti-AMC CAR to redirect the specificity of an effector cell (such as a primary T cell) to a complex comprising an AFP peptide and an MHC class I protein. Thus, the present invention also provides a method of stimulating an effector cell-mediated response (such as a T cell-mediated immune response) to a target cell population or tissue comprising AMC-presenting cells in a mammal, comprising the step of administering to the mammal an effector cell (such as a T cell) that expresses an anti-AMC CAR.

Anti-AMC CAR effector cells (such as T cells) expressing the anti-AMC CAR can be infused to a recipient in need thereof. The infused cell is able to kill AMC-presenting cells in the recipient. In some embodiments, unlike antibody therapies, anti-AMC CAR effector cells (such as T cells) are able to replicate in vivo resulting in long-term persistence that can lead to sustained tumor control.

In some embodiments, the anti-AMC CAR effector cells are anti-AMC CAR T cells that can undergo robust in vivo T cell expansion and can persist for an extended amount of time. In some embodiments, the anti-AMC CAR T cells of the invention develop into specific memory T cells that can be reactivated to inhibit any additional tumor formation or growth.

The anti-AMC CAR T cells of the invention may also serve as a type of vaccine for ex vivo immunization and/or in vivo therapy in a mammal. In some embodiments, the mammal is a human.

With respect to ex vivo immunization, of least one of the following occurs in vitro prior to administering the cell into a mammal: i) expansion of the cells, ii) introducing a nucleic acid encoding an anti-AMC CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing an anti-AMC CAR disclosed herein. The anti-AMC CAR cell can be administered to a mammalian recipient to provide a therapeutic benefit. The mammalian recipient may be a human and the anti-AMC CAR cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34$^+$ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

The anti-AMC CAR effector cells (such as T cells) of the present invention may be administered either alone, or as a pharmaceutical composition in combination with diluents and/or with other components such as IL-2 or other cytokines or cell populations. Briefly, pharmaceutical compositions of the present invention may comprise anti-AMC CAR effector cells (such as T cells), in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In some embodiments, anti-AMC CAR effector cell (such as T cell) compositions are formulated for intravenous administration.

The precise amount of the anti-AMC CAR effector cell (such as T cell) compositions of the present invention to be administered can be determined by a physician with consideration of individual differences in age, weight, tumor size, extent of infection or metastasis, and condition of the patient (subject). In some embodiments, a pharmaceutical composition comprising the anti-AMC CAR effector cells (such as T cells) is administered at a dosage of about $10^4$ to about $10^9$ cells/kg body weight, such any of about $10^4$ to about $10^5$, about $10^5$ to about $10^6$, about $10^6$ to about $10^7$, about $10^7$ to about $10^8$, or about $10^8$ to about $10^9$ cells/kg body weight, including all integer values within those ranges. Anti-AMC CAR effect cell (such as T cell) compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regimen for a particular patient can readily be determined by one skilled in the art of medicine by monitoring the patient for signs of disease and adjusting the treatment accordingly.

In some embodiments, it may be desired to administer activated anti-AMC CAR T cells to a subject and then subsequently redraw blood (or have an apheresis performed), activate T cells therefrom according to the present invention, and reinfuse the patient with these activated and expanded T cells. This process can be carried out multiple times every few weeks. In some embodiments, T cells can be activated from blood draws of from 10 cc to 400 cc. In some embodiments, T cells are activated from blood draws of 20 cc, 30 cc, 40 cc, 50 cc, 60 cc, 70 cc, 80 cc, 90 cc, or 100 cc.

The administration of the anti-AMC CAR effector cells (such as T cells) may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the anti-AMC CAR effector cell (such as T cell) compositions of the present invention are administered to a patient by intradermal or subcutaneous injection. In some embodiments, the anti-AMC CAR effector cell (such as T cell) compositions of the present invention are administered by i.v. injection. The compositions of anti-AMC CAR effector cells (such as T cells) may be injected directly into a tumor, lymph node, or site of infection.

Thus, for example, in some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein, b) a transmembrane domain, and c) an intracellular signaling domain comprising a CD3ζ intracellular signaling sequence and a CD28 intracellular signaling sequence. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP158 peptide (SEQ ID NO: 4) and HLA-A*02:01, b) a transmembrane domain, and c) an intracellular signaling domain comprising a CD3ζ intracellular signaling sequence and a CD28 intracellular signaling sequence. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, b) a transmembrane domain, and c) an intracellular signaling domain comprising a CD3ζ intracellular signaling sequence and a CD28 intracellular signaling sequence. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, b) a transmembrane domain, and c) an intracellular signaling domain comprising a CD3ζ intracellular signaling sequence and a CD28 intracellular signaling sequence. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions; b) a transmembrane domain, and c) an intracellular signaling domain comprising a CD3ζ intracellular signaling sequence and a CD28 intracellular signaling sequence. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences; b) a transmembrane domain, and c) an intracellular signaling domain comprising a CD3ζ intracellular signaling sequence and a CD28 intracellular signaling sequence. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; b) a transmembrane domain, and c) an intracellular signaling domain comprising a CD3ζ intracellular signaling sequence and a CD28 intracellular signaling sequence. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% sequence identity; b) a transmembrane domain, and c) an intracellular signaling domain comprising a CD3ζ intracellular signaling sequence and a CD28 intracellular signaling sequence. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising a heavy chain variable domain comprising the amino acid sequence of any one of SEQ ID NOs: 17-26 and a light chain variable domain comprising the amino acid sequence of any one of SEQ ID NOs: 27-36; b) a transmembrane domain, and c) an intracellular signaling domain comprising a CD3ζ intracellular signaling sequence and a CD28 intracellular signaling sequence. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein, b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP peptide is AFP158 (SEQ ID NO: 4). In some embodiments, the MHC class I protein is HLA-A02. In some embodiments, the MHC class I protein is HLA-A*02:01. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP158 peptide (SEQ ID NO: 4) and HLA-A*02:01, b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), or a variant thereof comprising up to about 3 (for example about any of 1, 2, or 3) amino acid substitutions, an HC-CDR2 comprising the amino acid sequence of I/S-K/S-X-H/Y-X-G-X-T (SEQ ID NO: 88), or a variant thereof comprising up to about 3 (for example about any of 1, 2, or 3) amino acid substitutions, and an HC-CDR3 comprising the amino acid sequence of A/G-X-W/Y-Y-X-X-X-F/Y-D (SEQ ID NO: 89), or a variant thereof comprising up to about 3 (for example about any of 1, 2, or 3) amino acid substitutions; and ii) a light chain variable domain comprising an LC-CDR1 comprising the amino acid sequence of S/T-G/S-D/N-I/V-A/G-A/S/V-X-H/Y (SEQ ID NO: 120), or a variant thereof comprising up to about 3 (for example about any of 1, 2, or 3) amino acid substitutions, and an LC-CDR3 comprising the amino acid sequence of Q-S/T-Y/W-D/T-S/T-A/S (SEQ ID NO: 121), or a variant thereof comprising up to about 3 (for example about any of 1, 2, or 3) amino acid substitutions; wherein X can be any amino acid, b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of G-F/Y-S/T-F-D/S/T-D/N/S-Y/A-A/G/W (SEQ ID NO: 87), an HC-CDR2 comprising the amino acid sequence of I/S-K/S-X-H/Y-X-G-X-T (SEQ ID NO: 88), and an HC-CDR3 comprising the amino acid sequence of A/G-X-W/Y-Y-X-X-X-F/Y-D (SEQ ID NO: 89); and ii) a light chain variable domain comprising an LC-CDR1 comprising the amino acid sequence of S/T-G/S-D/N-I/V-A/G-A/S/V-X-H/Y (SEQ ID NO: 120), and an LC-CDR3 comprising the amino acid sequence of Q-S/T-Y/W-D/T-S/T-A/S (SEQ ID NO: 121); wherein X can be any amino acid, b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66, or a variant thereof comprising up to about 5 (such as about any of 1, 2, 3, 4, or 5) amino acid substitutions, an HC-CDR2 comprising the amino acid sequence of any one of SEQ ID NOs: 67-76, or a variant thereof comprising up to about 5 (such as about any of 1, 2, 3, 4, or 5) amino acid substitutions, and an HC-CDR3 comprising the amino acid sequence of any one of SEQ ID NOs: 77-86, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 90-99, or a variant thereof comprising up to about 5 (such as about any of 1, 2, 3, 4, or 5) amino acid substitutions, an LC-CDR2 comprising the amino acid sequence of any one of SEQ ID NOs: 100-109, or a variant thereof comprising up to about 3 (such as about any of 1, 2, or 3) amino acid substitutions, and an LC-CDR3 comprising the amino acid sequence of any one of SEQ ID NOs: 110-119, or a variant thereof comprising up to about 5 (such as about any of 1, 2, 3, 4, or 5) amino acid substitutions; b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; or a variant thereof comprising up to about 5 (such as about any of 1, 2, 3, 4, or 5) amino acid substitutions in the LC-CDR sequences; b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain sequence comprising an HC-CDR1 comprising the amino acid sequence of any one of SEQ ID NOs: 57-66; an HC-CDR2 comprising the amino acid sequence of any one of SEQ ID NOs: 67-76; and an HC-CDR3 comprising the amino acid sequence of any one of SEQ ID NOs: 77-86; and ii) a light chain variable domain sequence comprising an LC-CDR1 comprising the amino acid sequence of any one of SEQ ID NOs: 90-99; an LC-CDR2 comprising the amino acid sequence of any one of SEQ ID NOs: 100-109; and an LC-CDR3 comprising the amino acid sequence of any one of SEQ ID NOs: 110-119; b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising i) a heavy chain variable domain comprising the amino acid sequence of any one of SEQ ID NOs: 17-26, or a variant thereof having at least about 95% (for example at least about any of 96%, 97%, 98%, or 99%) sequence identity, and a light chain variable domain comprising the amino acid sequence of any one of SEQ ID NOs: 27-36, or a variant thereof having at least about 95% sequence identity; b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating an AFP-positive disease in an individual comprising administering to the individual an effective amount of a composition comprising an effector cell (such as a T cell) expressing an anti-AMC CAR comprising a) an extracellular domain comprising an anti-AMC antibody moiety that specifically binds to a complex comprising an AFP peptide and an MHC class I protein comprising a heavy chain variable domain comprising the amino acid sequence of any one of SEQ ID NOs: 17-26 and a light chain variable domain comprising the amino acid sequence of any one of SEQ ID NOs: 27-36; b) a transmembrane domain, and c) an intracellular signaling domain comprising a CD3ζ intracellular signaling sequence and a CD28 intracellular signaling sequence, wherein the administering comprises local injection of the composition at an injection site distal to a site of the AFP-positive disease (such as an AFP-positive tumor). In some embodiments, the injection site is a first AFP-positive tumor (i.e., the administration is via intratumoral route). In some embodiments, the site of the AFP-positive disease is a second AFP-positive tumor. In some embodiments, the injection site is a first AFP-positive tumor and the site of the AFP-positive disease is a second AFP-positive tumor. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the cancer is hepatocellular carcinoma and the treating comprises preventing the spread of the cancer, e.g., inhibiting (such as preventing) metastasis of the cancer. In some embodiments, the cancer is metastatic hepatocellular carcinoma. In some embodiments, the individual is human.

In some embodiments, there is provided a method of treating metastatic hepatocellular carcinoma in an individual comprising administering to the individual an effective amount of a composition comprising an effector cell (such as a T cell) expressing an anti-AMC CAR according to any of the embodiments described above. In some embodiments, the individual is human.

In some embodiments, there is provided a method of inhibiting (such as preventing) metastasis of hepatocellular carcinoma in an individual comprising administering to the individual an effective amount of a composition comprising an effector cell (such as a T cell) expressing an anti-AMC CAR according to any of the embodiments described above. In some embodiments, the individual is human.

In some embodiments, there is provided a method of priming T cells in an individual comprising administering to the individual an effective amount of a composition comprising an effector cell (such as a T cell) expressing an anti-AMC CAR according to any of the anti-AMC CARs described above. In some embodiments, the individual has an AFP-positive disease. In some embodiments, the AFP-positive disease is cancer. In some embodiments, the cancer is, for example, hepatocellular carcinoma, germ cell tumor, or breast cancer. In some embodiments, the cancer is hepatocellular carcinoma. In some embodiments, the administration is via intravenous, intraperitoneal, or intratumoral route. In some embodiments, the administration is via intravenous route. In some embodiments, the administration is via intratumoral route. In some embodiments, the individual is human.

In some embodiments, according to any of the methods described above, the method further comprising administering antigen presenting cells, or APCs, (such as monocytes or monocyte-differentiated dendritic cells) to the individual. Dendritic cells can be generated ex vivo via culturing monocytes with specific cytokines (Palucka and Banchereau, *Nature Reviews Cancer* 12:265-277, 2012). In some embodiments, the APCs are administered simultaneously with the effector cell composition. In some embodiments, the APCs are administered concurrently with the effector cell composition. In some embodiments, the APCs are administered sequentially with the effector cell composition. In some embodiments, the APCs are administered via the same route as the effector cell composition. In some embodiments, the APCs are administered to the same site as the effector cell composition. In some embodiments, the effector cell composition comprises the APCs.

Cancers

The anti-AMC constructs and anti-AMC CAR cells in some embodiments can be useful for treating cancer. Cancers that may be treated using any of the methods described herein include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the anti-AMC constructs and anti-AMC CAR cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, the cancer is HCC. In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC. In some embodiments, the HCC is any one of liver cell carcinomas, fibrolamellar variants of HCC, and mixed hepatocellular cholangiocarcinomas.

In some embodiments, the cancer is a germ cell tumor.

Cancer treatments can be evaluated by, e.g., tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

Methods for Diagnosis and Imaging Using Anti-AMC Constructs

Labeled anti-AMC antibody moieties and derivatives and analogs thereof, which specifically bind to an AMC on the surface of a cell, can be used for diagnostic purposes to detect, diagnose, or monitor diseases and/or disorders associated with the expression, aberrant expression and/or activity of AFP, including any of the diseases and disorders described above, such as cancer (e.g., hepatocellular carcinoma, germ cell tumor, or breast cancer). For example, the anti-AMC antibody moieties of the invention can be used in in situ, in vivo, ex vivo, and in vitro diagnostic assays or imaging assays.

Additional embodiments of the invention include methods of diagnosing a disease or disorder associated with expression or aberrant expression of AFP in an individual (e.g., a mammal, such as a human) The methods comprise detecting AMC-presenting cells in the individual. In some embodiments, there is provided a method of diagnosing a disease or disorder associated with expression or aberrant expression of AFP in an individual (e.g., a mammal, such as a human) comprising (a) administering an effective amount of a labeled anti-AMC antibody moiety according to any of the embodiments described above to the individual; and (b) determining the level of the label in the individual, such that a level of the label above a threshold level indicates that the individual has the disease or disorder. The threshold level can be determined by various methods, including, for example, by detecting the label according to the method of diagnosing described above in a first set of individuals that have the disease or disorder and a second set of individuals that do not have the disease or disorder, and setting the threshold to a level that allows for discrimination between the first and second sets. In some embodiments, the threshold level is zero, and the method comprises determining the presence or absence of the label in the individual. In some embodiments, the method further comprises waiting for a time interval following the administering of step (a) to permit the labeled anti-AMC antibody moiety to preferentially concentrate at sites in the individual where the AMC is expressed (and for unbound labeled anti-AMC antibody moiety to be cleared). In some embodiments, the method further comprises subtracting a background level of the label. Background level can be determined by various methods, including, for example, by detecting the label in the individual prior to administration of the labeled anti-AMC antibody moiety, or by detecting the label according to the method of diagnosing described above in an individual that does not have the disease or disorder. In some embodiments, the disease or disorder is cancer. In some embodiments, the cancer is selected, for example, from the group consisting of hepatocellular carcinoma, germ cell tumor, and breast cancer. In some embodiments, the cancer is hepatocellular carcinoma. In some embodiments, the cancer is metastatic hepatocellular carcinoma. In some embodiments, the cancer is metastatic hepatocellular carcinoma, and the method further comprises determining the level of the label in the individual's blood. In some embodiments, the individual is human.

In some embodiments, there is provided a method of diagnosing metastatic hepatocellular carcinoma in an individual (e.g., a mammal, such as a human), comprising (a) administering an effective amount of a labeled anti-AMC antibody moiety according to any of the embodiments described above to the individual; and (b) determining the level of the label in the individual's blood, such that a level of the label above a threshold level indicates that the individual has metastatic hepatocellular carcinoma. The threshold level can be determined by various methods, including, for example, by detecting the label according to the method of diagnosing described above in a first set of individuals that have metastatic hepatocellular carcinoma and a second set of individuals that do not have metastatic hepatocellular carcinoma, and setting the threshold to a level that allows for discrimination between the first and second sets. In some embodiments, the threshold level is zero, and the method comprises determining the presence or absence of the label in the individual's blood. In some embodiments, the method further comprises waiting for a time interval following the administering of step (a) to permit the labeled anti-AMC antibody moiety to preferentially concentrate at sites in the individual where the AMC is expressed (and for unbound labeled anti-AMC antibody moiety to be cleared). In some embodiments, the method further comprises subtracting a background level of the label. Background level can be determined by various methods, including, for example, by detecting the label in the individual prior to administration of the labeled anti-AMC antibody moiety, or by detecting the label according to the method of diagnosing described above in an individual that does not have metastatic hepatocellular carcinoma. In some embodiments, the individual is human.

In some embodiments, there is provided a method of diagnosing a disease or disorder associated with expression or aberrant expression of AFP in an individual (e.g., a mammal, such as a human), comprising (a) contacting a labeled anti-AMC antibody moiety according to any of the embodiments described above with a sample (such as whole blood or homogenized tissue) derived from the individual; and (b) determining the number of cells bound with the labeled anti-AMC antibody moiety in the sample, such that a value for the number of cells bound with the labeled anti-AMC antibody moiety above a threshold level indicates that the individual has the disease or disorder. The threshold level can be determined by various methods, including, for example, by determining the number of cells bound with the labeled anti-AMC antibody moiety according to the method of diagnosing described above in a first set of individuals that have the disease or disorder and a second set of individuals that do not have the disease or disorder, and setting the threshold to a level that allows for discrimination between the first and second sets. In some embodiments, the threshold level is zero, and the method comprises determining the presence or absence of cells bound with the labeled anti-AMC antibody moiety in the sample. In some embodiments, the method further comprises subtracting a background level of the number of cells bound with the labeled anti-AMC antibody moiety. Background level can be determined by various methods, including, for example, by determining the number of cells bound with the labeled anti-AMC antibody moiety in the individual prior to administration of the labeled anti-AMC antibody moiety, or by determining the number of cells bound with the labeled anti-AMC antibody moiety according to the method of diagnosing described above in an individual that does not have the disease or disorder. In some embodiments, the disease or disorder is cancer. In some embodiments, the cancer is selected, for example, from the group consisting of hepatocellular carcinoma, germ cell tumor, and breast cancer. In some embodiments, the cancer is hepatocellular carcinoma. In some embodiments, the cancer is metastatic hepatocellular carcinoma. In some embodiments, the cancer is metastatic hepatocellular carcinoma, and the sample is a blood sample (such as whole blood). In some embodiments, the individual is human.

In some embodiments, there is provided a method of diagnosing metastatic hepatocellular carcinoma in an individual (e.g., a mammal, such as a human), comprising (a) contacting a labeled anti-AMC antibody moiety according to any of the embodiments described above with a sample (such as whole blood) derived from the individual; and (b) determining the number of cells bound with the labeled anti-AMC antibody moiety in the sample, such that a value for the number of cells bound with the labeled anti-AMC antibody moiety above a threshold level indicates that the individual has metastatic hepatocellular carcinoma. The threshold level can be determined by various methods, including, for example, by determining the number of cells bound with the labeled anti-AMC antibody moiety according to the method of diagnosing described above in a first set of individuals that have metastatic hepatocellular carcinoma and a second set of individuals that do not have metastatic hepatocellular carcinoma, and setting the threshold to a level that allows for discrimination between the first and second sets. In some embodiments, the threshold level is zero, and the method comprises determining the presence or absence of cells bound with the labeled anti-AMC antibody moiety in the sample. In some embodiments, the method further comprises subtracting a background level of the number of cells bound with the labeled anti-AMC antibody moiety. Background level can be determined by various methods, including, for example, by determining the number of cells bound with the labeled anti-AMC antibody moiety in the individual prior to administration of the labeled anti-AMC antibody moiety, or by determining the number of cells bound with the labeled anti-AMC antibody moiety according to the method of diagnosing described above in an individual that does not have metastatic hepatocellular carcinoma. In some embodiments, the sample is blood (such as whole blood). In some embodiments, the individual is human.

Anti-AMC antibody moieties of the invention can be used to assay levels of AMC-presenting cell in a biological sample using methods known to those of skill in the art. Suitable antibody labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), technetium ($^{90}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), samarium ($^{153}$Sm), lutetium ($^{177}$Lu), gadolinium ($^{159}$Gd), promethium ($^{149}$Pm), lanthanum ($^{140}$La), ytterbium ($^{175}$Yb), holmium ($^{166}$Ho), yttrium ($^{90}$Y), scandium ($^{47}$Sc), rhenium ($^{186}$Re, $^{188}$Re), praseodymium ($^{142}$Pr), rhodium ($^{105}$Rh) and ruthenium ($^{97}$Ru); luminol; fluorescent labels, such as fluorescein and rhodamine; and biotin.

Techniques known in the art may be applied to labeled anti-AMC antibody moieties of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003). Aside from the above assays, various in vivo and ex vivo assays are available to the skilled practitioner. For example, one can expose cells within the body of the subject to an anti-AMC antibody moiety which is optionally labeled with a detectable label, e.g., a radioactive isotope, and binding of the anti-AMC antibody moiety to the cells can be evaluated, e.g., by external scanning for radioactivity or by analyzing a sample (e.g., a biopsy or other biological sample) derived from a subject previously exposed to the anti-AMC antibody moiety.

Articles of Manufacture and Kits

In some embodiments of the invention, there is provided an article of manufacture containing materials useful for the treatment of an AFP-positive disease such as cancer (for example hepatocellular carcinoma, germ cell tumor, or breast cancer), for delivering an anti-AMC construct to a cell presenting an AMC on its surface, or for isolation or detection of AMC-presenting cells in an individual. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an anti-AMC construct of the invention. The label or package insert indicates that the composition is used for treating the particular condition. The label or package insert will further comprise instructions for administering the anti-AMC construct composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating cancer (such as hepatocellular carcinoma, germ cell tumor, or breast cancer).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of an AFP-positive disease or disorder described herein, for delivering an anti-AMC construct to a cell presenting an AMC on its surface, or for isolation or detection of AMC-presenting cells in an individual, optionally in combination with the articles of manufacture. Kits of the invention include one or more containers comprising an anti-AMC construct composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-AMC construct (e.g., a full-length anti-AMC antibody, a multi-specific anti-AMC molecule (such as a bispecific anti-AMC antibody), or an anti-AMC immunoconjugate). In some embodiments, the kit comprises a) a composition comprising an anti-AMC construct, and b) an effective amount of at least one other agent, wherein the other agent increases the expression of MHC class I proteins and/or enhances the surface presentation of AFP peptides by MHC class I proteins (e.g., IFNγ, IFNβ, IFNα, or Hsp90 inhibitor). In some embodiments, the kit comprises a) a composition comprising an anti-AMC construct, and b) instructions for administering the anti-AMC construct composition to an individual for treatment of an AFP-positive disease, such as HCC. In some embodiments, the kit comprises a) a composition comprising an anti-AMC construct, b) an effective amount of at least one other agent, wherein the other agent increases the expression of MHC class I proteins and/or enhances the surface presentation of AFP peptides by MHC class I proteins (e.g., IFNγ, IFNβ, IFNα, or Hsp90 inhibitor), and c) instructions for administering the anti-AMC construct composition and the other agent(s) to an individual for treatment of an AFP-positive disease, such as HCC. The anti-AMC construct and the other agent(s) can be present in separate containers or in a single container. For example, the kit may comprise one distinct composition or two or more compositions wherein one composition comprises an anti-AMC construct and another composition comprises another agent.

In some embodiments, the kit comprises a) a composition comprising an anti-AMC construct (e.g., a full-length anti-AMC antibody, a multi-specific anti-AMC molecule (such as a bispecific anti-AMC antibody), or an anti-AMC immunoconjugate), and b) instructions for combining the anti-AMC construct with cells (such as cells, e.g., immune cells, derived from an individual) to form a composition comprising anti-AMC construct/cell conjugates and administering the anti-AMC construct/cell conjugate composition to the individual for treatment of an AFP-positive disease (such as HCC). In some embodiments, the kit comprises a) a composition comprising an anti-AMC construct, and b) a cell (such as a cytotoxic cell). In some embodiments, the kit comprises a) a composition comprising an anti-AMC construct, b) a cell (such as a cytotoxic cell), and c) instructions for combining the anti-AMC construct with the cell to form a composition comprising anti-AMC construct/cell conjugates and administering the anti-AMC construct/cell conjugate composition to an individual for the treatment of an AFP-positive disease, such as HCC. In some embodiments, the kit comprises a composition comprising an anti-AMC construct in association with a cell (such as an cytotoxic cell). In some embodiments, the kit comprises a) a composition comprising an anti-AMC construct in association with a cell (such as a cytotoxic cell), and b) instructions for administering the composition to an individual for the treatment of an AFP-positive disease, such as HCC. In some embodiments, the association is by conjugation of the anti-AMC construct to a molecule on the surface of the cell. In some embodiments, the association is by insertion of a portion of the anti-AMC construct into the outer membrane of the cell.

In some embodiments, the kit comprises a nucleic acid (or set of nucleic acids) encoding an anti-AMC construct (e.g., a full-length anti-AMC antibody, a multi-specific anti-AMC molecule (such as a bispecific anti-AMC antibody), an anti-AMC CAR, or an anti-AMC immunoconjugate) or polypeptide portions thereof. In some embodiments, the kit comprises a) a nucleic acid (or set of nucleic acids) encoding an anti-AMC construct or polypeptide portions thereof, and b) a host cell (such as an effector cell) for expressing the nucleic acid (or set of nucleic acids). In some embodiments, the kit comprises a) a nucleic acid (or set of nucleic acids) encoding an anti-AMC construct or polypeptide portions thereof, and b) instructions for i) expressing the anti-AMC construct in a host cell (such as an effector cell, e.g., a T cell), ii) preparing a composition comprising the anti-AMC construct or the host cell expressing the anti-AMC construct, and iii) administering the composition comprising the anti-AMC construct or the host cell expressing the anti-AMC construct to an individual for the treatment of an AFP-positive disease, such as HCC. In some embodiments, the host cell is derived from the individual. In some embodiments, the kit comprises a) a nucleic acid (or set of nucleic acids) encoding an anti-AMC construct or polypeptide portions thereof, b) a host cell (such as an effector cell) for expressing the nucleic acid (or set of nucleic acids), and c) instructions for i) expressing the anti-AMC construct in the host cell, ii) preparing a composition comprising the anti-AMC construct or the host cell expressing the anti-AMC construct, and iii) administering the composition comprising the anti-AMC construct or the host cell expressing the anti-AMC construct to an individual for the treatment of an AFP-positive disease, such as HCC.

In some embodiments, the kit comprises a nucleic acid encoding an anti-AMC CAR. In some embodiments, the kit comprises a vector comprising a nucleic acid encoding an anti-AMC CAR. In some embodiments, the kit comprises a) a vector comprising a nucleic acid encoding an anti-AMC CAR, and b) instructions for i) introducing the vector into effector cells, such as T cells derived from an individual, ii) preparing a composition comprising the anti-AMC CAR effector cells, and iii) administering the anti-AMC CAR effector cell composition to the individual for treatment of an AFP-positive disease, such as HCC.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-AMC construct compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of an anti-AMC construct (e.g., a full-length anti-AMC antibody, a multi-specific anti-AMC molecule (such as a bispecific anti-AMC antibody), an anti-AMC CAR, or an anti-AMC immunoconjugate) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-AMC construct and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Exemplary Embodiments

Embodiment 1

In some embodiments, there is provided an isolated anti-AMC construct comprising an antibody moiety that specifically binds to a complex comprising an alpha-fetoprotein (AFP) peptide and a major histocompatibility (MHC) class I protein (an AFP/MHC class I complex, or AMC).

Embodiment 2

In some further embodiments of embodiment 1, the AFP/MHC class I complex is present on a cell surface.

Embodiment 3

In some further embodiments of embodiment 1, the AFP/MHC class I complex is present on the surface of a cancer cell.

Embodiment 4

In some further embodiments of any one of embodiments 1-3, the MHC class I protein is human leukocyte antigen (HLA)-A.

Embodiment 5

In some further embodiments of embodiment 4, the MHC class I protein is HLA-A02.

Embodiment 6

In some further embodiments of embodiment 5, the MHC class I protein is the HLA-A*02:01 subtype of the HLA-A02 allele.

Embodiment 7

In some further embodiments of any one of embodiments 1-6, the antibody moiety cross-reacts with a complex comprising the AFP peptide and a second MHC class I protein having a different HLA allele than the MHC class I protein.

Embodiment 8

In some further embodiments of any one of embodiments 1-7, the AFP peptide is 8 to 12 amino acids in length.

Embodiment 9

In some further embodiments of any one of embodiments 1-8, the AFP peptide is derived from human AFP.

Embodiment 10

In some further embodiments of any one of embodiments 1-9, the AFP peptide has an amino acid sequence selected from the group consisting of SEQ ID NOs: 3-13 and 16.

Embodiment 11

In some further embodiments of embodiment 9, the AFP peptide has the amino acid sequence of FMNKFIYEI (SEQ ID NO: 4).

Embodiment 12

In some further embodiments of any one of embodiments 1-11, the isolated anti-AMC construct cross-reacts with a complex comprising an interspecies variant of the AFP peptide and the MHC class I protein.

Embodiment 13

In some further embodiments of any one of embodiments 1-12, the antibody moiety is human, humanized, or semi-synthetic.

Embodiment 14

In some further embodiments of any one of embodiments 1-13, the antibody moiety is a full-length antibody, a Fab, a Fab', a (Fab')2, an Fv, or a single chain Fv (scFv).

Embodiment 15

In some further embodiments of any one of embodiments 1-14, the antibody moiety binds to the AFP/MHC class I complex with an equilibrium dissociation constant (Kd) from about 0.1 pM to about 500 nM.

Embodiment 16

In some further embodiments of any one of embodiments 1-15, the isolated anti-AMC construct binds to the AFP/MHC class I complex with a Kd from about 0.1 pM to about 500 nM.

Embodiment 17

In some further embodiments of any one of embodiments 1-16, the antibody moiety comprises:
i) a heavy chain variable domain comprising a heavy chain complementarity determining region (HC-CDR) 1 comprising the amino acid sequence of G-F/Y-S/T-F-D/S/T-D/N/S-Y/A-A/G/W (SEQ ID NO: 87), or a variant thereof comprising up to about 3 amino acid substitutions, an HC-CDR2 comprising the amino acid sequence of I/S-K/S-X-H/Y-X-G-X-T (SEQ ID NO: 88), or a variant thereof comprising up to about 3 amino acid substitutions, and an HC-CDR3 comprising the amino acid sequence of A/G-X-W/Y-Y-X-X-X-F/Y-D (SEQ ID NO: 89); or a variant thereof comprising up to about 3 amino acid substitutions; and
ii) a light chain variable domain comprising a light chain complementarity determining region (LC-CDR) 1 comprising the amino acid sequence of S/T-G/S-D/N-I/V-A/G-A/S/V-X-H/Y (SEQ ID NO: 120), or a variant thereof comprising up to about 3 amino acid substitutions, and an LC-CDR3 comprising the amino acid sequence of Q-S/T-Y/W-D/T-S/T-A/S (SEQ ID NO: 121); or a variant thereof comprising up to 3 amino acid substitutions, wherein
X can be any amino acid.

Embodiment 18

In some further embodiments of any one of embodiments 1-16, the antibody moiety comprises:
i) a heavy chain variable domain comprising an HC-CDR1 comprising the amino acid sequence of any one of SEQ ID NOs: 57-66, or a variant thereof comprising up to about 5 amino acid substitutions, an HC-CDR2 comprising the amino acid sequence of any one of SEQ ID NOs: 67-76, or a variant thereof comprising up to about 5 amino acid substitutions, and an HC-CDR3 comprising the amino acid sequence of any one of SEQ ID NOs: 77-86; or a variant thereof comprising up to about 5 amino acid substitutions; and
ii) a light chain variable domain comprising an LC-CDR1 comprising the amino acid sequence of any one of SEQ ID NOs: 90-99, or a variant thereof comprising up to about 5 amino acid substitutions, an LC-CDR2 comprising the amino acid sequence of any one of SEQ ID NOs: 100-109, or a variant thereof comprising up to about 3 amino acid substitutions, and an LC-CDR3 comprising the amino acid sequence of any one of SEQ ID NOs: 110-119; or a variant thereof comprising up to about 5 amino acid substitutions.

Embodiment 19

In some further embodiments of any one of embodiments 1-16, the antibody moiety comprises:
i) a heavy chain (HC) variable domain comprising an HC-CDR1 comprising the amino acid sequence of any one of SEQ ID NOs: 57-66, an HC-CDR2 comprising the amino acid sequence of any one of SEQ ID NOs: 67-76, and an HC-CDR3 comprising the amino acid sequence of any one of SEQ ID NOs: 77-86; or a variant thereof comprising up to about 5 amino acid substitutions in the HC-CDR regions; and
ii) a light chain (LC) variable domain comprising an LC-CDR1 comprising the amino acid sequence of any one of SEQ ID NOs: 90-99, an LC-CDR2 comprising the amino acid sequence of any one of SEQ ID NOs: 100-109, and an LC-CDR3 comprising the amino acid sequence of any one of SEQ ID NOs: 110-119; or a variant thereof comprising up to about 5 amino acid substitutions in the LC-CDR regions.

Embodiment 20

In some further embodiments of embodiment 18 or 19, the antibody moiety comprises a) a heavy chain variable domain comprising the amino acid sequence of any one of SEQ ID NOs: 17-26, or a variant thereof having at least about 95% sequence identify to any one of SEQ ID NOs: 17-26; and b) a light chain variable domain comprising the amino acid sequence of any one of SEQ ID NOs: 27-36, or a variant thereof having at least about 95% sequence identity to any one of SEQ ID NOs: 27-36.

Embodiment 21

In some further embodiments of embodiment 20, the antibody moiety comprises a heavy chain variable domain comprising the amino acid sequence of any one of SEQ ID NOs: 17-26 and a light chain variable domain comprising the amino acid sequence of any one of SEQ ID NOs: 27-36.

Embodiment 22

In some further embodiments of any one of embodiments 1-21, the isolated anti-AMC construct is a full-length antibody.

Embodiment 23

In some further embodiments of any one of embodiments 1-22, the isolated anti-AMC construct is monospecific.

Embodiment 24

In some further embodiments of any one of embodiments 1-22, the isolated anti-AMC construct is multispecific.

Embodiment 25

In some further embodiments of embodiment 24, the isolated anti-AMC construct is bispecific.

Embodiment 26

In some further embodiments of embodiment 24 or 25, the isolated anti-AMC construct is a tandem scFv, a diabody (Db), a single chain diabody (scDb), a dual-affinity retargeting (DART) antibody, a dual variable domain (DVD) antibody, a knob-into-hole (KiH) antibody, a dock and lock (DNL) antibody, a chemically cross-linked antibody, a heteromultimeric antibody, or a heteroconjugate antibody.

Embodiment 27

In some further embodiments of embodiment 26, the isolated anti-AMC construct is a tandem scFv comprising two scFvs linked by a peptide linker.

Embodiment 28

In some further embodiments of embodiment 27, the peptide linker comprises the amino acid sequence GGGGS.

Embodiment 29

In some further embodiments of any one of embodiments 24-28, the isolated anti-AMC construct further comprises a second antibody moiety that specifically binds to a second antigen.

Embodiment 30

In some further embodiments of embodiment 29, the second antigen is an antigen on the surface of a T cell.

Embodiment 31

In some further embodiments of embodiment 30, the second antigen is selected from the group consisting of CD3γ, CD3δ, CD3ε, CD3ζ, CD28, OX40, GITR, CD137, CD27, CD40L, and HVEM.

Embodiment 32

In some further embodiments of embodiment 30, the second antigen is CD3ε, and the isolated anti-AMC construct is a tandem scFv comprising an N-terminal scFv specific for the AFP/MHC class I complex and a C-terminal scFv specific for CD3ε.

Embodiment 33

In some further embodiments of embodiment 30, the T cell is selected from the group consisting of a cytotoxic T cell, a helper T cell, and a natural killer T cell.

Embodiment 34

In some further embodiments of embodiment 29, the second antigen is an antigen on the surface of a natural killer cell, a neutrophil, a monocyte, a macrophage or a dendritic cell.

Embodiment 35

In some further embodiments of any one of embodiments 1-21, the isolated anti-AMC construct is a chimeric antigen receptor.

Embodiment 36

In some further embodiments of embodiment 35, the chimeric antigen receptor comprises an extracellular domain comprising the antibody moiety, a transmembrane domain, and an intracellular signaling domain comprising a CD3ζ intracellular signaling sequence and a CD28 intracellular signaling sequence.

Embodiment 37

In some further embodiments of any one of embodiments 1-21, the isolated anti-AMC construct is an immunoconjugate comprising the antibody moiety and an effector molecule.

Embodiment 38

In some further embodiments of embodiment 36, the effector molecule is a therapeutic agent selected from the group consisting of a drug, a toxin, a radioisotope, a protein, a peptide, and a nucleic acid.

Embodiment 39

In some further embodiments of embodiment 38, the therapeutic agent is a drug or a toxin.

Embodiment 40

In some further embodiments of embodiment 37, the effector molecule is a label.

Embodiment 41

In some embodiments there is provided a pharmaceutical composition comprising the isolated anti-AMC construct of any one of embodiments 1-39.

Embodiment 42

In some embodiments there is provided a host cell expressing the isolated anti-AMC construct of any one of embodiments 1-40.

Embodiment 43

In some embodiments there is provided a nucleic acid encoding the polypeptide components of the isolated anti-AMC construct of any one of embodiments 1-40.

Embodiment 44

In some embodiments there is provided a vector comprising the nucleic acid of embodiment 43.

Embodiment 45

In some embodiments there is provided an effector cell expressing the isolated anti-AMC construct of embodiment 35 or 36.

Embodiment 46

In some further embodiments of embodiment 45, the effector cell is a T cell.

Embodiment 47

In some embodiments there is provided a method of detecting a cell presenting a complex comprising an AFP peptide and an MHC class I protein on its surface, comprising contacting the cell with the isolated anti-AMC construct of embodiment 40 and detecting the presence of the label on the cell.

Embodiment 48

In some embodiments there is provided a method of treating an individual having an AFP-positive disease, comprising administering to the individual an effective amount of the pharmaceutical composition of embodiment 41.

Embodiment 49

In some embodiments there is provided a method of treating an individual having an AFP-positive disease, comprising administering to the individual an effective amount of the effector cell of embodiments 45 or 46.

Embodiment 50

In some further embodiments of embodiment 48 or 49, the administration is via intravenous route.

Embodiment 51

In some further embodiments of embodiment 48 or 49, the administration is via intratumoral route.

Embodiment 52

In some further embodiments of embodiment 48 or 49, the administration is to an injection site distal to a first disease site.

Embodiment 53

In some further embodiments of embodiment 52, the injection site is a first tumor distal to the first disease site.

Embodiment 54

In some further embodiments of embodiment 52 or 53, the first disease site is an AFP-positive tumor.

Embodiment 55

In some embodiments there is provided a method of diagnosing an individual having an AFP-positive disease, comprising:
a) administering an effective amount of the isolated anti-AMC construct of embodiment 40 to the individual; and
b) determining the level of the label in the individual, wherein a level of the label above a threshold level indicates that the individual has the AFP-positive disease.

Embodiment 56

In some embodiments there is provided a method of diagnosing an individual having an AFP-positive disease, comprising:
a) contacting a sample derived from the individual with the isolated anti-AMC construct of embodiment 40; and
b) determining the number of cells bound with the isolated anti-AMC construct in the sample, wherein a value for the number of cells bound with the isolated anti-AMC construct above a threshold level indicates that the individual has the AFP-positive disease.

Embodiment 57

In some further embodiments of any one of embodiments 48-56, the AFP-positive disease is cancer.

Embodiment 58

In some further embodiments of embodiment 57, the cancer is hepatocellular carcinoma, germ cell tumor, or breast cancer.

Embodiment 59

In some further embodiments of embodiment 58, the cancer is hepatocellular carcinoma.

Embodiment 60

In some further embodiments of embodiment 59, the cancer is metastatic hepatocellular carcinoma.

Embodiment 61

In some further embodiments of any one of embodiments 48-54, the AFP-positive disease is hepatocellular carcinoma and metastasis is inhibited.

EXAMPLES

Materials
Cell Samples, Cell Lines, and Antibodies

The cell lines HepG2, SK-Hep1, MCF7, Malme-3M, CA46, THP-1, Colo205, ASPC1, OVCAR3, LnCAP, A498 and Hela were obtained from the American Type Culture Collection. SK-Hep1-MiniG (or SK-Hep1 AFP MG), MCF7-MiniG and Hela-MiniG (or Hela-MG) were generated by transducing the respective parental cell lines with an AFP158 peptide expressing minigene cassette, which results in a high level of cell surface expression of AFP158/HLA-A*02:01 complex in SK-Hep1 and MCF7 cells. Hela is HLA-A03- and HLA-A68-positive and HLA*A02:01-negative, and therefore Hela-MiniG served as AFP158 minigene expressing, but AFP158/HLA*A02:01 negative control cell line. The cell lines were cultured in RPMI 1640 supplemented with 10% FBS, 2 mM glutamine at 37° C./5% $CO_2$.

The following antibodies were purchased: monoclonal Ab against human HLA-A02 (clone BB7.2) conjugated to FITC or APC, and its isotype control mouse IgG2b/FITC or APC to human or mouse CD3, CD 19, CD56, CD33, CD34 (BD Biosciences, San Diego), goat F(ab)$_2$ anti-human IgG conjugated to PE or FITC and goat F(ab)$_2$ anti-mouse IgG (Invitrogen).

All peptides were synthesized by Genemed Synthesis, Inc. (San Antonio, Tex.). Peptides were >90% pure. The peptides were dissolved in DMSO and diluted in saline at 5 mg/mL and frozen at −180° C. Biotinylated single chain AFP peptide/HLA-A*02:01 and control peptide/HLA-A*02:01 complexes were synthesized by refolding the peptides with recombinant HLA-A*02:01 and β2 microglobulin ((β2M). 19 control peptides (SEQ ID NOs: 122-140) that bind HLA-A*02:01 were generated from the following 15 genes: BCR, BTG2, CALR, CD247, CSF2RA, CTSG, DDX5, DMTN, HLA-E, IFI30, IL7, PIM1, PPP2R1B, RPS6KB1, and SSR1.

Example 1. Production of Biotinylated AFP158/HLA-A*02:01 Complex Monomer

Figure 2:
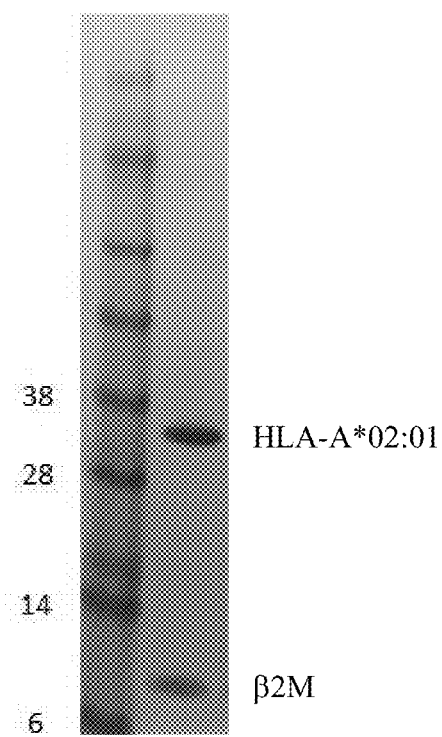
FIG. 2 shows reducing SDS-PAGE analysis to determine the purity of AFP158/HLA-A*02:01 complex isolated following SEC. Major bands correspond to HLA-A*02:01 and β2M subunits.

Biotinylated AFP158/HLA-A*02:01 complex monomers were prepared according to standard protocols (Altman, J. D. & Davis, M. M., *Current Protocols in Immunology* 17.3.1-17.3.33, 2003). In brief, DNA encoding full-length human β-2 microglobulin (β2M) was synthesized by Genewiz and cloned into vector pET-27b. The BirA substrate peptide (BSP) was added to the C-terminus of HLA-A*02:01 extracellular domain (ECD). DNA encoding HLA-A*02:01 ECD-BSP was also synthesized by Genewiz and cloned into vector pET-27b. The vectors expressing human β2M and HLA-A*02:01 ECD-BSP were transformed into *E. coli* BL21 cells separately, and isolated as inclusion bodies from bacterial culture. Peptide ligand AFP158 refolded with human β2M and HLA-A*02:01 ECD-BSP to form AFP158/HLA-A*02:01 complex monomer. Folded peptide/HLA-A*02:01 monomers were concentrated by ultrafiltration and further purified through size-exclusion chromatography. HiPrep 26/60 Sephacryl S-300 HR was equilibrated with 1.5 column volumes of Hyclone Dulbecco's Phosphate Buffered Saline solution (Thermo Scientific, Cat No. SH3002802). The unpurified sample was loaded and eluted with 1 column volume. The first peak, corresponding to misfolded aggregates, eluted at approximately 111.3 mL, the peak corresponding to the properly folded MHC complex was observed at 212.5 mL, and the peak corresponding to free β2M was observed at 267.2 mL (FIG. 1). SDS-PAGE of the purified AFP158/MHC complex was performed to determine protein purity. In brief, 1 μg of the protein complex was mixed with 2.5 μL of the NuPAGE LDS Sample Buffer (Life Technologies, NP0008) and brought up to 10 μL with deionized water. The sample was heated at 70° C. for 10 minutes, and then loaded onto the gel. Gel electrophoresis was performed at 180V for 1 hour. HLA-A*02:01 and β2M subunits were observed as the major bands on the gel (FIG. 2). Peptide/HLA-A*02:01 monomers were biotinylated via BirA-mediated enzymatic reaction and subsequently purified by high-resolution anion-exchange chromatography. Biotinylated peptide/HLA-A*02:01 monomers were stored in PBS at −80° C.

Example 2. Selection and Characterization of scFv Specific for AFP158/HLA-A*02:01 Complexes A collection of human scFv antibody phage display libraries (diversity=10×10$^{10}$) constructed by Eureka Therapeutics was used for the selection of human mAbs specific to AFP158/HLA-A*02:01. 15 fully human phage scFv libraries were used to pan against AFP158/HLA-A*02:01 complex. In order to reduce the conformational change of MHC1 complex introduced by immobilizing the protein complex onto plastic surfaces, solution panning and cell panning were used in place of conventional plate panning. In solution panning, biotinylated antigens were first mixed with the human scFv phage library after extended washing with PBS buffer, and then antigen-scFv antibody phage complexes were pulled down by streptavidin-conjugated Dynabeads M-280 through a magnetic rack. The bound clones were then eluted and used to infect *E. coli* XL1-Blue cells. In cell panning, T2 cells loaded with AFP158 peptide were first mixed with the human scFv phage library. T2 cells are a TAP-deficient, HLA-A*02:01$^+$ lymphoblast cell line. To load peptide, T2 cells were pulsed with peptides (50 ug/ml) in serum-free RPMI1640 medium in the presence of 20 μg/ml β2M overnight. After extended washing with PBS, peptide-loaded T2 cells with bound scFv antibody phage were spun down. The bound clones were then eluted and used to infect *E. coli* XL1-Blue cells. The phage clones expressed in bacteria were then purified. The panning was performed for 3-4 rounds with either solution panning, cell panning or a combination of solution and cell panning to enrich for scFv phage clones that bound AFP158/HLA-A*02:01 specifically.

Figure 3:
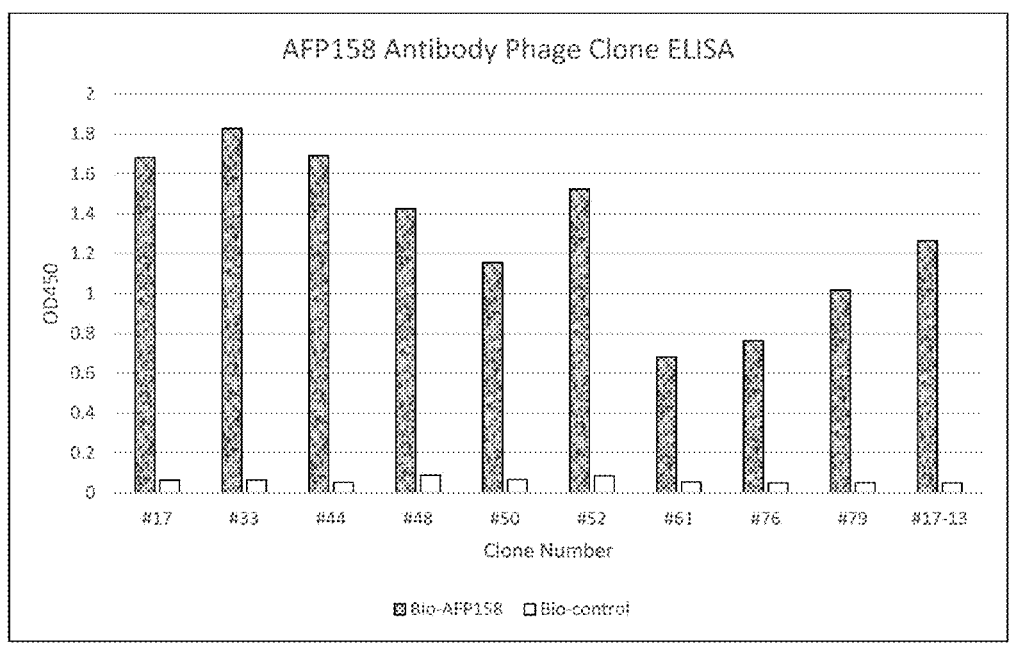
FIG. 3 shows the results of phage clone ELISA for specific binding of biotinylated AFP158 peptide/HLA-A*02:01 (Bio-AFP158) versus biotinylated control peptide/HLA-A*02:01 (Bio-control).

Streptavidin ELISA plates were coated with biotinylated AFP158/HLA-A*02:01 complex monomer (Bio-AFP158) or biotinylated control peptide/HLA-A*02:01 monomer (Bio-control), respectively. Individual phage clones from enriched phage display panning pools against AFP158/HLA-A*02:01 complex were incubated in the coated plates. Binding of the phage clones was detected by HRP-conjugated anti-M13 antibodies and developed using HRP substrate. The absorbance was read at 450 nm. 605 positive clones were identified through ELISA screening of 1260 phage clones enriched from phage panning. FIG. 3 provides an example of phage clone binding to biotinylated AFP158/

Figure 4:
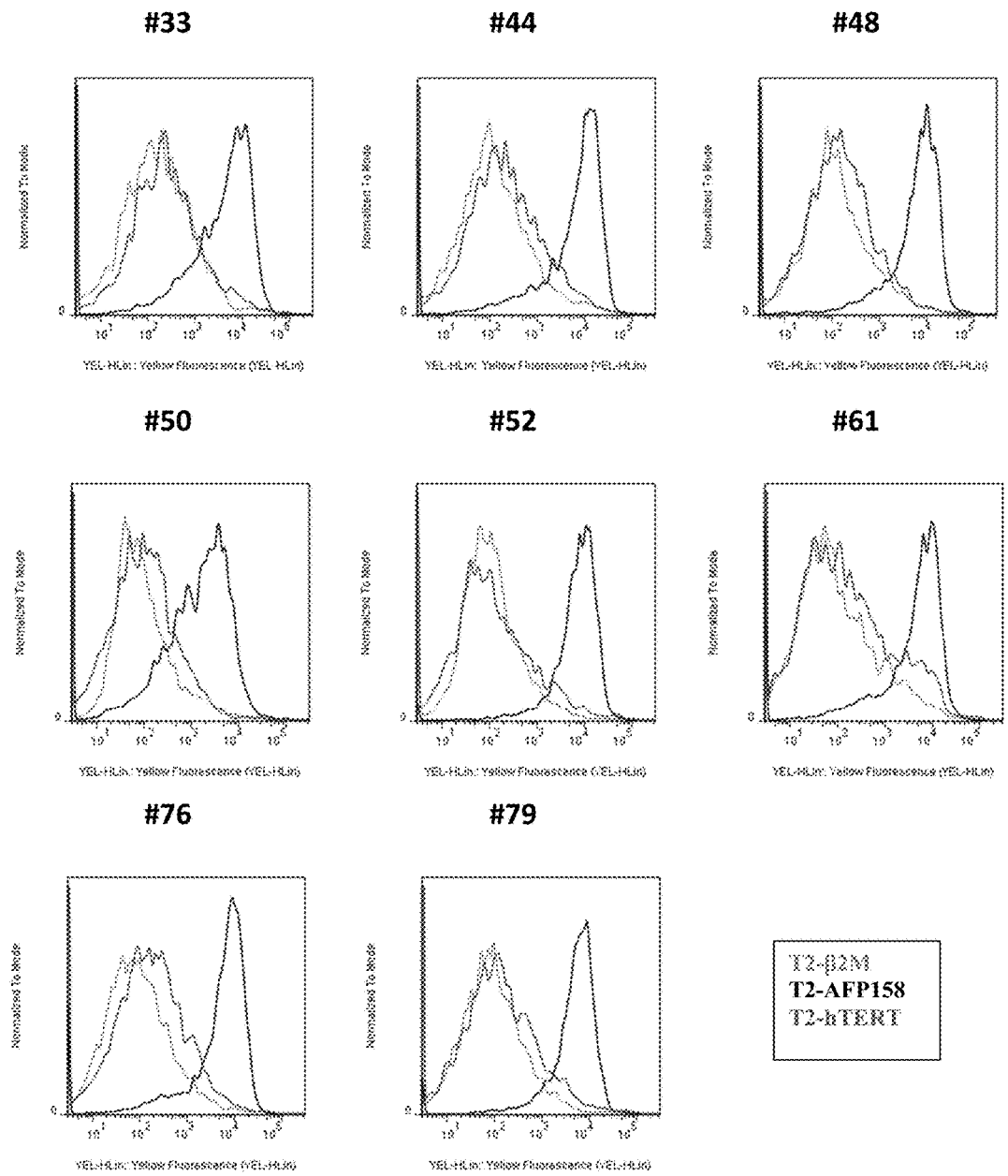
FIG. 4 shows the results of phage clone FACS binding assays for binding of β2M-loaded, β2M/AFP158 peptide-loaded and β2M/hTERT peptide-loaded T2 cells.

HLA-A*02:01 monomer in an ELISA assay. 82 unique clones were identified by DNA sequencing of the 605 ELISA positive phage clones. Positive clones were determined by standard ELISA against biotinylated AFP158/HLA-A*02:01 complex monomer. Then, unique antibody clones were identified through DNA sequencing of ELISA-positive clones. Specific and unique clones were further tested for their binding to HLA-A2/peptide complexes on live cell surfaces by flow cytometry (FACS analysis) using AFP158-loaded live T2 cells. T2 cells loaded with different peptides and β2M were first stained with purified scFv phage clones, followed by staining with a mouse anti-M13 mAb, and finally the R-PE conjugated horse anti-mouse IgG from Vector Labs. Each step of the staining was done between 30-60 minutes on ice and the cells were washed twice between staining. Among the 82 clones, 44 recognize AFP158-loaded T2 cells specifically. FIG. 4 provides an example of AFP158/HLA-A*02:01 specific phage clone binding to peptide-loaded T2 cells through FACS. The phage clones specifically bound to AFP158-loaded T2 cells and did not recognize T2 cells loaded with hTERT-derived peptide ILAKFLHWL (hTERT540, SEQ ID NO: 141) in the context of HLA-A*02:01, or T2 cells with β2M but without peptide loaded.

Example 3. Characterization of FACS-Positive AFP158-Specific Phage Clones

Cross-Reactivity to Mouse AFP158 Peptide

Figure 5:
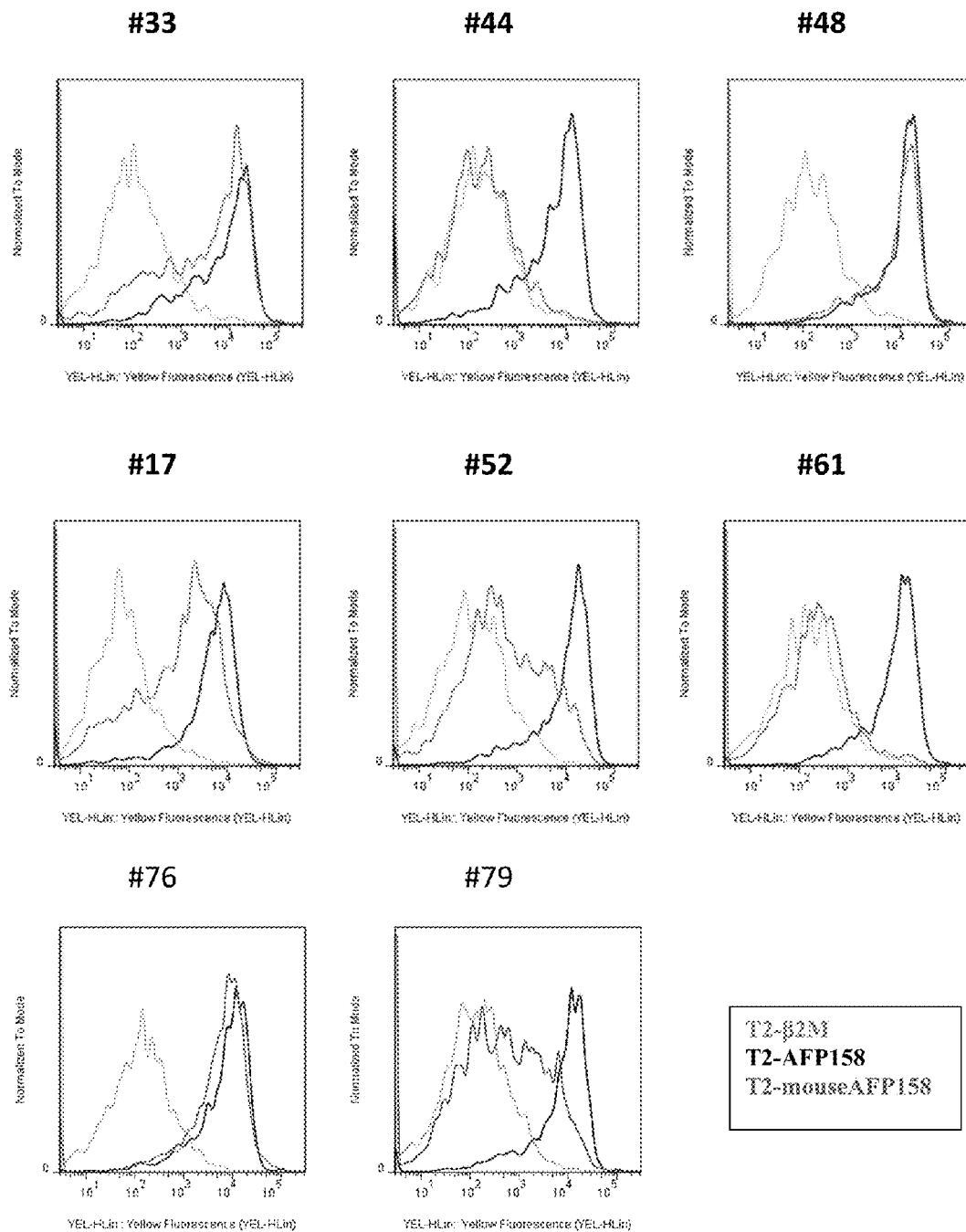
FIG. 5 shows the results of phage clone FACS binding assays for cross-reactivity with β2M/human AFP158 peptide-loaded T2 cells and β32M/mouse AFP158 peptide-loaded T2 cells versus β32M-loaded T2 cells.

Clones selected from FACS binding analysis against AFP158-loaded T2 cells were characterized further for cross-reactivity towards mouse AFP158 peptide/HLA-A*02:01 complex on live cell surfaces by FACS analysis using mouse AFP158-loaded live T2 cells. Mouse AFP158 peptide differs from human AFP158 peptide by two amino acids at position 4 and position 9. The mouse AFP158 peptide sequence is FMNRFIYEV (SEQ ID NO: 16), while the human AFP158 peptide sequence is FMNKFIYEI (SEQ ID NO: 4). Antibodies cross-reacting with both human and mouse AFP158 peptide/MHC complexes are useful for assessing antibody drug toxicity in HLA-A*02:01 transgenic mice. Among the phage clones tested, 4 clones (#17, #33, #48 and #76) recognized both human AFP158- and mouse AFP158-loaded T2 cells (FIG. 5). Clones #52 and #79 also bound to mouse AFP158-loaded T2 cells, but to a lesser degree.

Epitope Mapping by Alanine Walking

Figure 6:
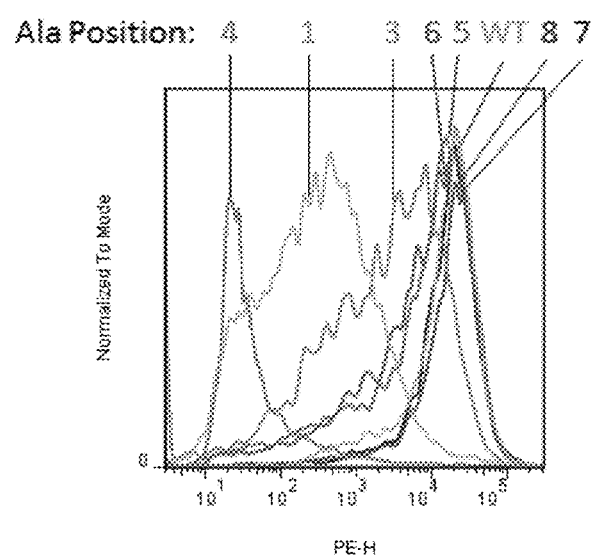
FIG. 6 shows the results of phage clone #52 FACS binding assays for T2 cells loaded with AFP158 peptide having single alanine substitutions at varying positions.

To investigate with precision the epitope for the mAb recognition, human AFP158 peptides with alanine substitutions at positions 1, 3, 4, 5, 6, 7 and 8 (SEQ ID NOs: 7-13) were pulsed onto T2 cells. Antibody phage clones were then tested for binding to these peptide-loaded T2 cells by FACS analysis. Although all the antibodies recognized the small conformational epitope formed by the AFP158 peptide and its surrounding MHCα chain residues, the key peptide residues interacting with different antibodies were quite different. For example, clone #52 is predicted to bind to the N-terminal half of the AFP158 peptide since alanine substitution at position 1 or 3 dramatically reduced binding to the peptide-loaded T2 cells, and alanine substitution at position 4 completely abrogated the binding of clone #52. In contrast, alanine substitutions at position 5, 6, 7 or 8 didn't change the binding of clone #52. Clone #17-13, on the other hand, was insensitive to alanine substitution at position 4, but was sensitive to changes at position 3, 5 and 7. FIG. 6 provides an example of FACS analysis, showing the binding of phage clone #52 to T2 cells loaded with the various AFP peptides. Table 6 summaries the binding of several AFP158/HLA-A*02:01-specific antibody clones to alanine-substituted human AFP158 peptide-loaded T2 cells.

TABLE 6

| Peptide | Ala Position | ET1402-52 | ET1402-61 | ET1402-76 | ET1402-79 | AM1402-17-13 |
|---|---|---|---|---|---|---|
| FMNKFIYEI |   | 37900 | 30400 | 14400 | 30100 | 83300 |
| AMNKFIYEI | 1 | 468 | 12300 | 5458 | 21000 | 55600 |
| FMAKFIYEI | 3 | 4470 | 38600 | 38200 | 786 | 2914 |
| FMNAFIYEI | 4 | 20.9 | 15.1 | 38.3 | 79.2 | 50800 |
| FMNKAIYEI | 5 | 21800 | 3719 | 49300 | 34.4 | 1500 |
| FMNKFAYEI | 6 | 18800 | 169 | 40300 | 27.7 | 28800 |
| FMNKFIAEI | 7 | 42500 | 1110 | 29300 | 907 | 572 |
| FMNKFIYAI | 8 | 38500 | 1748 | 53300 | 16100 | 43200 |
| Sensitive Position |   | 4, 1, 3 | 4, 6, 7, 8, 5 | 4, 1 | 5, 6, 4, 3, 7 | 7, 5, 6 |

Antibody Binding Specificity Evaluation against Endogenous Peptides

Figure 7:
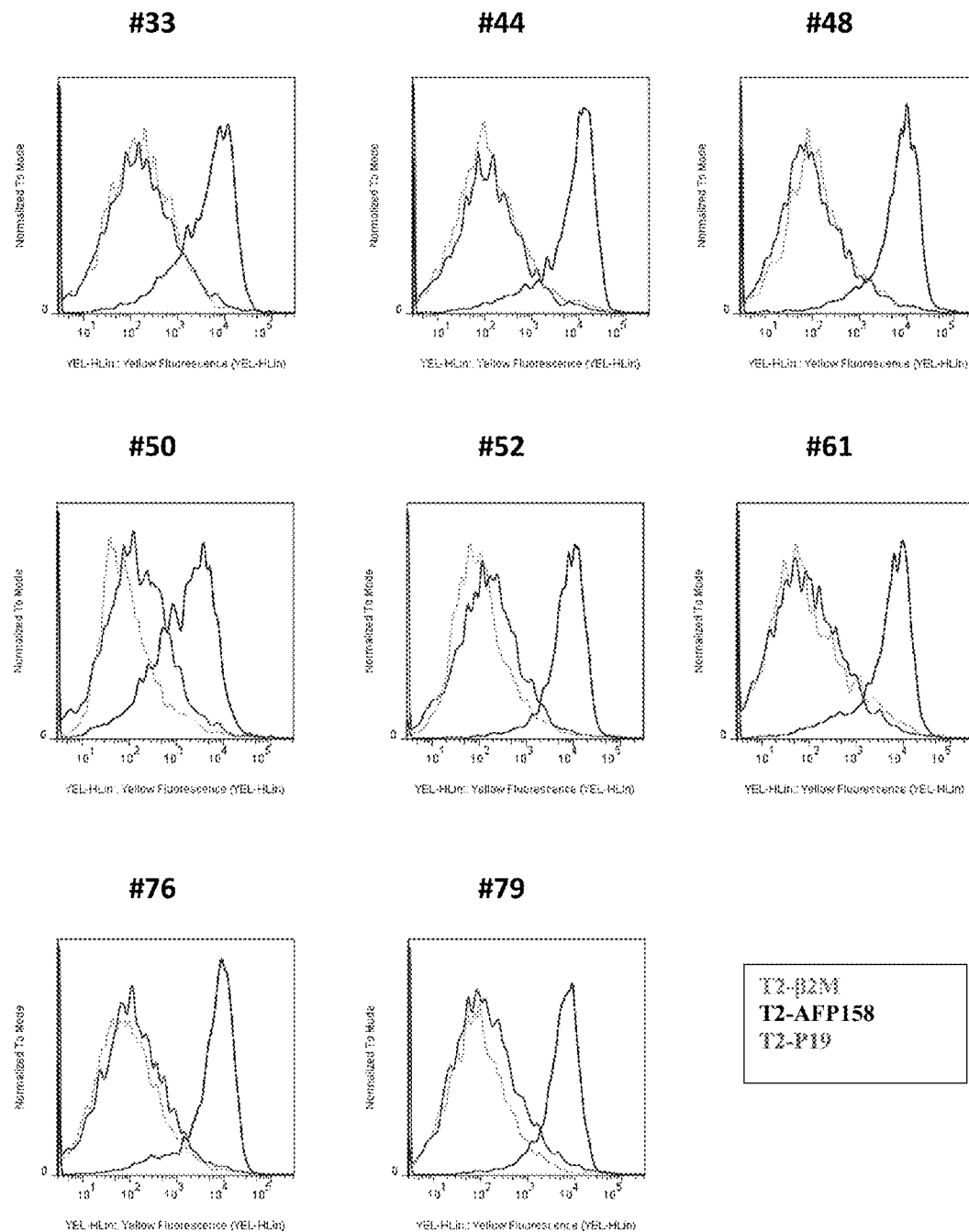
FIG. 7 shows the results of phage clone FACS binding assays for binding of β2M AFP158 peptide-loaded T2 cells, T2 cells loaded with β2M and a mixture of peptides derived from normally expressed endogenous proteins or β2M-loaded T2 cells.

On average, each nucleated cell in the human body expresses about half a million different peptide/MHC class I complexes. In order to develop anti-peptide/MHCI-complex antibodies into anti-cancer drugs with high specificity and therapeutic index, it is essential for the antibodies to specifically recognize the target peptide/MHCI complex, but not the MHCI molecule itself, or MHCI molecules bound to other peptides presented on cell surfaces. For the current study, the relevant MHCI molecule is HLA-A*02:01. During the early stages of our phage panning and screening, we eliminated antibodies that bound to the HLA-A*02:01 molecule alone (see, for example, FIGS. 3 and 4). The top phage clones were also screened against 19 endogenous HLA-A*02:01 peptides, which were derived from proteins normally expressed in multiple types of nucleated human cells, such as globin α chain, β chain, nuclear protein p68, and the like. The pool of endogenous peptides (P19, SEQ ID NOs: 122-140) was loaded into T2 cells and antibody binding was determined through FACS analysis. As shown in FIG. 7, the AFP158/HLA-A*02:01-specific antibody phage clones bound AFP158 peptide-loaded T2 cells, but not T2 cells loaded with endogenous peptides. We conclude that the identified antibodies are specific to AFP158 peptide/HLA-A*02:01 complexes, and do not recognize HLA-A*02:01 molecules bound to other HLA-A*02:01 peptides tested.

Example 4. Engineering Bispecific Antibodies

Figure 8:
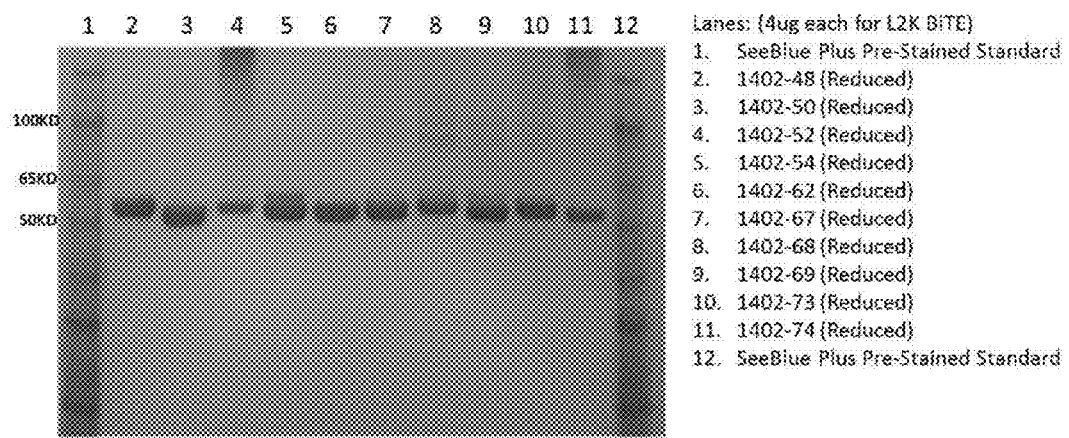
FIG. 8 shows SDS-PAGE analysis for molecular weight determination of purified anti-AFP158/MHC bispecific antibodies.
Figure 9:
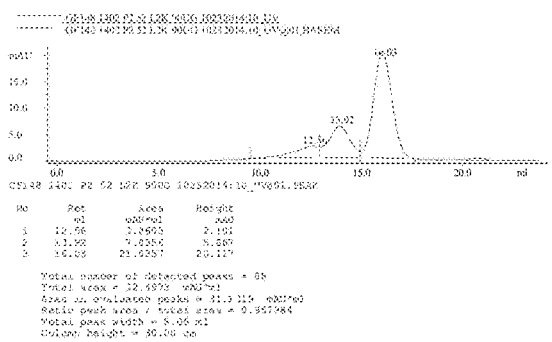
FIG. 9 shows SEC chromatograms of exemplary purified AFP158 bispecific antibodies to assess level of aggregation. anti-AFP158/MHC bispecific antibody monomer: ~15.8 mL.
Figure 9:
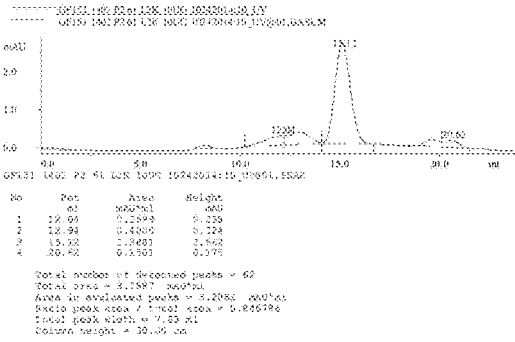
Figure 9:
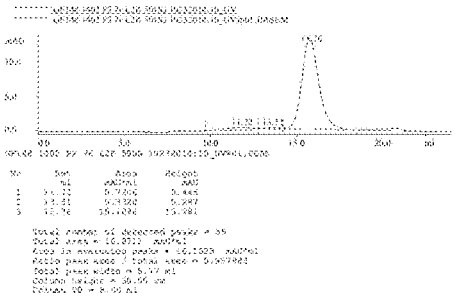
Figure 9:
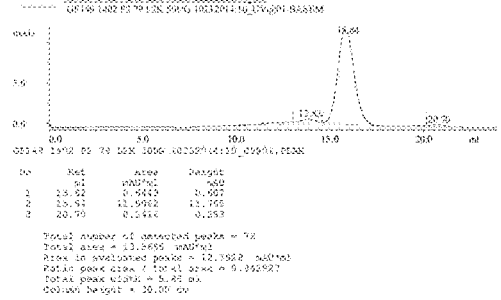

Bispecific antibodies (BsAbs) were generated using scFv sequences of the AFP158/HLA-A*02:01-specific phage clones. The BsAbs are single-chain bispecific antibodies comprising the scFv sequence of an AFP158/HLA-A*02:01-specific phage clone at the N-terminal end and an anti-human CD3ε mouse monoclonal scFv at the C-terminal end (Brischwein, K. et al., Mol. Immunol. 43:1129-1143, 2006). The DNA fragments coding for the AFP158 scFv and the anti-human CD3ε scFv were synthesized by Genewiz and subcloned into Eureka's mammalian expression vector pGSN-Hyg using standard DNA technology. A hexhistamine tag was inserted at the C-terminal end for antibody purification and detection. Chinese hamster ovary (CHO) cells were transfected with the BsAb expression vector, and then cultured for 7 days for BsAb antibody production. CHO cell supernatants containing secreted AFP158 BsAb molecules were collected. BsAb antibodies were purified using His-Trap HP column (GE healthcare) by FPLC AKTA system. Briefly, CHO cell culture was clarified and loaded onto the column with low imidazole concentration (20 mM), and then an isocratic high imidazole concentration elution buffer (500 mM) was used to elute the bound BsAb proteins. Molecular weights of the purified AFP158 BsAbs antibodies were measured under non-reducing conditions by gel electrophoresis. 4 μg of the protein was mixed with 2.5 μL of the NuPAGE LDS Sample Buffer (Life Technologies, NP0008) and brought up to 10 μL with deionized water. The sample was heated at 70° C. for 10 minutes, and then loaded onto the gel. Gel electrophoresis was performed at 180V for 1 hour. ~50 KD bands are observed as the major bands on the gel (FIG. 8). Antibody aggregation was assessed by size-exclusion chromatography (SEC). 50 μL of the sample was injected into the SEC column (Agilent, BioSEC-3,300A, 4.6×300 mm) while flowing a buffer consisting of Dulbecco's Phosphate Buffered Saline (Fisher Scientific, SH30028.FS) and 0.2M arginine adjusted to pH 7.0. BsAb was observed as the major peak at the retention time ~15.8 mL. (FIG. 9). BsAbs with high molecular weight aggregation less than 10% were used for further characterization.

Example 5. Characterization of AFP158 BsAb Antibodies

Binding Affinity of AFP158 BsAb Antibodies

The binding affinity of AFP158 BsAb antibodies to recombinant AFP158/HLA-A*02:01 complex was measured by Surface Plasma Resonance (BiaCore). The binding parameters between the AFP158 BsAb and the AFP158/HLA-A*02:01 complex were measured using a His Capture Kit (GE Healthcare, Cat #28995056) on a Biacore X100 (GE Healthcare) according to the manufacturer's protocol for multi-cycle kinetics measurement. All of the proteins used in the assay were diluted using HBS-E buffer. In brief, 1 μg/mL of the AFP158 BsAb was immobilized onto a Sensor Chip pre-functionalized with the anti-histidine antibody by flowing the solution through the flow cell 2 at 2 μL/min for 2 minutes. Binding towards the AFP158/A*02:01 complex was analyzed at 0.19, 0.38, 7.5, 15, and 30 μg/mL, each run consisting of a 3 minute association and 3 minute dissociation at 30 μL/min. At the end of cycle, the surface was regenerated using the regeneration buffer from the His Capture kit. Following the kinetics measurement, the surface was regenerated using the regeneration solution from the kit. The data were analyzed using 1:1 binding site mode with the BiaCore X-100 evaluation software. The binding parameters (association on rate constant $k_a$, dissociation constant $k_d$, and equilibrium dissociation constant $K_d$) were calculated. The binding affinities of AFP158 antibodies, in the monovalent scFv format, fall into the range of 10-500 nM. (Examples provided in Table 7).

TABLE 7

| Clone # | $k_a$ [1/Ms] | $k_d$ [1/s] | $K_d$ [nM] |
|---|---|---|---|
| #52 | 2.63E+05 | 1.71E−2 | 65 |
| #61 | 8.92E+04 | 3.08E−3 | 34 |
| #76 | 9.94E+04 | 1.42E−2 | 143 |
| #79 | 7.88E+04 | 2.51E−2 | 318 |
| #17-13 | 7.36E+04 | 3.45E−3 | 47 |

T-Cell Killing Assay

Tumor cytotoxicity was assayed by LDH Cytotoxicity Assay (Promega). Human T cells purchased from AllCells were activated and expanded with CD3/CD28 Dynabeads (Invitrogen) according to manufacturer's protocol. Activated T cells (ATC) were cultured and maintained in RPMI1640 medium with 10% FBS plus 100 U/ml IL-2, and used at day 7-14. The T cells were >99% CD3+ by FACS analysis. Activated T cells (Effector cells) and Target cells were co-cultured at a 5:1 ratio with different concentrations of BsAb antibodies for 16 hours. Cytotoxicities were then determined by measuring LDH activities in culture supernatants.

Figure 10:
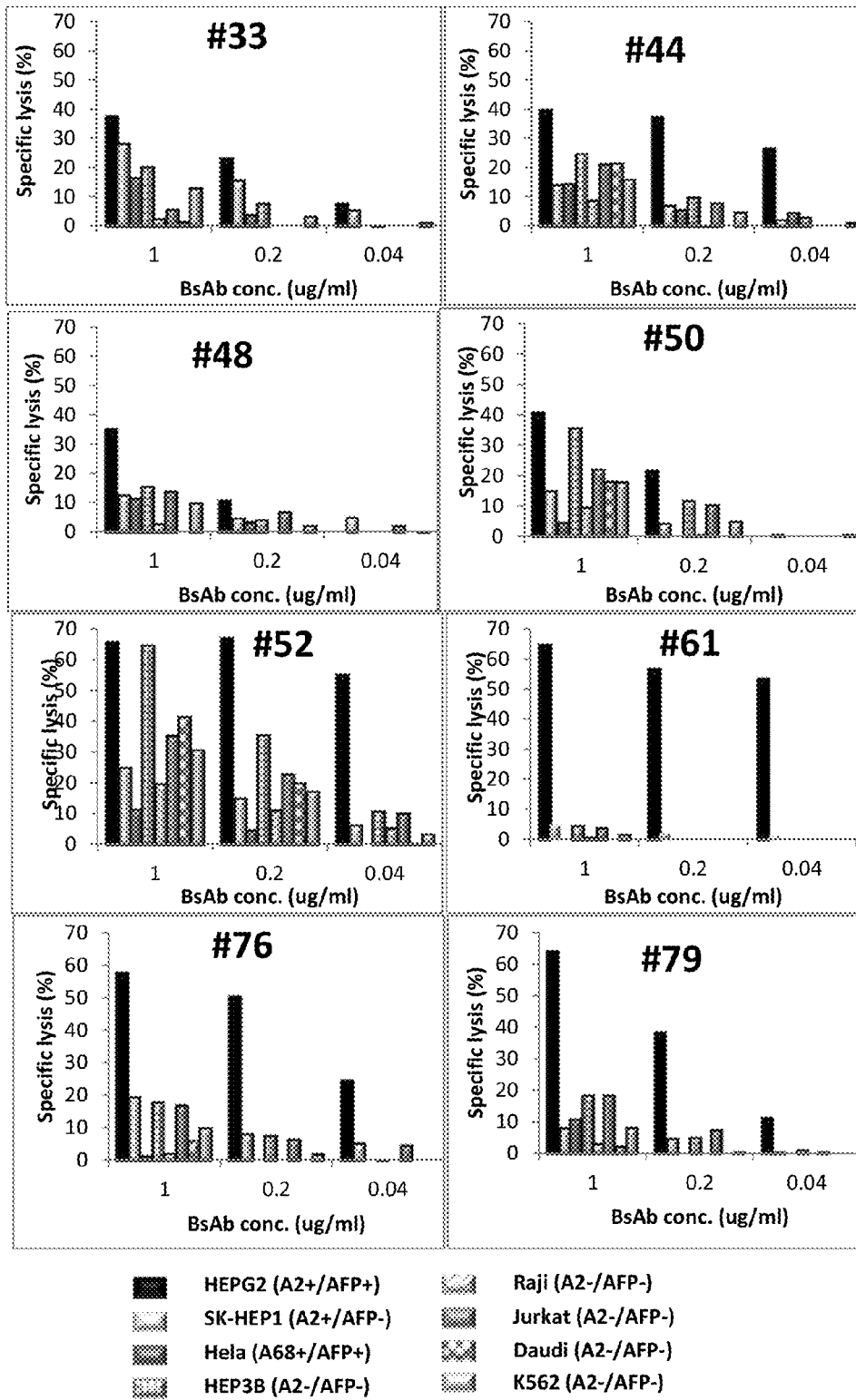
FIG. 10 shows the T-cell killing of multiple cancer cell lines mediated by anti-AFP158/MHC bispecific antibodies (BsAb) at varying concentrations. For each concentration, the bars from left to right represent HEPG2, SK-HEP1, Hela, HEP3B, Raji, Jurkat, Daudi, and K562 cells lines.

AFP158 BsAb antibodies killed cancer cells in an AFP and HLA-A*02:01-dependent manner Among all cell lines tested, HEPG2 (AFP and HLA-A*02:01 positive) was most effectively killed by T cells redirected through AFP158 BsAbs. Other cell lines tested that were either AFP negative or HLA-A02 negative, or negative for both were not killed as effectively under the same experimental settings (FIG. 10).

Cross-Reactivity of AFP158 BsAb Antibodies Against Multiple HLA-A02 Alleles

Human MHCI molecules consist of 6 class isoforms, HLA-A, -B, -C, -E, -F and G. The HLA-A, -B and-C heavy chain genes are highly polymorphic. For each isoform, the HLA genes are further grouped according to the similarity of heavy chain sequences. For example, HLA-A is divided into different alleles such as HLA-A01, -A02, -A03, etc. For the HLA-A02 allele, there are multiple subtypes, such as HLA-A*02:01, A*02:02, etc. Between the different subtypes of HLA-A02 group, the sequence differences are limited to only several amino acids. So in many cases, peptides that bind to HLA-A*02:01 molecule can also form complexes with multiple subtypes of the HLA-A02 allele. As shown in Table 8 (http://www.allelefrequencies.net/), although HLA-A*02:01 is the dominant HLA-A02 subtype among Caucasian populations, in Asia and Africa, A*02:03, A*02:05, A*02:06, A*02:07 and A*02:11 are also common HLA-A02 subtypes. The ability of AFP158 antibodies to recognize not only AFP158 peptide in the context of HLA-A*02:01, but also other subtypes of HLA-A02, will broaden the patient population that might be able to benefit from AFP158 antibody drug treatment. We therefore generated recombinant AFP158/MHCI complexes with other subtypes of the HLA-A02 allele and tested the binding affinity of the AFP158/HLA-A*02:01-specific antibodies for these other complexes. Binding affinity was determined using a ForteBio Octet QK. 5 μg/mL biotinylated HLA-A02 MHC complex of varying subtypes was loaded onto a streptavidin biosensor. After washing off excess antigen, BsAb antibodies were tested at 10 μg/mL for association and dissociation. Binding parameters were calculated using a 1:1 binding site, partial fit model. Table 9 shows binding affinities of several AFP158 BsAbs for multiple AFP158/HLA-A02 complexes with different subtypes. All of the antibodies tested were found to recognize AFP158 bound to multiple subtypes of the HLA-A02 allele.

1517, 2014), CLL (Brentjens, R. J. et al., *Blood.* 118(18): 4817-4828, 2011), and B cell lymphoma (Kochenderfer, J. N. et al., *Blood.* 116(20):4099-4102, 2010). In one study, a 90% complete remission rate in 30 patients with B-ALL treated with CD19-CAR T therapy was reported (Maude et al., supra).

Figure 11:
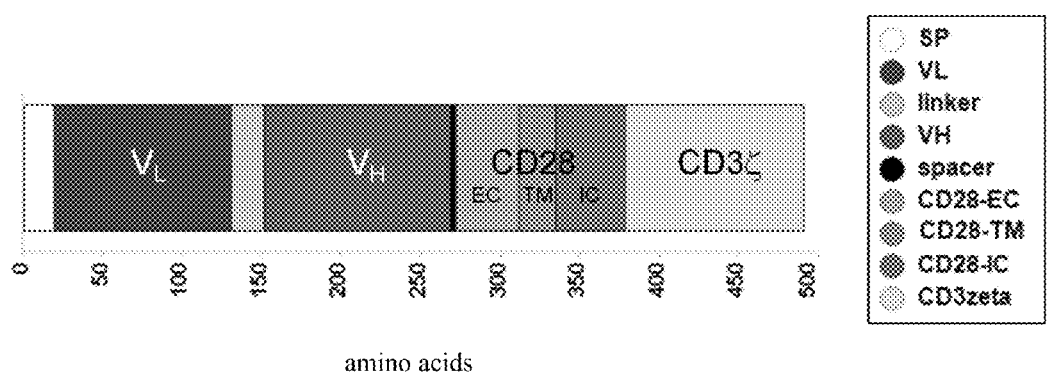
FIG. 11 shows a schematic representation of a chimeric antigen receptor construct.

To further explore the potency of the AFP158/HLA-A*02:01 specific antibodies, we constructed anti-AFP158/HLA-A*02:01 scFv expressing CARs and transduced T cells with these CARs. AFP158/HLA-A*02:01 specific CARs were constructed using a lentiviral CAR expression vector. Anti-AFP158/HLA-A*02:01 scFvs were grafted onto a second generation CAR (Mackall, C. L. et al., *Nat. Rev. Clin. Oncol.* 11 (12):693-703, 2014) with CD28 signaling domain and TCRζ engineered in cis to provide intracellular T cell stimulation signals and to activate T cells. FIG. 11 provides a schematic illustration of the anti-AFP158/HLA-A*02:01 CAR constructs.

TABLE 8

|  | australia | china | europe | india | north africa | sub-saharan africa | taiwan | us |
|---|---|---|---|---|---|---|---|---|
| A*02:01 | 97.8% | 39.5% | 94.0% | 53.9% | 73.3% | 56.3% | 35.1% | 79.4% |
| A*02:02 | 0.0% | 0.1% | 0.3% | 0.9% | 9.7% | 24.1% | 0.0% | 3.6% |
| A*02:03 | 0.0% | 15.3% | 0.2% | 4.9% | 0.0% | 0.4% | 19.3% | 2.2% |
| A*02:04 | 0.0% | 0.1% | 0.0% | 0.3% | 2.6% | 0.4% | 0.0% | 0.2% |
| A*02:05 | 1.1% | 0.9% | 3.2% | 5.8% | 13.8% | 15.9% | 0.1% | 4.5% |
| A*02:06 | 0.0% | 16.0% | 0.9% | 10.6% | 0.0% | 0.7% | 12.8% | 5.5% |
| A*02:07 | 1.1% | 26.1% | 0.4% | 0.4% | 0.0% | 0.0% | 32.7% | 2.4% |
| A*02:08 | 0.0% | 0.0% | 0.0% | 0.0% | 0.0% | 0.0% | 0.0% | 0.0% |
| A*02:09 | 0.0% | 0.0% | 0.0% | 0.0% | 0.0% | 0.0% | 0.0% | 0.0% |
| A*02:10 | 0.0% | 1.1% | 0.0% | 0.0% | 0.0% | 0.2% | 0.0% | 0.1% |
| A*02:11 | 0.0% | 0.1% | 0.1% | 22.3% | 0.0% | 1.5% | 0.0% | 1.7% |
| other A02 subtypes (A*02:12-A*02:93) | 0.0% | 0.7% | 0.8% | 0.9% | 0.5% | 0.5% | 0.0% | 0.6% |
|  | 100.0% | 100.0% | 100.0% | 100.0% | 100.0% | 100.0% | 100.0% | 100.0% |

TABLE 9

| HLA-A02 subtype | #17-13 $K_d$(nM) | #52 $K_d$(nM) | #61 $K_d$(nM) | #76 $K_d$(nM) | #79 $K_d$(nM) |
|---|---|---|---|---|---|
| A*02:02 | 233 | 16.8 | 394 | 16.8 | 115 |
| A*02:03 | 212 | 25.7 | 204* | 25.7* | — |
| A*02:05 | 183 | 18.6 | 2000 | 18.6 | 686 |
| A*02:06 | 26.4 | 9.4 | 2200* | 9.4* | 63.8 |
| A*02:07 | 373 | 6.9 | 3200* | 6.9* | 387 |
| A*02:11 | 11.3 | 10.4 | 433 | 10.4 | 68.5 |

*low fitting confidence

Example 6. Generation of AFP158/HLA-A*02:01 Specific Chimeric Antigen Receptor-Presenting T Cells (CAR-T)

Chimeric antigen receptor therapy (CAR-T therapy) is a new form of targeted immunotherapy. It merges the exquisite targeting specificity of monoclonal antibodies with the potent cytotoxicity and long-term persistence provided by cytotoxic T cells. This technology enables T cells to acquire long-term novel antigenic specificity independent of the endogenous TCR. Clinical trials have shown clinically significant anti-tumor activity of CAR-T therapy in neuroblastoma (Louis, C. U. et al., *Blood* 118(23):6050-6, 2011), B-ALL (Maude, S. L. et al., *N Engl J Med.* 371(16):1507-

Example 7. Characterization of AFP158 CAR-T Cells

AFP158 CAR Expressed in CD4+ and CD8+ Primary T Cells

Figure 24:
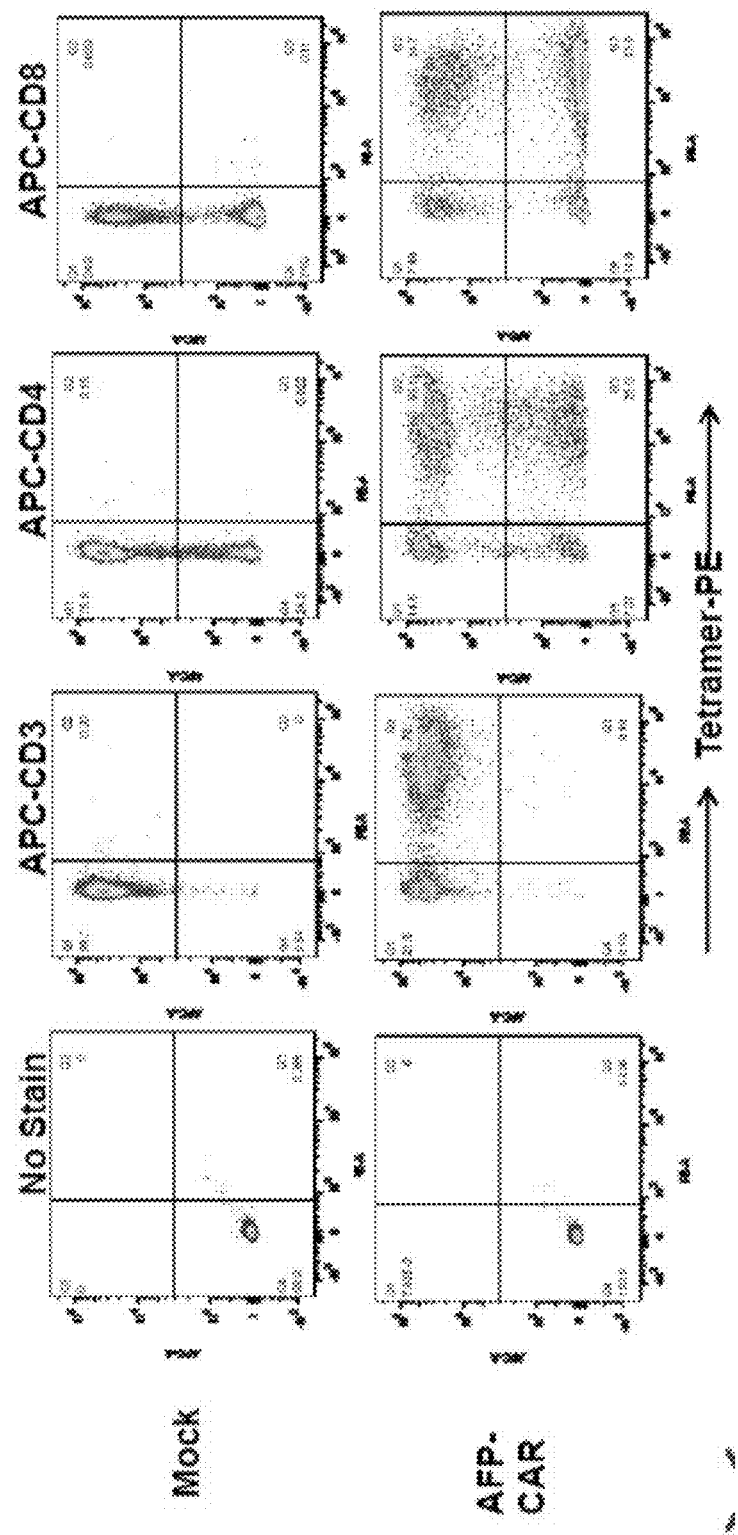
FIG. 24 shows flow cytometry analysis of AFP158 CAR-transduced peripheral blood lymphocytes; cells were stained with AFP158/HLA-A*02:01 tetramers and co-stained with anti-CD3, antibody, anti-CD4 antibody, or anti-CD8 antibody. Mock-transduced cells and cells without staining were included as controls.

Peripheral blood lymphocytes were isolated from healthy donors and transduced with an AFP158 CAR construct encoding an anti-AFP158/HLA-A*02:01 binding moiety. Five days after transduction, AFP158 CAR-T cells and mock-transduced cells were co-stained with AFP158 tetramer, and one of CD3, CD4 or CD8 antibodies and analyzed by flow cytometry. FIG. 24 shows flow cytometry results for AFP158 CAR- and mock-transfected cells indicating that the AFP158 CAR can be expressed in both CD4+ and CD8+ primary T cells.

Even Distribution of AFP158 CAR on T Cell Surface

Figure 26:
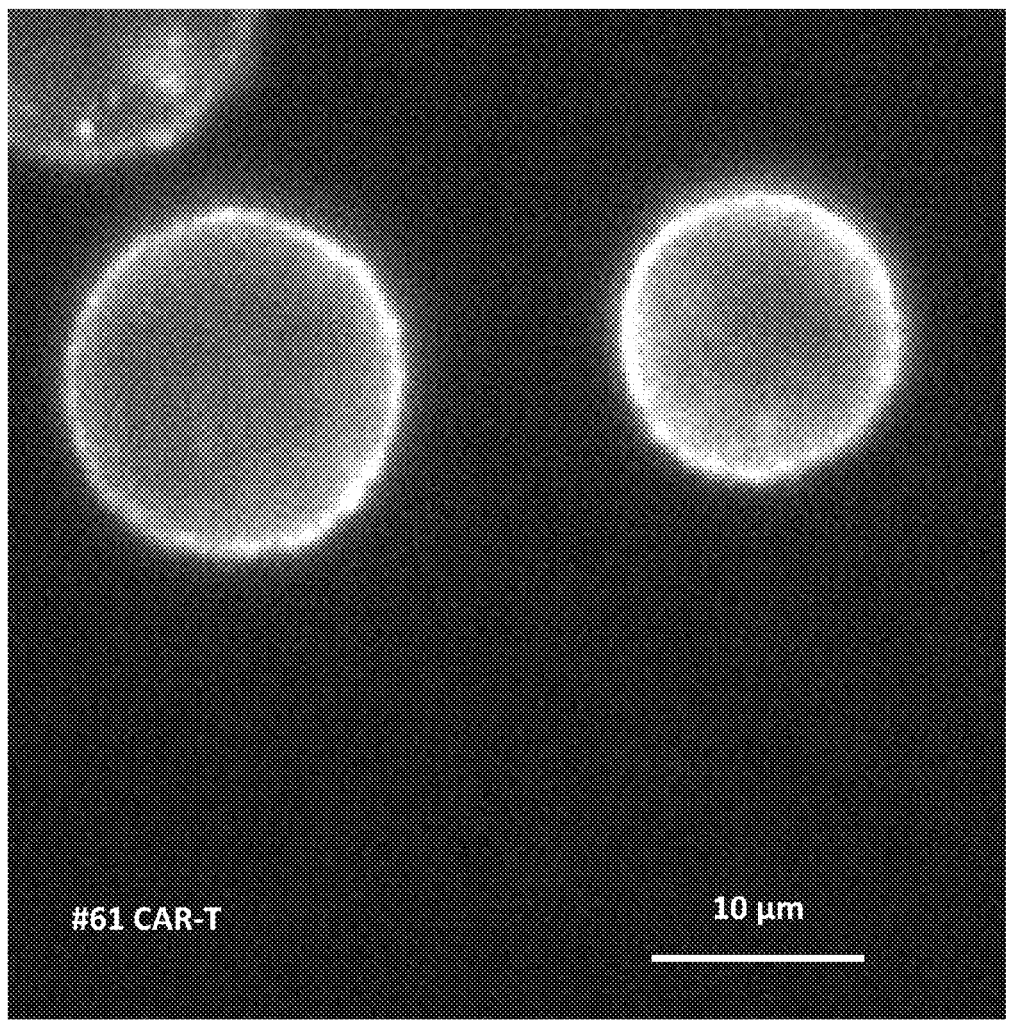
FIG. 26 shows CAR cell surface distribution in cells transduced to express a representative AFP158 CAR; cells were stained with AFP158/HLA-A*02:01 tetramer-PE.

It has been demonstrated that CAR-T cells with even cell surface distribution of CARs kill tumor cells more efficiently in vitro and in vivo than CAR-T cells with uneven cell surface distribution of CARs, and they exhaust much less easily after killing. The uneven distribution, such as aggregation, of CARs can lead to antigen-independent CAR activation, premature T cell exhaustion, and no anti-tumor activity in vivo. Therefore, even distribution of CARs on T cell surface is desirable. To determine the distribution of anti-AFP158/HLA-A*02:01 scFv expressing CARs on T cell membrane, we used a conjugate AFP158 peptide-HLA- A2 tetramer-PE to stain the AFP158 CAR-transduced T cells as described above. Primary human CD3+ T cells were first activated by anti-CD3 and CD28 beads, and then transduced with AFP158 CAR lentivirus. On day 8 after viral transduction, AFP158 CAR-transduced T cells were stained with AFP158 peptide-HLA-A2 tetramer-PE at 2 ng/ml in the presence of protein transport inhibitor for 30 minutes at room temperature. Images were acquired using an Olympus fluorescence microscope. We found that the distribution of AFP158 CAR on T cell membrane is even and smooth. No punctate CAR distribution was observed. A representative image is shown in FIG. 26.

In vitro Cytotoxicity Study of AFP158 CAR-T Cells

Lentiviruses containing AFP158/HLA-A*02:01-specific chimeric antigen receptors were produced by transfection of 293T cells with CAR vectors. Human T-cells were used for transduction after 1-day stimulation with CD3/CD28 beads (Dynabeads®, Invitrogen) in the presence of interleukin-2 at 100 U/ml. Concentrated lentiviruses were applied to T-cells in Retronectin (Takara) coated 6-well plates for 72 hours. Functional assessment of the transduced T cells (AFP158 CAR-T cells) was performed using LDH Cytotoxicity Assay. Effector-to-target ratios used were 5:1.

Figure 12:
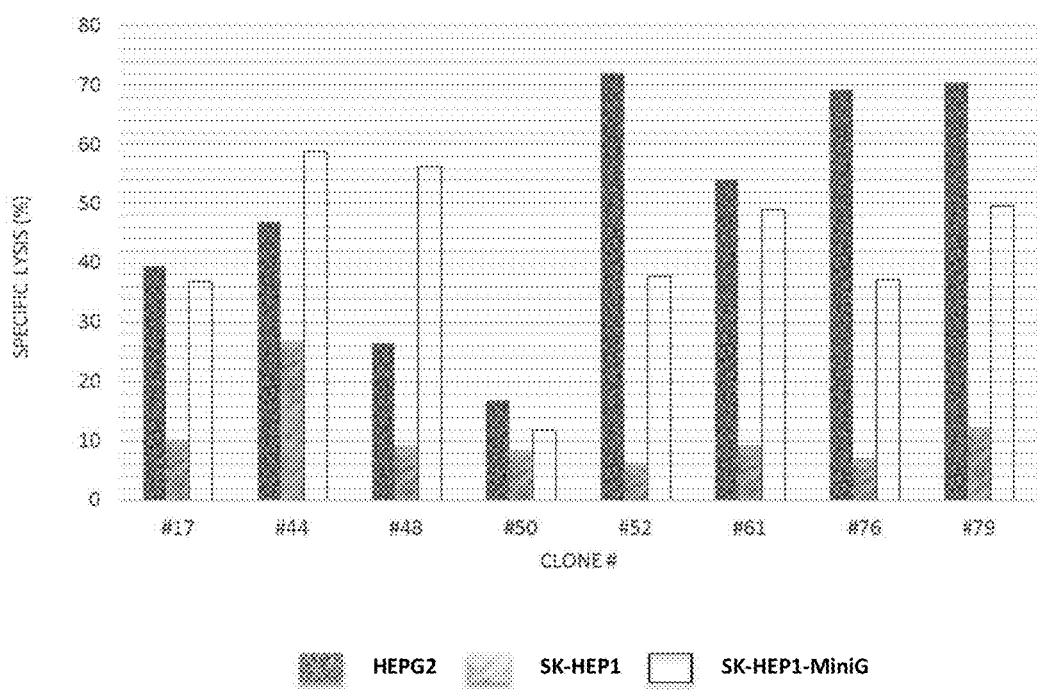
FIG. 12 shows the killing of HEPG2, SK-HEP1, and SK-HEP1-MiniG cell lines mediated by T cells expressing a panel of anti-AFP158/MHC CARs.

A panel of AFP158 CAR clones transduced into T cells was tested against the target cell lines HEPG2, SK-HEP1, and SK-HEP1-MiniG. T cells transduced with the AFP158 CAR clones specifically killed AFP158/HLA*A02:01 positive cell lines HEPG2 and SK-HEP1-MiniG (FIG. 12). The AFP158 CAR expressing T cells killed the target-positive cancer cells in a specific and highly efficient way for most of the antibody clones tested. Target-negative, wild-type SK-HEP1 cells, however, were poorly recognized by the same T cells, except for those transduced with clone #44, which showed some non-specific killing of wild-type SK-HEP1 cells.

Figure 13:
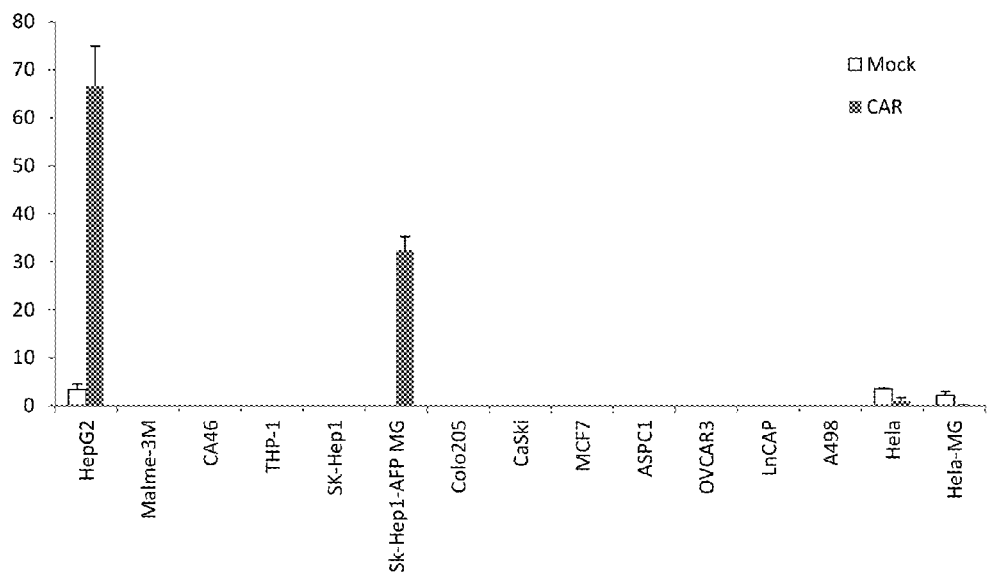
FIG. 13 shows the killing of a panel of cancer cell lines positive or negative for AFP158 and HLA-A*02:01, mediated by T cells expressing an exemplary anti-AFP158/MHC CAR. The tissue of origin of each cell line, the AFP/AFP158 peptide expression and whether the cells express the HLA-A02 allele are indicated in the table.

A large panel of cancer cell lines positive or negative for AFP158 and HLA*A02:01 was tested for killing by AFP158 CAR-T cells. Primary T cells that were mock-transduced or transduced with AFP158 CAR (a CAR construct encoding an exemplar anti-AFP158/HLA*A02:01 antibody) were tested for their ability to specifically kill AFP158/HLA*A02:01 positive cancer cells, at an effector-to-target ratio at 5:1. As shown in FIG. 13, AFP158 CAR-T cells specifically killed AFP158/HLA*A02:01 positive cell lines HepG2 and SK-Hep1-MiniG, but none of the other cell lines, which are either AFP negative or HLA*A02:01 negative. Importantly, this data demonstrates that our antibody is highly specific to AFP-expressing cells and does not mediate non-specific killing of a large panel of HLA-A02 cell lines across multiple tissues types that do not express AFP.

AFP158 CAR-Transduced T Cells Degranulate upon Antigen Stimulation

Figure 25:
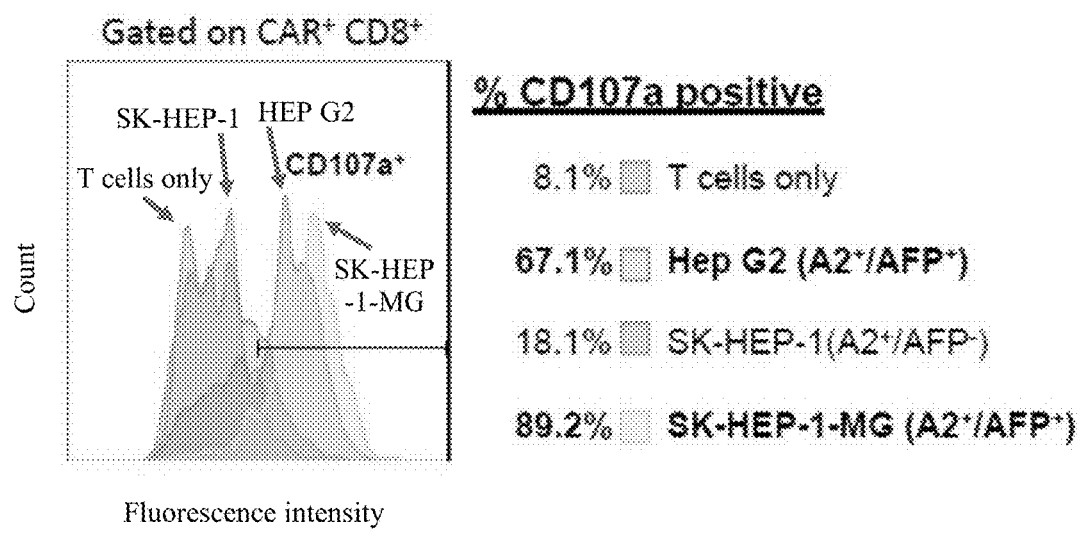

To further characterize the biological activities in AFP158 CAR-transduced T cells, we used a flow cytometry assay to detect CD107a surface expression as a measurement of degranulation activity. AFP158 CAR-transduced T cells were co-incubated with HepG2, SK-HEP-1 and SK-Hep1-MiniG cells for 4 hours in the presence of a 1:200 dilution of anti-CD107a antibody and protein transport inhibitor cocktail (eBioscience). After co-incubation with target cells, transduced T cells were stained with AFP158/HLA tetramers and anti-CD8. Degranulation in tetramer-positive, CD8-positive T cells is shown in FIG. 25. The highest level of degranulation, as measured by CD107a expression, was observed upon co-incubation with SK-Hep1-MiniG, followed by HepG2, while no degranulation was observed with the parental antigen-negative SK-HEP-1. This is consistent with the T-cell mediated cell lysis data above.

Cytokine Release

Figure 14A:
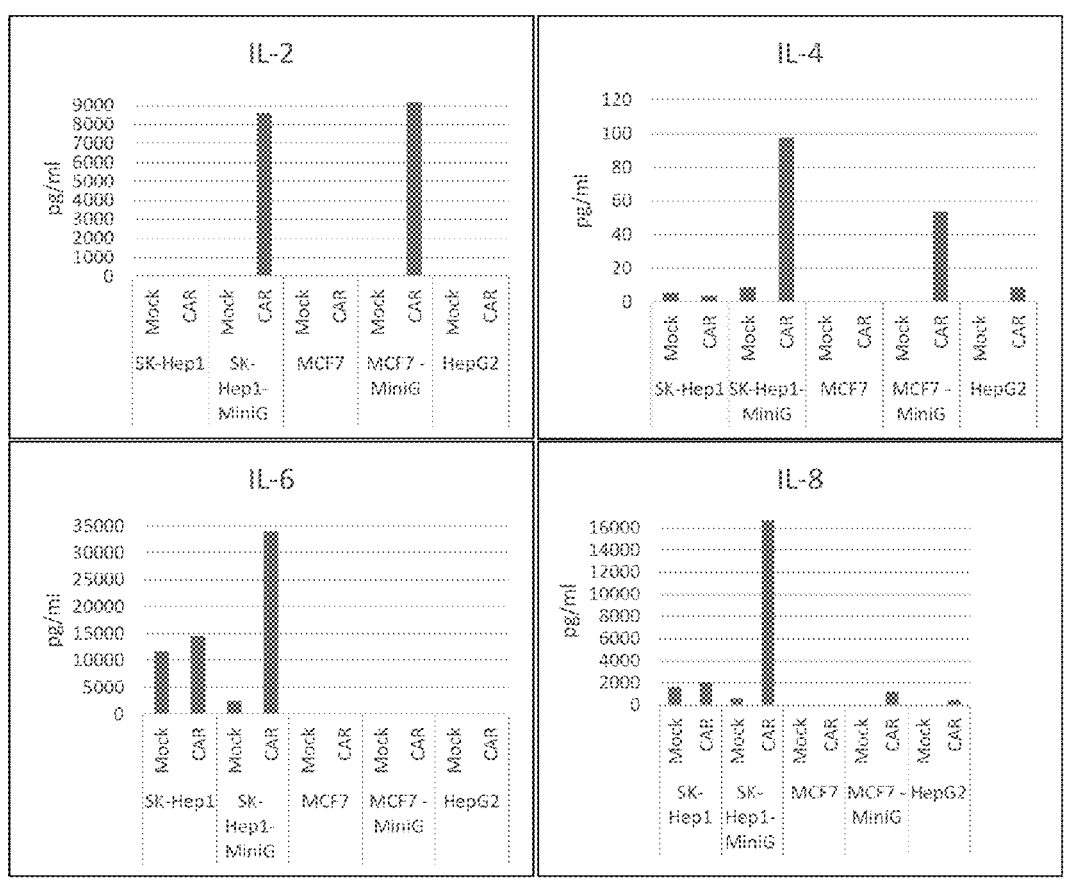
FIG. 14A shows the release of IL-2, IL-4, IL-6, and IL-8 after co-incubation of AFP158 CAR transduced T cells or mock-transduced T cells with cancer cell lines positive or negative for AFP158 and HLA-A*02:01.
Figure 14B:
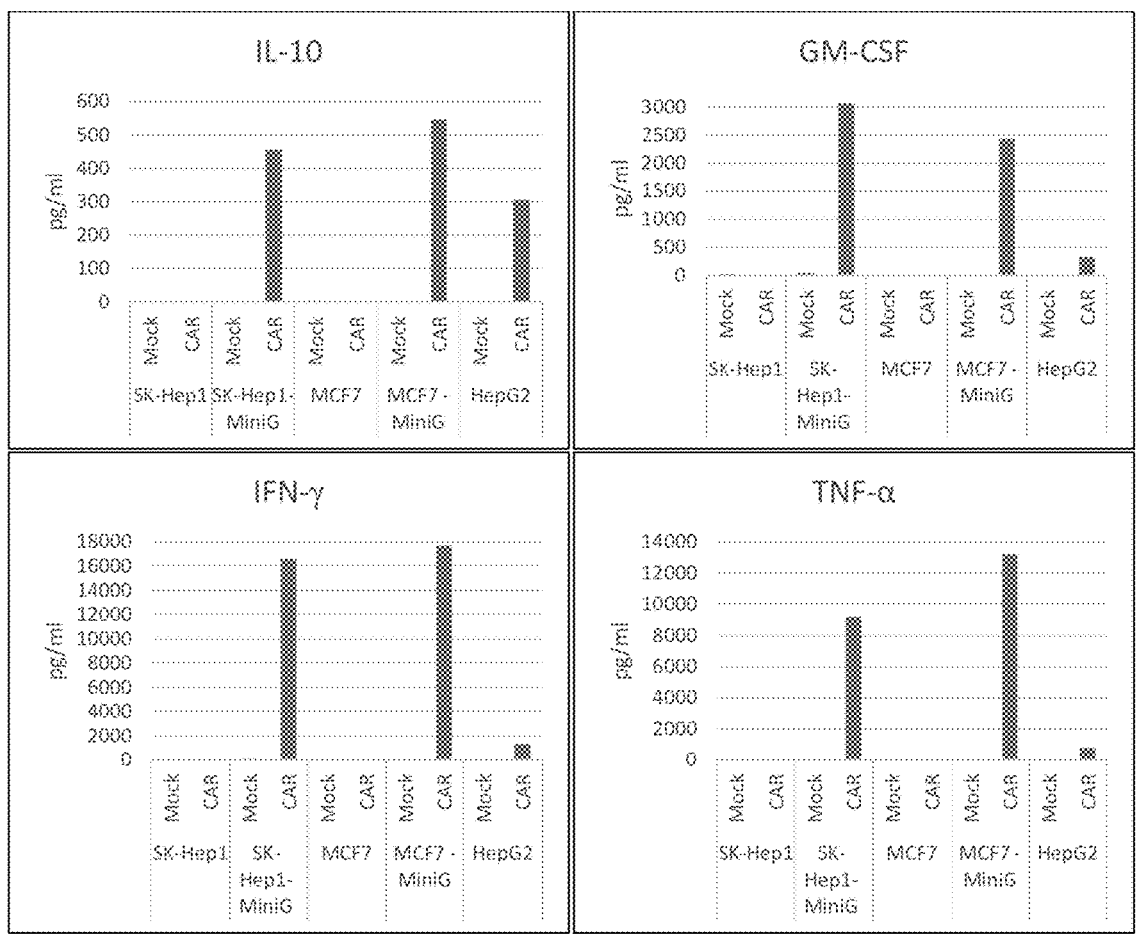
FIG. 14B shows the release of IL-10, GM-CSF, IFN-γ, and TNF-α after co-incubation of AFP158 CAR transduced T cells or mock-transduced T cells with cancer cell lines positive or negative for AFP158 and HLA-A*02:01.

The cytokine release profile upon treatment with activated AFP158 CAR-T cells was also examined. T cells were either mock-transduced or transduced with an exemplar AFP158 CAR and co-incubated with target cells as indicated. Release of IL-2, IL-4, IL-6, IL-8, IL-10, GM-CSF, IFN-γ and TNF-α into the media was measured after 16 hours using the Magpix multiplex system (Luminex) with the Bio-plex Pro Human Cytokine 8-plex Assay (BioRad). Cytokine concentrations were determined from a standard curve, after subtracting values from media, target cells alone and AFP158 CAR transduced T cells alone. As shown in FIGS. 14A and 14B, cytokine release was detected only when AFP158 CAR-T cells were co-incubated with AFP158/HLA*A02:01 positive cells: SK-Hep1-MiniG, MCF7-MiniG and HepG2, but not with AFP158/HLA*A02:01 negative cells: SK-Hep1 and MCF7. AFP158 CAR-T cells released much higher level of cytokines when they were exposed to SK-Hep1-MiniG and MCF7-MiniG. This is consistent with AFP158 minigene-transduced cancer cells expressing much higher levels of AFP158/HLA*A02:01 on the cell surface than HepG2. Mock-transduced T cells released only trace amounts, if any, of cytokines in the presence of AFP158/HLA*A02:01 positive cancer cells. IL-6 release after co-incubation with mock-transduced (AFP negative) SK-Hep1 is due to endogenous IL-6 expression in those cells (based on data not shown).

In Vivo Efficacy Study of AFP158 CAR T Cells in Human HCC Xenograft Model

The in vivo anti-tumor activity of AFP158 CAR-T cells was tested in several established human HCC xenograft models in SCID-beige immunocompromised mice. HepG2 was implanted subcutaneously (s.c.) over the right flank at $2.5 \times 10^6$ cells per mouse. When tumor volumes reached an average of 100 mm$^3$, mice were randomized based on tumor volume into four groups: 1) no treatment, 2) intravenous (i.v.) treatment with mock-transduced, donor-matched T cells (mock), 3) intravenous (i.v.) treatment with an exemplar AFP158 CAR transduced T cells, and 4) intratumoral (i.t.) injection of AFP158 CAR transduced T cells. All treatments were administered at a dose of $10^7$ cells per mouse and repeated every 2 weeks for a total of 3 doses.

Figure 15A:
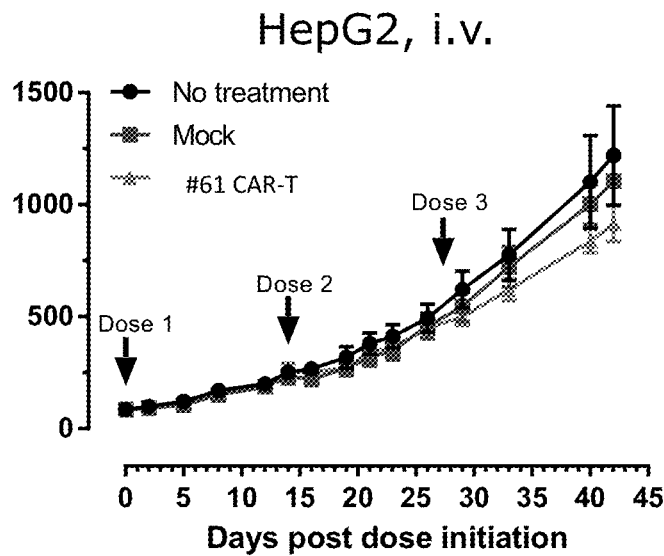
FIG. 15A shows tumor growth in HepG2 subcutaneous xenograft mice treated with intravenous injection of mock-transduced T cells or AFP158 CAR-transduced T cells, or left untreated.
Figure 15B:
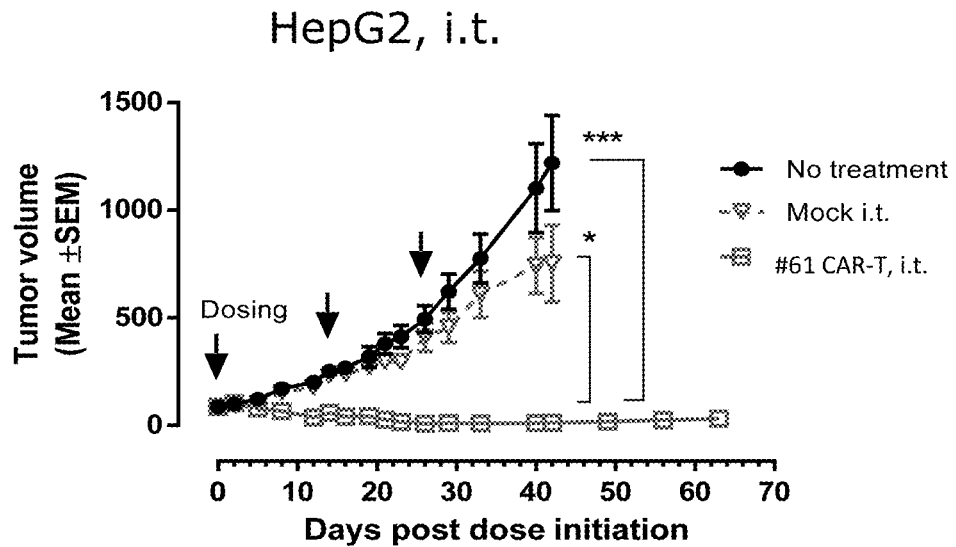
FIG. 15B shows tumor growth in HepG2 subcutaneous xenograft mice treated with intratumoral injection of mock-transduced T cells or AFP158 CAR-transduced T cells, or left untreated.

Both control and AFP158 CAR-T cells were well-tolerated at the given dose and schedule; no treatment-related adverse responses were observed during the study. Tumors in untreated mice, as well as control T cell-treated mice, grew continuously until they reached a size that required euthanasia. As shown in FIG. 15A, intravenous administration of AFP158 CAR-T cells in HepG2 tumor-bearing mice resulted in delayed tumor growth starting 28 days after the first dose. Approximately 25% tumor growth inhibition was observed after day 35 post the first dose (FIG. 15A). In contrast to the delayed effects of i.v. administration, i.t. injections of AFP158 CAR-T cells caused rapid, profound, and lasting tumor regression in all mice, with 80% (6/8) showing complete regression (FIG. 15B).

Peritoneal dissemination of HCC occurs in a subset of patients who have very limited treatment options as a result. Therefore the anti-tumor activity of AFP158 CAR-T cells was further tested in an established intraperitoneal HCC xenograft model. In this study, luciferase-tagged HepG2 cells (HepG2-luc2) were implanted intraperitoneally (i.p.) at $2.5 \times 10^6$ cells per mouse. Tumor burden was assessed weekly by measuring tumor-derived bioluminescence. One week post tumor implantation, animals were randomized based on total bioluminescent flux into four groups: 1) no treatment, 2) treatment with i.p. injection of $10^7$ control T cells, treatment with i.p. injection of $10^6$ AFP158 CAR-T cells, and 4) treatment with i.p. injection of $10^7$ AFP158 CAR-T cells (n=6 mice per group). Two doses of T cells were administered to each group, two weeks apart.

Figure 16A:
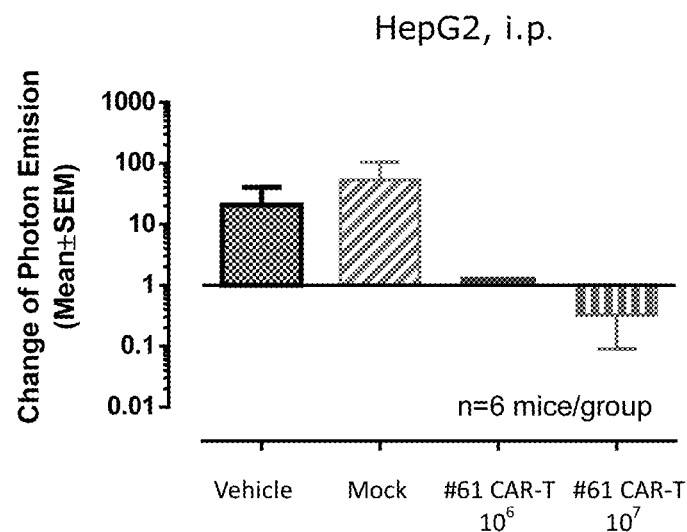
FIG. 16A shows the change in the photon emission from luciferase-tagged HepG2 (HepG2-Luc2) intraperitoneal xenograft mice at day 70 after treatment with intraperitoneal injection of mock-transduced T cells or AFP158 CAR-transduced T cells, or no treatment.
Figure 16B:
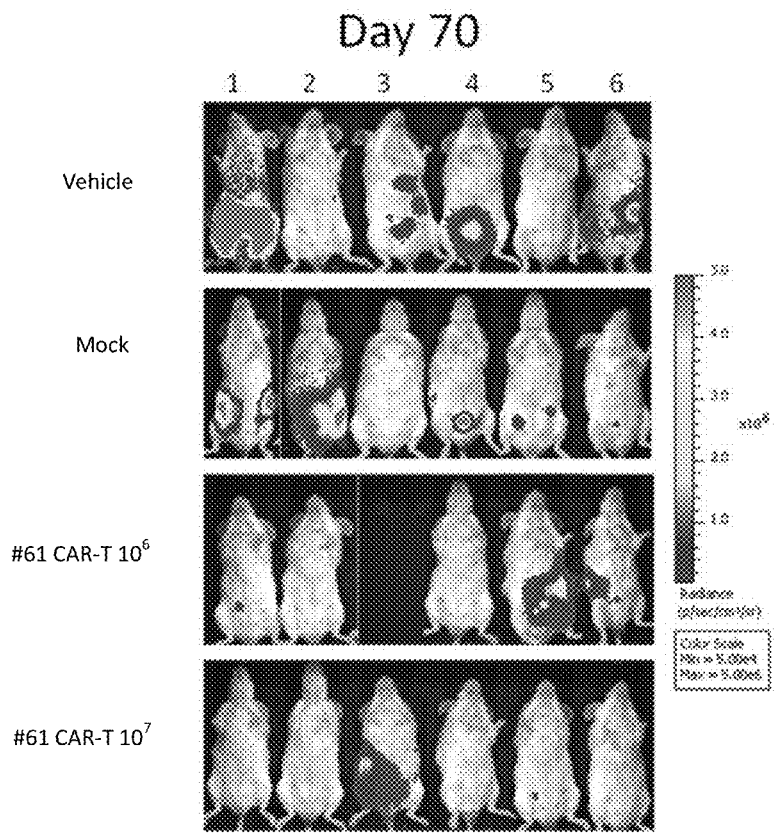
FIG. 16B shows photon emission images of the HepG2-Luc2 tumor-bearing mice at day 70.

As observed with i.v. and i.t. routes of administration, no clinical signs of adverse reactions were observed as a result of i.p. injections of either control or AFP158 CAR-T cells. As shown in FIGS. 16A (change of the photon emission from tumor-bearing mice at day 70 after treatment) and 16B (photon emission images of the HepG2-Luc2 tumor-bearing mice at day 70), the tumor burden in control T cell-treated animals showed no difference from that observed in the untreated control group. In contrast, mice treated with AFP158 CAR-T cells at $10^6$ or $10^7$ cells per mouse showed robust tumor regression. No dose-dependent anti-tumor activity was observed, indicating that both doses exceed the maximum efficacious dose in this model. Thus i.p. treatment with AFP158 CART cells in a model of peritoneal HCC is safe, potent and eradicated tumors effectively.

Figure 17:
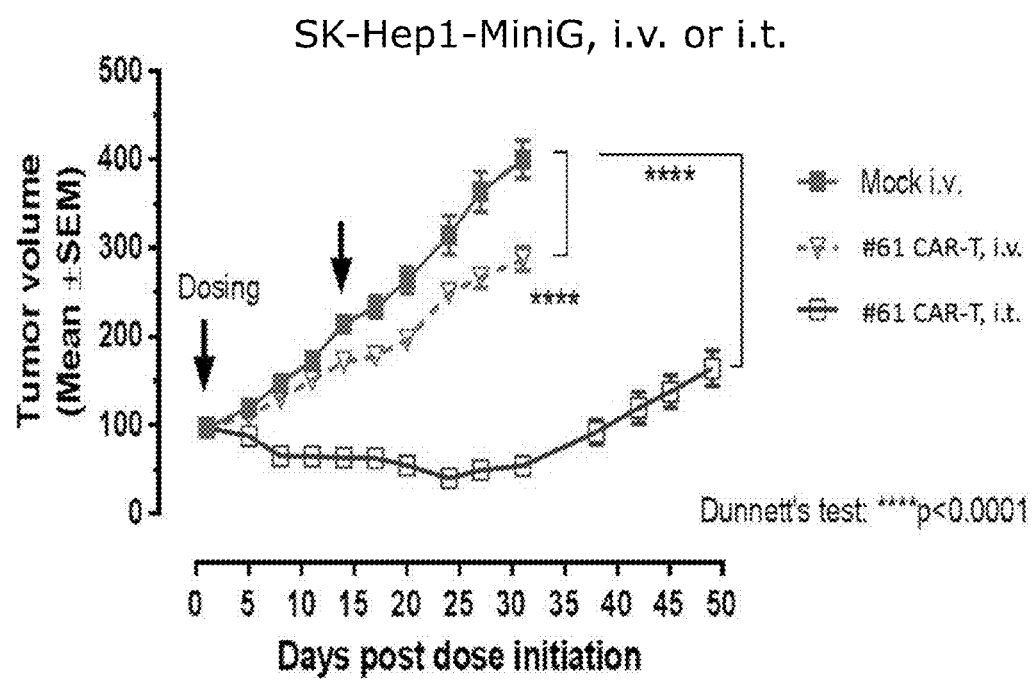
FIG. 17 shows tumor growth in SK-Hep1-MiniG subcutaneous xenograft mice treated with intravenous or intratumoral injection of AFP158 CAR-transduced T cells or intravenous injection of mock-transduced T cells.

The in vivo activity of AFP158 CAR-T cells was also evaluated in SK-Hep1-MiniG s.c. xenograft model. SK-Hep1-MiniG was implanted subcutaneously (s.c.) over the right flank at $2.5 \times 10^6$ cells per mouse. When tumor volume reached an average of 100 mm³, mice were randomized based on tumor volume into three groups: 1) intravenous (i.v.) treatment with mock-transduced, donor-matched T cells (mock), 2) intravenous (i.v.) treatment with exemplar AFP158 CAR transduced T cells, and 3) intratumoral (i.t.) injection of the same AFP158 CAR transduced T cells. All treatments were administered at a dose of $10^7$ cells per mouse and repeated once after 2 weeks of the first treatment. In this tumor model, i.v. administration of AFP158 CAR-T cells resulted in immediate tumor growth inhibition, slowing tumor growth by approximately 28% by day 31 following the first dose (FIG. 17). This suggests that the delayed tumor growth inhibition activity of i.v. AFP158 CAR-T cell administration in HepG2 tumors is a model-specific phenomenon. Similar to the results obtained in HepG2 tumors, i.t. injection of AFP158 CAR-T cells in the SK-Hep1-MiniG mouse model resulted in robust and prolonged tumor regression shortly after the first dose (FIG. 17).

Figure 18:
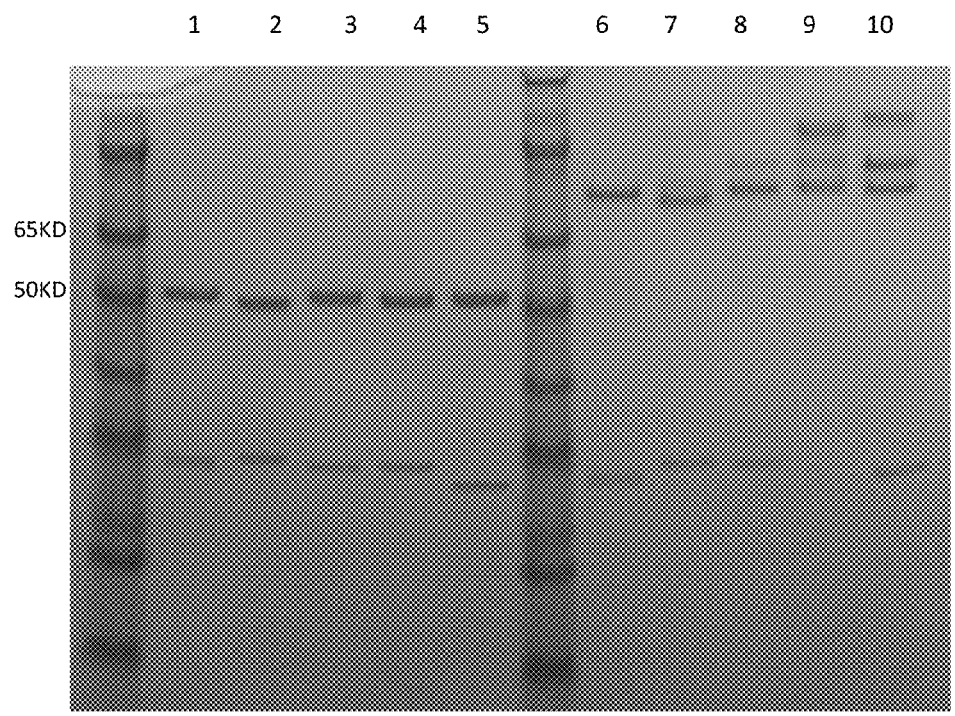
FIG. 18 shows SDS-PAGE analysis to determine the purity of full-length anti-AFP158/MHC mouse chimeric IgG1 antibodies.

Example 8. Generation and Characterization of the Full-Length IgG1 AFP158 Antibodies Full-length human IgG1 of the selected phage clones were produced in HEK293 and Chinese hamster ovary (CHO) cell lines, as described (Tomimatsu, K. et al., *Biosci. Biotechnol. Biochem.* 73(7):1465-1469, 2009) (data not shown). In brief, antibody variable regions were subcloned into mammalian expression vectors, with matching human lambda or kappa light chain constant region and human IgG1 constant region sequences. Applying the same cloning strategy, we also generated chimeric AFP158 full-length antibodies with mouse IgG1 heavy chain and light chain constant regions. Molecular weight of the purified full-length IgG antibodies was measured under both reducing and non-reducing conditions by electrophoresis. SDS-PAGE of purified AFP158 mouse chimeric IgG1 antibodies was performed to determine protein purity. In brief, 2 μg of the protein was mixed with 2.5 μL of the NuPAGE LDS Sample Buffer (Life Technologies, NP0008) and brought up to 10 μL with deionized water. The sample was heated at 70° C. for 10 minutes, and then loaded onto the gel. Gel electrophoresis was performed at 180V for 1 hour. Examples of SDS-PAGE are shown in FIG. 18.

Figure 19:
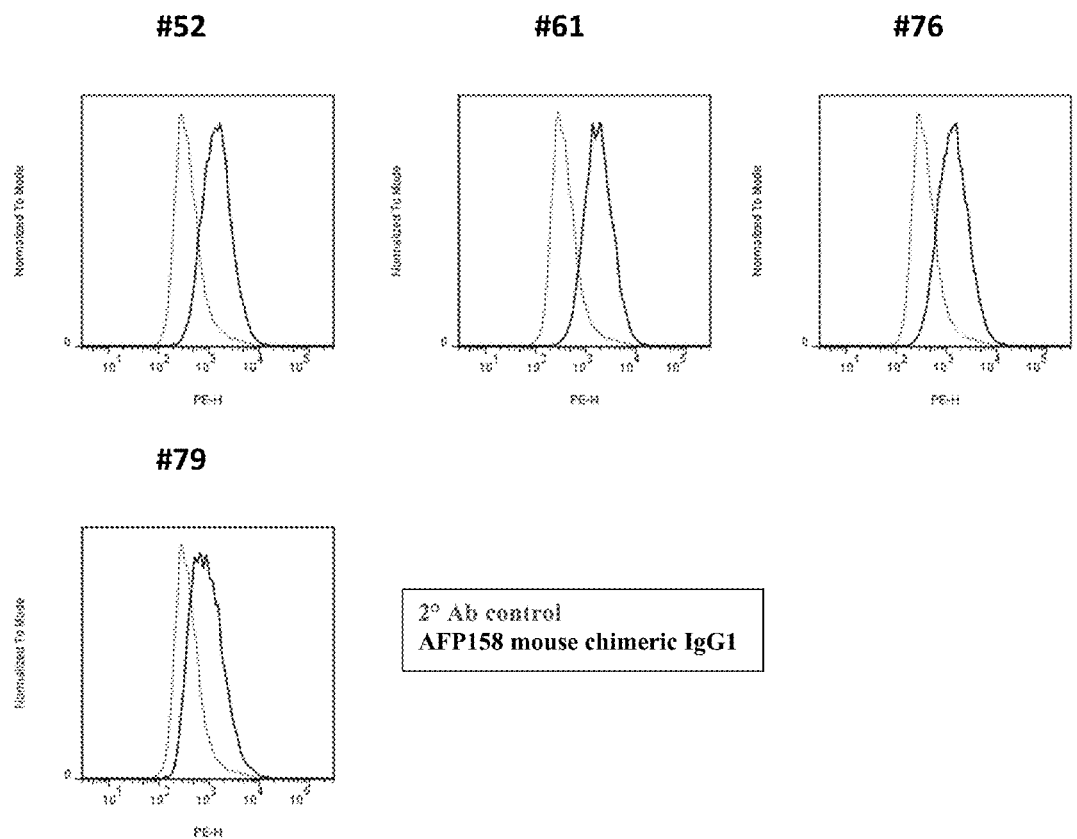
FIG. 19 shows FACS analysis of full-length anti-AFP158/MHC mouse chimeric IgG1 (black line) or negative control (secondary antibody alone, gray line) binding to SK-HEP1-miniG cells presenting AFP158/HLA-A*02:01.

AFP158 chimeric IgG1 antibody was tested for the binding towards AFP158 presenting SK-HEP1 cells by flow cytometry. SK-HEP1 is an HLA-A*02:01 positive and AFP negative cell line. An AFP158 minigene cassette was transfected into SK-HEP1 cells to generate the AFP158-presenting SK-HEP1-miniG cells. 10 μg/mL of antibody was added to cells on ice for 1 hour. After washing, R-PE conjugated anti-mouse IgG (H+L) (Vector Labs #EI-2007) was added to detect antibody binding. The AFP158 antibodies were found to bind to the minigene-transfected SK-HEP1-miniG cells, while secondary control antibody alone did not bind to the same cells (FIG. 19). Binding affinity of the mouse chimeric IgG1 AFP158 antibodies was determined by ForteBio. Converting the antibodies from monovalent BsAbs into bivalent IgG antibodies dramatically increased the binding affinity of AFP158 antibodies towards target antigen. The $K_d$'s of the full-length antibodies were determined to be in the picomolar range, a 100- to 1000-fold increase compared with the BsAb format. Table 10 shows examples of the $K_d$ data.

TABLE 10

| Clone # | $k_a$ [1/Ms] | $k_d$ [1/s] | $K_D$ [nM] |
|---|---|---|---|
| 1402-52 | 1.17E+06 | 2.35E−04 | 0.201 |
| 1402-61 | 5.13E+05 | 1.31E−05 | 0.0255 |
| 1402-76 | 6.32E+05 | 1.10E−04 | 0.173 |
| 1402-79 | 4.60E+05 | 5.33E−05 | 0.116 |

Figure 20:
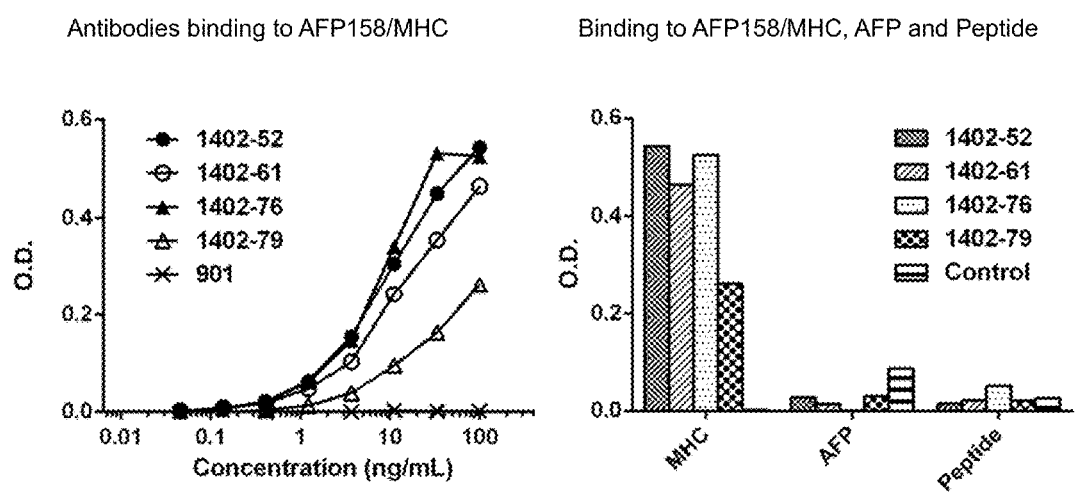
FIG. 20 shows the results of ELISA for full-length anti-AFP158/MHC mouse chimeric IgG1 binding to AFP158/HLA-A*02:01 complex, recombinant AFP protein or free AFP158 peptide. Left panel: dose dependence curve of full-length anti-AFP158/MHC mouse chimeric IgG1; Right: OD450 of antibody binding at 100 ng/mL for AFP158 peptide/MHC (MHC), AFP protein (AFP) and AFP158 peptide (Peptide).

AFP158-specific and negative control (ET901) mouse chimeric IgG1 were tested for the binding towards AFP158/HLA-A*02:01, AFP recombinant protein and free AFP158 peptide in an ELISA assay. Antibodies were tested at 3× serial dilution, starting from 100 ng/mL, for a total of 8 concentrations. Biotinlyated AFP158/A*02:01 MHC was coated onto streptavidin plates at 2 μg/mL, AFP protein was coated at 2 μg/mL and AFP158 peptide was coated at 40 ng/mL. It was confirmed that full-length AFP158 antibodies recognize the AFP158 peptide only in the context of HLA-A02, and do not bind recombinant AFP protein or free AFP158 peptide (FIG. 20).

Example 9. Efficacy of AFP158-CART in Distant SK-Hep1-MiniG s.c. Xenograft Model Example 7 showed that intratumoral administration of AFP158 CAR T cells into the subcutaneous (s.c.) liver tumor model significantly inhibited the growth of treated tumors in multiple xenograft models. The goal of the study described in this Example was to assess whether intratumoral treatment would also affect the growth of distant s.c. tumors.

In one representative study, the following materials and procedures were used:

1. Target tumor cell line SK-Hep1-MiniG (a.k.a. SK-Hep1-MG): Human HCC cell line SK-Hep1 expressing HLA-A*02:01 and AFP158 peptide minigene.

2. Animal: SCID-beige carries no T- and B-cells. Have functional NK, monocyte/macrophage, granulocytes and dendritic cells.

3. Animal study was carried out at a research contract lab.

4. CART Cells: human T cells were activated on Day 0; b) activated T cells were transduced by lentivirus on Day 1; c) lentivirus and beads were removed on Day 5; d) CAR T cells were cultured and expanded with IL-2 at 100 unit/ml;

e) APC cells were isolated by depleting CD3+ T cell from PBMC. The cells are mainly monocytes and B-cells.

5. Animal study. 6-8 weeks old female SCID Beige mice were used in this study. The SK-Hep1-MiniG cell line were cultured in DMEM Medium+10% FBS and 1% L-Glutamine at 37° C. in a humidified atmosphere with 5% $CO_2$. SK-Hep1-MiniG cells were resuspended in 50% PBS plus 50% Matrigel and implanted subcutaneously at both right and left flanks into 40 mice at $5\times10^6$ cells/100 ul/injection site.

When tumors reached 100 $mm^3$ on average, mice were randomized based on tumor size at right flank into the 6 groups described below, at 6 mice per group, and samples were injected into the tumors on the right flank of each mouse. For the AFP158-CART groups (groups 4-6), various antibody clones as described above were used in various experiments. Results from an experiment using a representative clone are shown below. Other clones produced similar results (data not shown).

Group 1: Vehicle (PBS), 100 μL/mouse, i.t. into the right site s.c. tumor, single dose.

Group 2: Mock* T-Cells 7 Million/100 μL/mouse, i.t. into the right site s.c. tumor, single dose. (Mock T-cells are the T-cells without CART transduction)

Group 3: Mock with APC Cells 7 Million (70% Mock+30% APC)/100 μL/mouse i.t. into the right site s.c. tumor, single dose.

Group 4: AFP158 CAR T Cells 7 Million/100 μL/mouse, i.v. via tail vein, single dose.

Group 5: AFP158 CART Cells 7 Million/100 μL/mouse, i.t. into the right site s.c. tumor, single dose.

Group 6: AFP158 CAR T Cells with APC, 7 Million (70% CART+30% APC)/100 μL/mouse, i.t. into the right site s.c. tumor, single dose.

AFP158-CART is Safe at the Current Dose/Schedule

Figure 21:
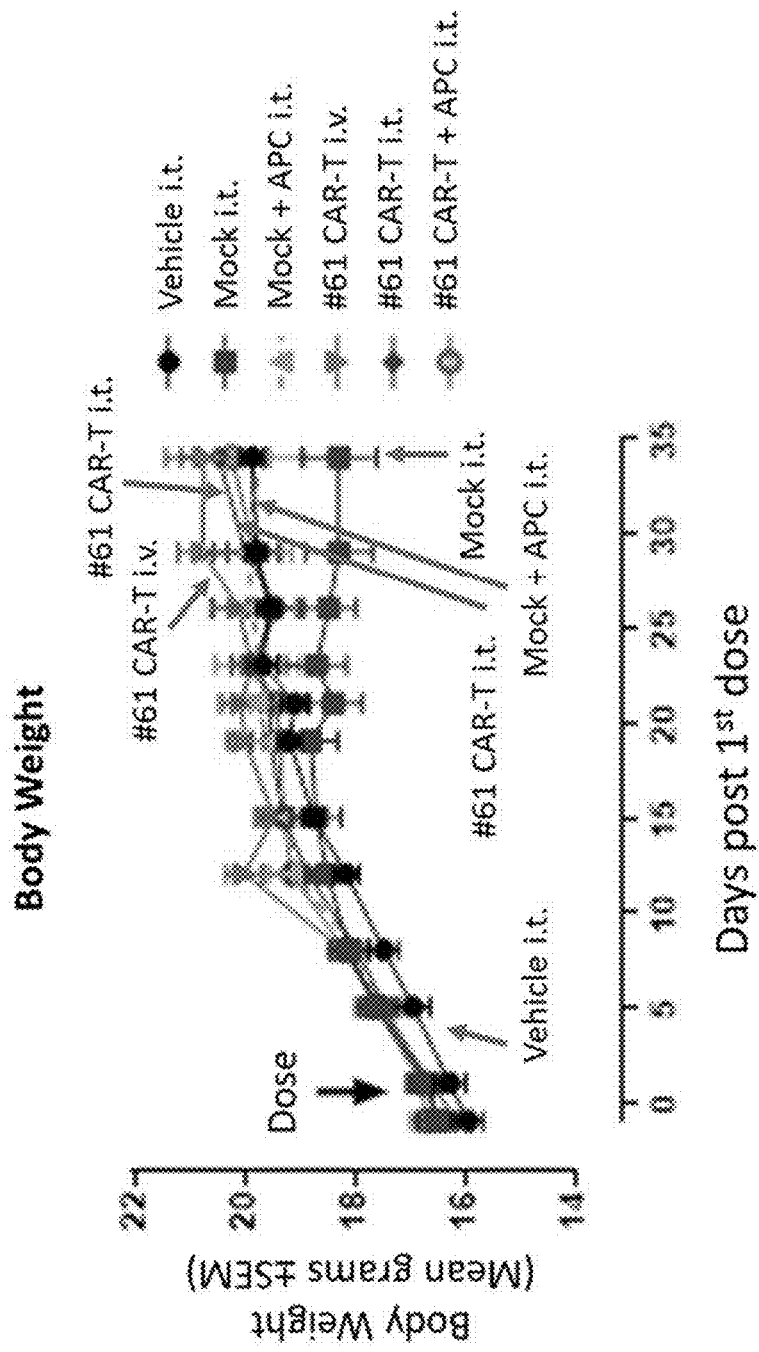
FIG. 21 shows body weight measurements over time (up to 35 days post $1^{st}$ dose) for mice injected intratumorally with AFP158 CAR-T cells or controls.

After dosing, body weight and other clinical behavior were closely monitored. As shown in FIG. 21, body weight loss was not observed in any of the groups. No other clinical signs of drug related toxicity were observed.

Figure 22:
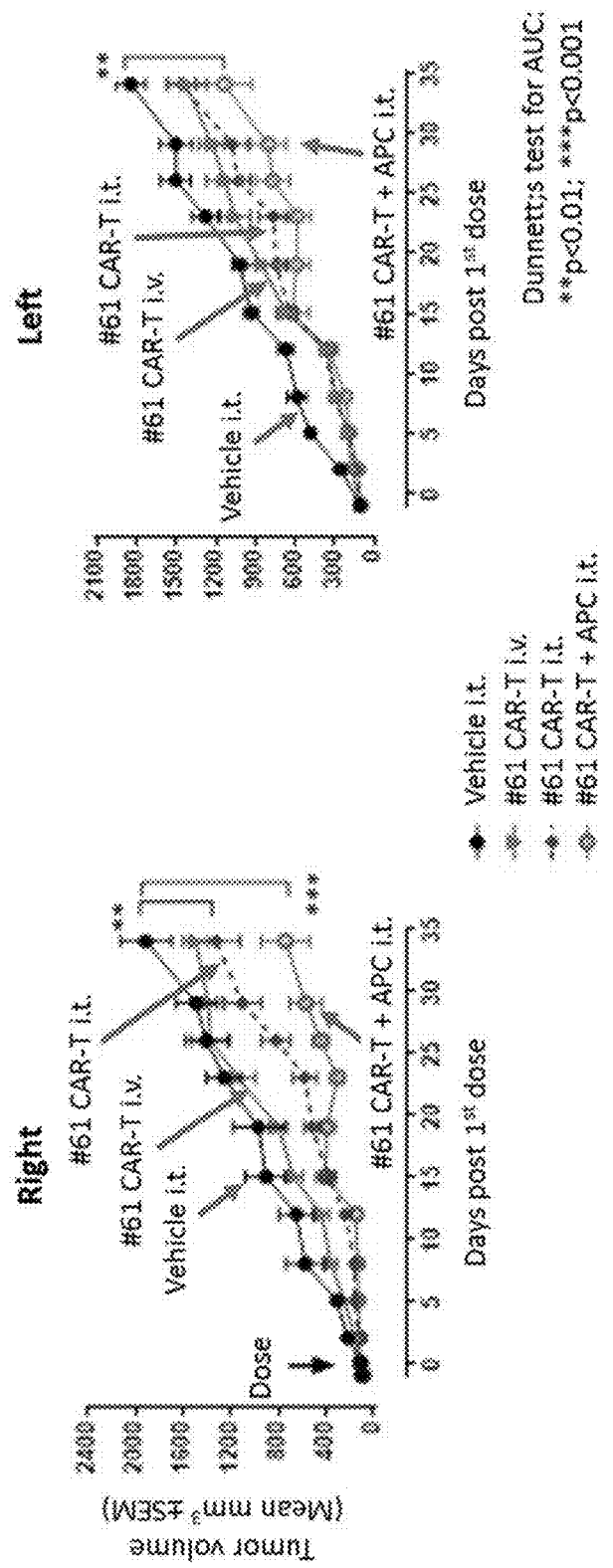
FIG. 22 shows tumor growth kinetics in bilateral SK-Hep1-MiniG subcutaneous xenograft mice treated with intravenous or intratumoral injection of AFP158 CAR-transduced T cells, intratumoral injection of AFP158 CAR-transduced T cells in combination with APCs, or intratumoral injection of mock-transduced T cells. Intratumoral injections were injected into right flank tumors.

Single i.t. Dose Resulted in Regression of Local Tumors and Inhibition of Distant Tumors As shown in FIG. 22, a single i.t. dose of AFP158-CART injected to only the right flank resulted in significant inhibition of tumors implanted on both the right flank and left flank (the side which AFP158-CAR T cells were not directly injected). Analysis by area under curve, reflecting the overall growth kinetics of the tumor, showed that i.t. injection of AFP158-CART alone resulted in 42% tumor growth inhibition on the right flank (Dunnett's test p<0.01) and 33% tumor growth inhibition on the left flank (p>0.05).

AFP158-CART+APC Enhanced Anti-Tumor Activity in Both Sides

As shown in FIG. 22, i.t. injection of AFP158-CART plus APC caused regression of right flank tumors with overall tumor inhibition of 68% when compared with the vehicle-treated group (p<0.001). A stronger inhibition of distant left flank tumor as compared to the respective vehicle-treated group was also observed (47%, p<0.01). This suggests the possible involvement of T-cell cross-priming in the additional inhibition of both right and left side tumors.

Figure 23:
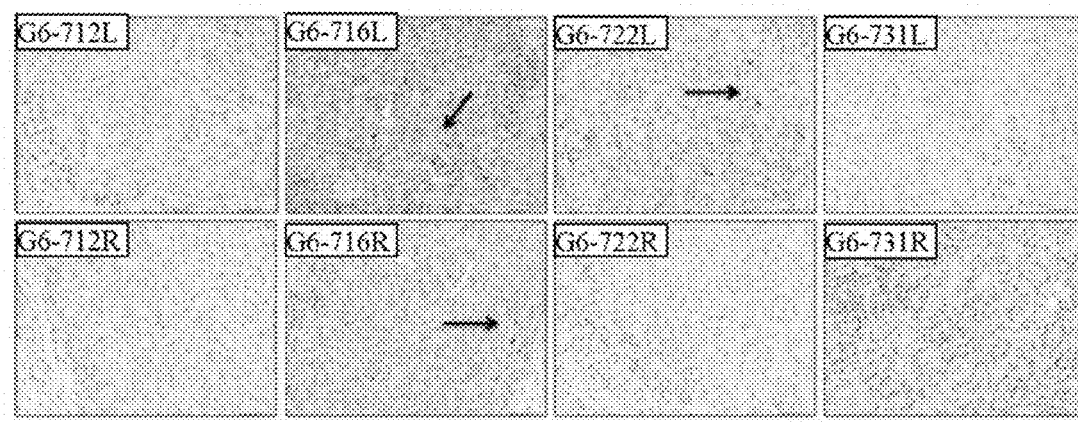
FIG. 23 shows immunohistochemical staining of human CD3 in tumor sections from bilateral SK-Hep1-MiniG subcutaneous xenograft mice treated with intratumoral injection into right flank tumors of AFP158 CAR-transduced T cells in combination with APCs. L, left tumor; R, right tumor.

CD3 Positive Cells were Observed in Both Right and Left Side Tumors in AFP158-CART+APC Treated Animals At the end of the study (34 days post dosing), tumors were harvested and histological staining of CD3 (T-cell marker) was performed. As shown in FIG. 23, CD3 positive cells were found in both right and left side tumors from i.t. injection of AFP158-CART plus APC cells. This suggests the involvement of the human T-cells in the tumor growth inhibition.

```
Sequence Listing hAFP protein (SEQ ID NO: 1)
MKWVESIFLIPLLNFTESRTLHRNEYGIASILDSYQCTAEISLADLATIFFAQFVQEATYKEVSKMVKDALTAIE
KPTGDEQSSGCLENQLPAFLEELCHEKEILEKYGHSDCCSQSEEGRHNCFLAHKKPTPASIPLFQVPEPVTSCEA
YEEDRETFMNKFIYEIARRHPFLYAPTILLWAARYDKIIPSCCKAENAVECFQTKAATVTKELRESSLLNQHACA
VMKNFGTRTFQAITVTKLSQKFTKVNFTEIQKLVLDVAHVHEHCCRGDVLDCLQDGEKIMSYICSQQDTLSNKIT
ECCKLTTLERGQCIIHAENDEKPEGLSPNLNRFLGDRDFNQFSSGEKNIFLASFVHEYSRRHPQLAVSVILRVAK
GYQELLEKCFQTENPLECQDKGEEELQKYIQESQALAKRSCGLFQKLGEYYLQNAFLVAYTKKAPQLTSSELMAI
TRKMAATAATCCQLSEDKLLACGEGAADIIIGHLCIRHEMTPVNPGVGQCCTSSYANRRPCFSSLVVDETYVPPA
FSDDKFIFHKDLCQAQGVALQTMKQEFLINLVKQKPQITEEQLEAVIADFSGLLEKCCQGQEQEVCFAEEGQKLI
SKTRAALGV hAFP CDS (SEQ ID NO: 2)
ATGAAGTGGGTGGAATCAATTTTTTTAATTTTCCTACTAAATTTTACTGAATCCAGAACACTGCATAGAAATGAA
TATGGAATAGCTTCCATATTGGATTCTTACCAATGTACTGCAGAGATAAGTTTAGCTGACCTGGCTACCATATTT
TTTGCCCAGTTTGTTCAAGAAGCCACTTACAAGGAAGTAAGCAAAATGGTGAAAGATGCATTGACTGCAATTGAG
AAACCCACTGGAGATGAACAGTCTTCAGGGTGTTTAGAAAACCAGCTACCTGCCTTTCTGGAAGAACTTTGCCAT
GAGAAAGAAATTTTGGAGAAGTACGGACATTCAGACTGCTGCAGCCAAAGTGAAGAGGGAAGACATAACTGTTTT
CTTGCACACAAAAAGCCCACTCCAGCATCGATCCCACTTTTCCAAGTTCCAGAACCTGTCACAAGCTGTGAAGCA
TATGAAGAAGACAGGGAGACATTCATGAACAAATTCATTTATGAGATAGCAAGAAGGCATCCCTTCCTGTATGCA
CCTACAATTCTTCTTTGGGCTGCTCGCTATGACAAAATAATTCCATCTTGCTGCAAAGCTGAAAATGCAGTTGAA
TGCTTCCAAACAAAGGCAGCAACAGTTACAAAAGAATTAAGAGAAAGCAGCTTGTTAAATCAACATGCATGTGCA
GTAATGAAAAATTTTGGGACCCGAACTTTCCAAGCCATAACTGTTACTAAACTGAGTCAGAAGTTTACCAAAGTT
AATTTTACTGAAATCCAGAAACTAGTCCTGGATGTGGCCCATGTACATGAGCACTGTTGCAGAGGAGATGTGCTG
GATTGTCTGCAGGATGGGGAAAAAATCATGTCCTACATATGTTCTCAACAAGACACTCTGTCAAACAAAATAACA
GAATGCTGCAAACTGACCACGCTGGAACGTGGTCAATGTATAATTCATGCAGAAAATGATGAAAAACCTGAAGGT
CTATCTCCAAATCTAAACAGGTTTTTAGGAGATAGAGATTTTAACCAATTTTCTTCAGGGGAAAAAAATATCTTC
TTGGCAAGTTTTGTTCATGAATATTCAAGAAGACATCCTCAGCTTGCTGTCTCAGTAATTCTAAGAGTTGCTAAA
GGATACCAGGAGTTATTGGAGAAGTGTTTCCAGACTGAAAACCCTCTTGAATGCCAAGATAAAGGAGAAGAAGAA
TTACAGAAATACATCCAGGAGAGCCAAGCATTGGCAAAGCGAAGCTGCGGCCTCTTCCAGAAACTAGGAGAATAT
TACTTACAAAATGCGTTTCTCGTTGCTTACACAAAGAAAGCCCCCCAGCTGACCTCGTCGGAGCTGATGGCCATC
ACCAGAAAAATGGCAGCCACACAGCAGCCACTTGTTGCCAACTCAGTGAGGACAAACTATTGGCCTGTGGCGAGGGA
GCGGCTGACATTATTATCGGACACTTATGTATCAGACATGAAATGACTCCAGTAAACCCTGGTGTTGGCCAGTGC
TGCACTTCTTCATATGCCAACAGGAGGCCATGCTTCAGCAGCTTGGTGGTGGATGAAACATATGTCCCTCCTGCA
TTCTCTGATGACAAGTTCATTTTCCATAAGGATCTGTGCCAAGCTCAGGGTGTAGCGCTGCAAACAATGAAGCAA
GAGTTTCTCATTAACCTTGTGAAGCAAAAGCCACAAATAACAGAGGAACAACTTGAGGCTGTCATTGCAGATTTC
```

Sequence Listing

```
TCAGGCCTGTTGGAGAAATGCTGCCAAGGCCAGGAACAGGAAGTCTGCTTTGCTGAAGAGGGACAAAAACTGATT
TCAAAAACTCGTGCTGCTTTGGGAGTTTAA hAFP137-145 (SEQ ID NO: 3)
PLFQVPEPV hAFP158-166 (SEQ ID NO: 4)
FMNKFIYEI hAFP325-334 (SEQ ID NO: 5)
GLSPNLNRFL hAFP542-550 (SEQ ID NO: 6)
GVALQTMKQ hAFP158 A1 (SEQ ID NO: 7)
AMNKFIYEI hAFP158 A3 (SEQ ID NO: 8)
FMAKFIYEI hAFP158 A4 (SEQ ID NO: 9)
FMNAFIYEI hAFP158 A5 (SEQ ID NO: 10)
FMNKAIYEI hAFP158 A6 (SEQ ID NO: 11)
FMNKFAYEI hAFP158 A7 (SEQ ID NO: 12)
FMNKFIAEI hAFP158 A8 (SEQ ID NO: 13)
FMNKFIYAI mAFP protein (SEQ ID NO: 14)
MKWITPASLILLLHFAASKALHENEFGIASTLDSSQCVTEKNVLSIATITFTQFVPEATEEEVNKMTSDVLAAMK
KNSGDGCLESQLSVFLDEICHETELSNKYGLSGCCSQSGVERHQCLLARKKTAPASVPPFQFPEPAESCKAHEEN
RAVFMNRFIYEVSRRNPFMYAPAILSLAAQYDKVVLACCKADNKEECFQTKRASIAKELREGSMLNEHVCSVIRK
FGSRNLQATTIIKLSQKLTEANFTEIQKLALDVAHIHEECCQGNSLECLQDGEKVMTYICSQQNILSSKIAECCK
LPMIQLGFCIIHAENGVKPEGLSLNPSQFLGDRNFAQFSSEEKIMFMASFLHEYSRTHPNLPVSVILRIAKTYQE
ILEKCSQSGNLPGCQDNLEEELQKHIEESQALSKQSCALYQTLGDYKLQNLFLIGYTRKAPQLTSAELIDLTGKM
VSIASTCCQLSEEKWSGCGEGMADIFIGHLCIRNEASPVNSGISHCCNSSYSNRRLCITSFLRDETYAPPPFSED
KPIFHKDLCQAQGKALQTMKQELLINLVKQKPELTEEQLAAVTADFSGLLEKCCKAQDQEVCFTEEGPKLISKTR
DALGV mAFP CDS (SEQ ID NO: 15)
ATGAAGTGGATCACACCCGCTTCCCTCATCCTCCTGCTACATTTCGCTGCGTCCAAAGCATTGCACGAAAATGAG
TTTGGGATAGCTTCCACGTTAGATTCCTCCCAGTGCGTGACGGAGAAGAATGTGCTTAGCATAGCTACCATCACC
TTTACCCAGTTTGTTCCGGAAGCCACCGAGGAGGAAGTGAACAAAATGACTAGCGATGTGTTGGCTGCAATGAAG
AAAAACTCTGGCGATGGGTGTTTAGAAAGCCAGCTATCTGTGTTTCTGGATGAAATTTGTCATGAGACGGAACTC
TCTAACAAGTATGGACTCTCAGGCTGCTGCAGCCAAAGTGGGTGGAAAGACATCAGTGTCTGCTGGCACGCAAG
AAGACTGCTCCGGCCTCTGTCCCACCCTTCCAGTTTCCAGAACCTGCCGAGAGTTGCAAAGCACATGAAGAAAC
AGGGCAGTGTTCATGAACAGGTTCATCTATGAAGTGTCAAGGAGGAACCCCTTCATGTATGCCCCAGCCATTCTG
TCCTTGGCTGCTCAGTACGACAAGGTCGTTCTGGCATGCTGCAAAGCTGACAACAAGGAGGAGTGCTTCCAGACA
AAGAGAGCATCCATTGCAAAGGAATTAAGAGAAGGAAGCATGTTAAATGAGCATGTATGTTCAGTGATAAGAAAA
TTTGGATCCCGAAACCTCCAGGCAACAACCATTATTAAGCTAAGTCAAAAGTTAACTGAAGCAAATTTTACTGAG
ATTCAGAAGCTGGCCCTGGATGTGGCTCACATCCACGAGGAGTGTTGCCAAGGAAACTCGCTGGAGTGTCTGCAG
GATGGGGAAAAAGTCATGACATATATATGTTCTCAACAAAATATTCTGTCAAGCAAAATAGCAGAGTGCTGCAAA
TTACCCATGATCCAACTAGGCTTCTGCATAATTCACGCAGAGAATGGCGTCAAACCTGAAGGCTTATCTCTAAAT
CCAAGCCAGTTTTTGGGAGACAGAAATTTTGCCCAATTTTCTTCAGAGGAAAAAATCATGTTCATGGCAAGCTTT
CTTCATGAATACTCAAGAACTCACCCCAACCTTCCTGTCTCAGTCATTCTAAGAATTGCTAAAACGTACCAGGAA
ATATTGGAGAAGTGTTCCCAGTCTGGAAATCTACCTGGATGTCAGGACAATCTGGAAGAAGAATTGCAGAAACAC
ATCGAGGAGAGCCAGGCACTGTCCAAGCAAAGCTGCGCTCTCTACCAGACCTTAGGAGACTACAAATTACAAAAT
CTGTTCCTTATTGGTTACACGAGGAAAGCCCCTCAGCTGACCTCAGCAGAGCTGATCGACCTCACCGGGAAGATG
GTGAGCATTGCCTCCACGTGCTGCCAGCTCAGCGAGGAGAAATGGTCCGGCTGTGGTGAGGGAATGGCCGACATT
TTCATTGGACATTTGTGTATAAGGAATGAAGCAAGCCCTGTGAACTCTGGTATCAGCCACTGCTGCAACTCTTCG
TATTCCAACAGGAGGCTATGCATCACCAGTTTTCTGAGGGATGAAACCTATGCCCCTCCCCCATTCTCTGAGGAT
AAATTCATCTTCCACAAGGATCTGTGCCAAGCTCAGGGCAAAGCCCTACAGACCATGAAACAAGAGCTTCTCATT
AACCTGGTGAAGCAAAAGCCTGAACTGACAGAGGAGCAGCTGGCGGCTGTCACTGCAGATTTCTCGGGCCTTTTG
GAGAAGTGCTGCAAAGCCCAGGACCAGGAAGTCTGTTTCACAGAAGAGGGTCCAAAGTTGATTTCCAAAACTCGT
GATGCTTTGGGCGTTTAA mAFP154-162 (SEQ ID NO: 16)
FMNRFIYEV
```

```
                        Sequence Listing

Clone 17 heavy chain variable domain, protein (SEQ ID NO: 17)
EVQLVQSGAEVKKPGASVKVSCKASGYTFTSYGISWVRQAPGQGLEWMGWISAYNGNTNYAQKLQGRVTMTTDTS
TSTAYMELRSLRSDDTAVYYCARYQDWWYLGQFDQWGQGTLVTVSS Clone 33 heavy chain variable domain, protein (SEQ ID NO: 18)
QVQLQQSGPGLVKPSQTLSLTCAISGDSVSSNSAAWNWIRQSPSRGLEWLGRTYYRSKWYNDYAVSVKSRITINP
DTSKNQFSLQLNSVTPEDTAVYYCARGSYYSGRYDAWGQGTLVTVSS Clone 44 heavy chain variable domain, protein (SEQ ID NO: 19)
QVQLVQSGAEVKKPGSSVKVSCKASGGTFSSYAISWVRQAPGQGLEWMGGIIPIFGTANYAQKFQGRVTITADES
TSTAYMELSSLRSEDTAVYYCAREIRGYYYYYGMDVWGQGTTVTVSS Clone 48 heavy chain variable domain, protein (SEQ ID NO: 20)
EVQLVESGGGLVQPGRSLRLSCAASGFTFDDYAMHWVRQAPGKGLEWVSGISWNSGRIGYADSVKGRFTISRDNA
KNSLYLQMNSLRAEDTAVYYCARADDYGAPYYYYGMDVWGQGTTVTVSS Clone 50 heavy chain variable domain, protein (SEQ ID NO: 21)
QVQLQESGPGLVKPSGTLSLTCAVSGGSISSSNWWSWVRQPPGKGLEWIGEIYHSGSTNYNPSLKSRVTISVDKS
KNQFSLKLSSVTAADTAVYYCATGYGGYFDYWGQGTLVTVSS Clone 52 heavy chain variable domain, protein (SEQ ID NO: 22)
EVQLVQSGAEVKKPGASVKVSCKASGYTFTSYGISWVRQAPGQGLEWMGWISAYNGNTNYAQKLQGRVTMTTDTS
TSTAYMELRSLRSDDTAVYYCARDSYYYYGMDVWGQGTTVTVSS Clone 61 heavy chain variable domain, protein (SEQ ID NO: 23)
EVQLVQSGAEVKKPGESLTISCKASGYSFPNYWITWVRQMSGGGLEWMGRIDPGDSYTTYNPSFQGHVTISIDKS
TNTAYLHWNSLKASDTAMYYCARYYVSLVDIWGQGTLVTVSS Clone 76 heavy chain variable domain, protein (SEQ ID NO: 24)
EVQLVESGGGLVKPGGSLRLSCAASGFTFSNAWMSWVRQAPGKGLEWVGFIRSKAYGGTTEYAASVKGRFTISRD
DSKSIAYLQMNNLKTEDTAVYYCARDGLYSSSWYDSDYWGQGTLVTVSS Clone 79 heavy chain variable domain, protein (SEQ ID NO: 25)
QMQLVQSGGGLVQPGRSLRLSCAASGFTFDDYAMHWVRQAPGKGLEWVSGISWNSGSIGYADSVKGRFTISRDNA
KNSLYLQMNSLRAEDTALYYCAKDIHSGSYYGLLYYAMDVWGQGTTVTVSS Clone 17-13 heavy chain variable domain, protein (SEQ ID NO: 26)
EVQLVQSGAEVKKPGASVKVSCKASGYTFTSYGISWVRQAPGQGLEWMGWISAYNGNTNYAQKLQGRVTMTTDTS
TSTAYMELRSLRSDDTAVYYCARFQDWWYLGQFDQWGQGTLVTVSS Clone 17 light chain variable domain, protein (SEQ ID NO: 27)
QSALTQPASVSGSPGQSITISCTATGSDVGVYYYVSWYQQHPGKAPKVMIYDVGNRPPGVSNRFSGSKSGNTASL
TISGLQAEDEADYYCASYTNRNSLGYVFGTGTKVTVLG Clone 33 light chain variable domain, protein (SEQ ID NO: 28)
NFMLTQPHSVSESPGKTVTISCTRSSGSIASNYVQWYQQRPGSSPTTVIYEDNQRPSGVPDRFSGSIDSSSNSAS
LTISGLKTEDEADYYCQSYDSSTVVFGGGTKLTVLG Clone 44 light chain variable domain, protein (SEQ ID NO: 29)
SYELTQPPSVSVAPGKTARITCGGDNIGTKSVTWYQQRPGQAPMMVIYYDTVRPSGIPERLSGSNSGNTATLTIT
RVEAGDEADYYCQVWDSSSDHPVFGGGTKLTVLG Clone 48 light chain variable domain, protein (SEQ ID NO: 30)
QSVLTQPPSVSGAPGQRVTISCTGSSSNIGAGYDVHWYQQLPGTAPKLLIYGNSNRPSGVPDRFSGSKSGTSASL
AITGLQAEDEADYYCQSYDSSLSGSVFGTGTKVTVLG Clone 50 light chain variable domain, protein (SEQ ID NO: 31)
QSVLTQPPSVSVAPGKTARITCGGNNIGSKSVHWYQQKPGQAPVLVIYYDSDRPSGIPERFSGSNSGNTATLTIS
RVEAGDEADYYCQVWDSSSDHVVFGGGTKLTVLG Clone 52 light chain variable domain, protein (SEQ ID NO: 32)
QAVVTQEPSLTVSPGGTVTLTCGSSTGAVTSGHYPYWFQQKPGQAPRTLIYDASDKHSWTPARFSGSLLGGKAAL
TLSGAQPEDEAEYYCLLSYSDALVFGGGTKLTVLG Clone 61 light chain variable domain, protein (SEQ ID NO: 33)
QSVLTQPASVSGSPGQSITISCTGTSSDVGGYNYVSWYQQHPGKAPKLMIYDVNNRPSEVSNRFSGSKSGNTASL
TISGLQAEDEADYYCSSYTTGSRAVFGGGTKLTVLG Clone 76 light chain variable domain, protein (SEQ ID NO: 34)
QSVVTQPPSVSAAPGQKVTISCSGSSSNIGNNYVSWYQQLPGTAPKLLIYDNNKRPSGIPDRFSGSKSGTSAT
LGITGLQTGDEADYYCGTWDGSLYTMLFGGGTKLTVLG Clone 79 light chain variable domain, protein (SEQ ID NO: 35)
QSVLTQPPSVSGAPGQRVTISCTGSSSNIGAGYDVHWYQQLPGTAPKLLIFGNSNRPSGVPDRFSGFKSGTSASL
AITGLQAEDEADYFCQSYDSSLSGSGVFGTGTKVTVLG Clone 17-13 light chain variable domain, protein (SEQ ID NO: 36)
```

```
QSALTQPASVSGSPGQSITISCTATGSDVGVYYYVSWYQQHPGKAPKVMIYDVDNRPPGVSNRFSGSKSGNTA
SLTISGLQAEDEADYYCASYTNRNSLGYVFGTGTKVTVLG

Clone 17 heavy chain variable domain, nucleic acid (SEQ ID NO: 37)
GAGGTCCAGCTGGTACAGTCTGGAGCTGAGGTGAAGAAGCCTGGGGCCTCAGTGAAGGTCTCCTGCAAGGCTTCT
GGTTACACCTTTACCAGCTATGGTATCAGCTGGGTGCGACAGGCCCCTGGACAAGGGCTTGAGTGGATGGGATGG
ATCAGCGCTTACAATGGTAACACAAACTATGCACAGAAGCTCCAGGGCAGAGTCACCATGACCACAGACACATCC
ACGAGCACAGCCTACATGGAGCTGAGGAGCCTGAGATCTGACGACACGGCCGTGTATTACTGTGCGCGCTACCAG
GACTGGTGGTACCTGGGTCAGTTCGATCAGTGGGGTCAAGGTACTCTGGTGACCGTCTCCTCA Clone 33 heavy chain variable domain, nucleic acid (SEQ ID NO: 38)
CAGGTACAGCTGCAGCAGTCAGGTCCAGGACTGGTGAAGCCCTCGCAGACCCTCTCACTCACCTGTGCCATTTCC
GGGGACAGTGTCTCTAGCAACAGTGCTGCTTGGAACTGGATCAGGCAGTCCCCATCGAGAGGCCTTGAGTGGCTG
GGAAGGACATACTACAGGTCCAAGTGGTATAATGATTATGCAGTATCTGTGAAAAGTCGAATAACCATCAACCCA
GACACATCCAAGAACCAGTTCTCCCTGCAGCTGAACTCTGTGACTCCCGAGGACACGGCTGTGTATTACTGTGCG
CGCGGTTCTTACTACTCTGGTCGTTACGATGCTTGGGGTCAAGGTACTCTGGTGACCGTCTCCTCA Clone 44 heavy chain variable domain, nucleic acid (SEQ ID NO: 39)
CAGGTCCAGCTGGTACAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCC
ACGAGCACAGCCTACATGGAGCTGAGCAGCCTGAGATCTGAGGACACGGCCGTGTATTACTGTGCGAGAGAAATT
AGGGGCTACTACTACTACTACGGTATGGACGTCTGGGGCCAAGGGACCACGGTCACCGTCTCCTCA Clone 48 heavy chain variable domain, nucleic acid (SEQ ID NO: 40)
GAGGTGCAGCTGGTGGAGTCTGGGGGAGGCTTGGTACAGCCTGGCAGGTCCCTGAGACTCTCCTGTGCAGCCTCT
GGATTCACCTTTGATGATTATGCCATGCACTGGGTCCGGCAAGCTCCAGGGAAGGGCCTGGAGTGGGTCTCAGGT
ATTAGTTGGAACAGTGGTAGAATAGGCTATGCGACTCTGTGAAGGGCCGATTCACCATCTCCAGAGACAACGCC
AAGAACTCCCTGTATCTGCAAATGAACAGTCTGAGAGCTGAGGACACGGCTGTGTATTACTGTGCGAGAGCCGAT
GACTACGGCGCCCCTACTACTACTACGGTATGGACGTCTGGGGCCAAGGGACCACGGTCACCGTCTCCTCA Clone 50 heavy chain variable domain, nucleic acid (SEQ ID NO: 41)
CAGGTGCAGCTGCAGGAGTCGGGCCCAGGACTGGTGAAGCCTTCGGGGACCCTGTCCCTCACCTGCGCTGTCTCT
GGTGGCTCCATCAGCAGTAGTAACTGGTGGAGTTGGGTCCGCCAGCCCCCAGGGAAGGGGCTGGAGTGGATTGGG
GAAATCTATCATAGTGGGAGCACCAACTACAACCCGTCCCTCAAGAGTCGAGTCACCATATCAGTAGACAAGTCC
AAGAACCAGTTCTCCCTGAAGCTGAGCTCTGTGACCGCCGCGGACACGGCCGTGTATTACTGTGCGACCGGTTAT
GGGGGGTACTTTGACTACTGGGGCCAGGGAACCCTGGNCACCGTCTCCTCA Clone 52 heavy chain variable domain, nucleic acid (SEQ ID NO: 42)
GAAGTGCAGCTGGTGCAGTCTGGAGCTGAGGTGAAGAAGCCTGGGGCCTCAGTGAAGGTCTCCTGCAAGGCTTCT
GGTTACACCTTTACCAGCTATGGTATCAGCTGGGTGCGACAGGCCCCTGGACAAGGGCTTGAGTGGATGGGATGG
ATCAGCGCTTACAATGGTAACACAAACTATGCACAGAAGCTCCAGGGCAGAGTCACCATGACCACAGACACATCC
ACGAGCACAGCCTACATGGAGCTGAGGAGCCTGAGATCTGACGACACGGCCGTGTATTACTGTGCGAGAGATTCC
TACTACTACTACTACGGTATGGACGTCTGGGGCCAAGGGACCACGGTCACCGTCTCCTCA Clone 61 heavy chain variable domain, nucleic acid (SEQ ID NO: 43)
GAGGTGCAGCTGGTGCAGTCTGGCGCCGAAGTGAAGAAGCCTGGCGAGAGCTGACCATCTCCTGCAAGGCCAGC
GGCTACAGCTTCCCCAACTACTGGATCACCTGGGTGCGCCAGATGTCCGGCGGAGGCCTGGAATGGATGGGCAGA
ATCGACCCCGGCGACAGCTACACAACCTACAACCCCAGCTTCCAGGGCCACGTGACCATCAGCATCGACAAGAGC
ACCAATACCGCCTACCTGCACTGGAACAGCCTGAAGGCCTCCGACACCGCCATGTACTACTGCGCCCGGTACTAT
GTGTCCCTGGTGGATATCTGGGGCCAGGGCACACTCGTGACCGTGTCTAGC Clone 76 heavy chain variable domain, nucleic acid (SEQ ID NO: 44)
GAGGTGCAGCTGGTGGAGTCTGGGGGAGGCTTGGTAAAGCCTGGGGGGTCCCTTAGACTCTCCTGTGCAGCCTCT
GGATTCACTTTCAGTAACGCCTGGATGAGCTGGGTCCGCCAGGCTCCAGGGAAGGGGCTGGAGTGGGTAGGTTTC
ATTAGAAGCAAAGCTTATGGTGGGACAACAGAATACGCCGCCTCTGTGAAAGGCAGATTCACCATCTCAAGAGAT
GATTCCAAAAGCATCGCCTATCTGCAAATGAACAACCTGAAAACCGAGGACACAGCCGTGTATTACTGTGCTAGA
GATGGGCTGTATAGCAGCAGCTGGTACGATTCTGACTACTGGGGCCAGGGAACCCTGGTCACCGTCTCCTCA Clone 79 heavy chain variable domain, nucleic acid (SEQ ID NO: 45)
CAGATGCAGCTGGTGCAGTCTGGGGGAGGCTTGGTACAGCCTGGCAGGTCCCTGAGACTCTCCTGTGCAGCCTCT
GGATTCACCTTTGATGATTATGCCATGCACTGGGTCCGGCAAGCTCCAGGGAAGGGCCTGGAGTGGGTCTCAGGT
ATTAGTTGGAATAGTGGTAGCATAGGCTATGCGGACTCTGTGAAGGGCCGATTCACCATCTCCAGAGACAACGCC
AAGAACTCCCTGTATCTGCAAATGAACAGTCTGAGAGCTGAGGACACGGCCTTGTATTACTGTGCAAAAGATATC
CATAGTGGGAGCTACTACGGCCTACTCTACTACGCTATGGACGTCTGGGGCCAAGGGACCACGGTCACCGTCTCC
TCA Clone 17-13 heavy chain variable domain, nucleic acid (SEQ ID NO: 46)
GAGGTGCAGCTGGTGCAGTCTGGCGCCGAAGTGAAGAAACCAGGCGCCAGCGTGAAGGTGTCCTGCAAGGCCAGC
GGCTACACCTTTACCAGCTACGGCATCAGCTGGGTGCGCCAGGCTCCTGGACAGGGCCTGGAATGGATGGGCTGG
ATCAGCGCCTACAACGGCAATACCAACTACGCCCAGAAACTGCAGGGCAGAGTGACCATGACCACCGACACCAGC
ACCTCCACCGCCTACATGGAACTGCGGAGCCTGAGAAGCGACGACACCGCCGTGTACTATTGCGCCCGGTTCCAG
GACTGGTGGTATCTGGGCCAGTTCGACCAGTGGGGCCAGGGCACACTCGTGACCGTGTCTAGC Clone 17 light chain variable domain, nucleic acid (SEQ ID NO: 47)
CAATCTGCCCTGACTCAGCCTGCCTCCGTGTCTGGGTCTCCTGGACAGTCGATCACCATCTCCTGCACTGCAACC
GGCAGTGACGTTGGTGTTTATTACTATGTCTCCTGGTACCAACAACACCCAGGCAAAGCCCCCAAAGTGATGATT
```

```
TATGATGTCGGTAATCGGCCCCCAGGGGTTTCTAATCGCTTCTCTGGCTCCAAGTCTGGCAACACGGCCTCCCTG
ACCATCTCTGGGCTCCAGGCTGAGGACGAGGCTGATTATTACTGCGCCTCATATACAAACAGGAACAGTCTCGGC
TATGTCTTCGGAACCGGGACCAAGGTCACCGTCCTAGG

Clone 33 light chain variable domain, nucleic acid (SEQ ID NO: 48)
AATTTTATGCTGACTCAGCCCCACTCTGTGTCGGAGTCTCCGGGGAAGACGGTAACCATCTCCTGCACCCGCAGC
AGTGGCAGCATTGCCAGCAACTATGTGCAGTGGTACCAGCAGCGCCCGGGCAGTTCCCCCACCACTGTGATCTAT
GAGGATAACCAAAGACCCTCTGGGGTCCCTGATCGGTTCTCTGGCTCCATCGACAGCTCCTCCAACTCTGCCTCC
CTCACCATCTCTGGACTGAAGACTGAGGACGAGGCTGACTACTACTGTCAGTCTTATGATAGCAGCACCGTGGTA
TTCGGCGGAGGGACCAAGCTGACCGTCCTAGGT Clone 44 light chain variable domain, nucleic acid (SEQ ID NO: 49)
TCCTATGAGCTGACTCAGCCACCCTCGGTGTCAGTGGCCCCTGGCAAGACGGCCAGGATTACCTGTGGGGGTGAC
AACATTGGAACTAAAAGTGTGACCTGGTACCAACAGAGGCCAGGCCAGGCCCCTATGATGGTCATCTATTATGAT
ACCGTCCGGCCCTCAGGGATCCCTGAGCGACTCTCTGGCTCCAACTCTGGGAACACGGCCACCCTGACCATCACC
AGGGTCGAAGCCGGGGATGAGGCCGACTATTACTGTCAGGTGTGGGATAGTAGTAGTGATCATCCGGTGTTCGGC
GGAGGGACCAAGCTGACCGTCCTAGGT Clone 48 light chain variable domain, nucleic acid (SEQ ID NO: 50)
CAGTCTGTGTTGACGCAGCCGCCCTCAGTGTCTGGGGCCCCGGGGCAGAGGGTCACCATCTCCTGCACTGGGAGC
AGCTCCAACATCGGGGCAGGTTATGATGTACACTGGTACCAGCAGCTTCCAGGAACAGCCCCCAAACTCCTCATC
TATGGTAACAGCAATCGGCCCTCAGGGGTCCCTGACCGATTCTCTGGCTCCAAGTCTGGCACCTCAGCCTCCCTG
GCCATCACTGGGCTCCAGGCTGAGGATGAGGCTGATTATTACTGCCAGTCCTATGACAGCAGCCTGAGTGGTTCA
GTCTTCGGAACTGGGACCAAGGTCACCGTCCTAGGT Clone 50 light chain variable domain, nucleic acid (SEQ ID NO: 51)
CAGTCTGTGTTGACTCAGCCACCCTCAGTGTCAGTGGCCCCAGGAAAGACGGCCAGGATTACCTGTGGGGGAAAC
AACATTGGAAGTAAAAGTGTGCACTGGTACCAGCAGAAGCCAGGCCAGGCCCCTGTGCTGGTCATCTATTATGAT
AGCGACCGGCCCTCAGGGATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAGTGATCATGTGGTATTCGGC
GGAGGGACCAAGCTGACCGTCCTAGGT Clone 52 light chain variable domain, nucleic acid (SEQ ID NO: 52)
CAGGCTGTGGTGACTCAGGAGCCCTCACTGACTGTGTCCCCAGGAGGGACAGTCACTCTCACCTGTGGCTCCAGC
ACTGGAGCTGTCACCAGTGGTCATTATCCCTACTGGTTCCAGCAGAAGCCTGGCCAAGCCCCCAGGACACTGATT
TATGATGCAAGCGACAAACACTCCTGGACACCTGCCCGGTTCTCAGGCTCCCTCCTTGGGGGCAAAGCTGCCCTG
ACCCTTTCGGGTGCGCAGCCTGAGGATGAGGCTGAGTATTACTGCTTGCTCTCCTATAGTGATGCTCTGGTGTTC
GGCGGAGGGACCAAGCTGACCGTCCTAGGT Clone 61 light chain variable domain, nucleic acid (SEQ ID NO: 53)
CAGAGCGTGCTGACACAGCCTGCCTCCGTGTCTGGCTCTCCTGGCCAGTCCATCACCATCAGCTGTACCGGCACC
AGCTCCGACGTGGGCGGCTACAATTACGTGTCCTGGTATCAGCAGCATCCCGGCAAGGCCCCCAAGCTGATGATC
TACGACGTGAACAACCGGCCCAGCGAGGTGTCCAACAGATTCAGCGGCAGCAAGAGCGGCAACACCGCCAGCCTG
ACAATCAGCGGACTGCAGGCCGAGGACGAGGCCGACTACTACTGCAGCAGCTACACCACCGGCAGCAGAGCCGTG
TTTGGCGGAGGCACCAAGCTGACAGTGCTGGGC Clone 76 light chain variable domain, nucleic acid (SEQ ID NO: 54)
CAGTCTGTCGTGACGCAGCCGCCCTCAGTGTCTGCGGCCCCAGGACAGAAGGTCACCATCTCCTGCTCTGGAAGC
AGCTCCAACATTGGGAATAATTATGTATCCTGGTACCAGCAGCTCCCAGGAACAGCCCCCAAACTCCTCATTTAT
GACAATAATAAGCGACCCTCAGGGATTCCTGACCGATTCTCTGGCTCCAAGTCTGGCACGTCAGCCACCCTGGGC
ATCACCGGACTCCAGACTGGGGACGAGGCCGATTACTACTGCGGAACATGGGATGGCAGCCTCTATACTATGTTA
TTCGGCGGAGGGACCAAGCTGACCGTCCTAGGT Clone 79 light chain variable domain, nucleic acid (SEQ ID NO: 55)
CAGTCTGTGTTGACGCAGCCGCCCTCAGTGTCTGGGGCCCCAGGGCAGAGGGTCACCATCTCCTGCACTGGGAGC
AGCTCCAACATCGGGGCAGGTTATGATGTACACTGGTACCAGCAGCTTCAGGAACAGCCCCCAAACTCCTCATC
TTTGGTAACAGCAATCGGCCCTCAGGGGTCCCTGACCGATTCTCTGGCTTCAAGTCTGGCACCTCAGCCTCCCTG
GCCATCACTGGGCTCCAGGCTGAGGATGAGGCTGACTATTTCTGCCAGTCGTATGACAGTAGCCTGAGTGGTTCG
GGGGTCTTCGGAACTGGGACCAAGGTCACCGTCCTAGGT Clone 17-13 light chain variable domain, nucleic acid (SEQ ID NO: 56)
CAGAGCGCCCTGACACAGCCTGCCTCCGTGTCTGGATCTCCCGGCCAGAGCATCACCATCAGCTGCACAGCCACC
GGCTCCGACGTGGGCGTGTACTACTACGTGTCCTGGTATCAGCAGCATCCCGGCAAGGCCCCCAAAGTGATGATC
TACGACGTGGACAACCGGCCTCCCGGCGTGTCCAATAGATTCAGCGGCAGCAAGAGCGGCAACACCGCCAGCCTG
ACAATCAGCGGACTGCAGGCCGAGGACGAGGCCGATTACTACTGCGCCAGCTACACCAACCGGAACAGCCTGGGC
TACGTGTTCGGCACCGGCACCAAAGTGACAGTGCTGGGC Clone 17 HCDR1 (SEQ ID NO: 57)
GYTFTSYG Clone 33 HCDR1 (SEQ ID NO: 58)
VSSNSAAWN Clone 44 HCDR1 (SEQ ID NO: 59)
GGTFSSYA Clone 48 HCDR1 (SEQ ID NO: 60)
```

```
                        Sequence Listing
GFTFDDYA

Clone 50 HCDR1 (SEQ ID NO: 61)
GGSISSSNW

Clone 52 HCDR1 (SEQ ID NO: 62)
GYTFTSYG

Clone 61 HCDR1 (SEQ ID NO: 63)
GYSFPNYW

Clone 76 HCDR1 (SEQ ID NO: 64)
GFTFSNAW

Clone 79 HCDR1 (SEQ ID NO: 65)
GFTFDDYA

Clone 17-13 HCDR1 (SEQ ID NO: 66)
GYTFTSYG

Clone 17 HCDR2 (SEQ ID NO: 67)
ISAYNGNT

Clone 33 HCDR2 (SEQ ID NO: 68)
YRSKWYN

Clone 44 HCDR2 (SEQ ID NO: 69)
IIPIFGTA

Clone 48 HCDR2 (SEQ ID NO: 70)
ISWNSGRI

Clone 50 HCDR2 (SEQ ID NO: 71)
IYHSGST

Clone 52 HCDR2 (SEQ ID NO: 72)
ISAYNGNT

Clone 61 HCDR2 (SEQ ID NO: 73)
IDPGDSYT

Clone 76 HCDR2 (SEQ ID NO: 74)
IRSKAYGGTT

Clone 79 HCDR2 (SEQ ID NO: 75)
ISWNSGSI

Clone 17-13 HCDR2 (SEQ ID NO: 76)
ISAYNGNT

Clone 17 HCDR3 (SEQ ID NO: 77)
ARYQDWWYLGQFDQ

Clone 33 HCDR3 (SEQ ID NO: 78)
ARGSYYSGRYDA

Clone 44 HCDR3 (SEQ ID NO: 79)
AREIRGYYYYYGMDV

Clone 48 HCDR3 (SEQ ID NO: 80)
ARADDYGAPYYYYGMDV

Clone 50 HCDR3 (SEQ ID NO: 81)
ATGYGGYFDY

Clone 52 HCDR3 (SEQ ID NO: 82)
ARDSYYYYGMDV

Clone 61 HCDR3 (SEQ ID NO: 83)
ARYYVSLVDI

Clone 76 HCDR3 (SEQ ID NO: 84)
ARDGLYSSSWYDSDY

Clone 79 HCDR3 (SEQ ID NO: 85)
AKDIHSGSYYGLLYYAMDV
```

| Sequence Listing |
|---|

Clone 17-13 HCDR3 (SEQ ID NO: 86)
ARFQDWWYLGQFDQ

HCCDR1 consensus (SEQ ID NO: 87)
G-F/Y-S/T-F-D/S/T-D/N/S-Y/A-A/G/W

HCCDR2 consensus (SEQ ID NO: 88)
I/S-K/S-X-H/Y-X-G-X-T

HCCDR3 consensus (SEQ ID NO: 89)
A/G-X-W/Y-Y-X-X-F/Y-D

Clone 17 LCDR1 (SEQ ID NO: 90)
GSDVGVYYY

Clone 33 LCDR1 (SEQ ID NO: 91)
SGSIASNY

Clone 44 LCDR1 (SEQ ID NO: 92)
NIGTKS

Clone 48 LCDR1 (SEQ ID NO: 93)
SSNIGAGYD

Clone 50 LCDR1 (SEQ ID NO: 94)
NIGSKS

Clone 52 LCDR1 (SEQ ID NO: 95)
TGAVTSGHY

Clone 61 LCDR1 (SEQ ID NO: 96)
SSDVGGYNY

Clone 76 LCDR1 (SEQ ID NO: 97)
SSNIGNNY

Clone 79 LCDR1 (SEQ ID NO: 98)
SSNIGAGYD

Clone 17-13 LCDR1 (SEQ ID NO: 99)
GSDVGVYYY

Clone 17 LCDR2 (SEQ ID NO: 100)
DVG

Clone 33 LCDR2 (SEQ ID NO: 101)
EDN

Clone 44 LCDR2 (SEQ ID NO: 102)
YDT

Clone 48 LCDR2 (SEQ ID NO: 103)
GNS

Clone 50 LCDR2 (SEQ ID NO: 104)
YDS

Clone 52 LCDR2 (SEQ ID NO: 105)
DAS

Clone 61 LCDR2 (SEQ ID NO: 106)
DVN

Clone 76 LCDR2 (SEQ ID NO: 107)
DNN

Clone 79 LCDR2 (SEQ ID NO: 108)
GNS

Clone 17-13 LCDR2 (SEQ ID NO: 109)
DVD

Clone 17 LCDR3 (SEQ ID NO: 110)
ASYTNRNSLGYV

Clone 33 LCDR3 (SEQ ID NO: 111)
QSYDSSTVV

-continued

Sequence Listing

Clone 44 LCDR3 (SEQ ID NO: 112)
QVWDSSSDHPV

Clone 48 LCDR3 (SEQ ID NO: 113)
QSYDSSLSGSV

Clone 50 LCDR3 (SEQ ID NO: 114)
QVWDSSSDHVV

Clone 52 LCDR3 (SEQ ID NO: 115)
LLSYSDALV

Clone 61 LCDR3 (SEQ ID NO: 116)
SSYTTGSRAV

Clone 76 LCDR3 (SEQ ID NO: 117)
GTWDGSLYTML

Clone 79 LCDR3 (SEQ ID NO: 118)
QSYDSSLSGSGV

Clone 17-13 LCDR3 (SEQ ID NO: 119)
ASYTNRNSLGYV

LCCDR1 consensus (SEQ ID NO: 120)
S/T-G/S-D/N-I/V-A/G-A/S/V-X-H/Y

LCCDR3 consensus (SEQ ID NO: 121)
Q-S/T-Y/W-D/T-S/T-A/S

IFI30 control (SEQ ID NO: 122)
LLDVPTAAV

BTG2 control (SEQ ID NO: 123)
TLWVDPYEV

BCR control (SEQ ID NO: 124)
FLLDHLKRV

IFI30 control (SEQ ID NO: 125)
LLLDVPTAAV

SSR1 control (SEQ ID NO: 126)
VLFRGGPRGLLAV

PPP2R1B control (SEQ ID NO: 127)
SLLPAIVEL

DDX5 control (SEQ ID NO: 128)
YLLPAIVHI

CTSG control (SEQ ID NO: 129)
FLLPTGAEA

CD247 control (SEQ ID NO: 130)
LLDPKLCYLL

DMTN control (SEQ ID NO: 131)
SLPHFHHPET

CALR control (SEQ ID NO: 132)
MLLSVPLLLG

PIM1 control (SEQ ID NO: 133)
LLYDMVCGDIP

IFI30 control (SEQ ID NO: 134)
LLLDVPTAAVQ

IFI30 control (SEQ ID NO: 135)
LLLDVPTAAVQA

SSR1 control (SEQ ID NO: 136)
VLFRGGPRGLLAVA

HLA-E control (SEQ ID NO: 137)

MVDGTLLLL

RPS6KB1 control (SEQ ID NO: 138)
YMAPEILMRS

CSF2RA control (SEQ ID NO: 139)
FIYNADLMNC

IL7 control (SEQ ID NO: 140)
KQYESVLMVSI hTERT540 control (SEQ ID NO: 141)
ILAKFLHWL

What is claimed is:

1. An isolated anti-AMC construct comprising an antibody moiety that specifically binds to a complex comprising an alpha-fetoprotein (AFP) peptide and a major histocompatibility (MHC) class I protein (AFP/MHC class I complex, or AMC), wherein the AFP peptide comprises the amino acid sequence of SEQ ID NO: 4, wherein the MHC class I protein is HLA-A02, and wherein the antibody moiety comprises:
 a heavy chain variable domain comprising a heavy chain complementarity determining region (HC-CDR)1 comprising the amino acid sequence of SEQ ID NO: 63, an HC-CDR2 comprising the amino acid sequence of SEQ ID NO: 73, and an HC-CDR3 comprising the amino acid sequence of SEQ ID NO: 83; and
 a light chain variable domain comprising a light chain complementarity determining region (LC-CDR)1 comprising the amino acid sequence of SEQ ID NO: 96, an LC-CDR2 comprising the amino acid sequence of SEQ ID NO: 106, and an LC-CDR3 comprising the amino acid sequence of SEQ ID NO: 116.

2. The isolated anti-AMC construct of claim 1, wherein the heavy chain variable domain comprises the amino acid sequence of SEQ ID NO: 23 and the light chain variable domain comprises the amino acid sequence of SEQ ID NO: 33.

3. The isolated anti-AMC construct of claim 1, wherein the isolated anti-AMC construct is a chimeric antigen receptor (CAR) comprising an extracellular domain comprising the antibody moiety, a transmembrane domain, and an intracellular signaling domain capable of activating an immune cell.

4. The isolated anti-AMC construct of claim 3, wherein the intracellular signaling domain comprises a CD3ζ intracellular signaling sequence and a co-stimulatory signaling sequence.

5. The isolated anti-AMC construct of claim 4, wherein the co-stimulatory signaling sequence comprises a CD28 or 4-1BB intracellular signaling sequence.

6. The isolated anti-AMC construct of claim 5, wherein the co-stimulatory signaling sequence comprises a CD28 intracellular signaling sequence.

7. The isolated anti-AMC construct of claim 6, wherein the transmembrane domain comprises a CD28 transmembrane region.

8. The isolated anti-AMC construct of claim 3, wherein the antibody moiety is an scFv.

9. The isolated anti-AMC construct of claim 1, wherein the isolated anti-AMC construct is a tandem scFv comprising a first scFv linked by a peptide linker to a second scFv, wherein the first scFv is the antibody moiety that specifically binds to the AFP/MHC class I complex.

10. The isolated anti-AMC construct of claim 9, wherein the second scFv is specific for CD3ε.

11. The isolated anti-AMC construct of claim 10, wherein the first scFv is N-terminal to the second scFv.

12. The isolated anti-AMC construct of claim 1, wherein the isolated anti-AMC construct is an immunoconjugate comprising the antibody moiety and an effector molecule, wherein the effector molecule is a therapeutic agent selected from the group consisting of a drug, a toxin, a radioisotope, a protein, a peptide, and a nucleic acid.

13. The isolated anti-AMC construct of claim 1, wherein the isolated anti-AMC construct is an immunoconjugate comprising the antibody moiety and a label.

14. A nucleic acid encoding the polypeptide components of the isolated anti-AMC construct of claim 1.

15. A host cell expressing the isolated anti-AMC construct of claim 1.

16. An effector cell expressing the isolated anti-AMC construct of claim 1.

17. A CAR T cell expressing the isolated anti-AMC construct of claim 3, wherein the intracellular signaling domain is capable of activating a T cell.

18. A pharmaceutical composition comprising the CART cell of claim 17.

19. A method of treating an individual having an AFP-positive cancer, comprising administering to the individual an effective amount of the pharmaceutical composition of claim 18, wherein the cancer expresses human AFP and HLA-A02.

20. The method of claim 19, wherein the administration is via intravenous or intratumoral route.

21. The method of claim 19, wherein the cancer is hepatocellular carcinoma, germ cell tumor, or breast cancer.

22. The method of claim 21, wherein the cancer is hepatocellular carcinoma.

23. The method of claim 22, wherein the cancer is metastatic hepatocellular carcinoma.

24. The isolated anti-AMC construct of claim 1, wherein the MHC class I protein is the HLA-A*02:01 subtype of the HLA-A02 allele.

* * * * *

SEQUENCE LISTING

<160> NUMBER OF SEQ ID NOS: 141

<210> SEQ ID NO 1
<211> LENGTH: 609
<212> TYPE: PRT
<213> ORGANISM: Homo sapiens

<400> SEQUENCE: 1

```
Met Lys Trp Val Glu Ser Ile Phe Leu Ile Phe Leu Leu Asn Phe Thr
 1               5                  10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255
```

Lys Leu Val Leu Asp Val Ala His Val His Glu His Cys Cys Arg Gly
                260                 265                 270

Asp Val Leu Asp Cys Leu Gln Asp Gly Glu Lys Ile Met Ser Tyr Ile
            275                 280                 285

Cys Ser Gln Gln Asp Thr Leu Ser Asn Lys Ile Thr Glu Cys Cys Lys
290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
    370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
        435                 440                 445

Ala Ile Thr Arg Lys Met Ala Ala Thr Ala Thr Cys Cys Gln Leu
    450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
    530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val

<210> SEQ ID NO 2
<211> LENGTH: 1830
<212> TYPE: DNA
<213> ORGANISM: Homo sapiens

<400> SEQUENCE: 2
atgaagtggg tggaatcaat ttttttaatt ttcctactaa attttactga atccagaaca     60
ctgcatagaa atgaatatgg aatagcttcc atattggatt cttaccaatg tactgcagag    120

```
ataagtttag ctgacctggc taccatattt tttgcccagt tgttcaaga agccacttac      180 aaggaagtaa gcaaaatggt gaaagatgca ttgactgcaa ttgagaaacc cactggagat      240
gaacagtctt cagggtgttt agaaaaccag ctacctgcct ttctggaaga actttgccat      300
gagaaagaaa ttttggagaa gtacggacat tcagactgct gcagccaaag tgaagaggga      360
agacataact gttttcttgc acacaaaaag cccactccag catcgatccc acttttccaa      420
gttccagaac ctgtcacaag ctgtgaagca tatgaagaag acaggagac attcatgaac       480 aaattcattt atgagatagc aagaaggcat cccttcctgt atgcacctac aattcttctt      540
tgggctgctc gctatgacaa ataattcca tcttgctgca aagctgaaaa tgcagttgaa       600
tgcttccaaa caaaggcagc aacagttaca aaagaattaa gagaaagcag cttgttaaat      660
caacatgcat gtgcagtaat gaaaaatttt gggacccgaa ctttccaagc cataactgtt      720
actaaactga gtcagaagtt taccaaagtt aattttactg aaatccagaa actagtcctg      780
gatgtggccc atgtacatga gcactgttgc agaggagatg tgctggattg tctgcaggat      840
ggggaaaaaa tcatgtccta catatgttct caacaagaca ctctgtcaaa caaaataaca      900
gaatgctgca aactgaccac gctggaacgt ggtcaatgta taattcatgc agaaaatgat      960
gaaaaacctg aaggtctatc tccaaatcta acaggttttt aggagatag agattttaac      1020 caattttctt caggggaaaa aaatatcttc ttggcaagtt ttgttcatga atattcaaga      1080
agacatcctc agcttgctgt ctcagtaatt ctaagagttg ctaaaggata ccaggagtta      1140
ttggagaagt gtttccagac tgaaaaccct cttgaatgcc aagataaagg agaagaagaa      1200
ttacagaaat acatccagga gagccaagca ttggcaaagc gaagctgcgg cctcttccag      1260
aaactaggag aatattactt acaaaatgcg tttctcgttg cttacacaaa gaaagccccc      1320
cagctgacct cgtcggagct gatggccatc accagaaaaa tggcagccac agcagccact      1380
tgttgccaac tcagtgagga caaactattg gcctgtggcg agggagcggc tgacattatt      1440
atcggacact tatgtatcag acatgaaatg actccagtaa accctggtgt tggccagtgc      1500
tgcacttctt catatgccaa caggaggcca tgcttcagca gcttggtggt ggatgaaaca      1560
tatgtccctc ctgcattctc tgatgacaag ttcattttcc ataaggatct gtgccaagct      1620
cagggtgtag cgctgcaaac aatgaagcaa gagtttctca ttaaccttgt gaagcaaaag      1680
ccacaaataa cagaggaaca acttgaggct gtcattgcag atttctcagg cctgttggag      1740
aaatgctgcc aaggccagga acaggaagtc tgctttgctg aagagggaca aaaactgatt      1800
tcaaaaactc gtgctgcttt gggagtttaa                                      1830
```

<210> SEQ ID NO 3
<211> LENGTH: 9
<212> TYPE: PRT
<213> ORGANISM: Homo sapiens

<400> SEQUENCE: 3

Pro Leu Phe Gln Val Pro Glu Pro Val
 1               5

<210> SEQ ID NO 4
<211> LENGTH: 9
<212> TYPE: PRT
<213> ORGANISM: Homo sapiens

<400> SEQUENCE: 4

Phe Met Asn Lys Phe Ile Tyr Glu Ile

```
                           1               5

<210> SEQ ID NO 5
<211> LENGTH: 10
<212> TYPE: PRT
<213> ORGANISM: Homo sapiens

<400> SEQUENCE: 5

Gly Leu Ser Pro Asn Leu Asn Arg Phe Leu
 1               5                  10

<210> SEQ ID NO 6
<211> LENGTH: 9
<212> TYPE: PRT
<213> ORGANISM: Homo sapiens

<400> SEQUENCE: 6

Gly Val Ala Leu Gln Thr Met Lys Gln
 1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Ala Met Asn Lys Phe Ile Tyr Glu Ile
 1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Phe Met Ala Lys Phe Ile Tyr Glu Ile
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Phe Met Asn Ala Phe Ile Tyr Glu Ile
 1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Phe Met Asn Lys Ala Ile Tyr Glu Ile
 1               5

<210> SEQ ID NO 11
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 11

Phe Met Asn Lys Phe Ala Tyr Glu Ile
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Phe Met Asn Lys Phe Ile Ala Glu Ile
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Phe Met Asn Lys Phe Ile Tyr Ala Ile
1               5

<210> SEQ ID NO 14
<211> LENGTH: 605
<212> TYPE: PRT
<213> ORGANISM: Mus musculus

<400> SEQUENCE: 14

Met Lys Trp Ile Thr Pro Ala Ser Leu Ile Leu Leu Leu His Phe Ala
1               5                   10                  15

Ala Ser Lys Ala Leu His Glu Asn Glu Phe Gly Ile Ala Ser Thr Leu
                20                  25                  30

Asp Ser Ser Gln Cys Val Thr Glu Lys Asn Val Leu Ser Ile Ala Thr
            35                  40                  45

Ile Thr Phe Thr Gln Phe Val Pro Glu Ala Thr Glu Glu Val Asn
        50                  55                  60

Lys Met Thr Ser Asp Val Leu Ala Ala Met Lys Lys Asn Ser Gly Asp
65                  70                  75                  80

Gly Cys Leu Glu Ser Gln Leu Ser Val Phe Leu Asp Glu Ile Cys His
                85                  90                  95

Glu Thr Glu Leu Ser Asn Lys Tyr Gly Leu Ser Gly Cys Cys Ser Gln
                100                 105                 110

Ser Gly Val Glu Arg His Gln Cys Leu Leu Ala Arg Lys Lys Thr Ala
            115                 120                 125

Pro Ala Ser Val Pro Pro Phe Gln Phe Pro Glu Pro Ala Glu Ser Cys
        130                 135                 140

Lys Ala His Glu Glu Asn Arg Ala Val Phe Met Asn Arg Phe Ile Tyr
145                 150                 155                 160

Glu Val Ser Arg Arg Asn Pro Phe Met Tyr Ala Pro Ala Ile Leu Ser
                165                 170                 175

Leu Ala Ala Gln Tyr Asp Lys Val Val Leu Ala Cys Cys Lys Ala Asp
                180                 185                 190
```

```
Asn Lys Glu Glu Cys Phe Gln Thr Lys Arg Ala Ser Ile Ala Lys Glu
        195                 200                 205

Leu Arg Glu Gly Ser Met Leu Asn Glu His Val Cys Ser Val Ile Arg
    210                 215                 220

Lys Phe Gly Ser Arg Asn Leu Gln Ala Thr Thr Ile Ile Lys Leu Ser
225                 230                 235                 240

Gln Lys Leu Thr Glu Ala Asn Phe Thr Glu Ile Gln Lys Leu Ala Leu
                245                 250                 255

Asp Val Ala His Ile His Glu Glu Cys Cys Gln Gly Asn Ser Leu Glu
                260                 265                 270

Cys Leu Gln Asp Gly Glu Lys Val Met Thr Tyr Ile Cys Ser Gln Gln
            275                 280                 285

Asn Ile Leu Ser Ser Lys Ile Ala Glu Cys Cys Lys Leu Pro Met Ile
        290                 295                 300

Gln Leu Gly Phe Cys Ile Ile His Ala Glu Asn Gly Val Lys Pro Glu
305                 310                 315                 320

Gly Leu Ser Leu Asn Pro Ser Gln Phe Leu Gly Asp Arg Asn Phe Ala
                325                 330                 335

Gln Phe Ser Ser Glu Glu Lys Ile Met Phe Met Ala Ser Phe Leu His
            340                 345                 350

Glu Tyr Ser Arg Thr His Pro Asn Leu Pro Val Ser Val Ile Leu Arg
        355                 360                 365

Ile Ala Lys Thr Tyr Gln Glu Ile Leu Glu Lys Cys Ser Gln Ser Gly
    370                 375                 380

Asn Leu Pro Gly Cys Gln Asp Asn Leu Glu Glu Leu Gln Lys His
385                 390                 395                 400

Ile Glu Glu Ser Gln Ala Leu Ser Lys Gln Ser Cys Ala Leu Tyr Gln
                405                 410                 415

Thr Leu Gly Asp Tyr Lys Leu Gln Asn Leu Phe Leu Ile Gly Tyr Thr
            420                 425                 430

Arg Lys Ala Pro Gln Leu Thr Ser Ala Glu Leu Ile Asp Leu Thr Gly
        435                 440                 445

Lys Met Val Ser Ile Ala Ser Thr Cys Cys Gln Leu Ser Glu Glu Lys
    450                 455                 460

Trp Ser Gly Cys Gly Glu Gly Met Ala Asp Ile Phe Ile Gly His Leu
465                 470                 475                 480

Cys Ile Arg Asn Glu Ala Ser Pro Val Asn Ser Gly Ile Ser His Cys
                485                 490                 495

Cys Asn Ser Ser Tyr Ser Asn Arg Arg Leu Cys Ile Thr Ser Phe Leu
            500                 505                 510

Arg Asp Glu Thr Tyr Ala Pro Pro Phe Ser Glu Asp Lys Phe Ile
        515                 520                 525

Phe His Lys Asp Leu Cys Gln Ala Gln Gly Lys Ala Leu Gln Thr Met
    530                 535                 540

Lys Gln Glu Leu Leu Ile Asn Leu Val Lys Gln Lys Pro Glu Leu Thr
545                 550                 555                 560

Glu Glu Gln Leu Ala Ala Val Thr Ala Asp Phe Ser Gly Leu Leu Glu
                565                 570                 575

Lys Cys Cys Lys Ala Gln Asp Gln Glu Val Cys Phe Thr Glu Glu Gly
            580                 585                 590

Pro Lys Leu Ile Ser Lys Thr Arg Asp Ala Leu Gly Val
        595                 600                 605
```

<210> SEQ ID NO 15
<211> LENGTH: 1818
<212> TYPE: DNA
<213> ORGANISM: Mus musculus

<400> SEQUENCE: 15

| | | | | | |
|---|---|---|---|---|---|
| atgaagtgga | tcacacccgc | ttccctcatc | ctcctgctac | atttcgctgc | gtccaaagca | 60 |
| ttgcacgaaa | atgagtttgg | gatagcttcc | acgttagatt | cctcccagtg | cgtgacggag | 120 |
| aagaatgtgc | ttagcatagc | taccatcacc | tttacccagt | tgttccgga | agccaccgag | 180 |
| gaggaagtga | acaaaatgac | tagcgatgtg | ttggctgcaa | tgaagaaaaa | ctctggcgat | 240 |
| gggtgtttag | aaagccagct | atctgtgttt | ctggatgaaa | tttgtcatga | cggaactc | 300 |
| tctaacaagt | atggactctc | aggctgctgc | agccaaagtg | gagtggaaag | acatcagtgt | 360 |
| ctgctggcac | gcaagaagac | tgctccggcc | tctgtcccac | ccttccagtt | tccagaacct | 420 |
| gccgagagtt | gcaaagcaca | tgaagaaaac | agggcagtgt | tcatgaacag | gttcatctat | 480 |
| gaagtgtcaa | ggaggaaccc | cttcatgtat | gccccagcca | ttctgtcctt | ggctgctcag | 540 |
| tacgacaagg | tcgttctggc | atgctgcaaa | gctgacaaca | aggaggagtg | cttccagaca | 600 |
| aagagagcat | ccattgcaaa | ggaattaaga | aaggaagca | tgttaaatga | gcatgtatgt | 660 |
| tcagtgataa | gaaaatttgg | atcccgaaac | ctccaggcaa | caaccattat | taagctaagt | 720 |
| caaaagttaa | ctgaagcaaa | ttttactgag | attcagaagc | tggccctgga | tgtggctcac | 780 |
| atccacgagg | agtgttgcca | aggaaactcg | ctggagtgtc | tgcaggatgg | ggaaaaagtc | 840 |
| atgacatata | tatgttctca | acaaaatatt | ctgtcaagca | aaatagcaga | gtgctgcaaa | 900 |
| ttacccatga | tccaactagg | cttctgcata | attcacgcag | agaatggcgt | caaacctgaa | 960 |
| ggcttatctc | taaatccaag | ccagttttg | ggagacagaa | attttgccca | attttcttca | 1020 |
| gaggaaaaaa | tcatgttcat | ggcaagcttt | cttcatgaat | actcaagaac | tcaccccaac | 1080 |
| cttcctgtct | cagtcattct | aagaattgct | aaaacgtacc | aggaaatatt | ggagaagtgt | 1140 |
| tcccagtctg | gaaatctacc | tggatgtcag | gacaatctgg | aagaagaatt | gcagaaacac | 1200 |
| atcgaggaga | gccaggcact | gtccaagcaa | agctgcgctc | tctaccagac | cttaggagac | 1260 |
| tacaaattac | aaaatctgtt | ccttattggt | tacacgagga | aagcccctca | gctgacctca | 1320 |
| gcagagctga | tcgacctcac | cgggaagatg | gtgagcattg | cctccacgtg | ctgccagctc | 1380 |
| agcgaggaga | atggtccgg | ctgtggtgag | ggaatggccg | acattttcat | ggacatttg | 1440 |
| tgtataagga | atgaagcaag | ccctgtgaac | tctggtatca | gccactgctg | caactcttcg | 1500 |
| tattccaaca | ggaggctatg | catcaccagt | tttctgaggg | atgaaaccta | tgcccctccc | 1560 |
| ccattctctg | aggataaatt | catcttccac | aaggatctgt | gccaagctca | gggcaaagcc | 1620 |
| ctacagacca | tgaaacaaga | gcttctcatt | aacctggtga | agcaaaagcc | tgaactgaca | 1680 |
| gaggagcagc | tggcggctgt | cactgcagat | ttctcgggcc | ttttggagaa | gtgctgcaaa | 1740 |
| gcccaggacc | aggaagtctg | tttcacagaa | gagggtccaa | agttgatttc | caaaactcgt | 1800 |
| gatgctttgg | gcgtttaa | | | | | 1818 |

<210> SEQ ID NO 16
<211> LENGTH: 9
<212> TYPE: PRT
<213> ORGANISM: Mus musculus

<400> SEQUENCE: 16

Phe Met Asn Arg Phe Ile Tyr Glu Val

```
<210> SEQ ID NO 17
<211> LENGTH: 121
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Gln Asp Trp Trp Tyr Leu Gly Gln Phe Asp Gln Trp Gly
            100                 105                 110

Gln Gly Thr Leu Val Thr Val Ser Ser
        115                 120

<210> SEQ ID NO 18
<211> LENGTH: 122
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Ser Tyr Tyr Ser Gly Arg Tyr Asp Ala Trp
            100                 105                 110

Gly Gln Gly Thr Leu Val Thr Val Ser Ser
        115                 120

<210> SEQ ID NO 19
<211> LENGTH: 122
<212> TYPE: PRT
<213> ORGANISM: Artificial Sequence
<220> FEATURE:
<223> OTHER INFORMATION: Synthetic Construct

<400> SEQUENCE: 19
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ile Arg Gly Tyr Tyr Tyr Tyr Gly Met Asp Val Trp
                100                 105                 110

Gly Gln Gly Thr Thr Val Thr Val Ser Ser
            115                 120

<210> SEQ ID NO 20
<211> LENGTH: 124
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Asp Tyr Gly Ala Pro Tyr Tyr Tyr Tyr Gly Met Asp
                100                 105                 110

Val Trp Gly Gln Gly Thr Thr Val Thr Val Ser Ser
            115                 120

<210> SEQ ID NO 21
<211> LENGTH: 117
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu

```
                  50                  55                  60
Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                     85                  90                  95

Ala Thr Gly Tyr Gly Gly Tyr Phe Asp Tyr Trp Gly Gln Gly Thr Leu
                100                 105                 110

Val Thr Val Ser Ser
            115

<210> SEQ ID NO 22
<211> LENGTH: 120
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
         50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Ser Tyr Tyr Tyr Tyr Gly Met Asp Val Trp Gly Gln
                100                 105                 110

Gly Thr Thr Val Thr Val Ser Ser
            115                 120

<210> SEQ ID NO 23
<211> LENGTH: 117
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Gln Ser Gly Ala Glu Val Lys Lys Pro Gly Glu
  1               5                  10                  15

Ser Leu Thr Ile Ser Cys Lys Ala Ser Gly Tyr Ser Phe Pro Asn Tyr
                 20                  25                  30

Trp Ile Thr Trp Val Arg Gln Met Ser Gly Gly Leu Glu Trp Met
             35                  40                  45

Gly Arg Ile Asp Pro Gly Asp Ser Tyr Thr Thr Tyr Asn Pro Ser Phe
         50                  55                  60

Gln Gly His Val Thr Ile Ser Ile Asp Lys Ser Thr Asn Thr Ala Tyr
 65                  70                  75                  80

Leu His Trp Asn Ser Leu Lys Ala Ser Asp Thr Ala Met Tyr Tyr Cys
                 85                  90                  95

Ala Arg Tyr Tyr Val Ser Leu Val Asp Ile Trp Gly Gln Gly Thr Leu
                100                 105                 110
```

Val Thr Val Ser Ser
        115

<210> SEQ ID NO 24
<211> LENGTH: 124
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Asn Leu Lys Thr Glu Asp Thr Ala Val Tyr
                85                  90                  95

Tyr Cys Ala Arg Asp Gly Leu Tyr Ser Ser Trp Tyr Asp Ser Asp
            100                 105                 110

Tyr Trp Gly Gln Gly Thr Leu Val Thr Val Ser Ser
        115                 120

<210> SEQ ID NO 25
<211> LENGTH: 126
<212> TYPE: PRT
<213> ORGANISM: Artificial Sequence
<220> FEATURE:
<223> OTHER INFORMATION: Synthetic Construct

<400> SEQUENCE: 25

Gln Met Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile His Ser Gly Ser Tyr Tyr Gly Leu Leu Tyr Tyr Ala
            100                 105                 110

Met Asp Val Trp Gly Gln Gly Thr Thr Val Thr Val Ser Ser
        115                 120                 125

<210> SEQ ID NO 26
<211> LENGTH: 121
<212> TYPE: PRT
<213> ORGANISM: Artificial Sequence
<220> FEATURE:
<223> OTHER INFORMATION: Synthetic Construct

```
<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Phe Gln Asp Trp Trp Tyr Leu Gly Phe Asp Gln Trp Gly
                100                 105                 110

Gln Gly Thr Leu Val Thr Val Ser Ser
            115                 120

<210> SEQ ID NO 27
<211> LENGTH: 113
<212> TYPE: PRT
<213> ORGANISM: Artificial Sequence
<220> FEATURE:
<223> OTHER INFORMATION: Synthetic Construct

<400> SEQUENCE: 27

Gln Ser Ala Leu Thr Gln Pro Ala Ser Val Ser Gly Ser Pro Gly Gln
1               5                   10                  15

Ser Ile Thr Ile Ser Cys Thr Ala Thr Gly Ser Asp Val Gly Val Tyr
                20                  25                  30

Tyr Tyr Val Ser Trp Tyr Gln Gln His Pro Gly Lys Ala Pro Lys Val
            35                  40                  45

Met Ile Tyr Asp Val Gly Asn Arg Pro Pro Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Thr Asn Arg
                85                  90                  95

Asn Ser Leu Gly Tyr Val Phe Gly Thr Gly Thr Lys Val Thr Val Leu
                100                 105                 110

Gly

<210> SEQ ID NO 28
<211> LENGTH: 111
<212> TYPE: PRT
<213> ORGANISM: Artificial Sequence
<220> FEATURE:
<223> OTHER INFORMATION: Synthetic Construct

<400> SEQUENCE: 28

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
```

```
                50                  55                  60
Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Thr Val Val Phe Gly Gly Gly Thr Lys Leu Thr Val Leu Gly
            100                 105                 110

<210> SEQ ID NO 29
<211> LENGTH: 109
<212> TYPE: PRT
<213> ORGANISM: Artificial Sequence
<220> FEATURE:
<223> OTHER INFORMATION: Synthetic Construct

<400> SEQUENCE: 29

Ser Tyr Glu Leu Thr Gln Pro Pro Ser Val Ser Val Ala Pro Gly Lys
 1               5                  10                  15

Thr Ala Arg Ile Thr Cys Gly Gly Asp Asn Ile Gly Thr Lys Ser Val
             20                  25                  30

Thr Trp Tyr Gln Gln Arg Pro Gly Gln Ala Pro Met Met Val Ile Tyr
         35                  40                  45

Tyr Asp Thr Val Arg Pro Ser Gly Ile Pro Glu Arg Leu Ser Gly Ser
     50                  55                  60

Asn Ser Gly Asn Thr Ala Thr Leu Thr Ile Thr Arg Val Glu Ala Gly
 65                  70                  75                  80

Asp Glu Ala Asp Tyr Tyr Cys Gln Val Trp Asp Ser Ser Ser Asp His
                 85                  90                  95

Pro Val Phe Gly Gly Gly Thr Lys Leu Thr Val Leu Gly
            100                 105

<210> SEQ ID NO 30
<211> LENGTH: 112
<212> TYPE: PRT
<213> ORGANISM: Artificial Sequence
<220> FEATURE:
<223> OTHER INFORMATION: Synthetic Construct

<400> SEQUENCE: 30

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Val Phe Gly Thr Gly Thr Lys Val Thr Val Leu Gly
            100                 105                 110

<210> SEQ ID NO 31
<211> LENGTH: 109
<212> TYPE: PRT
<213> ORGANISM: Artificial Sequence
<220> FEATURE:
```

<223> OTHER INFORMATION: Synthetic Construct

<400> SEQUENCE: 31

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 32
<211> LENGTH: 110
<212> TYPE: PRT
<213> ORGANISM: Artificial Sequence
<220> FEATURE:
<223> OTHER INFORMATION: Synthetic Construct

<400> SEQUENCE: 32

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Ala Ser Asp Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Asp
                85                  90                  95

Ala Leu Val Phe Gly Gly Gly Thr Lys Leu Thr Val Leu Gly
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Synthetic Construct

<400> SEQUENCE: 33

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu

```
              65                  70                  75                  80
Gln Ala Glu Asp Glu Ala Asp Tyr Tyr Cys Ser Ser Tyr Thr Thr Gly
                    85                  90                  95

Ser Arg Ala Val Phe Gly Gly Gly Thr Lys Leu Thr Val Leu Gly
                100                 105                 110
```

<210> SEQ ID NO 34
<211> LENGTH: 111
<212> TYPE: PRT
<213> ORGANISM: Artificial Sequence
<220> FEATURE:
<223> OTHER INFORMATION: Synthetic Construct

<400> SEQUENCE: 34

```
Gln Ser Val Val Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
         50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Gly Ser Leu
                 85                  90                  95

Tyr Thr Met Leu Phe Gly Gly Gly Thr Lys Leu Thr Val Leu Gly
                100                 105                 110
```

<210> SEQ ID NO 35
<211> LENGTH: 113
<212> TYPE: PRT
<213> ORGANISM: Artificial Sequence
<220> FEATURE:
<223> OTHER INFORMATION: Synthetic Construct

<400> SEQUENCE: 35

```
Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
             35                  40                  45

Leu Ile Phe Gly Asn Ser Asn Arg Pro Ser Gly Val Pro Asp Arg Phe
         50                  55                  60

Ser Gly Phe Lys Ser Gly Thr Ser Ala Ser Leu Ala Ile Thr Gly Leu
 65                  70                  75                  80

Gln Ala Glu Asp Glu Ala Asp Tyr Phe Cys Gln Ser Tyr Asp Ser Ser
                 85                  90                  95

Leu Ser Gly Ser Gly Val Phe Gly Thr Gly Thr Lys Val Thr Val Leu
                100                 105                 110

Gly
```

<210> SEQ ID NO 36
<211> LENGTH: 113
<212> TYPE: PRT
<213> ORGANISM: Artificial Sequence
<220> FEATURE:
<223> OTHER INFORMATION: Synthetic Construct

<400> SEQUENCE: 36

Gln Ser Ala Leu Thr Gln Pro Ala Ser Val Ser Gly Ser Pro Gly Gln
1               5                   10                  15

Ser Ile Thr Ile Ser Cys Thr Ala Thr Gly Ser Asp Val Gly Val Tyr
            20                  25                  30

Tyr Tyr Val Ser Trp Tyr Gln Gln His Pro Gly Lys Ala Pro Lys Val
        35                  40                  45

Met Ile Tyr Asp Val Asp Asn Arg Pro Pro Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ala Ser Tyr Thr Asn Arg
                85                  90                  95

Asn Ser Leu Gly Tyr Val Phe Gly Thr Gly Thr Lys Val Thr Val Leu
            100                 105                 110

Gly

<210> SEQ ID NO 37
<211> LENGTH: 363
<212> TYPE: DNA
<213> ORGANISM: Artificial Sequence
<220> FEATURE:
<223> OTHER INFORMATION: Synthetic Construct

<400> SEQUENCE: 37
gaggtccagc tggtacagtc tggagctgag gtgaagaagc tggggcctc  agtgaaggtc      60 tcctgcaagg cttctggtta cacctttacc agctatggta tcagctgggt gcgacaggcc    120
cctggacaag gcttgagtg  gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gcgctaccag    300
gactggtggt acctgggtca gttcgatcag tggggtcaag gtactctggt gaccgtctcc    360
tca                                                                  363

<210> SEQ ID NO 38
<211> LENGTH: 366
<212> TYPE: DNA
<213> ORGANISM: Artificial Sequence
<220> FEATURE:
<223> OTHER INFORMATION: Synthetic Construct

<400> SEQUENCE: 38
caggtacagc tgcagcagtc aggtccagga ctggtgaagc cctcgcagac cctctcactc      60
acctgtgcca tttccgggga cagtgtctct agcaacagtg ctgcttggaa ctggatcagg    120
cagtccccat cgagaggcct tgagtggctg gaaggacat  actacaggtc caagtggtat    180
aatgattatg cagtatctgt gaaaagtcga ataaccatca cccagacac  atccaagaac    240 cagttctccc tgcagctgaa ctctgtgact cccgaggaca cggctgtgta ttactgtgcg    300
cgcggttctt actactctgg tcgttacgat gcttggggtc aaggtactct ggtgaccgtc    360
tcctca                                                              366

<210> SEQ ID NO 39
<211> LENGTH: 366
<212> TYPE: DNA
<213> ORGANISM: Artificial Sequence

```
<220> FEATURE:
<223> OTHER INFORMATION: Synthetic Construct

<400> SEQUENCE: 39
caggtccagc tggtacagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccta tctttggtac agcaaactac      180
gcacagaagt tccagggcag agtcacgatt accgcggacg aatccacgag cacagcctac     240
atggagctga gcagcctgag atctgaggac acggccgtgt attactgtgc gagagaaatt     300
aggggctact actactacta cggtatggac gtctggggcc aagggaccac ggtcaccgtc     360
tcctca                                                                 366

<210> SEQ ID NO 40
<211> LENGTH: 372
<212> TYPE: DNA
<213> ORGANISM: Artificial Sequence
<220> FEATURE:
<223> OTHER INFORMATION: Synthetic Construct

<400> SEQUENCE: 40
gaggtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga acagtggtag aataggctat      180
gcggactctg tgaagggccg attcaccatc tccagagaca acgccaagaa ctccctgtat     240
ctgcaaatga acagtctgag agctgaggac acggctgtgt attactgtgc gagagccgat     300
gactacggcg ccccctacta ctactacggt atggacgtct ggggccaagg gaccacggtc     360
accgtctcct ca                                                          372

<210> SEQ ID NO 41
<211> LENGTH: 351
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 338
<223> OTHER INFORMATION: n = A,T,C or G

<400> SEQUENCE: 41
caggtgcagc tgcaggagtc gggcccagga ctggtgaagc cttcgggac cctgtccctc       60 acctgcgctg tctctggtgg ctccatcagc agtagtaact ggtggagttg ggtccgccag     120
cccccaggga aggggctgga gtggattggg gaaatctatc atagtgggag caccaactac     180
aacccgtccc tcaagagtcg agtcaccata tcagtagaca gtccaagaa ccagttctcc      240 ctgaagctga gctctgtgac cgccgcggac acggccgtgt attactgtgc gaccggttat     300 gggggggtact ttgactactg gggccaggga accctggnca ccgtctcctc a              351

<210> SEQ ID NO 42
<211> LENGTH: 360
<212> TYPE: DNA
<213> ORGANISM: Artificial Sequence
<220> FEATURE:
<223> OTHER INFORMATION: Synthetic Construct

<400> SEQUENCE: 42
```

| | |
|---|---:|
| gaagtgcagc tggtgcagtc tggagctgag gtgaagaagc ctggggcctc agtgaaggtc | 60 |
| tcctgcaagg cttctggtta cacctttacc agctatggta tcagctgggt gcgacaggcc | 120 |
| cctggacaag ggcttgagtg gatgggatgg atcagcgctt acaatggtaa cacaaactat | 180 |
| gcacagaagc tccagggcag agtcaccatg accacagaca catccacgag cacagcctac | 240 |
| atggagctga ggagcctgag atctgacgac acggccgtgt attactgtgc gagagattcc | 300 |
| tactactact actacggtat ggacgtctgg ggccaaggga ccacggtcac cgtctcctca | 360 |

<210> SEQ ID NO 43
<211> LENGTH: 351
<212> TYPE: DNA
<213> ORGANISM: Artificial Sequence
<220> FEATURE:
<223> OTHER INFORMATION: Synthetic Construct

<400> SEQUENCE: 43

| | |
|---|---:|
| gaggtgcagc tggtgcagtc tggcgccgaa gtgaagaagc ctggcgagag cctgaccatc | 60 |
| tcctgcaagg ccagcggcta cagcttcccc aactactgga tcacctgggt gcgccagatg | 120 |
| tccggcggag gcctggaatg gatgggcaga atcgaccccg cgacagcta cacaacctac | 180 |
| aaccccagct ccagggcca cgtgaccatc agcatcgaca gagcaccaa taccgcctac | 240 |
| ctgcactgga acagcctgaa ggcctccgac accgccatgt actactgcgc ccggtactat | 300 |
| gtgtccctgg tggatatctg gggccagggc acactcgtga ccgtgtctag c | 351 |

<210> SEQ ID NO 44
<211> LENGTH: 372
<212> TYPE: DNA
<213> ORGANISM: Artificial Sequence
<220> FEATURE:
<223> OTHER INFORMATION: Synthetic Construct

<400> SEQUENCE: 44

| | |
|---|---:|
| gaggtgcagc tggtggagtc tgggggaggc ttggtaaagc ctggggggtc ccttagactc | 60 |
| tcctgtgcag cctctggatt cactttcagt aacgcctgga tgagctgggt ccgccaggct | 120 |
| ccagggaagg ggctggagtg ggtaggtttc attagaagca agcttatgg tgggacaaca | 180 |
| gaatacgccg cctctgtgaa aggcagattc accatctcaa gagatgattc aaaagcatc | 240 |
| gcctatctgc aaatgaacaa cctgaaaacc gaggacacag ccgtgtatta ctgtgctaga | 300 |
| gatgggctgt atagcagcag ctggtacgat tctgactact ggggccaggg aaccctggtc | 360 |
| accgtctcct ca | 372 |

<210> SEQ ID NO 45
<211> LENGTH: 378
<212> TYPE: DNA
<213> ORGANISM: Artificial Sequence
<220> FEATURE:
<223> OTHER INFORMATION: Synthetic Construct

<400> SEQUENCE: 45

| | |
|---|---:|
| cagatgcagc tggtgcagtc tgggggaggc ttggtacagc ctggcaggtc cctgagactc | 60 |
| tcctgtgcag cctctggatt cacctttgat gattatgcca tgcactgggt ccggcaagct | 120 |
| ccagggaagg gcctggagtg ggtctcaggt attagttgga atagtggtag cataggctat | 180 |
| gcggactctg tgaagggccg attcaccatc tccagagaca acgccaagaa ctccctgtat | 240 |
| ctgcaaatga acagtctgag agctgaggac acggccttgt attactgtgc aaaagatatc | 300 |
| catagtggga gctactacgg cctactctac tacgctatgg acgtctgggg ccaagggacc | 360 |

```
acggtcaccg tctcctca                                                  378

<210> SEQ ID NO 46
<211> LENGTH: 363
<212> TYPE: DNA
<213> ORGANISM: Artificial Sequence
<220> FEATURE:
<223> OTHER INFORMATION: Synthetic Construct

<400> SEQUENCE: 46
gaggtgcagc tggtgcagtc tggcgccgaa gtgaagaaac caggcgccag cgtgaaggtg      60
tcctgcaagg ccagcggcta cacctttacc agctacggca tcagctgggt gcgccaggct     120
cctggacagg gcctggaatg gatgggctgg atcagcgcct acaacggcaa taccaactac     180
gcccagaaac tgcagggcag agtgaccatg accaccgaca ccagcacctc caccgcctac     240
atggaactgc ggagcctgag aagcgacgac accgccgtgt actattgcgc ccggttccag     300
gactggtggt atctgggcca gttcgaccag tggggccagg gcacactcgt gaccgtgtct     360
agc                                                                  363

<210> SEQ ID NO 47
<211> LENGTH: 338
<212> TYPE: DNA
<213> ORGANISM: Artificial Sequence
<220> FEATURE:
<223> OTHER INFORMATION: Synthetic Construct

<400> SEQUENCE: 47
caatctgccc tgactcagcc tgcctccgtg tctgggtctc ctggacagtc gatcaccatc      60
tcctgcactg caaccggcag tgacgttggt gtttattact atgtctcctg gtaccaacaa     120
cacccaggca aagcccccaa agtgatgatt tatgatgtcg gtaatcggcc cccagggggtt    180 tctaatcgct tctctggctc caagtctggc aacacggcct ccctgaccat ctctgggctc     240
caggctgagg acgaggctga ttattactgc gcctcatata caaacaggaa cagtctcggc     300
tatgtcttcg gaaccgggac caaggtcacc gtcctagg                             338

<210> SEQ ID NO 48
<211> LENGTH: 333
<212> TYPE: DNA
<213> ORGANISM: Artificial Sequence
<220> FEATURE:
<223> OTHER INFORMATION: Synthetic Construct

<400> SEQUENCE: 48
aattttatgc tgactcagcc ccactctgtg tcggagtctc cggggaagac ggtaaccatc      60
tcctgcaccc gcagcagtgg cagcattgcc agcaactatg tgcagtggta ccagcagcgc     120
ccgggcagtt cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caccgtggta     300
ttcggcggag ggaccaagct gaccgtccta ggt                                  333

<210> SEQ ID NO 49
<211> LENGTH: 327
<212> TYPE: DNA
<213> ORGANISM: Artificial Sequence
<220> FEATURE:
<223> OTHER INFORMATION: Synthetic Construct
```

<400> SEQUENCE: 49

```
tcctatgagc tgactcagcc accctcggtg tcagtggccc ctggcaagac ggccaggatt    60
acctgtgggg gtgacaacat tggaactaaa agtgtgacct ggtaccaaca gaggccaggc   120
caggccccta tgatggtcat ctattatgat accgtccggc cctcagggat ccctgagcga   180
ctctctggct ccaactctgg gaacacggcc accctgacca tcacccgggt cgaagccggg   240
gatgaggccg actattactg tcaggtgtgg gatagtagta gtgatcatcc ggtgttcggc   300
ggagggacca agctgaccgt cctaggt                                       327
```

<210> SEQ ID NO 50
<211> LENGTH: 336
<212> TYPE: DNA
<213> ORGANISM: Artificial Sequence
<220> FEATURE:
<223> OTHER INFORMATION: Synthetic Construct

<400> SEQUENCE: 50

```
cagtctgtgt tgacgcagcc gccctcagtg tctggggccc cggggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggttca   300
gtcttcggaa ctgggaccaa ggtcaccgtc ctaggt                             336
```

<210> SEQ ID NO 51
<211> LENGTH: 327
<212> TYPE: DNA
<213> ORGANISM: Artificial Sequence
<220> FEATURE:
<223> OTHER INFORMATION: Synthetic Construct

<400> SEQUENCE: 51

```
cagtctgtgt tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatgt ggtattcggc   300
ggagggacca agctgaccgt cctaggt                                       327
```

<210> SEQ ID NO 52
<211> LENGTH: 330
<212> TYPE: DNA
<213> ORGANISM: Artificial Sequence
<220> FEATURE:
<223> OTHER INFORMATION: Synthetic Construct

<400> SEQUENCE: 52

```
caggctgtgg tgactcagga gccctcactg actgtgtccc caggagggac agtcactctc    60
acctgtggct ccagcactgg agctgtcacc agtggtcatt atcccrtactg gttccagcag   120
aagcctggcc aagcccccag gacactgatt tatgatcaa gcgacaaaca ctcctggaca   180
cctgcccggt tctcaggctc cctccttggg ggcaaagctg ccctgaccct ttcgggtgcg   240
cagcctgagg atgaggctga gtattactgc ttgctctcct atagtgatgc tctggtgttc   300
ggcggaggga ccaagctgac cgtcctaggt                                    330
```

<210> SEQ ID NO 53
<211> LENGTH: 333
<212> TYPE: DNA
<213> ORGANISM: Artificial Sequence
<220> FEATURE:
<223> OTHER INFORMATION: Synthetic Construct

<400> SEQUENCE: 53

| | | |
|---|---|---|
| cagagcgtgc tgacacagcc tgcctccgtg tctggctctc ctggccagtc catcaccatc | 60 |
| agctgtaccg gcaccagctc cgacgtgggc ggctacaatt acgtgtcctg gtatcagcag | 120 |
| catcccggca aggcccccaa gctgatgatc tacgacgtga acaaccggcc cagcgaggtg | 180 |
| tccaacagat tcagcggcag caagagcggc aacaccgcca gcctgacaat cagcggactg | 240 |
| caggccgagg acgaggccga ctactactgc agcagctaca ccaccggcag cagagccgtg | 300 |
| tttggcggag gcaccaagct gacagtgctg ggc | 333 |

<210> SEQ ID NO 54
<211> LENGTH: 333
<212> TYPE: DNA
<213> ORGANISM: Artificial Sequence
<220> FEATURE:
<223> OTHER INFORMATION: Synthetic Construct

<400> SEQUENCE: 54

| | | |
|---|---|---|
| cagtctgtcg tgacgcagcc gccctcagtg tctgcggccc caggacagaa ggtcaccatc | 60 |
| tcctgctctg gaagcagctc caacattggg aataattatg tatcctggta ccagcagctc | 120 |
| ccaggaacag cccccaaact cctcatttat gacaataata gcgaccctc agggattcct | 180 |
| gaccgattct ctggctccaa gtctggcacg tcagccaccc tgggcatcac cggactccag | 240 |
| actggggacg aggccgatta ctactgcgga acatgggatg cagcctcta tactatgtta | 300 |
| ttcggcggag ggaccaagct gaccgtccta ggt | 333 |

<210> SEQ ID NO 55
<211> LENGTH: 339
<212> TYPE: DNA
<213> ORGANISM: Artificial Sequence
<220> FEATURE:
<223> OTHER INFORMATION: Synthetic Construct

<400> SEQUENCE: 55

| | | |
|---|---|---|
| cagtctgtgt tgacgcagcc gccctcagtg tctggggccc cagggcagag ggtcaccatc | 60 |
| tcctgcactg ggagcagctc caacatcggg gcaggttatg atgtacactg gtaccagcag | 120 |
| cttccaggaa cagcccccaa actcctcatc tttggtaaca gcaatcggcc ctcaggggtc | 180 |
| cctgaccgat tctctggctt caagtctggc acctcagcct ccctggccat cactgggctc | 240 |
| caggctgagg atgaggctga ctatttctgc cagtcgtatg acagtagcct gagtggttcg | 300 |
| ggggtcttcg gaactgggac caaggtcacc gtcctaggt | 339 |

<210> SEQ ID NO 56
<211> LENGTH: 339
<212> TYPE: DNA
<213> ORGANISM: Artificial Sequence
<220> FEATURE:
<223> OTHER INFORMATION: Synthetic Construct

<400> SEQUENCE: 56

| | | |
|---|---|---|
| cagagcgccc tgacacagcc tgcctccgtg tctggatctc ccggccagag catcaccatc | 60 |

```
agctgcacag ccaccggctc cgacgtgggc gtgtactact acgtgtcctg gtatcagcag    120
catcccggca aggccccaa agtgatgatc tacgacgtgg acaaccgcc tcccggcgtg      180 tccaatagat tcagcggcag caagagcggc aacaccgcca gcctgacaat cagcggactg    240
caggccgagg acgaggccga ttactactgc gccagctaca ccaaccggaa cagcctgggc    300
tacgtgttcg gcaccggcac caaagtgaca gtgctgggc                           339
```

```
<210> SEQ ID NO 57
<211> LENGTH: 8
<212> TYPE: PRT
<213> ORGANISM: Artificial Sequence
<220> FEATURE:
<223> OTHER INFORMATION: Synthetic Construct

<400> SEQUENCE: 57

Gly Tyr Thr Phe Thr Ser Tyr Gly
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

Val Ser Ser Asn Ser Ala Ala Trp Asn
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Gly Gly Thr Phe Ser Ser Tyr Ala
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Gly Phe Thr Phe Asp Asp Tyr Ala
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gly Gly Ser Ile Ser Ser Ser Asn Trp
1               5

<210> SEQ ID NO 62
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 62

Gly Tyr Thr Phe Thr Ser Tyr Gly
 1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic Construct

<400> SEQUENCE: 63

Gly Tyr Ser Phe Pro Asn Tyr Trp
 1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Construct

<400> SEQUENCE: 64

Gly Phe Thr Phe Ser Asn Ala Trp
 1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic Construct

<400> SEQUENCE: 65

Gly Phe Thr Phe Asp Asp Tyr Ala
 1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic Construct

<400> SEQUENCE: 66

Gly Tyr Thr Phe Thr Ser Tyr Gly
 1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic Construct

<400> SEQUENCE: 67

Ile Ser Ala Tyr Asn Gly Asn Thr
 1               5

<210> SEQ ID NO 68
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 68

Tyr Arg Ser Lys Trp Tyr Asn
 1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic Construct

<400> SEQUENCE: 69

Ile Ile Pro Ile Phe Gly Thr Ala
 1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Construct

<400> SEQUENCE: 70

Ile Ser Trp Asn Ser Gly Arg Ile
 1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic Construct

<400> SEQUENCE: 71

Ile Tyr His Ser Gly Ser Thr
 1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Construct

<400> SEQUENCE: 72

Ile Ser Ala Tyr Asn Gly Asn Thr
 1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Construct

<400> SEQUENCE: 73

Ile Asp Pro Gly Asp Ser Tyr Thr
 1               5

<210> SEQ ID NO 74
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 74

Ile Arg Ser Lys Ala Tyr Gly Gly Thr Thr
1               5                   10

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Ile Ser Trp Asn Ser Gly Ser Ile
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Construct

<400> SEQUENCE: 76

Ile Ser Ala Tyr Asn Gly Asn Thr
1               5

<210> SEQ ID NO 77
<211> LENGTH: 14
<212> TYPE: PRT
<213> ORGANISM: Artificial Sequence
<220> FEATURE:
<223> OTHER INFORMATION: Synthetic Construct

<400> SEQUENCE: 77

Ala Arg Tyr Gln Asp Trp Trp Tyr Leu Gly Gln Phe Asp Gln
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic Construct

<400> SEQUENCE: 78

Ala Arg Gly Ser Tyr Tyr Ser Gly Arg Tyr Asp Ala
1               5                   10

<210> SEQ ID NO 79
<211> LENGTH: 15
<212> TYPE: PRT
<213> ORGANISM: Artificial Sequence
<220> FEATURE:
<223> OTHER INFORMATION: Synthetic Construct

<400> SEQUENCE: 79

Ala Arg Glu Ile Arg Gly Tyr Tyr Tyr Tyr Tyr Gly Met Asp Val
1               5                   10                  15

<210> SEQ ID NO 80
<211> LENGTH: 17
<212> TYPE: PRT
<213> ORGANISM: Artificial Sequence
<220> FEATURE:
<223> OTHER INFORMATION: Synthetic Construct
```

<400> SEQUENCE: 80

Ala Arg Ala Asp Asp Tyr Gly Ala Pro Tyr Tyr Tyr Tyr Gly Met Asp
1               5                   10                  15
Val

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Ala Thr Gly Tyr Gly Gly Tyr Phe Asp Tyr
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Synthetic Construct

<400> SEQUENCE: 82

Ala Arg Asp Ser Tyr Tyr Tyr Tyr Tyr Gly Met Asp Val
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic Construct

<400> SEQUENCE: 83

Ala Arg Tyr Tyr Val Ser Leu Val Asp Ile
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Synthetic Construct

<400> SEQUENCE: 84

Ala Arg Asp Gly Leu Tyr Ser Ser Ser Trp Tyr Asp Ser Asp Tyr
1               5                   10                  15

<210> SEQ ID NO 85
<211> LENGTH: 19
<212> TYPE: PRT
<213> ORGANISM: Artificial Sequence
<220> FEATURE:
<223> OTHER INFORMATION: Synthetic Construct

<400> SEQUENCE: 85

Ala Lys Asp Ile His Ser Gly Ser Tyr Tyr Gly Leu Leu Tyr Tyr Ala
1               5                   10                  15
Met Asp Val

<210> SEQ ID NO 86
<211> LENGTH: 14
<212> TYPE: PRT

```
<213> ORGANISM: Artificial Sequence
<220> FEATURE:
<223> OTHER INFORMATION: Synthetic Construct

<400> SEQUENCE: 86

Ala Arg Phe Gln Asp Trp Trp Tyr Leu Gly Gln Phe Asp Gln
 1               5                   10

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = F or Y
<220> FEATURE:
<221> NAME/KEY: VARIANT
<222> LOCATION: 3
<223> OTHER INFORMATION: Xaa = S or T
<220> FEATURE:
<221> NAME/KEY: VARIANT
<222> LOCATION: 5
<223> OTHER INFORMATION: Xaa = D or S or T
<220> FEATURE:
<221> NAME/KEY: VARIANT
<222> LOCATION: 6
<223> OTHER INFORMATION: Xaa = D or N or S
<220> FEATURE:
<221> NAME/KEY: VARIANT
<222> LOCATION: 7
<223> OTHER INFORMATION: Xaa = Y or A
<220> FEATURE:
<221> NAME/KEY: VARIANT
<222> LOCATION: 8
<223> OTHER INFORMATION: Xaa = A or G or W

<400> SEQUENCE: 87

Gly Xaa Xaa Phe Xaa Xaa Xaa Xaa
 1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = I or S
<220> FEATURE:
<221> NAME/KEY: VARIANT
<222> LOCATION: 2
<223> OTHER INFORMATION: Xaa = K or S
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 4
<223> OTHER INFORMATION: Xaa = H or Y
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: 7
<223> OTHER INFORMATION: Xaa = Any Amino Acid

<400> SEQUENCE: 88
```

```
Xaa Xaa Xaa Xaa Xaa Gly Xaa Thr
 1               5
```

```
<210> SEQ ID NO 89
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = A or G
<220> FEATURE:
<221> NAME/KEY: VARIANT
<222> LOCATION: 2, 5, 6, 7
<223> OTHER INFORMATION: Xaa = Any Amino Acid
<220> FEATURE:
<221> NAME/KEY: VARIANT
<222> LOCATION: 3
<223> OTHER INFORMATION: Xaa = W or Y
<220> FEATURE:
<221> NAME/KEY: VARIANT
<222> LOCATION: 8
<223> OTHER INFORMATION: Xaa = F or Y

<400> SEQUENCE: 89

Xaa Xaa Xaa Tyr Xaa Xaa Xaa Xaa Asp
 1               5
```

```
<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

Gly Ser Asp Val Gly Val Tyr Tyr Tyr
 1               5
```

```
<210> SEQ ID NO 91
<211> LENGTH: 8
<212> TYPE: PRT
<213> ORGANISM: Artificial Sequence
<220> FEATURE:
<223> OTHER INFORMATION: Synthetic Construct

<400> SEQUENCE: 91

Ser Gly Ser Ile Ala Ser Asn Tyr
 1               5
```

```
<210> SEQ ID NO 92
<211> LENGTH: 6
<212> TYPE: PRT
<213> ORGANISM: Artificial Sequence
<220> FEATURE:
<223> OTHER INFORMATION: Synthetic Construct

<400> SEQUENCE: 92

Asn Ile Gly Thr Lys Ser
 1               5
```

```
<210> SEQ ID NO 93
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 93

Ser Ser Asn Ile Gly Ala Gly Tyr Asp
1               5

<210> SEQ ID NO 94
<211> LENGTH: 6
<212> TYPE: PRT
<213> ORGANISM: Artificial Sequence
<220> FEATURE:
<223> OTHER INFORMATION: Synthetic Construct

<400> SEQUENCE: 94

Asn Ile Gly Ser Lys Ser
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Construct

<400> SEQUENCE: 95

Thr Gly Ala Val Thr Ser Gly His Tyr
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Construct

<400> SEQUENCE: 96

Ser Ser Asp Val Gly Gly Tyr Asn Tyr
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic Construct

<400> SEQUENCE: 97

Ser Ser Asn Ile Gly Asn Asn Tyr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Construct

<400> SEQUENCE: 98

Ser Ser Asn Ile Gly Ala Gly Tyr Asp
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 99

Gly Ser Asp Val Gly Val Tyr Tyr Tyr
1               5

<210> SEQ ID NO 100
<211> LENGTH: 3
<212> TYPE: PRT
<213> ORGANISM: Artificial Sequence
<220> FEATURE:
<223> OTHER INFORMATION: Synthetic Construct

<400> SEQUENCE: 100

Asp Val Gly
1

<210> SEQ ID NO 101
<211> LENGTH: 3
<212> TYPE: PRT
<213> ORGANISM: Artificial Sequence
<220> FEATURE:
<223> OTHER INFORMATION: Synthetic Construct

<400> SEQUENCE: 101

Glu Asp Asn
1

<210> SEQ ID NO 102
<211> LENGTH: 3
<212> TYPE: PRT
<213> ORGANISM: Artificial Sequence
<220> FEATURE:
<223> OTHER INFORMATION: Synthetic Construct

<400> SEQUENCE: 102

Tyr Asp Thr
1

<210> SEQ ID NO 103
<211> LENGTH: 3
<212> TYPE: PRT
<213> ORGANISM: Artificial Sequence
<220> FEATURE:
<223> OTHER INFORMATION: Synthetic Construct

<400> SEQUENCE: 103

Gly Asn Ser
1

<210> SEQ ID NO 104
<211> LENGTH: 3
<212> TYPE: PRT
<213> ORGANISM: Artificial Sequence
<220> FEATURE:
<223> OTHER INFORMATION: Synthetic Construct

<400> SEQUENCE: 104

Tyr Asp Ser
1

<210> SEQ ID NO 105
<211> LENGTH: 3
<212> TYPE: PRT
<213> ORGANISM: Artificial Sequence
<220> FEATURE:
<223> OTHER INFORMATION: Synthetic Construct

<400> SEQUENCE: 105
```

```
Asp Ala Ser
  1

<210> SEQ ID NO 106
<211> LENGTH: 3
<212> TYPE: PRT
<213> ORGANISM: Artificial Sequence
<220> FEATURE:
<223> OTHER INFORMATION: Synthetic Construct

<400> SEQUENCE: 106

Asp Val Asn
  1

<210> SEQ ID NO 107
<211> LENGTH: 3
<212> TYPE: PRT
<213> ORGANISM: Artificial Sequence
<220> FEATURE:
<223> OTHER INFORMATION: Synthetic Construct

<400> SEQUENCE: 107

Asp Asn Asn
  1

<210> SEQ ID NO 108
<211> LENGTH: 3
<212> TYPE: PRT
<213> ORGANISM: Artificial Sequence
<220> FEATURE:
<223> OTHER INFORMATION: Synthetic Construct

<400> SEQUENCE: 108

Gly Asn Ser
  1

<210> SEQ ID NO 109
<211> LENGTH: 3
<212> TYPE: PRT
<213> ORGANISM: Artificial Sequence
<220> FEATURE:
<223> OTHER INFORMATION: Synthetic Construct

<400> SEQUENCE: 109

Asp Val Asp
  1

<210> SEQ ID NO 110
<211> LENGTH: 12
<212> TYPE: PRT
<213> ORGANISM: Artificial Sequence
<220> FEATURE:
<223> OTHER INFORMATION: Synthetic Construct

<400> SEQUENCE: 110

Ala Ser Tyr Thr Asn Arg Asn Ser Leu Gly Tyr Val
  1               5                  10

<210> SEQ ID NO 111
<211> LENGTH: 9
<212> TYPE: PRT
<213> ORGANISM: Artificial Sequence
<220> FEATURE:
<223> OTHER INFORMATION: Synthetic Construct

<400> SEQUENCE: 111
```

Gln Ser Tyr Asp Ser Ser Thr Val Val
1               5

<210> SEQ ID NO 112
<211> LENGTH: 11
<212> TYPE: PRT
<213> ORGANISM: Artificial Sequence
<220> FEATURE:
<223> OTHER INFORMATION: Synthetic Construct

<400> SEQUENCE: 112

Gln Val Trp Asp Ser Ser Ser Asp His Pro Val
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Synthetic Construct

<400> SEQUENCE: 113

Gln Ser Tyr Asp Ser Ser Leu Ser Gly Ser Val
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Synthetic Construct

<400> SEQUENCE: 114

Gln Val Trp Asp Ser Ser Ser Asp His Val Val
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Synthetic Construct

<400> SEQUENCE: 115

Leu Leu Ser Tyr Ser Asp Ala Leu Val
1               5

<210> SEQ ID NO 116
<211> LENGTH: 10
<212> TYPE: PRT
<213> ORGANISM: Artificial Sequence
<220> FEATURE:
<223> OTHER INFORMATION: Synthetic Construct

<400> SEQUENCE: 116

Ser Ser Tyr Thr Thr Gly Ser Arg Ala Val
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic Construct

<400> SEQUENCE: 117

Gly Thr Trp Asp Gly Ser Leu Tyr Thr Met Leu

```
                   1               5                   10

<210> SEQ ID NO 118
<211> LENGTH: 12
<212> TYPE: PRT
<213> ORGANISM: Artificial Sequence
<220> FEATURE:
<223> OTHER INFORMATION: Synthetic Construct

<400> SEQUENCE: 118

Gln Ser Tyr Asp Ser Ser Leu Ser Gly Ser Gly Val
 1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic Construct

<400> SEQUENCE: 119

Ala Ser Tyr Thr Asn Arg Asn Ser Leu Gly Tyr Val
 1               5                   10

<210> SEQ ID NO 120
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = S or T
<220> FEATURE:
<221> NAME/KEY: VARIANT
<222> LOCATION: 2
<223> OTHER INFORMATION: Xaa = G or S
<220> FEATURE:
<221> NAME/KEY: VARIANT
<222> LOCATION: 3
<223> OTHER INFORMATION: Xaa = D or N
<220> FEATURE:
<221> NAME/KEY: VARIANT
<222> LOCATION: 4
<223> OTHER INFORMATION: Xaa = I or V
<220> FEATURE:
<221> NAME/KEY: VARIANT
<222> LOCATION: 5
<223> OTHER INFORMATION: Xaa = A or G
<220> FEATURE:
<221> NAME/KEY: VARIANT
<222> LOCATION: 6
<223> OTHER INFORMATION: Xaa = A or S or V
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 8
<223> OTHER INFORMATION: Xaa = H or Y

<400> SEQUENCE: 120

Xaa Xaa Xaa Xaa Xaa Xaa Xaa Xaa
 1               5

<210> SEQ ID NO 121
<211> LENGTH: 6
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: 2
<223> OTHER INFORMATION: Xaa = S or T
<220> FEATURE:
<221> NAME/KEY: VARIANT
<222> LOCATION: 3
<223> OTHER INFORMATION: Xaa = Y or W
<220> FEATURE:
<221> NAME/KEY: VARIANT
<222> LOCATION: 4
<223> OTHER INFORMATION: Xaa = D or T
<220> FEATURE:
<221> NAME/KEY: VARIANT
<222> LOCATION: 5
<223> OTHER INFORMATION: Xaa = S or T
<220> FEATURE:
<221> NAME/KEY: VARIANT
<222> LOCATION: 6
<223> OTHER INFORMATION: Xaa = A or S

<400> SEQUENCE: 121

Gln Xaa Xaa Xaa Xaa Xaa
 1               5

<210> SEQ ID NO 122
<211> LENGTH: 9
<212> TYPE: PRT
<213> ORGANISM: Homo sapiens

<400> SEQUENCE: 122

Leu Leu Asp Val Pro Thr Ala Ala Val
 1               5

<210> SEQ ID NO 123
<211> LENGTH: 9
<212> TYPE: PRT
<213> ORGANISM: Homo sapiens

<400> SEQUENCE: 123

Thr Leu Trp Val Asp Pro Tyr Glu Val
 1               5

<210> SEQ ID NO 124
<211> LENGTH: 9
<212> TYPE: PRT
<213> ORGANISM: Homo sapiens

<400> SEQUENCE: 124

Phe Leu Leu Asp His Leu Lys Arg Val
 1               5

<210> SEQ ID NO 125
<211> LENGTH: 10
<212> TYPE: PRT
<213> ORGANISM: Homo sapiens

<400> SEQUENCE: 125

Leu Leu Leu Asp Val Pro Thr Ala Ala Val
 1               5                  10

<210> SEQ ID NO 126
<211> LENGTH: 13
<212> TYPE: PRT
<213> ORGANISM: Homo sapiens

<400> SEQUENCE: 126
```

Val Leu Phe Arg Gly Gly Pro Arg Gly Leu Leu Ala Val
1               5                   10

<210> SEQ ID NO 127
<211> LENGTH: 9
<212> TYPE: PRT
<213> ORGANISM: Homo sapiens

<400> SEQUENCE: 127

Ser Leu Leu Pro Ala Ile Val Glu Leu
1               5

<210> SEQ ID NO 128
<211> LENGTH: 9
<212> TYPE: PRT
<213> ORGANISM: Homo sapiens

<400> SEQUENCE: 128

Tyr Leu Leu Pro Ala Ile Val His Ile
1               5

<210> SEQ ID NO 129
<211> LENGTH: 9
<212> TYPE: PRT
<213> ORGANISM: Homo sapiens

<400> SEQUENCE: 129

Phe Leu Leu Pro Thr Gly Ala Glu Ala
1               5

<210> SEQ ID NO 130
<211> LENGTH: 10
<212> TYPE: PRT
<213> ORGANISM: Homo sapiens

<400> SEQUENCE: 130

Leu Leu Asp Pro Lys Leu Cys Tyr Leu Leu
1               5                   10

<210> SEQ ID NO 131
<211> LENGTH: 10
<212> TYPE: PRT
<213> ORGANISM: Homo sapiens

<400> SEQUENCE: 131

Ser Leu Pro His Phe His His Pro Glu Thr
1               5                   10

<210> SEQ ID NO 132
<211> LENGTH: 10
<212> TYPE: PRT
<213> ORGANISM: Homo sapiens

<400> SEQUENCE: 132

Met Leu Leu Ser Val Pro Leu Leu Leu Gly
1               5                   10

<210> SEQ ID NO 133
<211> LENGTH: 11
<212> TYPE: PRT
<213> ORGANISM: Homo sapiens

<400> SEQUENCE: 133

Leu Leu Tyr Asp Met Val Cys Gly Asp Ile Pro
1               5                   10

<210> SEQ ID NO 134
<211> LENGTH: 11
<212> TYPE: PRT
<213> ORGANISM: Homo sapiens

<400> SEQUENCE: 134

Leu Leu Leu Asp Val Pro Thr Ala Ala Val Gln
1               5                   10

<210> SEQ ID NO 135
<211> LENGTH: 12
<212> TYPE: PRT
<213> ORGANISM: Homo sapiens

<400> SEQUENCE: 135

Leu Leu Leu Asp Val Pro Thr Ala Ala Val Gln Ala
1               5                   10

<210> SEQ ID NO 136
<211> LENGTH: 14
<212> TYPE: PRT
<213> ORGANISM: Homo sapiens

<400> SEQUENCE: 136

Val Leu Phe Arg Gly Gly Pro Arg Gly Leu Leu Ala Val Ala
1               5                   10

<210> SEQ ID NO 137
<211> LENGTH: 9
<212> TYPE: PRT
<213> ORGANISM: Homo sapiens

<400> SEQUENCE: 137

Met Val Asp Gly Thr Leu Leu Leu Leu
1               5

<210> SEQ ID NO 138
<211> LENGTH: 10
<212> TYPE: PRT
<213> ORGANISM: Homo sapiens

<400> SEQUENCE: 138

Tyr Met Ala Pro Glu Ile Leu Met Arg Ser
1               5                   10

<210> SEQ ID NO 139
<211> LENGTH: 10
<212> TYPE: PRT
<213> ORGANISM: Homo sapiens

<400> SEQUENCE: 139

Phe Ile Tyr Asn Ala Asp Leu Met Asn Cys
1               5                   10

<210> SEQ ID NO 140
<211> LENGTH: 11
<212> TYPE: PRT
<213> ORGANISM: Homo sapiens

<400> SEQUENCE: 140

Lys Gln Tyr Glu Ser Val Leu Met Val Ser Ile
1               5                   10

```
<210> SEQ ID NO 141
<211> LENGTH: 9
<212> TYPE: PRT
<213> ORGANISM: Homo sapiens

<400> SEQUENCE: 141

Ile Leu Ala Lys Phe Leu His Trp Leu
 1               5
```